(12) United States Patent
Dalton et al.

(10) Patent No.: US 7,645,898 B2
(45) Date of Patent: Jan. 12, 2010

(54) SELECTIVE ANDROGEN RECEPTOR MODULATORS AND METHOD OF USE THEREOF

(75) Inventors: James T. Dalton, Arlington, OH (US); Duane D. Miller, Germantown, TN (US)

(73) Assignee: University of Tennessee Research Foundation, Knoxville, TN (US)

(*) Notice: Subject to any disclaimer, the term of this patent is extended or adjusted under 35 U.S.C. 154(b) by 0 days.

(21) Appl. No.: 11/505,499

(22) Filed: Aug. 17, 2006

(65) Prior Publication Data

US 2007/0123563 A1 May 31, 2007

Related U.S. Application Data

(63) Continuation-in-part of application No. 11/353,225, filed on Feb. 14, 2006, now Pat. No. 7,518,013, which is a continuation-in-part of application No. 11/125,159, filed on May 10, 2005, now Pat. No. 7,205,437, which is a continuation-in-part of application No. 11/062,752, filed on Feb. 23, 2005, which is a continuation-in-part of application No. 10/863,524, filed on Jun. 9, 2004, now abandoned.

(51) Int. Cl.
*C07C 255/50* (2006.01)
*A61K 31/275* (2006.01)

(52) U.S. Cl. ...................... 558/414; 514/522

(58) Field of Classification Search .......... 514/522, 514/524, 616, 617; 564/153, 157, 158, 175; 558/417, 414

See application file for complete search history.

(56) References Cited

U.S. PATENT DOCUMENTS

| | | | |
|---|---|---|---|
| 3,239,345 A | 3/1966 | Hodge et al. | |
| 3,865,801 A | 2/1975 | Chiba et al. | |
| 3,875,229 A | 4/1975 | Gold | |
| 4,036,979 A | 7/1977 | Asato | |
| 4,139,638 A | 2/1979 | Neri et al. | |
| 4,191,775 A | 3/1980 | Glen | |
| 4,239,776 A | 12/1980 | Glen et al. | |
| 4,282,218 A | 8/1981 | Glen et al. | |
| 4,386,080 A | 5/1983 | Crossley et al. | |
| 4,411,890 A | 10/1983 | Momany et al. | |
| 4,465,507 A | 8/1984 | Konno et al. | |
| 4,636,505 A | 1/1987 | Tucker | |
| 4,880,839 A | 11/1989 | Tucker | |
| 4,977,288 A | 12/1990 | Kassis et al. | |
| 5,162,504 A | 11/1992 | Horoszewicz | |
| 5,179,080 A | 1/1993 | Rothkopf et al. | |
| 5,441,868 A | 8/1995 | Lin et al. | |
| 5,547,933 A | 8/1996 | Lin et al. | |
| 5,609,849 A | 3/1997 | Kung | |
| 5,612,359 A | 3/1997 | Murugesan et al. | |
| 5,618,698 A | 4/1997 | Lin et al. | |
| 5,621,080 A | 4/1997 | Lin et al. | |
| 5,656,651 A | 8/1997 | Sovak et al. | |
| 6,019,957 A | 2/2000 | Miller et al. | |
| 6,043,265 A | 3/2000 | Murugesan et al. | |
| 6,071,957 A | 6/2000 | Miller et al. | |
| 6,160,011 A | 12/2000 | Miller et al. | |
| 6,482,861 B2 | 11/2002 | Miller et al. | |
| 6,492,554 B2 | 12/2002 | Dalton et al. | |
| 6,548,529 B1 | 4/2003 | Robl et al. | |
| 6,569,896 B2 | 5/2003 | Dalton et al. | |
| 6,777,427 B2 | 8/2004 | Miyakawa et al. | |
| 6,838,484 B2 * | 1/2005 | Steiner et al. | ............... 514/616 |
| 6,899,888 B2 | 5/2005 | Steiner et al. | |
| 6,960,474 B2 | 11/2005 | Salvati et al. | |
| 6,995,284 B2 | 2/2006 | Dalton et al. | |
| 6,998,500 B2 | 2/2006 | Dalton et al. | |
| 7,026,500 B2 * | 4/2006 | Dalton et al. | ............... 558/417 |
| 7,041,844 B2 | 5/2006 | Miller et al. | |
| 7,205,437 B2 | 4/2007 | Dalton et al. | |
| 7,344,700 B2 | 3/2008 | Dalton et al. | |
| 7,518,013 B2 | 4/2009 | Dalton et al. | |
| 7,547,728 B2 | 6/2009 | Dalton et al. | |
| 2001/0012839 A1 | 8/2001 | Miller et al. | |
| 2002/0173445 A1 | 11/2002 | Salvati et al. | |
| 2003/0232792 A1 | 12/2003 | Dalton et al. | |
| 2004/0014975 A1 | 1/2004 | Dalton et al. | |
| 2004/0029913 A1 | 2/2004 | Dalton et al. | |
| 2004/0053897 A1 | 3/2004 | Steiner et al. | |
| 2004/0087557 A1 | 5/2004 | Steiner et al. | |

(Continued)

FOREIGN PATENT DOCUMENTS

AU 2002364949 6/2003

(Continued)

OTHER PUBLICATIONS

U.S. Appl. No. 09/644,970, filed Aug. 2, 2000, Dalton et al.
U.S. Appl. No. 09/935,044, filed Aug. 23, 2001, Dalton et al.
U.S. Appl. No. 09/935,045, filed Aug. 23, 2001, Dalton et al.
U.S. Appl. No. 10/298,229, filed Nov. 28, 2002, Miller et al.
U.S. Appl. No. 10/270,232, filed Oct. 15, 2002, Dalton et al.
U.S. Appl. No. 10/277,108, filed Oct. 23, 2002, Dalton et al.
U.S. Appl. No. 10/270,233, filed Oct. 15, 2002, Dalton et al.
U.S. Appl. No. 10/270,732, filed Oct. 15, 2002, Dalton et al.
U.S. Appl. No. 10/310,150, filed Dec. 5, 2002, Steiner et at.
Howard Tucker and Glynne J. Chesterson, J. Med Chem. 1988, 31, pp. 885-887, "Resolution of the Nonsteroidal Antiandrogen -4'-Cyano-3[(4-fluorophenyl)sulfonyl]-2-hydroxy-2-methyl-3'-(trifluoromethyl)-propionanilide and the Determination of the Absolute Configuration of the Active Enantiomer".

(Continued)

*Primary Examiner*—Shailendra Kumar
(74) *Attorney, Agent, or Firm*—Mark S. Cohen; Pearl Cohen Zedek Latzer, LLP

(57) ABSTRACT

This invention provides SARM compounds and uses thereof in treating a variety of diseases or conditions in a subject, including, inter-alia, a muscle wasting disease and/or disorder or a bone-related disease and/or disorder.

7 Claims, 42 Drawing Sheets

U.S. PATENT DOCUMENTS

| | | | |
|---|---|---|---|
| 2004/0087810 A1 | 5/2004 | Dalton et al. |
| 2004/0147489 A1 | 7/2004 | Dalton et al. |
| 2004/0260092 A1 | 12/2004 | Miller et al. |
| 2004/0260108 A1 | 12/2004 | Dalton et al. |
| 2004/0265916 A1 | 12/2004 | Dalton et al. |
| 2005/0038110 A1 | 2/2005 | Steiner et al. |
| 2005/0137172 A1 | 6/2005 | Dalton et al. |
| 2006/0004042 A1 | 1/2006 | Dalton et al. |
| 2006/0009529 A1 | 1/2006 | Dalton et al. |
| 2006/0035965 A1 | 2/2006 | Dalton et al. |
| 2006/0111441 A1 | 5/2006 | Dalton et al. |
| 2006/0183931 A1 | 8/2006 | Dalton et al. |
| 2006/0229362 A1 | 10/2006 | Dalton et al. |
| 2007/0066568 A1 | 3/2007 | Dalton et al. |
| 2007/0123563 A1 | 5/2007 | Dalton et al. |
| 2007/0173546 A1 | 7/2007 | Dalton et al. |

FOREIGN PATENT DOCUMENTS

| | | |
|---|---|---|
| AU | 2003216174 | 9/2003 |
| CA | 2420279 | 2/2002 |
| CA | 2477737 | 9/2003 |
| CA | 2502209 | 4/2004 |
| CA | 2505355 | 4/2004 |
| CA | 2538095 | 4/2004 |
| CA | 2529464 | 1/2005 |
| EP | 0 040 932 | 2/1981 |
| EP | 0 040 932 | 12/1981 |
| EP | 0 100 172 | 2/1984 |
| EP | 00 02 892 | 2/1985 |
| EP | 000 2892 | 2/1985 |
| EP | 0 253 503 | 1/1988 |
| EP | 00198352 | 1/1989 |
| EP | 0253 503 | 12/1991 |
| EP | 0253503 | 12/1991 |
| EP | 668351 | 8/1995 |
| EP | 1221439 | 7/2002 |
| EP | 1401801 | 11/2006 |
| EP | 1801140 | 6/2007 |
| GB | 1360001 | 3/1970 |
| JP | 52-128329 | 10/1977 |
| JP | 54-63047 | 12/1980 |
| JP | 59-033250 | 2/1984 |
| WO | WO 89/07110 | 8/1989 |
| WO | WO 89/07111 | 8/1989 |
| WO | WO 91/05867 | 5/1991 |
| WO | WO 93/04081 | 3/1993 |
| WO | 95/19770 | 7/1995 |
| WO | WO 95/19770 | 7/1995 |
| WO | 98 05962 | 2/1998 |
| WO | WO 98/05962 | 2/1998 |
| WO | WO 98 05962 | 2/1998 |
| WO | 98/53826 | 12/1998 |
| WO | 98/55153 | 12/1998 |
| WO | WO 98/53826 | 12/1998 |
| WO | WO 98/55153 | 12/1998 |
| WO | WO 00/01389 | 1/2000 |
| WO | 01 27622 | 4/2001 |
| WO | 01 28990 | 4/2001 |
| WO | WO 01/27086 | 4/2001 |
| WO | WO/01/27086 | 4/2001 |
| WO | WO 01/27622 | 4/2001 |
| WO | WO 01 27622 | 4/2001 |
| WO | WO 01 28990 | 4/2001 |
| WO | WO 01/28990 | 4/2001 |
| WO | 01 34563 | 5/2001 |
| WO | WO 01 34563 | 5/2001 |
| WO | WO 01/34563 | 5/2001 |
| WO | WO 01/68603 | 9/2001 |
| WO | 02 00617 | 1/2002 |
| WO | WO 02 00617 | 1/2002 |
| WO | WO 02/00617 | 1/2002 |
| WO | 02/16310 | 2/2002 |
| WO | WO 02/16310 | 2/2002 |
| WO | WO 02/22585 | 3/2002 |
| WO | WO/02/22585 | 3/2002 |
| WO | WO 03/011302 | 2/2003 |
| WO | WO 03/049675 | 6/2003 |
| WO | WO 03/065992 | 8/2003 |
| WO | WO 03/074449 | 9/2003 |
| WO | WO/03/077919 | 9/2003 |
| WO | WO 2004/035736 | 4/2004 |
| WO | WO 2005/000794 | 1/2005 |
| WO | WO 2005/060647 | 7/2005 |
| WO | WO 03/077919 | 9/2009 |

OTHER PUBLICATIONS

D. McKillop, et al., "Enantioselective metabolism and pharmacokinetics of Casodex in the male rat", Xenobiotica, 1995, vol. 25, No. 6, 623-634.

Leonid Kirkovsky, et al., "[$^{125}$I]-Radionated Bicalutamide Analogs as Potential Imaging Agents for Prostate Cancer", Poster Presentation MEDI 155, 214th ACS National Meeting, Las Vegas, NV, Sep. 7-11, 1997, Department of Pharmaceutical Sciences, University of Tennessee, Memphis, TN 38163.

David T. Baird and Anna F. Glasier, "Hormonal Contraception—Drug Therapy", The New England Journal of Medicine, May 27, 1993, pp. 1543-1549.

F.C. W. Wu, "Male Contraception: Current Status and Future Prospects", Clinical Endocrinology, (1988), 29, pp. 443-465.

Carl Djerassi and S.P. Leibo, "A new look at male contraception", Nature, vol. 370, pp. 11-12, 1994.

World Health Organisation Task Force on Methods for the Regulation of Male Fertility, "Contraceptive efficacy of testosterone-induced azoospermia in normal men", The Lancet, vol. 336, Oct. 20, 1990, pp. 955-959 and 1517-1518.

C. G. Francisco, et al., "Long-acting contraceptive agents: testosterone esters of unsaturated acids", Steroids, Jan. 1990, vol. 55, Butterworths.

John M. Hoberman and Charles E. Yesalis, "The History of Synthetic Testosterone", Scientific American, Feb. 1995, pp. 76-81.

Leonid Kirkovsky, et al., "Approaches to Irreversible non-steroidal chiral antiandrogens", Department of Pharmaceutical Sciences, University of Tennessee, 47th Southeast/51st Southwest Joint Regional Meeting of the American Chemical Society, Memphis, TN, Nov. 29-Dec. 1, 1995.

David J. Handelsman, "Bridging the gender gap in contraception: another hurdle cleared" The Medical Journal of Australia, vol. 154, Feb. 18, 1996, pp. 230-233.

Edwards JP, Higuchi RI, Winn DT, Pooley CLF, Caferro TR, Hamann LG, Zhi L, Marschke KB, Goldman ME, and Jones TK. Nonsteroidal androgen receptor agonists based on 4-(trifluoromethyl)-2H-pyrano[3,2-g]quinolin-2-one. Bioorg. Med. Chem. Lett., 9: 1003, 1999.

Zhi L, Tegley CM, Marschke KB, and Jones TK. Switching androgen receptor antagonists to agonists by modifying C-ring substituents on piperidino[3,2-g]quinolone. Bioorg. Med. Chem. Lett., 9: 1009, 1999.

Higuchi RI, Edwards JP, Caferro TR, Ringgenberg JD, Kong JW, Hamann LG, Arienti KL., Marschke KB, Davis RL, Farmer LJ, and Jones TK. 4-Alkyl- and 3,4-diaklyl-1,2,3,4-tetrahydro-8-pyridono[5,6-g]quinolines: potent, nonsteroidal androgen receptor agonists. Bioorg. Med. Chem. Lett., 9:1335,1999.

Hamann LG, Mani NS, Davis RL, Wang XN, Marschke KB, and Jones TK. Discovery of a potent, orally active nonsteroidal androgen receptor agonist: 4-ethyl-1,2,3,4-tetrahydro-6-(trifluoromethyl)-8-pyridono[5,6-g]-quinoline (LG121071). J. Med. Chem., 42: 210, 1999.

Rosen J, Day A, Jones TK, Jones ET, Nathan AM, and Stein RB. Intracellular receptors and signal transducers and activators of transcription superfamilies: novel targets for small-molecule drug discovery. J. Med. Chem., 38: 4855, 1995.

Dalton JT, Mukherjee A, Zhu Z, Kirkovsky L, and Miller DD. Discovery of Nonsteroidal Androgens. Biochem. Biophys. Res. Commun.,244(1):1-4, 1998.

Edwards JP, West SJ, Pooley CLF, Marschke KB, Farmer LJ, and Jones TK. New nonsteroidal androgen receptor modulators based on 4-(trifluoromethyl)-2-(1H)-Pyrololidino[3,2-g]quinolone. Bioorg. Med. Chem. Lett, 8: 745, 1998.

Eliason et al., "High Throughput Fluorescence Polarization-Based Screening Assays for the Identification of Novel Nuclear Receptor Ligands," Abstracts of Papers, 223rd ACS National Meeting, Orlando, FL, United States, (2002), Apr. 7, 2002.

Berger et al., "Concepts and limitations in the application of radiolabeled antiandrogens, estrogens, or androgens as isotropic scanning agents for the prostate", Invest. Urol, (1975), 1391, 10-16.

Wanner, et al (1984) "Assesment of Bone Mineral Part 1 " J Nucl. Medicine, 1134-1141.

Wahner, et al (1985) "Bone Mineral Density of the Radius" J. Nucl Medicine 26 13-39.

Faulkner KG, et al (1991) "Noninvasive measurements of bone mass, structure, and strength: current methods and experimental techniques." Am J Rosentgenology 157:1229-1237.

Hanada, K., et al (2003) "Bone anabolic effects of S-40503, a novel nonsteroidal selective androgen receptor modulator (SARM), in rat models of osteoporosis." Biol. Pharm. Bull. 26:1563-1569.

Kalu, DN, (1991) "The ovariectomized rat model of postmenopausal bone loss. Bone Miner," 15Δ 175-91.

Langer (1990) "New methods of drug delivery." Science 249:1527-1533.

Negro-Vilar, A. (1999) "Selective androgen receptor modulators (SARMs): a novel approach to androgen therapy for the new illennium." J. Clin. Endocrin Metabol. 84: 3459-3462.

Eliason et al., "High Throughput Fluorescence Polarization-Based Screening Assays for the Identification of Novel Nuclear Receptor Ligands," Abstracts of Papers, 223rd ACS National Meeting, Orlando, FL, United States, (2002), Apr. 7, 2002.

D. McKillop, et al., "Enantioselective metabolism and pharmacokinetics of Casodex in the male rat", Xenobiotica, 1995, vol. 25, No. 6, 623-634.

Carl Djerassi and S.P. Leibo, "A new look at male contraception", Nature, vol. 370, pp. 11-12.

Buchwald, et Long-term, continuous intravenous heparin administration by an implantable infusion pump in ambulatory patients with recurrent venous thrombosis.Surgery. 1980 88(4):507-16.

Goodson, et al (1984) "Goodson, in Medical Applications of Controlled Release, supra, vol. 2. pp. 115-138 (1984)" Medical Applications of Controlled Release vol. 2, 115-138.

Langer, et al (1987)" "CRC Crit. Ref. Biomed. Eng. 14;201.

Langer, et al New methods of drug delivery. Science. Sep 28, 1990; 249(4976):1527-33. Review.

Saudek et al A preliminary trial of the programmable implantable medication system for insulin delivery. N Engl J Med. Aug 31, 1989; 321(9):574-9.

Treat, et al (1989) Liposomes in the Therapy of Infectious Disease and Cancer 353-365.

Campfield et al., 1995, "Recombinant mouse OB protein: evidence for a peripheral signal linking adiposity and central neural networks" Science 269:546-549.

Considine et al., 1995, "Evidence against either a premature stop codon or the absence of obese gene mRNA in human obesity." J. Clin. Invest. 95:2986-2988.

Grundy, 1990, *Disease-a-Month* 36:645-696.

Halaas et al., 1995, "Weight-reducing effects of the plasma protein encoded by the obese gene." *Science* 269:543-546.

Hamilton et al., 1995, <<Increased obese mRNA expression in omental fat cells from massively obese humans. Nature Med. 1:953.

Lonnquist et al., 1995, Nature Med. 1:950.

Matsumoto, 1994, "Hormonal therapy of male hypogonadism" Endocrinol. Met. Clin. N. Am. 23:857-75.

Pelleymounter et al., 1995. "Effects of the obese gene product on body weight regulation in ob/ob mice." *Science* 269:540-543.

Singh et al., 2003, "Androgens stimulate myogenic differentiation and inhibit adipogenesis in C3H 10T1/2 pluripptent cells through an androgen receptor-mediated pathway." *Endocrinology*, 144(11):5081-8.

Sefton, 1987, "Implantable pumps." CRC Crit. Ref. Biomed. Eng. 14:201.

Narayanan, et al "Steroidal Androgens and Nonsteroidal, Tissue Selective Androgen Receptor Modulators (SARM) Regulate Androgen Receptor Function Through Distinct Genomic and Non-Genomic Signaling Pathways." The Endocrine Society—Programs and Abstracts—89$^{th}$ Annual Meeting—Paper P1-595.

Yepuru, et al "AN Angrogen Receptor-b Specific selective Estrogen Receptor Modulator (SERM) Inhibits the Growth of the Prostate Cancer Cells and Stromal-Epithilial Tumor Xenograft." The Endocrine Society—Programs and Abstracts—89$^{th}$ Annual Meeting—Paper OR6-3.

Dalton, et al "Therapeutic Promise of Selective Androgen Receptor Modulators (SARSs): Preclinical and Clinical Proof-of-Concept Studies." The Endocrine Society—Programs and Abstracts—89$^{th}$ Annual Meeting—Paper S41-2.

Matsumoto, "Hormonal terapy of male hypogonadism" Endocrinol. Met. Clin. N. Am.: 23:857-75 (1994).

Zhou et al., Molec. Endocrinol. 9: 208-18 (1995).

Sundaram et al., "7 Alpha-Methyl-Nortestosterone (MENT): The Optimal Androgen for Male Contraception", Ann. Med., 25:199-205 (1993).

Wahner H W et al., "Assesment of Bone Mineral Part 1", J Nucl Medicine, pp. 1134-1141 (1984).

Wahner H W et al., "Bone Mineral Density of the Radius", J Nucl Medicine, 26:13-39 (1985).

Singh et al., "Androgens stimulate myogenic differentiation and inhibit adipogenesis in C3H 10T1/2 pluripotent cells through an androgen receptor-mediated pathway" Endocrinology,144(11):5081-8, Jul. 24, 2003.

Langer, "New methods of drug delivery", Science 249:1527-1533(1990).

Treat et al., in Liposomes in the Therapy of infections disease and cancer, Lopez-Berestein and Fidler (eds.), Liss New York, pp. 353-365 (1989).

Sefton, "Implantable pumps" CRC Crit. Ref. Biomed. Eng. 14:201 (1987).

Campfield et al., 1995, "Recombinant mouse OB protein: evidence for a peripheral signal linking adiposity and central neural networks" Science 269:546-549.

Dalton et al., "Therapeutic Promise of Selective Androgen Receptor Modulators (SARSs): Preclinical and Clinical Proof-of-Concept Studies"—The Endocrine Society—Programs and Abstracts—89$^{th}$ Annual Meeting—Paper S41-2.

Goodson, in Medical Applications of controlled Release, supra, vol. 2, pp. 115-138 (1984).

Narayanan et al., "Steroidal Androgens and Nonsteroidal, Tissue Selective Androgen Receptor Modulators (SARM) Regulate Androgen Receptor Function Through Distinct Genomic and Non-Genomic Signaling Pathways" The Endocrine Society—Programs and Abstracts—89$^{th}$ Annual Meeting—Paper P1-595.

Edwards, J. P. et al., Bio. Med. Chem. Let., 9, 1003-1008(1999).

Pelleymounter et al., 1995, "Effects of the Obese gene product on body weight regulation in ob/ob mice", Science 269:540-543.

Steinberger et al., Effect of chronic Administration of Testosterone Enanthateon Sperm Production and Plasma Testosterone, Follicle Stimulating Hormone, and Luteinizing Hormone Levels: a Preliminary Evaluation of possible Male Contraceptive, Fertility and Sterility 28:1320-28 (1977).

World Health Organization Task Force on Methods and Regulation of Male Fertility "Contraceptive Efficacy of Testosterone-Induced Azoospermia and Oligospermia in Normal Men", Fertility & Sterility 65:821-29 (1996).

Wu, "Effects of Testosterone Enanthate in Normal Men: Experience from a Multicenter contraceptive efficacy study", Fertility and Sterility 65:626-36 (1996).

International Search Report of Application No. PCT/US08/04816 issued on Jul. 08, 2008.

International Search Report of Application No. PCT/US05/19788 issued on Jun. 16, 2006.

Georgian Search Report of Application No. AP 2005 009805 issued on Jan. 23, 2008.

Supplementary European Search Report of Application No. EP 05 75 8756 issued on May 29, 2008.

Kalu, DN (1991) "The ovariectomized rat model of postmenopausal bone loss Bone Miner" 15:175-91.

Considine et al., 1995, "Evidence against either a premature stop codon or the absence of obese gene Mrna in human obesity", J. Clin. Invest. 95:2986-2988.

Tucker et al "Nonsteroidal antiandrogens. Synthesis and structure-activity relationships of 3-substituted derivatives of 2-hydroxypropionanilides." *J. Med Chem* (1988), 31, 954-959.

Buchwald et al. "Long-term, continuous intravenous heparin administration by an implantable infusion pump in ambulatory patients with recurrent venous thrombosis."Surgery 88:507 (1980).

Saudek et al."A preliminary trial of the programmable implantable medication system for insulin delivery." N. Engl. J. Med. 321:574 (1989).

Corey (1987) "Asymmetric Bromolactonization Reaction: Synthesis of Optically Active 2-hydroxy-2-Methylalkanoic Acids from 2-Methylalkanoic Acids" Tetrahedron Letters vol. 28, No. 25 2801-2804.

Kirkovsky et al., "Approaches to Irreversible non-steroidal chiral antiandrogen", Department of Pharmaceutical Sciences, University of Tennessee, 47$^{th}$ Southeast/51$^{st}$ Southeast Joint Regional Meeting of the American Chemical Society, Memphis, TN, Nov. 29-Dec. 1, 1995.

Berger et al., "Concepts and Limitations in the application of radiolabeled antiandrogens, estrogens, or androgen as isotropic scanning agents for the prostate", Invest. Urol, (1975), 1391, 10-16.

Tucker and Chesterson, J. Med Chem. 1988, 31, pp. 885-887, "Resolution of the Nonsteroidal Antiandrogen -4'-Cyano-3-[(4-fluorophenyl)sulfonyl]-2-hydroxy-2-methyl-3'-(trifluoromethyl)-propionanilide and the Determination of the Absolute Configuration of the Active Enantiomer".

Wu, "Male Contraception: Current Status and Future Prospects", Clinical Endocrinology, (1988), 29, pp. 443-465.

Mukherjee A, Kirkovsky L, Yao XT, Yates CR, and Dalton JT. Enantioselective Binding of Casodex to the Androgen Receptor. Xenobiotica 26(2): 117-122, 1996.

Dalton JT, Mukherjee A, Zhu Z, Kirkovsky L; and Miller DD. Discovery of Nonsteroidal Androgens. Biochemical and Biophysical Research Communications, 244(1): 1-4, 1998.

Mukherjee A, Kirkovsky LI, Kimura Y, Marvel MM, Miller DD, and Dalton JT. Affinity Labeling of the Androgen Receptor with Nonsteroidal Chemoaffinity Ligands. Biochemical Pharmacology, 58: 1259-1267, 1999.

Kirkovsky L, Mukherjee A, Yin D, Dalton JT, and Miller DD. Chiral Nonsteroidal Affinity Ligands for the Androgen Receptor. 1, Bicalutamide Analogs bearing Electrophilic Groups at the Aromatic Ring B. Journal of Medicinal Chemistry, 43: 581-590, 2000.

Marhefka CA, Moore IIBM, Bishop TC, Kirkovsky L, Mukherjee A, Dalton JT, Miller DD. Homology Modeling Using Multiple Molecular Dynamics Simulations and Docking Studies of the Human Androgen Receptor Ligand Binding Domain Bound to Testosterone and Nonsteroidal Ligands. Journal of Medicinal Chemistry, 44: 1729-1740, 2001.

He Y, Yin D, Perera MA, Kirkovsky L, Stourman N, Dalton JT, and Miller DD. Novel Nonsteroidal Ligands with High Affinity and Potent Functional Activity for the Human Androgen Receptor. European Journal of Medicinal Chemistry, 37: 619-634, 2002.

Yin D, He YS Hong SS, Marhefka CA, Stourman N, Kirkovsky L, Miller DD, and Dalton JT. Key Structural Features of Nonsteroidal Ligands for Binding and Activation of the Androgen Receptor. Molecular Pharmacology, 63:211-223, 2003.

Yin D, Xu H, He Y, Kirkovsky L, Miller DD, and Dalton JT, Pharmacology, Pharmacokinetics and Metabolism of Acetothiolutamide, A Novel Nonsteroidal Agonist For the Androgen Receptor. Journal of Pharmacology and Experimental Therapeutics, 304(3):1323-1333, 2003.

Yin D, Gao W, Kearbey JD, Xu H, Chung K, Miller DD, and Dalton JT. Pharmacodynamics of Selective Androgen Receptor Modulators. Journal of Pharmacology and Experimental Therapeutics, 304(3): 1334-1340, 2003.

Wu Z, Gao W, Phelps M, Wu D, Miller DD, and Dalton JT. The Favorable Effects of Weak Acids on Negative-Ion Electrospray Mass Spectrometry. Analytical Chemistry, 76(3):839-847, 2004.

Kearbey, J. D., Wu, D., Gao, W., Miller, D. D., and Dalton, J. T. (2004). Pharmacokinetics of S-3-(4-acetylamino-phenoxy)-2-hydroxy-2-methyl-N-(4-nitro-3-trifluoromethyl-phenyl)-propionamide in rats, a non-steroidal selective androgen receptor modulator. Xenobiotica 34(3), 273-80.

Marhefka, C. A., Gao, W., Chung, K., Kim, J., He, Y., Yin, D., Bohl, C., Dalton, J. T., and Miller, D. D. (2004). Design, synthesis, and biological characterization of metabolically stable selective androgen receptor modulators. *J Med Chem* 47(4), 993-8.

Bohl CE, Chang C, Mohler ML, Miller DD, Swaan PW, and Dalton JT. A Ligand-Based Approach to Identify Quantitative Structure-Activity Relationships for the Androgen Receptor. Journal of Medicinal Chemistry, 47(15):3765-3776, 2004.

Gao, W., Kearbey, J.D., Nair, V.A., Chung, K., Parlow, A.F., Miller, D.D., and Dalton, J.T. Comparison of the Pharmacological Effects of a Novel Selective Androgen Receptor Modulator (SARM), the 5{alpha}-Reductase Inhibitor Finasteride, and the Antiandrogeo Hydroxyflutamide in Intact Rats: New Approach for Benign Prostate Hyperplasia (BPH). Endocrinology, 145(12): 5420-5428,2004.

Nair VA, Mustafa $SM_3$ Mohler ML, Fisher SJ, Dalton JT, and Miller DD. Synthesis of Novel lodo Derived Bicalutamide Analogs. Tetrahedron Letters, 45:9475-9477, 2004.

Chen J, Hwang DJ, Bohl CE, Miller DD, and Dalton JT. A Selective Androgen Receptor Modulator (SARM) for Hormonal Male Contraception. Journal of Pharmacology and Experimental Therapeutics, 312(2): 546-553,2005.

Nair V, Mustafa SM, Mohler ML, Fisher S J, Dalton JT, and Miller DD. Synthesis of irreversibly binding bicalutamide analogs for imaging studies. Tetrahedron Letters. 46:4821-4823, 2005.

Bohl CE, Gao W, Miller DD, Bell CE, Dalton JT. Structural Basis for Antagonism and Resistance of Bicalutamide in Prostate Cancer. Proc Nati Acad Sci USA. 102(17): 6201-6206, 2005.

Chen J, Kim J, and Dalton JT. Discovery and Therapeutic Promise of Selective Androgen Receptor Modulators. Molecular Interventions, 5(3)173-188, 2005.

Kim J, Wu D, Hwang DJ, Miller DD, and Dalton JT. The 4-Para-Substituent of S-3-(Phenoxy)-2-hydroxy-2-methyl-N-(4-nitro-3-trifluoromethyl]-phenyl)-propionamides is a Major Structural Determinant of In Vivo Disposition and Activity of Selective Androgen Receptor Modulators. Journal of Pharmacology and Experimental Therapeutics, 315(I):230-239, 2005.

Gao W, Reiser PJ, Coss CC, Phelps MA, Kearbey JD, Miller DD, and Dalton JT. Selective Androgen Receptor Modulator (SARM) Treatment Improves Muscle Strength and Body Composition, and Prevents Bone Loss in Orchidectomized Rats. Endocrinology, 146(11):48B7-4897, 2005.

Bohl CE, Miller DD, Chen J, Bell CE, and Dalton JT. Structural Basis for Accomodation of Nonsteroidal Ligaiids in the Androgen Receptor. Journal of Biological Chemistry, 280(45):37747-37754, 2005.

Gao W, Bohl CE, and Dalton JT. Chemistry and structural biology of androgen receptor. Chemical Reviews, 1G5(9):3352-70,2005.

Chen J, Hwang DJ, Chung K, Bohl CE, Fisher SJ, Miller DD, Dalton JT. In vitro and in vivo structure-activity relationships of novel androgen receptor ligands with multiple substituents in the B-ring. Endocrinology, 146(12):5444-54, 2005.

Segal S, Narayanan R, Dalton JT. Therapeutic potential of the SARMs: revisiting the androgen receptor for drug discovery. Expert Opinion in Investigational Drugs. 15(4):377-87, 2006.

Gao W, Johnston JS, Miller DD, Dalton JT. Inter-Species Differences in Pharmacokinetics and Metabolism of S-3-(4-acelylamino-phenoxy)-2-hydroxy-2-methyl-N-(4-nitro- 3-trifluoromethyi-phenyl>propionarnide: The Role of N-Acetyltransferase. Drug Metabolism and Disposition, 34(2):254-260, 2006.

Gao W, Wu Z, Bohl CE, Yang J, Miller DD, Dalton JT. Characterization of the In vitro Metabolism of Selective Androgen Receptor Modulator (SARM) Using Human, Rat and Dog Liver Enzyme Preparations. Drug Metabolism and Disposition, 34(2):243-253, 2006.

Wu D, Wu Z, Yang J, Nair VA, Miller DD, Dalton JT. Pharmacokinetics and metabolism of a selective androgen receptor modulator (SARM) in rats—implication of molecular properties and intensive metabolic profile to investigate ideal pharmacokinetic characteristics of a propanamide in preclinical study. Drug Metabolism and Disposition, 34(3):483-494, 2006.

Yang J, Bohl CE, Nair VA, Mustafa SM, Hong SS, Miller DD, Dalton JT. Preclinical pharmacology of a nonsteroidal ligand for androgen receptor mediated imaging of prostate cancer. Journal of Pharmacology and Experimental Therapeutics, 317(I):402-408, 2006.

Gao W, Kim J, Dalton JT, Pharmacokinetics and Pharmacodynamics of Nonsteroidal Androgen Receptor Ligands. Pharmaceutical Research, 23(8):1641-165B, 2006.

Hwang DJ, Yang J, Xu H, Rakov IM, Mohler ML, Dalton JT, Miller DD—Aryl isothiocyanato selective androgen receptor modulators (SARMs) for prostate cancer. Bioorganic and Medicinal Chemistry, ,14(19):6525-6538, 2006.

Bhasin S, Calof OM, Storer TW, Lee ML, Mazer NA, Jasuja R, Montori VM, Gao W, Dalton JT. Drug insight: Testosterone and selective androgen receptor modulators as anabolic therapies for chronic illness and aging. Nature, Clinical Practice in Endocrinology and Metabolism, 2(3): 146-159,2006.

Nair VA; Mustafa SM; Mohler ML; Dalton JT; Miller DD.Synthesis of oxazolidinedione derived bicalutamide analogs . Tetrahedron Letters, 47 (23): 3953-3955, 2006.

Patil R, Li W, Ross CR, Kraka E, Cremer D, Mohler ML, Dalton JT, and Miller DD. Cesium fluoride and tetra-n-butylammonium fluoride mediated 1,4-N-O shiftof disubstituted phenyl ring of a bicalutamide derivative. Tetrahedron Letters, 47:3941-3944, 2006.

Kearbey JD, Gao W, Narayanan R, Fisher SJ, Wu D, Miller DD, Dalton JT. Selective Androgen Receptor Modulator (SARM) Treatment Prevents Bone Loss and Reduces Body Fat in Ovariectomized Rats. Pharmaceutical Research, 24(2):328-335, 2006.

Bohl CE, Wu Z, Miller DD, Bell CE, Dalton JT. Crystal structure of the TS77A human androgen receptor Ugand-binding domain completed to cyproterone acetate provides insight for ligand-induced conformational changes and structure-based drug design. Journal of Biological Chemistry, 282(18)13648-13655,2007.

Gao W, Dalton JT, Expanding the therapeutic use of androgens via selective androgen receptor modulators (SARMs). Drug Discovery Today, 12(5-6):241-248, 2007.

Gao W, Dalton JT. Ockham's razor and selective androgen receptor modulators (SARMs): are we overlooking the role of 5a-reductase? Molecular Interventions, 7(1):1Q-13, 2007.

Sharifi N, Hamel E, Lill MA, Risbood P, Kane CT Jr, Hossain $MT_3$ Jones A, Dalton JT, Farrar WL. A bifunctional colchicinoid that binds to the androgen receptor. Molecular Cancer Therapeutics, 6(8):2328-2336, 2007.

Bisson WH, Cheltsov $AV_5$ Bruey-Sedano N, Lin B, Chen J, Goldberger N, May LT, Christopoulos A, Dalton JT, Sexton PM, Zhang XK, Abagyan R. Discovery of antiandrogen activity of nonsteroidal scaffolds of marketed drugs. Proceedings of the National Academy of Sciences, U S A. 104(29): 1192741932, 2007.

Mukherjee A, Kirkovsky L, Marvel M, Miller DD, and Dalton JT, Development of Nonsteroidal Androgen Receptor Ligands for Imaging Prostate Tumors. PharmSci, 1(1):S-681, 1998.

Yin D, Kirkovsky L, Stourman N, Miller DD and Dalton JT. In Vitro Pharmacology and In Vivo Pharmacokinetics Of (R)-Para-Acetamido-Bicalutamide. PharmSci, 1(4):S-3185, 1999.

Gao W, Chung K, Miller DD, and Dalton JT. In Vitro Metabolism and In Vivo Tissue Selectivity of Andarine. PharmSci 4(4): 2002.

Perera MA, Yin D, Chung K, Miller DD, and Dalton JT. Pharmacokinetics and Allometric Scaling of Andarine. PharmSci 4(4): 2002.

Xu H, Chung K, Hwang DJ, Miller $DD_7$ and Dalton JT. Pharmacodynamics of Electrophilic Androgen Receptor Ligands in Prostate Cancer Cell Lines. PharmSci 4(4): 2002.

Wang L, Miller DD, and Dalton JT, Androgen Receptor Mediated Transcriptional Activation of SARMs is Enhanced by Nuclear Receptor Coactivators. The Endocrine Society, Philadelphia, Jun. 2003, Abstract #P2-95.

Gao W, Kearbey JD, Chung K, Miller DD, and Dalton JT. Pharmacologic Effects of a Novel Selective Androgen Receptor Modulator (SARM), Flutamide and Finasteride in Intact Male Rats. The Endocrine Society, Philadelphia, Jun. 2003, Abstract #P3-221.

Kim J, Hwang DJ, Miller DD, and Dalton JT. In vitro and In vivo Pharmacologic Activity of 4-Halo Substituted SARMs. The Endocrine Society, Philadelphia, Jun. 2003, Abstract #P3-198.

Higuchi RI, Edwards JP, Caferro TR, Ringgenberg JD, Kong JW, Hamann LG, Arienti KL, Marschke KB, Davis RL, Farmer LJ, and Jones TK. 4-Alkyl- and 3,4-diaklyl-1,2,3,4-tetrahydro-8-pyridono[5,6-g]quinolines: potent, nonsteroidal androgen receptor agonists. Bioorg. Med. Chem. Lett., 9:1335, 1999.

Rosen J, Day A, Jones TK, Jones ET, Nadzan AM, and Stein RB. Intracellular receptors and signal transducers and activators of transcription superfamilies: novel targets for small-molecule drug discovery. J. Med. Chem., 38:4855, 1995.

Dalton JT, et al "Pharrnacokinetics of Aminolevulinic Acid after Oral and Intravenous Dosing in Dogs." Drug Metabolism and Disposition, 27 (4):432-435, 1999.

Grundy, Metabolic and health complications of obesity, 1990, Disease-a-Month 36:Dec; 36(12):641-731.

Halaas et al., 1995, 'Weight-reducing effects of the plasma protein encoded by the obese gene, Science 269:543-546.

Hamilton et al., 1995 "Increased obese mRNA expression in omental fat cells from massively obese humans", Nature Med., 1:953.

Kim J, Hwang DJ, Rakov I, Miller DD, and Dalton JT. Structure-Activity Relationships for Modification of the Linkage Group and B-Ring of Selective Androgen Receptor Modulators. The AAPS Journal, vol. 7(S2):T2117,2005.

Hwang DJ,Yang J, Mohler ML, Dalton JT, Miller DD.Synth.esis and testing of both reversible and irreversible selective androgen receptor modulators (SARMs) for prostate cancer. Abstracts of Papers of the American Chemical Society, 231: 274-MEDI, Mar. 26, 2006.

Narayanan R, Bohl CE, Kearbey JD, Coss CC, Miller DD, and Dalton JT. Molecular Mechanism for the Tissue Selectivity of a Novel Non-Steroidal Selective Androgen Receptor Modulator: Genome-Wide Mapping of Androgen Receptor Binding Sites, The Endocrine Society, Boston, Abstract # OR49-1, Jun. 2006.

Narayanan R, Coss CC; Yepuru MM, Miller DD and Dalton JT. Steroidal Androgens and Nonsteroidal, Tissue Selective Androgen Receptor Modulators (SARM) Regulate Androgen Receptor Function Through Distinct Genomic and Non-Genomic Signaling Pathways. The Endocrine Society, Toronto, Abstract #PI-595, Jun. 2007.

Gao W, Reiser PJ, Kearbey JD, Phelps MA, Coss $CC_7$ Miller DD, and Dalton JT. Effects of a Novel Selective Androgen Receptor Modulator (SARM) on Skeletal Muscle Mass and Strength in Castrated Male Rats. The Endocrine Society, New Orleans, Abstract #P2-120, Jun. 2005.

Wu D, Wu Z, Nair V, Miller DD, and Dalton JT—Urinary Metabolites of S-I, A Novel Selective Androgen Receptor Modulator (SARM), In Rats. The AAPS Journal, vol. 6, No. 4, Abstract #W53OO, Nov. 2004.

Fisher SJ, Hong SS, Miller DD, and Dalton JT. Preclinical Pharmacology And Pharmacokinetics Of a Novel A-ring Substituted Selective Androgen Receptor Modulator (SARM) In Rats. The AAPS Journal, vol. 6, No. 4, Abstract #T2256, Nov. 2004.

Bohl CE, Chang C, Mohler M, Miller DD, Swaan PW, and Dalton JT. A Ligand-based Approach To Identify Quantitative Structure Activity Relationships For The Androgen Receptor. The AAPS Journal, vol. 6, No. 4, Abstract #W4111, Nov. 2004.

Hwang DJ, Chen JY, Kim J, Dalton JT, Miller DD. Synthesis and biological testing of (2S)-multU halogenated B-ring 2-hydroxy-2-methylpropionamide selective androgen receptor modulators (SARMs): Probing the B-ring pocket. Abstracts of Papers of the American Chemical Society, 229: U140-U140 176- MEDI Part 2, Mar. 13, 2005.

Hwang DJ, Chen JY, Xu HP, Mustafa SM, Dalton JT, Miller DD. Synthesis of isothiocyanate derivatives of irreversible selective androgen receptor modulators (SARMs) and biological testing in prostate cancer cell lines. Abstracts of Papers of the American Chemical Society, 229: U140-U140 177- MEDI Part 2, Mar. 13, 2005.

Gao W, Stuart LB, Yates CR, Miller DD, and Dalton JT. Regulation of Cytochrome P450s by Selective Androgen Receptor Modulators (SARMs) in Primary Culture of Human Hepatocytes.). PharmSci 5 (4): T3338,2003.

Gao W; Veverka KA, Chung K, Miller DD, and Dalton JT. Species Difference in the Metabolism of Selective Androgen Receptor Modulators (SARMs). PharmSci 5 (4): T3336, 2003.

Kearbey JD, Gao W, Miller DD, and Dalton JT. Selective androgen receptor modulators inhibit bone resorption in rats. PharmSci 5(4): R6167, 2003.

Xu H, Hwang DJ, Miller DD, and Dalton JT. In Vitro and In Vivo Anticancer Activity of S-NTBA for Prostate Cancer. PharmSci 5 (4): T2378, 2003.

U.S. Appl. No. 10/683,156, filed Oct. 14, 2003, Dalton, James T. et al.

* cited by examiner

Compound of Formula III (mg/day)

Compound of Formula III (mg/day)

• p < 0.05; **p<0.01

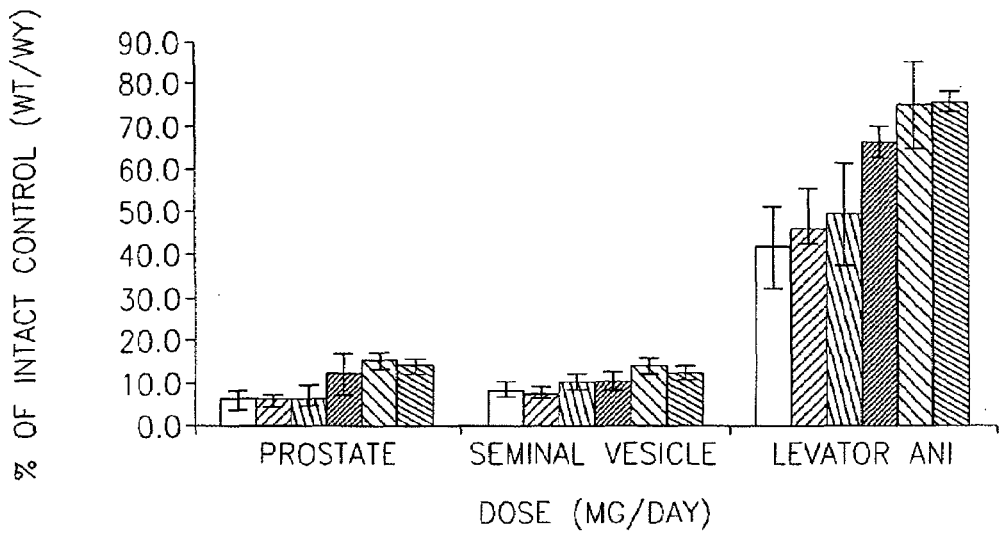
FIG.24A
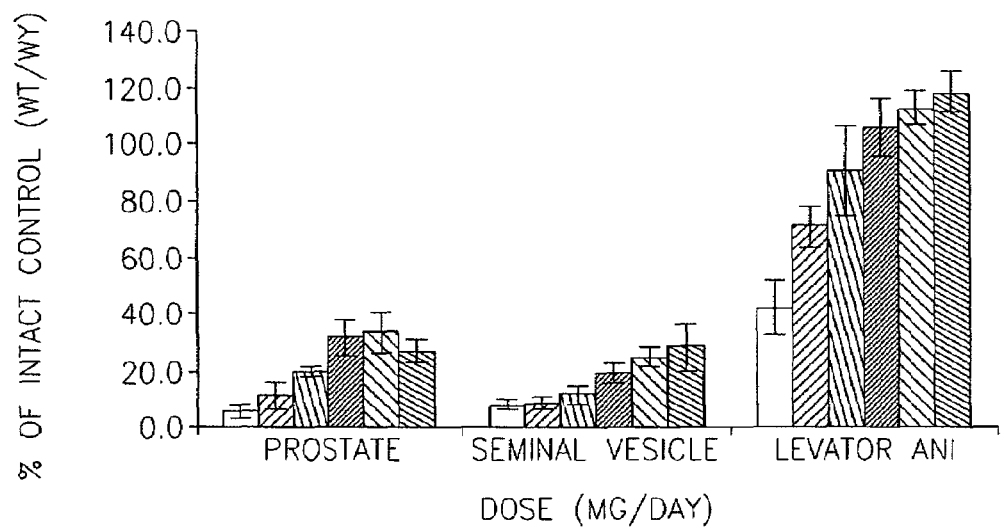
FIG.24B
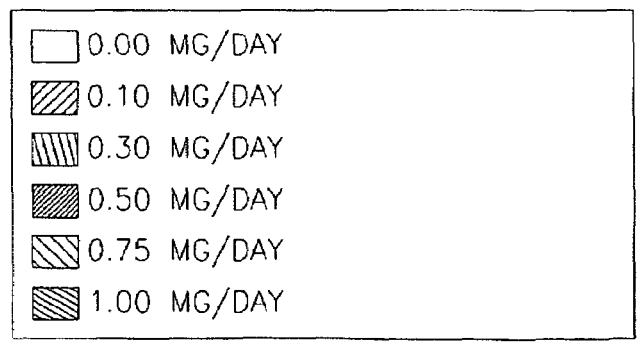

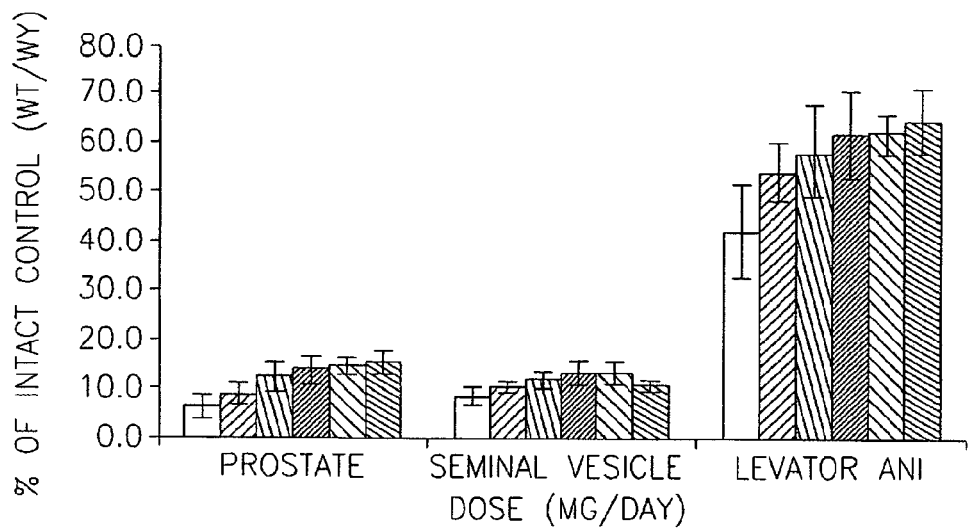
FIG.24C
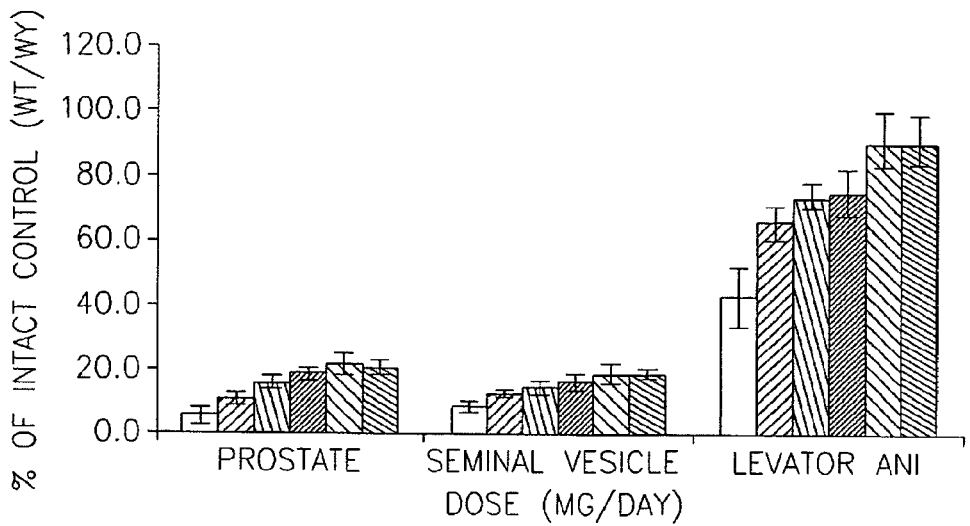
FIG.24D
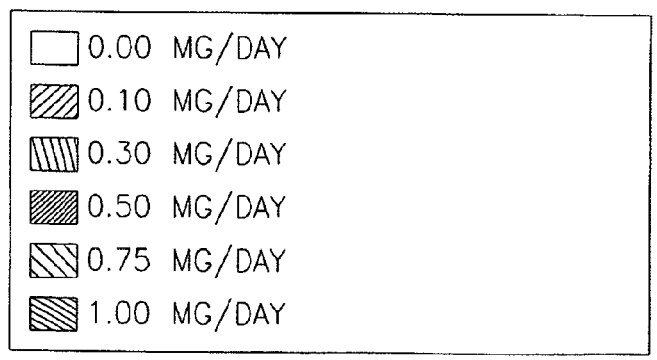

SELECTIVE ANDROGEN RECEPTOR MODULATORS AND METHOD OF USE THEREOF

CROSS-REFERENCE TO RELATED APPLICATIONS

This Application is a Continuation-in-Part Application of U.S. Ser. No. 11/353,225, filed Feb. 14, 2006 now U.S. Pat. No. 7,518,013 which is a Continuation-in-Part Application of U.S. Ser. No. 11/125,159, filed May 10, 2005, now U.S. Pat. No. 7,205,437, which is a Continuation-in-Part Application of U.S. Ser. No. 11/062,752, filed Feb. 23, 2005, which is Continuation-in-Part Application of U.S. Ser. No. 10/863,524 filed Jun. 9, 2004, now abandoned, all of which are hereby incorporated by reference in their entirety.

GOVERNMENT INTEREST STATEMENT

This invention was made in whole or in part with government support under grant number R29 CA068096, awarded by the National Cancer Institute, National Institute of Health, and under grant number R15 HD35329, awarded by the National Institute of Child Health and Human Development, National Institute of Health. The government may have certain rights in the invention.

BACKGROUND OF THE INVENTION

The androgen receptor ("AR") is a ligand-activated transcriptional regulatory protein that mediates induction of male sexual development and function through its activity with endogenous androgens. Androgens are generally known as the male sex hormones. The androgenic hormones are steroids which are produced in the body by the testes and the cortex of the adrenal gland or can be synthesized in the laboratory. Androgenic steroids play an important role in many physiologic processes, including the development and maintenance of male sexual characteristics such as muscle and bone mass, prostate growth, spermatogenesis, and the male hair pattern (Matsumoto, Endocrinol. Met. Clin. N. Am. 23:857-75 (1994)). The endogenous steroidal androgens include testosterone and dihydrotestosterone ("DHT"). Testosterone is the principal steroid secreted by the testes and is the primary circulating androgen found in the plasma of males. Testosterone is converted to DHT by the enzyme 5 alpha-reductase in many peripheral tissues. DHT is thus thought to serve as the intracellular mediator for most androgen actions (Zhou, et al., Molec. Endocrinol. 9:208-18 (1995)). Other steroidal androgens include esters of testosterone, such as the cypionate, propionate, phenylpropionate, cyclopentylpropionate, isocarporate, enanthate, and decanoate esters, and other synthetic androgens such as 7-Methyl-Nortestosterone ("MENT") and its acetate ester (Sundaram et al., "7 Alpha-Methyl-Nortestosterone (MENT): The Optimal Androgen For Male Contraception," Ann. Med., 25:199-205 (1993) ("Sundaram")). Because the AR is involved in male sexual development and function, the AR is a likely target for effecting male contraception or other forms of hormone replacement therapy.

Worldwide population growth and social awareness of family planning have stimulated a great deal of research in contraception. Contraception is a difficult subject under any circumstance. It is fraught with cultural and social stigma, religious implications, and, most certainly, significant health concerns. This situation is only exacerbated when the subject focuses on male contraception. Despite the availability of suitable contraceptive devices, historically, society has looked to women to be responsible for contraceptive decisions and their consequences. Although concern over sexually transmitted diseases has made men more aware of the need to develop safe and responsible sexual habits, women still often bear the brunt of contraceptive choice. Women have a number of choices, from temporary mechanical devices such as sponges and diaphragms to temporary chemical devices such as spermicides. Women also have at their disposal more permanent options, such as physical devices including IUDs and cervical caps as well as more permanent chemical treatments such as birth control pills and subcutaneous implants. However, to date, the only options available for men include the use of condoms and vasectomy. Condom use, however is not favored by many men because of the reduced sexual sensitivity, the interruption in sexual spontaneity, and the significant possibility of pregnancy caused by breakage or misuse. Vasectomies are also not favored. If more convenient methods of birth control were available to men, particularly long-term methods which require no preparative activity immediately prior to a sexual act, such methods could significantly increase the likelihood that men would take more responsibility for contraception.

Administration of the male sex steroids (e.g., testosterone and its derivatives) has shown particular promise in this regard due to the combined gonadotropin-suppressing and androgen-substituting properties of these compounds (Steinberger et al., "Effect of Chronic Administration of Testosterone Enanthate on Sperm Production and Plasma Testosterone, Follicle Stimulating Hormone, and Luteinizing Hormone Levels: A Preliminary Evaluation of a Possible Male Contraceptive, Fertility and Sterility 28:1320-28 (1977)). Chronic administration of high doses of testosterone completely abolishes sperm production (azoospermia) or reduces it to a very low level (oligospermia). The degree of spermatogenic suppression necessary to produce infertility is not precisely known. However, a recent report by the World Health Organization showed that weekly intramuscular injections of testosterone enanthate result in azoospermia or severe oligospermia (i.e., less than 3 million sperm per mil) and infertility in 98% of men receiving therapy (World Health Organization Task Force on Methods And Regulation of Male Fertility, "Contraceptive Efficacy of Testosterone-Induced Azoospermia and Oligospermia in Normal Men," Fertility and Sterility 65:821-29 (1996)).

A variety of testosterone esters have been developed which are more slowly absorbed after intramuscular injection and thus result in greater androgenic effect. Testosterone enanthate is the most widely used of these esters. While testosterone enanthate has been valuable in terms of establishing the feasibility of hormonal agents for male contraception, it has several drawbacks, including the need for weekly injections and the presence of supraphysiologic peak levels of testosterone immediately following intramuscular injection (Wu, "Effects of Testosterone Enanthate in Normal Men: Experience From a Multicenter Contraceptive Efficacy Study," Fertility and Sterility 65:626-36 (1996)).

Bone mineral density (BMD) decreases with age in both males and females. Decreased amounts of bone mineral content (BMC) and BMD correlate with decreased bone strength and predispose patients to fracture.

Osteoporosis is a systemic skeletal disease, characterized by low bone mass and deterioration of bone tissue, with a consequent increase in bone fragility and susceptibility to fracture. In the U.S., the condition affects more than 25 million people and causes more than 1.3 million fractures each year, including 500,000 spine, 250,000 hip and 240,000 wrist fractures annually. Hip fractures are the most serious consequence of osteoporosis, with 5-20% of patients dying within one year, and over 50% of survivors being incapacitated. The elderly are at greatest risk of osteoporosis, and the problem is therefore predicted to increase significantly with the aging of the population. Worldwide fracture incidence is forecasted to increase three-fold over the next 60 years, and one study estimated that there will be 4.5 million hip fractures worldwide in 2050.

Women are at greater risk of osteoporosis than men. Women experience a sharp acceleration of bone loss during the five years following menopause. Other factors that increase the risk include smoking, alcohol abuse, a sedentary lifestyle and low calcium intake. However, osteoporosis also occurs frequently in males. It is well established that the bone mineral density of males decrease with age. Decreased amounts of bone mineral content and density correlates with decreased bone strength, and predisposes to fracture. The molecular mechanisms underlying the pleiotropic effects of sex-hormones in non-reproductive tissues are only beginning to be understood, but it is clear that physiologic concentrations of androgens and estrogens play an important role in maintaining bone homeostasis throughout the life-cycle. Consequently, when androgen or estrogen deprivation occurs there is a resultant increase in the rate of bone remodeling that tilts the balance of resorption and formation to the favor of resorption that contributes to the overall loss of bone mass. In males, the natural decline in sex-hormones at maturity (direct decline in androgens as well as lower levels of estrogens derived from peripheral aromatization of androgens) is associated with the frailty of bones. This effect is also observed in males who have been castrated.

Muscle wasting refers to the progressive loss of muscle mass and/or to the progressive weakening and degeneration of muscles, including the skeletal or voluntary muscles, which control movement, cardiac muscles, which control the heart (cardiomyopathics), and smooth muscles. Chronic muscle wasting is a chronic condition (i.e. persisting over a long period of time) characterized by progressive loss of muscle mass, weakening and degeneration of muscle.

The loss of muscle mass that occurs during muscle wasting can be characterized by muscle protein degradation by catabolism. Protein catabolism occurs because of an unusually high rate of protein degradation, an unusually low rate of protein synthesis, or a combination of both. Muscle protein catabolism, whether caused by a high degree of protein degradation or a low degree of protein synthesis, leads to a decrease in muscle mass and to muscle wasting.

Muscle wasting is associated with chronic, neurological, genetic or infectious pathologies, diseases, illnesses or conditions. These include Muscular Dystrophies such as Duchenne Muscular Dystrophy and Myotonic Dystrophy; Muscle Atrophies such as Post-Polio Muscle Atrophy (PPMA); Cachexias such as Cardiac Cachexia, AIDS Cachexia and Cancer Cachexia, malnutrition, Leprosy, Diabetes, Renal Disease, Chronic Obstructive Pulmonary Disease (COPD), Cancer, end stage Renal failure, Sarcopenia, Emphysema, Osteomalacia, HIV Infection, AIDS, and Cardiomyopathy.

In addition, other circumstances and conditions are linked to and can cause muscle wasting. These include chronic lower back pain, advanced age, central nervous system (CNS) injury, peripheral nerve injury, spinal cord injury, chemical injury, central nervous system (CNS) damage, peripheral nerve damage, spinal cord damage, chemical damage, burns, disuse deconditioning that occurs when a limb is immobilized, long term hospitalization due to illness or injury, and alcoholism.

An intact androgen receptor (AR) signaling pathway is crucial for appropriate development of skeletal muscles. Furthermore, an intact AR-signaling pathway increases lean muscle mass, muscle strength and muscle protein synthesis.

Muscle wasting, if left unabated, can have dire health consequences. For example, the changes that occur during muscle wasting can lead to a weakened physical state that is detrimental to an individual's health, resulting in increased susceptibility to infraction and poor performance status. In addition, muscle wasting is a strong predictor of morbidity and mortality in patients suffering from cachexia and AIDS.

New innovative approaches are urgently needed at both the basic science and clinical levels to develop compounds which are useful for a) male contraception; b) treatment of a variety of hormone-related conditions, for example conditions associated with Androgen Decline in Aging Male (ADAM), such as fatigue, depression, decreased libido, sexual dysfunction, erectile dysfunction, hypogonadism, osteoporosis, hair loss, anemia, obesity, sarcopenia, osteopenia, osteoporosis, benign prostate hyperplasia, alterations in mood and cognition and prostate cancer; c) treatment of conditions associated with ADIF, such as sexual dysfunction, decreased sexual libido, hypogonadism, sarcopenia, osteopenia, osteoporosis, alterations in cognition and mood, depression, anemia, hair loss, obesity, endometriosis, breast cancer, uterine cancer and ovarian cancer; d) treatment and/or prevention of chronic muscular wasting; e) decreasing the incidence of, halting or causing a regression of prostate cancer; f) oral androgen replacement and/or other clinical therapeutic and/or diagnostic areas.

SUMMARY OF THE INVENTION

In one embodiment, the present invention relates to novel androgen receptor targeting agents (ARTA), and processes for producing the same. The agents are nonsteroidal ligands for the androgen receptor and demonstrate androgenic and/or anabolic activity. The agents are selective androgen receptor modulators (SARMs) useful in a) male contraception; b) the treatment of a variety of hormone-related conditions, for example conditions associated with Androgen Decline in Aging Male (ADAM); c) the treatment of conditions associated with Androgen Decline in Female (ADIF); d) the treatment of conditions associated with osteoporosis; e) the treatment and/or prevention of chronic muscular wasting; and/or; e) decreasing the incidence of, halting or causing regression of prostate cancer; f) oral androgen relacement and/or other clinical therapeutic and/or diagnostic areas.

In one embodiment the present invention provides for a SARM compound represented by the structure of formula (I):

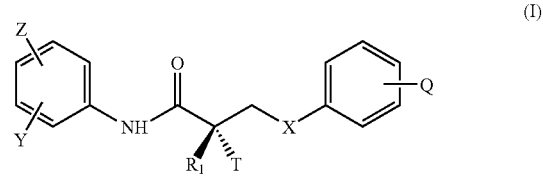

wherein
X is O;
Z is a hydrogen bond acceptor, $NO_2$, CN, COR, COOH or CONHR;
Y is a lipid soluble group, I, $CF_3$, H, $CH_3$, Br, Cl, or $Sn(R)_3$;
$R_1$ is $CH_3$, $CF_3$, $CH_2CH_3$, or $CF_2CF_3$;

T is OH, OR, —NHCOCH$_3$, or NHCOR;

Q is CN, halogen, acetamido-, trifluroacetamido-, alkylamines, ether, alkyl, N-sulfonyl, O-sulfonyl, alkylsulfonyl, carbonyl, ketone, Q is alkyl, halogen, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR NHSO$_2$CH$_3$, NHSO$_2$R, OR, COR, OCOR, OSO$_2$R, SO$_2$R or SR;

or Q together with the benzene ring to which it is attached is a fused ring system represented by structure A, B or C:

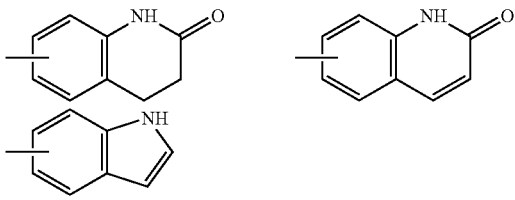

$R_1$ is CH$_3$, CF$_3$, CH$_2$CH$_3$, or CF$_2$CF$_3$; and

T is OH, OR, —NHCOCH$_3$, or NHCOR; and

R is a C$_1$-C$_4$ alkyl, aryl, phenyl, alkenyl, hydroxyl, a C$_1$-C$_4$ haloalkyl, halogen, or haloalkenyl.

In another embodiment, this invention provides, a pharmaceutical composition comprising an effective amount of the SARM compound of formula I, and/or its analog, isomer, metabolite, derivative, pharmaceutically acceptable salt, pharmaceutical product, polymorph, crystal, impurity, N-oxide, hydrate; and a pharmaceutically acceptable carrier, diluent or salt.

In another embodiment, this invention provides, a method of binding a SARM compound to an androgen receptor, comprising the step of contacting the androgen receptor with the SARM compound of formula I and/or its analog, derivative, isomer, metabolite, pharmaceutically acceptable salt, pharmaceutical product, polymorph, crystal, impurity, hydrate, N-oxide or any combination thereof, in an amount effective to bind the SARM compound to the androgen receptor.

In one embodiment, this invention provides a method of contraception in a male subject, comprising the step of administering to said subject the SARM compound of formula I and/or its analog, derivative, isomer, metabolite, pharmaceutically acceptable salt, pharmaceutical product, polymorph, crystal, impurity, hydrate, N-oxide or any combination thereof, in an amount effective to suppress sperm production in said subject, thereby effecting contraception in said subject.

In one embodiment, this invention provides a method of hormone therapy comprising the step of contacting an androgen receptor of a subject with the SARM compound of formula I and/or its analog, derivative, isomer, metabolite, pharmaceutically acceptable salt, pharmaceutical product, polymorph, crystal, impurity, hydrate, N-oxide or any combination thereof, in an amount effective to effect a change in an androgen-dependent condition.

In one embodiment, this invention provides a method of treating a subject suffering from prostate cancer, comprising the step of administering to said subject the SARM compound of formula I and/or its analog, derivative, isomer, metabolite, pharmaceutically acceptable salt, pharmaceutical product, polymorph, crystal, impurity, hydrate, N-oxide or any combination thereof, in an amount effective to treat prostate cancer in said subject.

In one embodiment, this invention provides a method of delaying the progression of prostate cancer in a subject suffering from prostate cancer, comprising the step of administering to said subject the SARM compound of formula I and/or its analog, derivative, isomer, metabolite, pharmaceutically acceptable salt, pharmaceutical product, polymorph, crystal, impurity, hydrate, N-oxide or any combination thereof, in an amount effective to delay the progression of prostate cancer in said subject.

BRIEF DESCRIPTION OF THE DRAWINGS

FIG. 24: Androgenic and Anabolic activity of compounds 1-4 (see Table 6). Rats were left untreated (intact control), castrated (0 mg/day control), or treated with 0.1, 0.3, 0.5, 0.75 and 1.0 mg/day of compound 1 (FIG. 24A), compound 2 (FIG. 24B), compound 3 (FIG. 24C) or compound 4 (FIG. 24D), and the weight of androgen-responsive tissues (prostate, semimal vesicles and levator ani muscle) was determined.

FIG. 28: Synthetic schemes for the preparation of compound of formula III.

DETAILED DESCRIPTION OF THE PRESENT INVENTION

Figure 1:
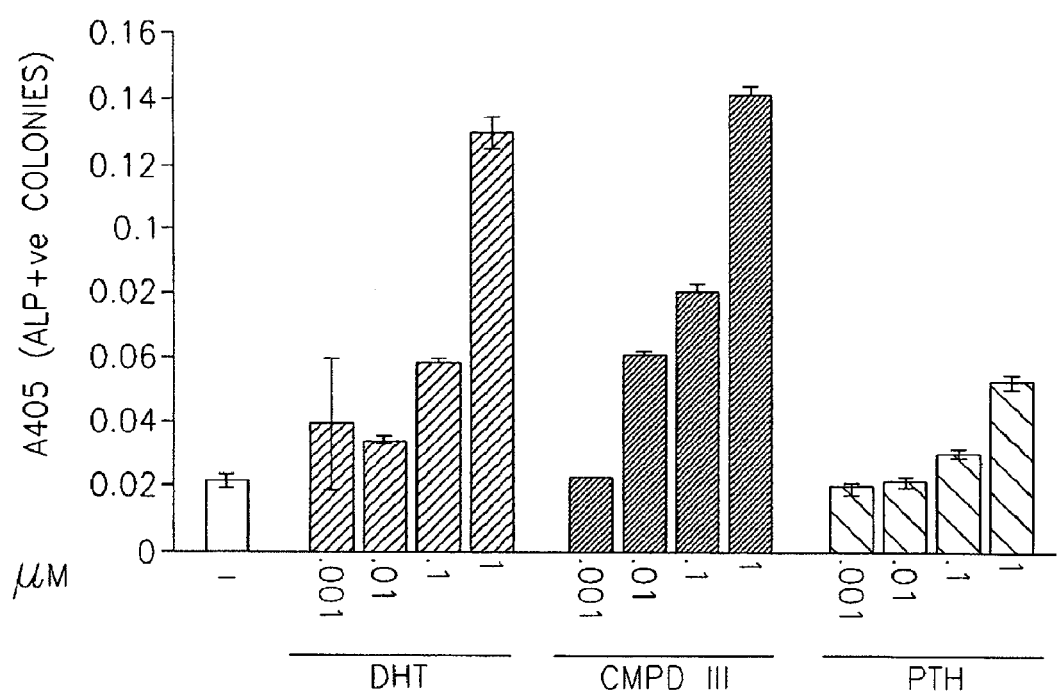
FIG. 1: Effect of SARMs, DHT and PTH on Differentiation of Rat Bone Marrow Cells Towards the Osteoblast Lineage.

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

This invention provides, in one embodiment, a novel class of tissue-selective androgen receptor targeting agents (ARTA). The agents are tissue-SARMs, which are useful, in some embodiments, for oral testosterone replacement therapy, male contraception, maintaining sexual desire in women, osteoporosis, treating prostate cancer and/or imaging prostate cancer. These agents are nonsteroidal ligands for the AR and have, in some embodiments, an unexpected and tissue-selective in-vivo androgenic and/or anabolic activity. In some embodiments, the agents are partial agonists or antagonists in some tissues, yet full agonists in other tissues, providing a novel and unexpected means for eliciting tissue-selective androgenic or anabolic effects. These agents may be active alone or in combination with progestins or estrogens, or any other agent. In other embodiments, the agents are agonists, antagonists, partial agonists or partial antagonists.

In some embodiments, this invention provides synthetic processes of preparation of the SARM compounds of this invention. In some embodiments, the invention provides compositions comprising the selective androgen modulator compounds or use of the same for binding an AR, modulating spermatogenesis, bone formation and/or resorption, treating muscle wasting or diseases associated with muscle wasting, treating prostate cancer, and/or providing hormonal therapy for androgen-dependent conditions.

In one embodiment, this invention provides a SARM compound represented by the structure of formula (I):

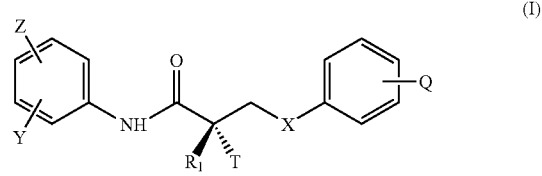

wherein
X is O;
Z is a hydrogen bond acceptor, $NO_2$, CN, COR, COOH or CONHR;
Y is a lipid soluble group, I, $CF_3$, H, $CH_3$, Br, Cl, or $Sn(R)_3$;

$R_1$ is $CH_3$, $CF_3$, $CH_2CH_3$, or $CF_2CF_3$;

T is OH, OR, —NHCOCH$_3$, or NHCOR;

Q is CN, halogen, acetamido-, trifluroacetamido-, alkylamines, ether, alkyl, N-sulfonyl, O-sulfonyl, alkylsulfonyl, carbonyl, ketone, Q is alkyl, halogen, $N(R)_2$, NHCOCH$_3$, NHCOCF$_3$, NHCOR, NHCONHR, NHCOOR, OCONHR, CONHR, NHCSCH$_3$, NHCSCF$_3$, NHCSR NHSO$_2$CH$_3$, NHSO$_2$R, OR, COR, OCOR, OSO$_2$R, SO$_2$R or SR;

or Q together with the benzene ring to which it is attached is a fused ring system represented by structure A, B or C:

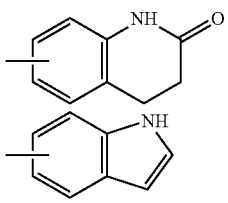
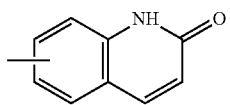

$R_1$ is $CH_3$, $CF_3$, $CH_2CH_3$, or $CF_2CF_3$; and

T is OH, OR, —NHCOCH$_3$, or NHCOR; and

R is a $C_1$-$C_4$ alkyl, aryl, phenyl, alkenyl, hydroxyl, a $C_1$-$C_4$ haloalkyl, halogen, or haloalkenyl.

In one embodiment, Q is in the para position. In another embodiment, X is O, or in another embodiment, T is OH, or in another embodiment, $R_1$ is $CH_3$, or in another embodiment, Z is $NO_2$, or in another embodiment, Z is CN, or in another embodiment, Z is in the para position, or in another embodiment, Y is $CF_3$, $CF_3$, or H, or in another embodiment, Y is in the meta position, or in another embodiment, Q is in the para position, or in another embodiment, Q is para alkyl, halogen, $N(R)_2$, CN, NHCOCH$_3$, NHCOCF$_3$, NHCOR, NHCONHR, NHCOOR, OCONHR, CONHR, NHCSCH$_3$, NHCSCF$_3$, NHCSR NHSO$_2$CH$_3$, NHSO$_2$R, OR, COR, OCOR, OSO$_2$R, SO$_2$R or SR, or in another embodiment, any combination thereof.

In one embodiment, this invention provides a racemate SARM compound represented by the structure of formula (Ia):

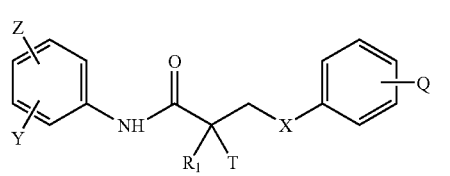

(Ia)

wherein

X is a bond, O, $CH_2$, NH, Se, PR, or NR;

Z is $NO_2$, CN, COR, COOH or CONHR;

Y is I, $CF_3$, $CH_3$, H, Br, Cl, or $Sn(R)_3$;

Q is alkyl, halogen, $N(R)_2$, CN, NHCOCH$_3$, NHCOCF$_3$, NHCOR, NHCONHR, NHCOOR, OCONHR, CONHR, NHCSCH$_3$, NHCSCF$_3$, NHCSR NHSO$_2$CH$_3$, NHSO$_2$R, OR, COR, OCOR, OSO$_2$R, SO$_2$R or SR;

or Q together with the benzene ring to which it is attached is a fused ring system represented by structure A, B or C:

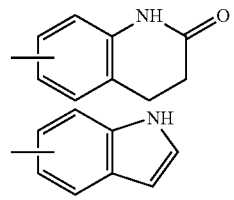
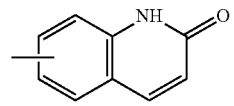

$R_1$ is $CH_3$, $CF_3$, $CH_2CH_3$, or $CF_2CF_3$; and

T is OH, OR, —NHCOCH$_3$, or NHCOR;

wherein

R is a $C_1$-$C_4$ alkyl, aryl, phenyl, alkenyl, hydroxyl, a $C_1$-$C_4$ haloalkyl, halogen, or haloalkenyl.

In one embodiment, Q is in the para position. In another embodiment, X is O. In another embodiment, Q is in the para position and X is O. In another embodiment, Q is para alkyl, halogen, $N(R)_2$, NHCOCH$_3$, NHCOCF$_3$, NHCOR, NHCONHR, NHCOOR, OCONHR, CONHR, NHCSCH$_3$, NHCSCF$_3$, NHCSR NHSO$_2$CH$_3$, NHSO$_2$R, OR, COR, OCOR, OSO$_2$R, SO$_2$R or SR wherein R is a aryl, phenyl, hydroxyl, $C_1$-$C_4$ alkyl, $C_1$-$C_4$ haloalkyl, halogen, alkenyl or haloalkenyl.

In one embodiment the present invention provides, a SARM compound or its prodrug, analog, isomer, metabolite, derivative, pharmaceutically acceptable salt, pharmaceutical product, polymorph, crystal, impurity, N-oxide, hydrate or any combination thereof, represented by a structure of formula (I):

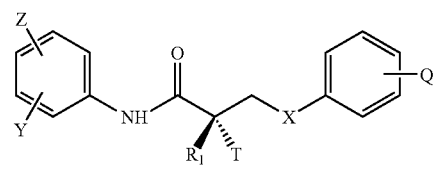

I wherein

X is O;

Z is $NO_2$, CN, COR, or CONHR;

Y is I, $CF_3$, $CH_3$, H, Br, Cl, F or $Sn(R)_3$;

Q is CN;

T is OH, OR, —NHCOCH$_3$, NHCOR or OC(O)R;

R is alkyl, haloalkyl, dihaloalkyl, trihaloalkyl, $CH_2F$, $CHF_2$, $CF_3$, $CF_2CF_3$, aryl, phenyl, halogen, alkenyl, haloalkenyl or OH; and $R_1$ is $CH_3$, $CH_2F$, $CHF_2$, $CF_3$, $CH_2CH_3$, or $CF_2CF_3$.

In one embodiment, Q is in the para position. In another embodiment, X is O, or in another embodiment, T is OH, or in another embodiment, $R_1$ is $CH_3$, or in another embodiment, Z is $NO_2$, or in another embodiment, Z is CN, or in another embodiment, Z is in the para position, or in another embodiment, Y is $CF_3$, or in another embodiment, Y is in the meta position, or in another embodiment, Q is in the para position, or in another embodiment, Q is para alkyl, halogen, $N(R)_2$, NHCOCH$_3$, NHCOCF$_3$, NHCOR, NHCONHR, NHCOOR, OCONHR, CONHR, NHCSCH$_3$, NHCSCF$_3$, NHCSR NHSO$_2$CH$_3$, NHSO$_2$R, OR, COR, OCOR, OSO$_2$R, SO$_2$R or SR, or in another embodiment, any combination thereof.

The present invention relates to a SARM compound having in vivo androgenic and anabolic activity of a nonsteroidal ligand for the androgen receptor, the SARM compound represented by the structure of formula (II):

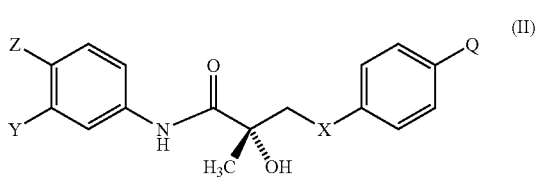

wherein
X is O, CH$_2$, NH, Se, PR, or NR;
Z is a hydrogen bond acceptor, NO$_2$, CN, COR, CONHR;
Y is a lipid soluble group, I, CF$_3$, Br, Cl, Sn(R)$_3$;
R is an alkyl, aryl, phenyl, alkenyl, haloalkyl, haloalkenyl, halogen or OH;
and Q is CN, halogen, acetamido-, trifluroacetamido-, alkylamines, ether, alkyl, N-sulfonyl, O-sulfonyl, alkylsulfonyl, carbonyl, or a ketone.

The present invention relates to a SARM compound having in vivo androgenic and anabolic activity of a nonsteroidal ligand for the androgen receptor, the SARM compound represented by the structure of formula (II):

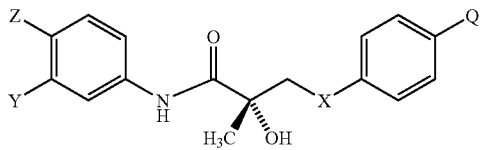

wherein
X is O, CH$_2$, NH, Se, PR, or NR;
Z is a hydrogen bond acceptor, NO$_2$, CN, COR, CONHR;
Y is a lipid soluble group, I, CF$_3$, CH$_3$, H, Br, Cl, Sn(R)$_3$;
R is an alkyl, aryl, phenyl, alkenyl, haloalkyl, haloalkenyl, halogen or OH;
and Q is alkyl, halogen, N(R)$_2$, CN, NHCOCH$_3$, NHCOCF$_3$, NHCOR, NHCONHR, NHCOOR, OCONHR, CONHR, NHCSCH$_3$, NHCSCF$_3$, NHCSR NHSO$_2$CH$_3$, NHSO$_2$R, OR, COR, OCOR, OSO$_2$R, SO$_2$R or SR, CN, halogen, acetamido-, trifluroacetamido-, alkylamines, ether, alkyl, N-sulfonyl, O-sulfonyl, alkylsulfonyl, carbonyl, or a ketone.

In one embodiment, X is O, or in another embodiment, T is OH, or in another embodiment, R$_1$ is CH$_3$, or in another embodiment, Z is NO$_2$, or in another embodiment, Z is CN, or in another embodiment, Y is CF$_3$, or in another embodiment, Q is alkyl, halogen, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR NHSO$_2$CH$_3$, NHSO$_2$R, OR, COR, OCOR, OSO$_2$R, SO$_2$R or SR, CN, halogen, acetamido-, trifluroacetamido-, alkylamines, ether, alkyl, N-sulfonyl, O-sulfonyl, alkylsulfonyl, carbonyl, or a ketone or in another embodiment, any combination thereof.

The present invention also relates to a SARM compound having in vivo androgenic and anabolic activity of a nonsteroidal ligand for the androgen receptor the, SARM compound represented by the structure of formula (II):

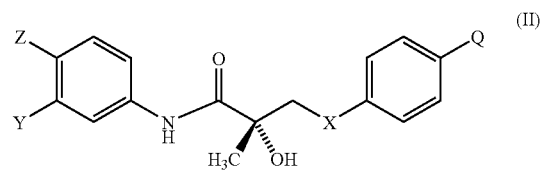

wherein,
X is O, CH$_2$, NH, Se, PR, or NR;
Z is NO$_2$, CN, COR, CONHR;
Y is a lipid soluble group, I, CF$_3$, CH$_3$, H, Br, Cl, Sn(R)$_3$;
R is an alkyl, aryl, phenyl, alkenyl, haloalkyl, haloalkenyl, halogen or OH; and
Q is acetamido or trifluroacetamido.

In another embodiment, the present invention provides a SARM represented by a structure of formula (II):

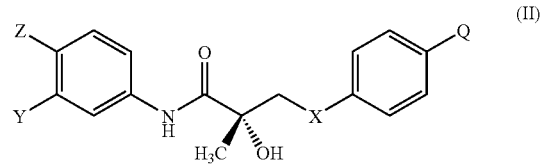

wherein
X is O;
Z is NO$_2$, CN, COR, or CONHR;
Y is I, CF$_3$, CH$_3$, H, Br, Cl, F or Sn(R)$_3$;
R is an alkyl, aryl, phenyl, alkenyl, haloalkyl, haloalkenyl, halogen or OH; and
Q is CN.

In one embodiment, the invention provides a SARM compound or its prodrug, analog, isomer, metabolite, derivative, pharmaceutically acceptable salt, pharmaceutical product, polymorph, crystal, impurity, N-oxide, hydrate or any combination thereof, represented by a structure of formula (III):

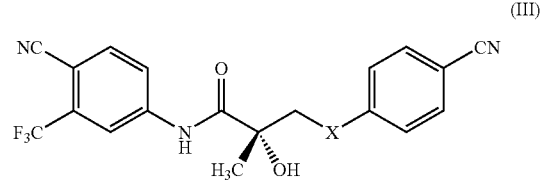

In another embodiment, this invention provides a SARM compound or its prodrug, analog, isomer, metabolite, derivative, pharmaceutically acceptable salt, pharmaceutical product, polymorph, crystal, impurity, N-oxide, hydrate or any combination thereof, represented by a structure of formula (IV):

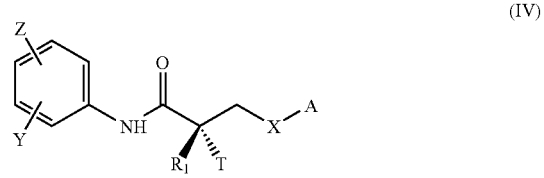

wherein
X is O or NH;
T is OH, OR, NHCOCH$_3$, NHCOR or OC(O)R;
Z is hydrogen, alkyl, NO$_2$, CN, COOH, COR, NHCOR or CONHR;

Y is hydrogen, alkyl, $CF_3$, halogen, hydroxyalkyl or alkyl aldehyde;

R is alkyl, haloalkyl, dihaloalkyl, trihaloalkyl, $CH_2F$, $CHF_2$, $CF_3$, $CF_2CF_3$, aryl, phenyl, halogen, haloalkenyl, alkenyl or OH; and $R_1$ is $CH_3$, $CH_2F$, $CHF_2$, $CF_3$, $CH_2CH_3$, or $CF_2CF_3$.

A is a group selected from:

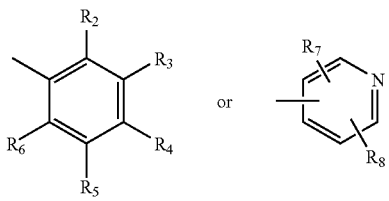

wherein $R_2$, $R_3$, $R_4$, $R_5$, $R_6$ are independently is H, halogen, $NO_2$, CN, $NHCOR_9$, $N(COR_9)_2$, $COR_{10}$, $OR_{11}$, $OSO_2R_{12}$, $SO_2R_{13}$, $NHSO_2R_{12}$, $SR_{14}$, an imide ring, alkyl or substituted alkyl with at least one substituent of halogen, CN, $NH_2$, OH, alkoxy; or $R_2$ and $R_3$, $R_3$ and $R_4$, $R_4$ and $R_5$, or $R_5$ and $R_6$ form, together with any of the ring atom(s) to which they are attached, a condensed 5 to 7 membered aliphatic or aromatic carbocyclic ring or a condensed 5 to 7 membered heterocyclic ring containing 1 to 3 heteroatom(s) selected from N, O, S; or represented by structures A, B or C:

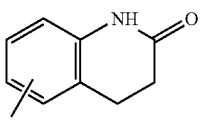 A

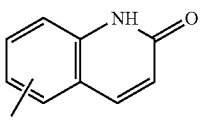 B

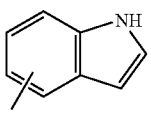 C $R_7$ and $R_8$ are independently H, halogen, alkyl or alkenyl $R_9$ and $R_{10}$ are independently alkyl, alkenyl, haloalkyl, aminoalkyl, mono- or di alkylaminoalkyl, aryl, $N(R_{15})_2$ or $-OR_{16}$;

$R_{11}$ and $R_{14}$ independently H, alkyl, alkenyl, haloalkyl, aminoalkyl, mono- or di alkylaminoalkyl, aryl, $-COR_{17}$;

$R_{12}$ and $R_{13}$ are independently alkyl or alkenyl, haloalkyl or aryl;

$R_{15}$ and $R_{16}$ are independently H, alkyl, alkenyl, haloalkyl, aminoalkyl or aryl;

$R_{17}$ is alkyl, alkenyl, haloalkyl or aryl.

In one embodiment, according to this aspect of the invention, X is O, or in another embodiment, T is OH, or in another embodiment, $R_1$ is $CH_3$, or in another embodiment, Z is $NO_2$, or in another embodiment, Z is CN, or in another embodiment, $R_2$, $R_3$, $R_5$, $R_6$ are hydrogens and $R_4$ is $NHCOCF_3$, or in another embodiment, $R_2$, $R_3$, $R_5$, $R_6$ are hydrogens and $R_4$ is F, or in another embodiment, $R_2$, $R_3$, $R_5$, $R_6$ are hydrogens, or in another embodiment, Z is in the para position, or in another embodiment, Y is in the meta position, or in another embodiment, any combination thereof.

In another embodiment, this invention provides a SARM compound or its prodrug, analog, isomer, metabolite, derivative, pharmaceutically acceptable salt, pharmaceutical product, polymorph, crystal, impurity, N-oxide, hydrate or any combination thereof, represented by a structure of formula (IV):

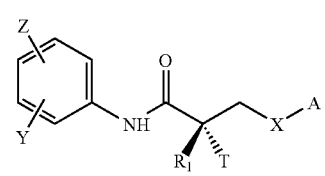

wherein

X is O, NH;

T is OH, OR, $NHCOCH_3$, or NHCOR;

Z is $NO_2$, CN, COOH, COR, NHCOR or CONHR;

Y is H;

A is a group selected from:

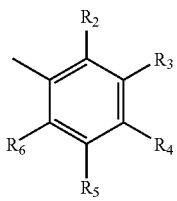

wherein $R_2$, $R_3$, $R_4$, $R_5$, $R_6$ are independently H, halogen, CN, $NHCOCH_3$, $NHCOCF_3$;

R is alkyl, haloalkyl, dihaloalkyl, trihaloalkyl, $CH_2F$, $CHF_2$, $CF_3$, $CF_2CF_3$, aryl, phenyl, halogen, alkenyl or OH; and $R_1$ is $CH_3$, $CH_2F$, $CHF_2$, $CF_3$, $CH_2CH_3$, or $CF_2CF_3$.

In one embodiment, the compound of formula II is represented by the compound of formula (V):

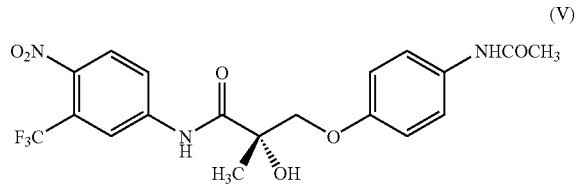

In one embodiment, a compound of formula II is represented by the compound of formula (VI):

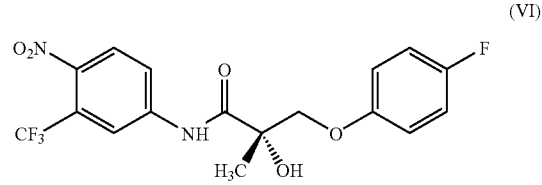

In another embodiment, a compound of formula II is represented by the structure of formula (VII):

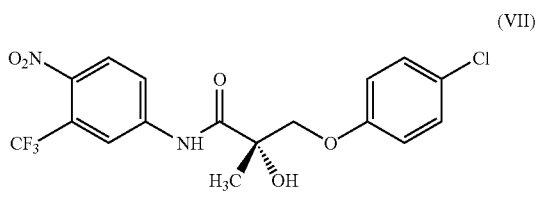

In another embodiment, a compound of formula II is represented by the structure of formula (VIII):

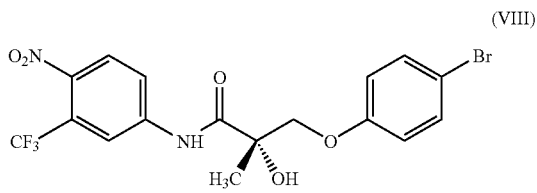

In another embodiment, a compound of formula II is represented by the structure of formula (IX):

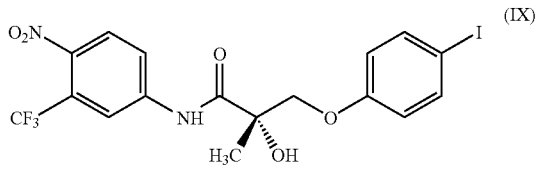

In another embodiment, a compound of formula II is represented by the structure of formula (X):

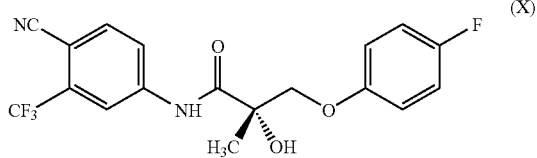

In one embodiment, a compound of formula II is represented by the structure of formula (XI):

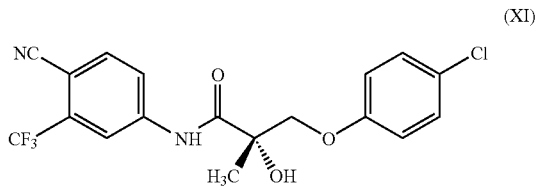

In one embodiment, a compound of formula II is represented by the structure of formula (XII):

In another embodiment, a compound of formula II is represented by the structure of formula (XIII):

In another embodiment, a compound of formula II is represented by the structure of formula (XIV):

In another embodiment, a compound of formula II is represented by the structure of formula (XV):

In another embodiment, a compound of formula II is represented by the compound of formula (XVI):

In another embodiment, a compound of formula II is represented by the compound of formula (XVII):

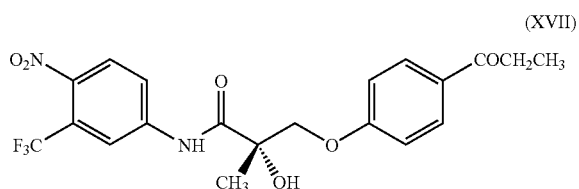
(XVII)

In another embodiment, a compound of formula II is represented by the compound of formula (XVIII):

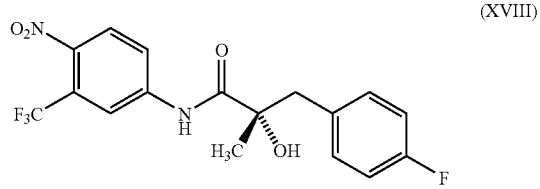
(XVIII)

In another embodiment, a compound of formula II is represented by the compound of formula (XIX):

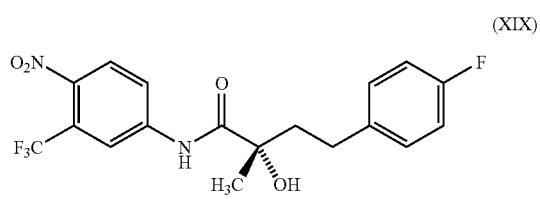
(XIX)

In one embodiment, the compound of formula II, wherein X is a bond or $CH_2$ is an agonist with minimal or no antagonist activity. In another embodiment, compound XVIII and XIX are agonists with minimal or no antagonist activity.

The present invention relates to a non-steroidal agonist compound, the non-steroidal agonist compound represented by the structure of formula (XX):

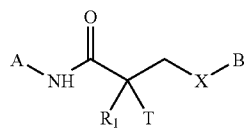
(XX)

wherein

X is O, $CH_2$, NH, Se, PR, or NR;

$R_1$ is $CH_3$, $CF_3$, $CH_2CH_3$, or $CF_2 CF_3$;

T is OH, OR, $NHCOCH_3$, or NHCOR;

wherein R is a $C_1$-$C_4$ alkyl, a $C_1$-$C_4$ haloalkyl, aryl, phenyl, halogen, alkenyl, haloalkenyl, or hydroxyl;

A is a 5 or 6 membered saturated, unsaturated or aromatic carbocyclic or heterocyclic ring represented by the structure:

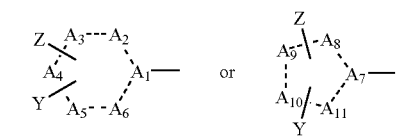

B is a 5 or 6 membered saturated, unsaturated or aromatic carbocyclic or heterocyclic ring represented by the structure:

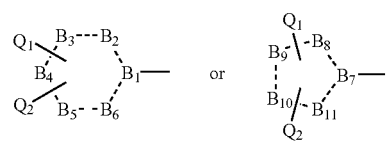

wherein $A_1$-$A_{11}$ are each C, CH, $CH_2$, O, S, N, or NH;

$B_1$-$B_{11}$ are each C, CH, $CH_2$, O, S, N, or NH;

Z is a hydrogen bond acceptor, alkyl, H, $NO_2$, CN, COOH, COR, NHCOR or CONHR;

Y is a lipid soluble group, hydrogen, alkyl, hydroxylalkyl, alkylaldehyde, $CF_3$, F, I, Br, Cl, CN, $C(R)_3$ or $Sn(R)_3$; and $Q_1$ and $Q_2$ are independently of each other H, alkyl, halogen, CN, $N(R)_2$, $NHCOCH_3$, $NHCOCF_3$, NHCOR, NHCONHR, NHCOOR, OCONHR, CONHR, NHCSCH_3$, $NHCSCF_3$, NHCSR, $NHSO_2CH_3$, $NHSO_2R$, OR, COR, OCOR, $OSO_2R$, $SO_2R$ or SR;

wherein R is a $C_1$-$C_4$ alkyl, a $C_1$-$C_4$ haloalkyl, aryl, phenyl, halogen, alkenyl, haloalkenyl, or hydroxyl. In one embodiment, the alkyl group is $CH_3$.

The substitutents Z and Y can be in any position of the five or 6 membered ring carrying these substitutents (hereinafter "A ring"). Similarly, the substituent Q can be in any position of the five or 6 membered ring carrying this substitutent (hereinafter "B ring"). It is understood that when any of the ring members $A_1$-$A_{11}$ or $B_1$-$B_{11}$ are O or S, then these ring members are unsubstituted. It is further understood that when any of the ring members $A_1$-$A_{11}$ or $B_1$-$B_{11}$ are O or S, then the dotted line between O or S atoms and adjacent ring members represents a single bond.

In one embodiment, the A ring includes any type of saturated or unsaturated carbocyclic ring. In one embodiment, the A ring is a 6 membered saturated carbocyclic ring, which may be unsubstituted, monosubstituted or polysubstituted by any of the substitutents described hereinabove. In one embodiment, the A ring is a 5 membered saturated carbocyclic ring, which may be unsubstituted, monosubstituted or polysubstituted by any of the substitutents described hereinabove. In another embodiment, the A ring is a 6 membered carbocyclic ring containing one or more double bonds, which ring may be unsubstituted, monosubstituted or polysubstituted by any of the substitutents described hereinabove. In another embodiment, the A ring is a 5 membered carbocyclic ring containing one or more double bonds, which ring may be unsubstituted, monosubstituted or polysubstituted by any of the substitutents described hereinabove.

In another embodiment, the A ring includes any type of saturated, unsaturated or aromatic heterocyclic ring. In another embodiment, the A ring is a 6 membered saturated heterocyclic ring, which may be unsubstituted, monosubstituted or polysubstituted by any of the substituents described hereinabove. In another embodiment, the A ring is a 5 membered saturated heterocyclic ring, which may be unsubstituted, monosubstituted or polysubstituted by any of the substituents described hereinabove. In another embodiment, the A ring is a 6 membered heterocyclic ring containing one or more double bonds, which ring may be unsubstituted, monosubstituted or polysubstituted by any of the substitutents described hereinabove. In another embodiment, the A ring is a 5 membered heterocyclic ring containing one or more double bonds, which ring may be unsubstituted, monosubstituted or polysubstituted by any of the substitutents described hereinabove. In another embodiment, the A ring is a 6 membered heteroaromatic ring which may be unsubstituted, monosubstituted or polysubstituted by any of the substitutents described hereinabove. In another embodiment, the A ring is a 5 membered heteroaromatic ring which may be unsubstituted, monosubstituted or polysubstituted by any of the substitutents described hereinabove.

Similarly, the B ring includes any type of saturated or unsaturated carbocyclic ring. In one embodiment, the B ring is a 6 membered saturated carbocyclic ring, which may be unsubstituted, monosubstituted or polysubstituted by any of the substitutents described hereinabove. In one embodiment, the B ring is a 5 membered saturated carbocyclic ring, which may be unsubstituted, monosubstituted or polysubstituted by any of the substitutents described hereinabove. In another embodiment, the B ring is a 6 membered carbocyclic ring containing one or more double bonds, which ring may be unsubstituted, monosubstituted or polysubstituted by any of the substitutents described hereinabove. In another embodiment, the B ring is a 5 membered carbocyclic ring containing one or more double bonds, which ring may be unsubstituted, monosubstituted or polysubstituted by any of the substitutents described hereinabove.

In another embodiment, the B ring includes any type of saturated, unsaturated or aromatic heterocyclic ring. In another embodiment, the B ring is a 6 membered saturated heterocyclic ring, which may be unsubstituted, monosubstituted or polysubstituted by any of the substituents described hereinabove. In another embodiment, the B ring is a 5 membered saturated heterocyclic ring, which may be unsubstituted, monosubstituted or polysubstituted by any of the substituents described hereinabove. In another embodiment, the B ring is a 6 membered heterocyclic ring containing one or more double bonds, which ring may be unsubstituted, monosubstituted or polysubstituted by any of the substitutents described hereinabove. In another embodiment, the B ring is a 5 membered heterocyclic ring containing one or more double bonds, which ring may be unsubstituted, monosubstituted or polysubstituted by any of the substitutents described hereinabove. In another embodiment, the B ring is a 6 membered heteroaromatic ring which may be unsubstituted, monosubstituted or polysubstituted by any of the substituents described hereinabove. In another embodiment, the B ring is a 5 membered heteroaromatic ring which may be unsubstituted, monosubstituted or polysubstituted by any of the substitutents described hereinabove.

Nonlimiting examples of suitable A rings and/or B rings are carbocyclic rings such as cyclopentane, cyclopentene, cyclohexane, and cyclohexene rings, and heterocyclic rings such as pyran, dihydropyran, tetrahydropyran, pyrrole, dihydropyrrole, tetrahydropyrrole, pyrazine, dihydropyrazine, tetrahydropyrazine, pyrimidine, dihydropyrimidine, tetrahydropyrimidone, pyrazol, dihydropyrazol, tetrahydropyrazol, piperidine, piperazine, pyridine, dihydropyridine, tetrahydropyridine, morpholine, thiomorpholine, furan, dihydrofuran, tetrahydrofuran, thiophene, dihydrothiophene, tetrahydrothiophene, thiazole, imidazole, isoxazole, and the like.

An "alkyl" group refers, in one embodiment, to a saturated aliphatic hydrocarbon, including straight-chain, branched-chain and cyclic alkyl groups. In one embodiment, the alkyl group has 1-12 carbons. In another embodiment, the alkyl group has 1-7 carbons. In another embodiment, the alkyl group has 1-6 carbons. In another embodiment, the alkyl group has 1-4 carbons. The alkyl group may be unsubstituted or substituted by one or more groups selected from halogen, hydroxy, alkoxy carbonyl, amido, alkylamido, dialkylamido, nitro, amino, alkylamino, dialkylamino, carboxyl, thio and thioalkyl. In one embodiment, the alkyl group is $CH_3$.

An "alkenyl" group refers, in another embodiment, to an unsaturated hydrocarbon, including straight chain, branched chain and cyclic groups having one or more double bond. The alkenyl group may have one double bond, two double bonds, three double bonds etc. Examples of alkenyl groups are ethenyl, propenyl, butenyl, cyclohexenyl etc. The alkenyl group may be unsubstituted or substituted by one or more groups selected from halogen, hydroxy, alkoxy carbonyl, amido, alkylamido, dialkylamido, nitro, amino, alkylamino, dialkylamino, carboxyl, thio and thioalkyl.

A "haloalkyl" group refers to an alkyl group as defined above, which is substituted by one or more halogen atoms, in one embodiment by F, in another embodiment by Cl, in another embodiment by Br, in another embodiment by I.

An "aryl" group refers to an aromatic group having at least one carbocyclic aromatic group or heterocyclic aromatic group, which may be unsubstituted or substituted by one or more groups selected from halogen, haloalkyl, hydroxy, alkoxy carbonyl, amido, alkylamido, dialkylamido, nitro, amino, alkylamino, dialkylamino, carboxy or thio or thioalkyl. Nonlimiting examples of aryl rings are phenyl, naphthyl, pyranyl, pyrrolyl, pyrazinyl, pyrimidinyl, pyrazolyl, pyridinyl, furanyl, thiophenyl, thiazolyl, imidazolyl, isoxazolyl, and the like.

A "hydroxyl" group refers to an OH group. It is understood by a person skilled in the art that when T is OR, R is not OH.

In one embodiment, the term "halogen refers to in one embodiment to F, in another embodiment to Cl, in another embodiment to Br, in another embodiment to I.

An "arylalkyl" group refers, in another embodiment, to an alkyl bound to an aryl, wherein alkyl and aryl are as defined above. An example of an arylalkyl group is a benzyl group.

In one embodiment, this invention provides a SARM compound and/or, analog, derivative, isomer, metabolite, pharmaceutically acceptable salt, pharmaceutical product, hydrate, N-oxide, prodrug, polymorph, impurity or crystal or combinations thereof. In one embodiment, this invention provides an analog of the SARM compound. In another embodiment, this invention provides a derivative of the SARM compound. In another embodiment, this invention provides an isomer of the SARM compound. In another embodiment, this invention provides a metabolite of the SARM compound. In another embodiment, this invention provides a pharmaceutically acceptable salt of the SARM compound. In another embodiment, this invention provides a pharmaceutical product of the SARM compound. In another embodiment, this invention provides a hydrate of the SARM compound. In another embodiment, this invention provides an N-oxide of the SARM compound. In another embodiment, this invention provides a prodrug of the SARM compound. In another embodiment, this invention provides a polymorph of the SARM compound. In another embodiment, this invention provides a crystal of the SARM compound. In another embodiment, this invention provides an impurity of the SARM compound. In another embodiment, this invention provides composition comprising a SARM compound, as described herein, or, in another embodiment, a combination of an analog, derivative, isomer, metabolite, pharmaceutically acceptable salt, pharmaceutical product, hydrate, N-oxide, prodrug, polymorph, impurity or crystal of the SARM compounds of the present invention.

In one embodiment, the term "isomer" includes, but is not limited to, optical isomers and analogs, structural isomers and analogs, conformational isomers and analogs, and the like.

In one embodiment, the term "isomer" is meant to encompass optical isomers of the SARM compound. It will be appreciated by those skilled in the art that the SARMs of the present invention contain at least one chiral center. Accordingly, the SARMs used in the methods of the present invention may exist in, and be isolated in, optically-active or racemic forms. Some compounds may also exhibit polymorphism. It is to be understood that the present invention encompasses any racemic, optically-active, polymorphic, or stereoisomeric form, or mixtures thereof, which form possesses properties useful in the treatment of androgen-related conditions described herein. In one embodiment, the SARMs are the pure (R)-isomers. In another embodiment, the SARMs are the pure (S)-isomers. In another embodiment, the SARMs are a mixture of the (R) and the (S) isomers. In another embodiment, the SARMs are a racemic mixture comprising an equal amount of the (R) and the (S) isomers. It is well known in the art how to prepare optically-active forms (for example, by resolution of the racemic form by recrystallization techniques, by synthesis from optically-active starting materials, by chiral synthesis, or by chromatographic separation using a chiral stationary phase).

The invention includes "pharmaceutically acceptable salts" of the SARMs of this invention, which may be produced, in one embodiment, using an amino-substituted SARM and organic and inorganic acids, for example, citric acid and hydrochloric acid. Pharmaceutically acceptable salts can be prepared, from the phenolic compounds, in other embodiments, by treatment with inorganic bases, for example, sodium hydroxide. In another embodiment, esters of the phenolic compounds can be made with aliphatic and aromatic carboxylic acids, for example, acetic acid and benzoic acid esters.

The invention also includes N-oxides of the amino substituents of the SARMs described herein.

This invention provides derivatives of the SARM compounds In one embodiment, "derivatives" includes but is not limited to ether derivatives, acid derivatives, amide derivatives, ester derivatives and the like. In another embodiment, this invention further includes hydrates of the SARM compounds. In one embodiment, "hydrate" includes but is not limited to hemihydrate, monohydrate, dihydrate, trihydrate and the like.

This invention provides, in other embodiments, metabolites of the SARM compounds. In one embodiment, "metabolite" means any substance produced from another substance by metabolism or a metabolic process.

This invention provides, in other embodiments, pharmaceutical products of the SARM compounds. The term "pharmaceutical product" refers, in other embodiments, to a composition suitable for pharmaceutical use (pharmaceutical composition), for example, as described herein.

In one embodiment, the present invention provides a process for preparing a SARM compound represented by the structure of formula (I):

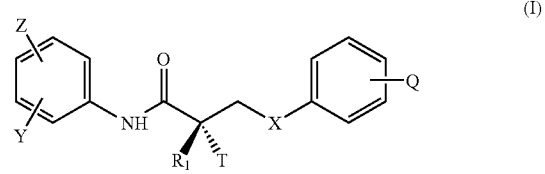

wherein

X is O, NH, Se, PR, or NR;

T is OH, OR, NHCOCH$_3$, or NHCOR;

Z is a hydrogen bond acceptor, hydrogen, alkyl, NO$_2$, CN, COOH, COR, NHCOR or CONHR;

Y is a lipid soluble group, hydrogen, alkyl, hydroxylalkyl, alkylaldehyde, CF$_3$, F, I, Br, Cl, CN, C(R)$_3$ or Sn(R)$_3$;

Q is alkyl, halogen, CF$_3$, CN, C(R)$_3$, Sn(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR; or Q together with the benzene ring to which it is attached is a fused ring system represented by structure A, B or C:

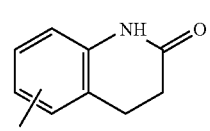

A

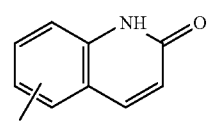

B

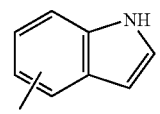

C

R is alkyl, haloalkyl, dihaloalkyl, trihaloalkyl, CH$_2$F, CHF$_2$, CF$_3$, CF$_2$CF$_3$, aryl, phenyl, halogen, alkenyl or OH; and R$_1$ is CH$_3$, CH$_2$F, CHF$_2$, CF$_3$, CH$_2$CH$_3$, or CF$_2$CF$_3$;

the process comprising the step of coupling an amide of formula (XXII):

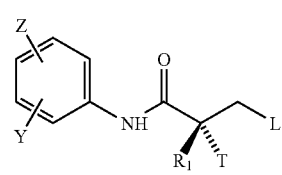

(XXII)

wherein Z, Y, R$_1$ and T are as defined above and L is a leaving group, with a compound of formula (XXIII):

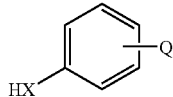
(XXIII)

wherein Q and X are as defined above.

In one embodiment, the amide of formula XXII is prepared by the following steps:
a) preparing a carboxylic acid of formula XXV by ring opening of a cyclic compound of formula XXIV

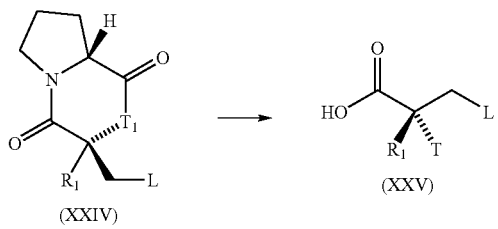
(XXIV) → (XXV)

wherein L, $R_1$ and T are as defined above, and $T_1$ is O or NH; and b) reacting an amine of formula XXVI:

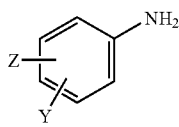
(XXVI)

wherein Z and Y are as defined above, with the carboxylic acid of formula XXV in the presence of a coupling reagent, to produce the amide of formula XXII.

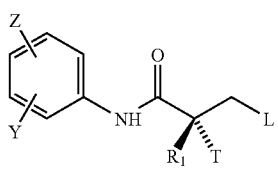
(XXII)

In one embodiment, step (a) is carried out in the presence of HBr.

In one embodiment, whereby compound XXV of step (a) is reacted with a coupling agent prior to step (b).

In one embodiment, the present invention provides a process for preparing a SARM compound represented by the structure of formula (I):

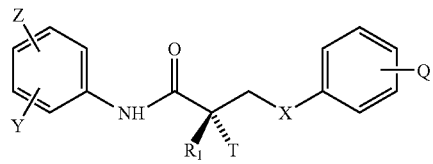
(I)

wherein
X is O;
T is OH;
Z is a hydrogen bond acceptor, hydrogen, alkyl, $NO_2$, CN, COOH, COR, NHCOR or CONHR;
Y is a lipid soluble group, hydrogen, alkyl, hydroxyalkyl, alkylaldehyde, $CF_3$, F, I, Br, Cl, CN, $C(R)_3$ or $Sn(R)_3$;
Q is alkyl, halogen, $CF_3$, CN, $C(R)_3$, $Sn(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR;
R is alkyl, haloalkyl, dihaloalkyl, trihaloalkyl, $CH_2F$, $CHF_2$, $CF_3$, $CF_2CF_3$, aryl, phenyl, halogen, alkenyl or OH; and
$R_1$ is $CH_3$;

the process comprising the step of coupling an amide of formula (XXII-a):

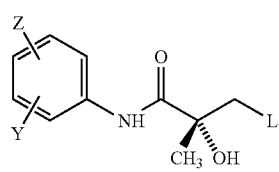
(XXII-a)

wherein Z, Y, $R_1$ and T are as defined above and L is a leaving group, with a compound of formula (XXIII-a):

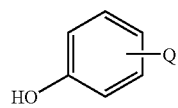
(XXIII-a)

wherein Q is as defined above.

In one embodiment, the amide of formula (XXII-a) has a structure as follows:

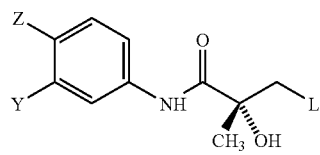

In one embodiment, the amide of formula (XXII-a) has a structure as follows:

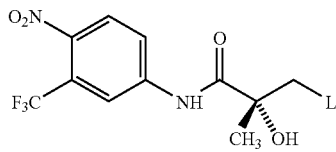

In one embodiment, the amide of formula (XXII-a) has a structure as follows:

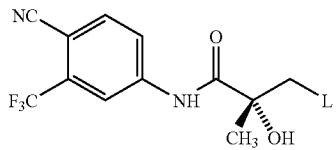

In one embodiment, the amide of formula XXII is prepared by the following steps:

c) preparing a carboxylic acid of formula XXV by ring opening of a cyclic compound of formula XXIV

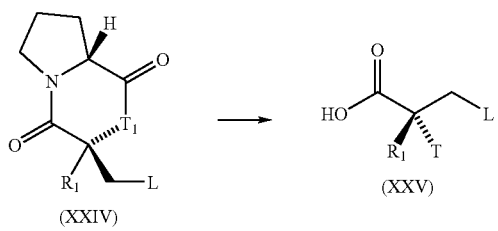

wherein L, $R_1$ and T are as defined above, and $T_1$ is O or NH; and d) reacting an amine of formula XXVI:

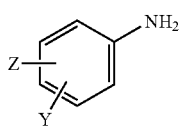

wherein Z and Y are as defined above, with the carboxylic acid of formula XXV in the presence of a coupling reagent, to produce the amide of formula XXII.

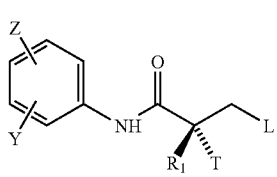

In one embodiment, the amine of formula XXVI, has a structure as follows:

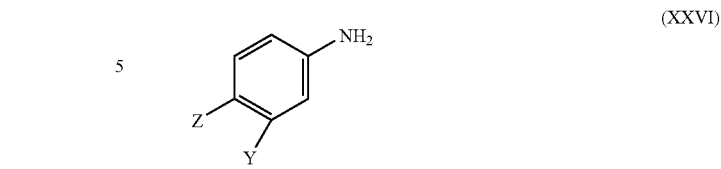

wherein Z and Y are as defined above.

In another embodiment, the amine of formula XXVI, has a structure as follows:

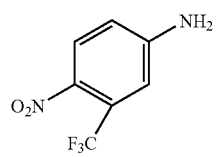

In another embodiment, the amine of formula XXVI, has a structure as follows:

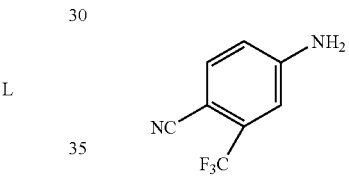

In another embodiment, the amide of formula XXII corresponds to any embodiment of such an amide as described herein, for example, the amide of formula XXII-a, as described hereinabove.

In one embodiment, the carboxylic acid of formula XXV has a structure as follows:

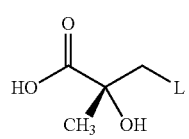

In another embodiment, the carboxylic acid of formula XXV has a structure as follows:

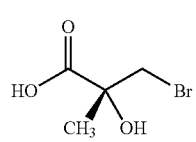

In one embodiment, the compound of formula XXIV has a structure as follows:

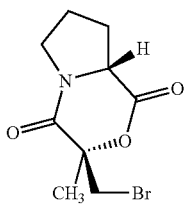

In one embodiment, step (a) is carried out in the presence of HBr.

It is to be understood that any embodiment, for any compound, which may be used for the preparation of a SARM as described herein, is to be considered as part of this invention, and can be used in a process to obtain a SARM of this invention.

In one embodiment, compound XXV of step (a) is reacted with a coupling agent prior to step (b).

Furthermore, in another embodiment, the present invention provides a process for preparing a SARM compound represented by the structure of formula (I):

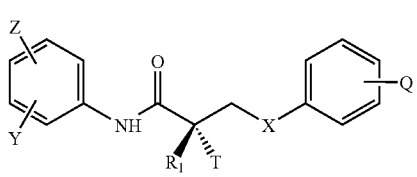
(I)

wherein

X is O, NH, Se, PR, or NR;

T is OH, OR, NHCOCH$_3$, or NHCOR;

Z is a hydrogen bond acceptor, hydrogen, alkyl, NO$_2$, CN, COOH, COR, NHCOR or CONHR;

Y is a lipid soluble group, hydrogen, alkyl, hydroxylalkyl, alkylaldehyde, CF$_3$, F, I, Br, Cl, CN, C(R)$_3$ or Sn(R)$_3$;

Q is alkyl, halogen, CF$_3$, CN, C(R)$_3$, Sn(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR; or Q together with the benzene ring to which it is attached is a fused ring system represented by structure A, B or C:

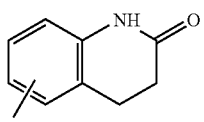
(A)

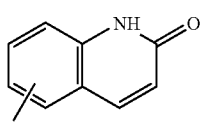
(B)

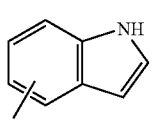
(C)

R is alkyl, haloalkyl, dihaloalkyl, trihaloalkyl, CH$_2$F, CHF$_2$, CF$_3$, CF$_2$CF$_3$, aryl, phenyl, halogen, alkenyl or OH; and R$_1$ is CH$_3$, CH$_2$F, CHF$_2$, CF$_3$, CH$_2$CH$_3$, or CF$_2$CF$_3$;

said process comprising the steps of:

a) preparing a carboxylic acid of formula XXV by ring opening of a cyclic compound of formula XXIV

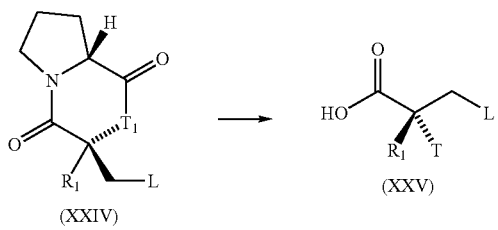

wherein L, R$_1$ and T are as defined above, and T$_1$ is O or NH;

b) reacting an amine of formula XXVI:

(XXVI)

wherein Z and Y are as defined above, with the carboxylic acid of formula XXV in the presence of a coupling reagent, to produce an amide of formula XXII

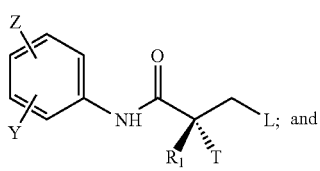
XXII c) coupling the amide of formula XXII with a compound of formula XXIII:

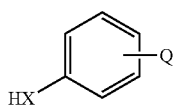
XXIII wherein Q and X are as defined above.

In one embodiment, step (a) is carried out in the presence of HBr.

In one embodiment, whereby compound XXV of step (a) is reacted with a coupling agent prior to step (b).

In one embodiment, the coupling step is carried out in the presence of a base. In another embodiment, the leaving group L is Br.

In another embodiment, this invention provides a large scale process for the preparation of compound of formula I, wherein the process comprises the same steps as described herein above, wherein compound of formula XXIV is prepared according to the following scheme, in the presence of 4N NaOH:

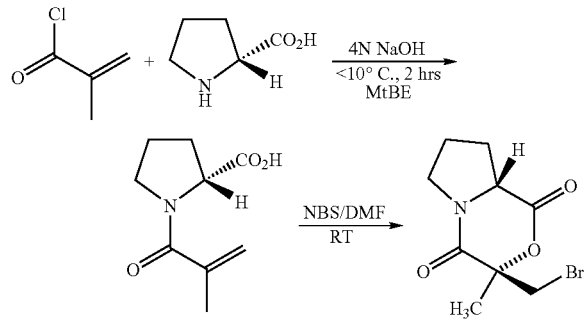

Figure 28A:
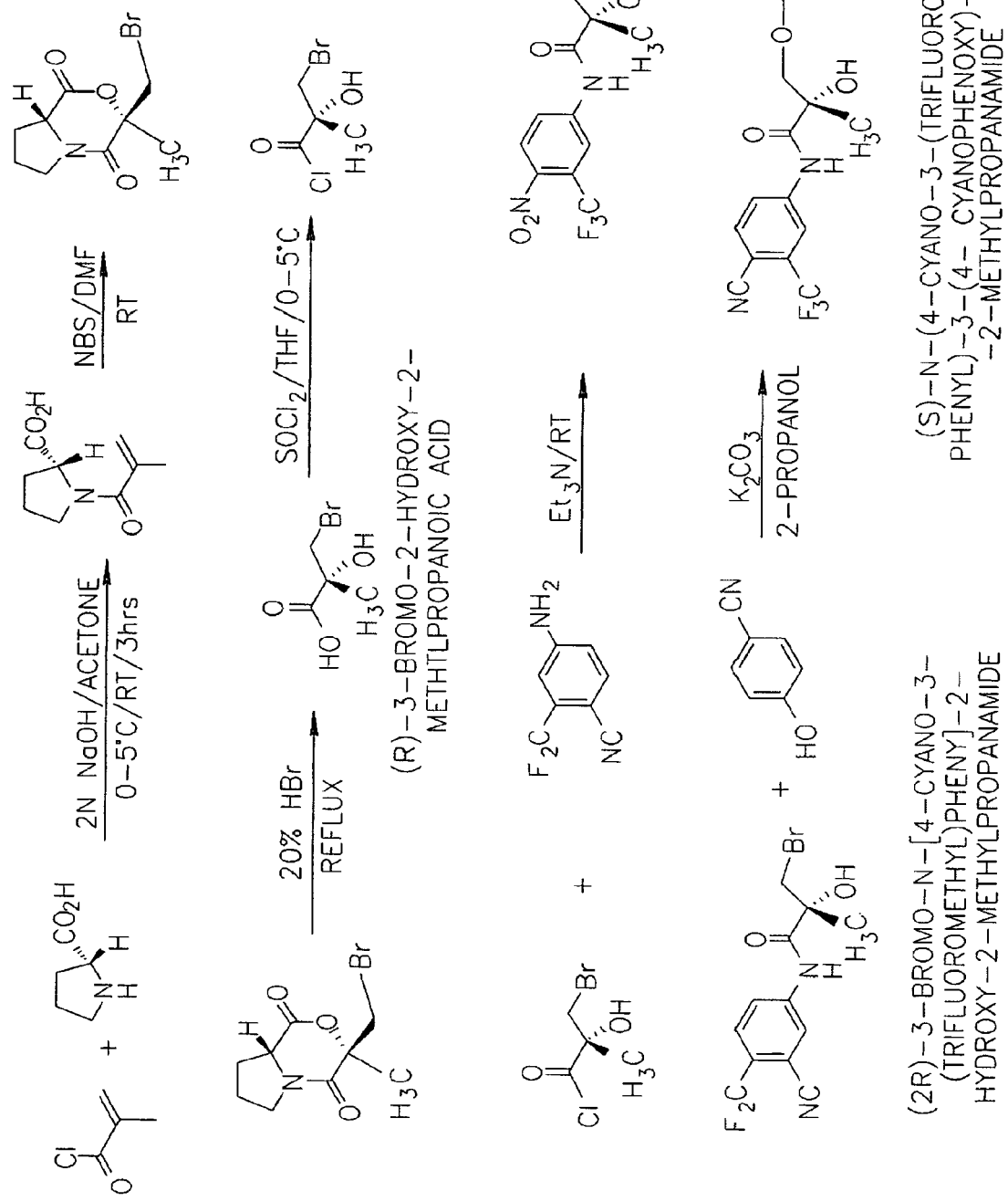
FIG. 28A is a synthetic scheme for the preparation of an (S) enantiomer of a compound of formula III (S-III).
Figure 28B:
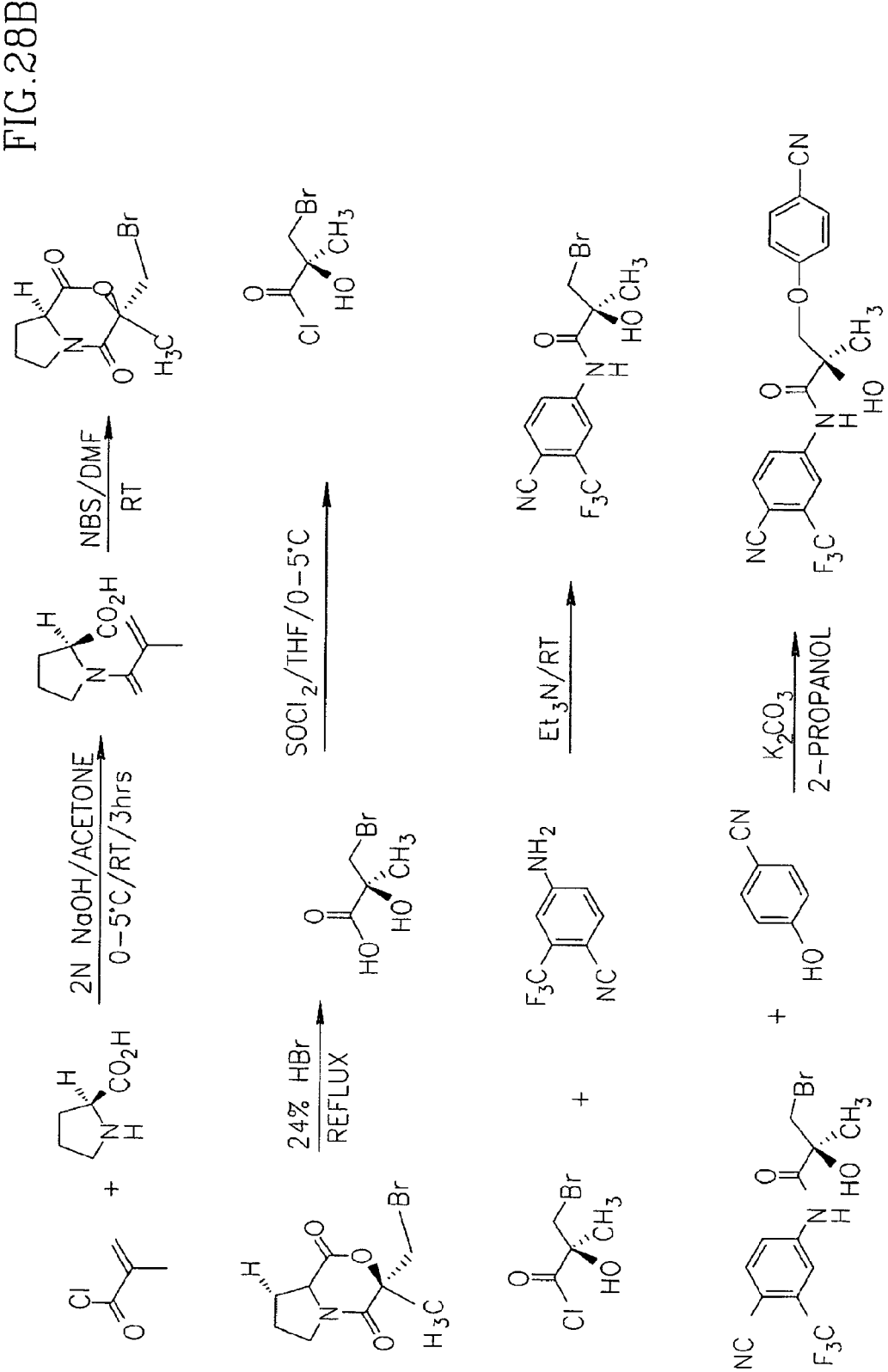
FIG. 28B is a synthetic scheme for the preparation of an (R) enantiomer of a compound of formula III (R-III).
Figure 28C:
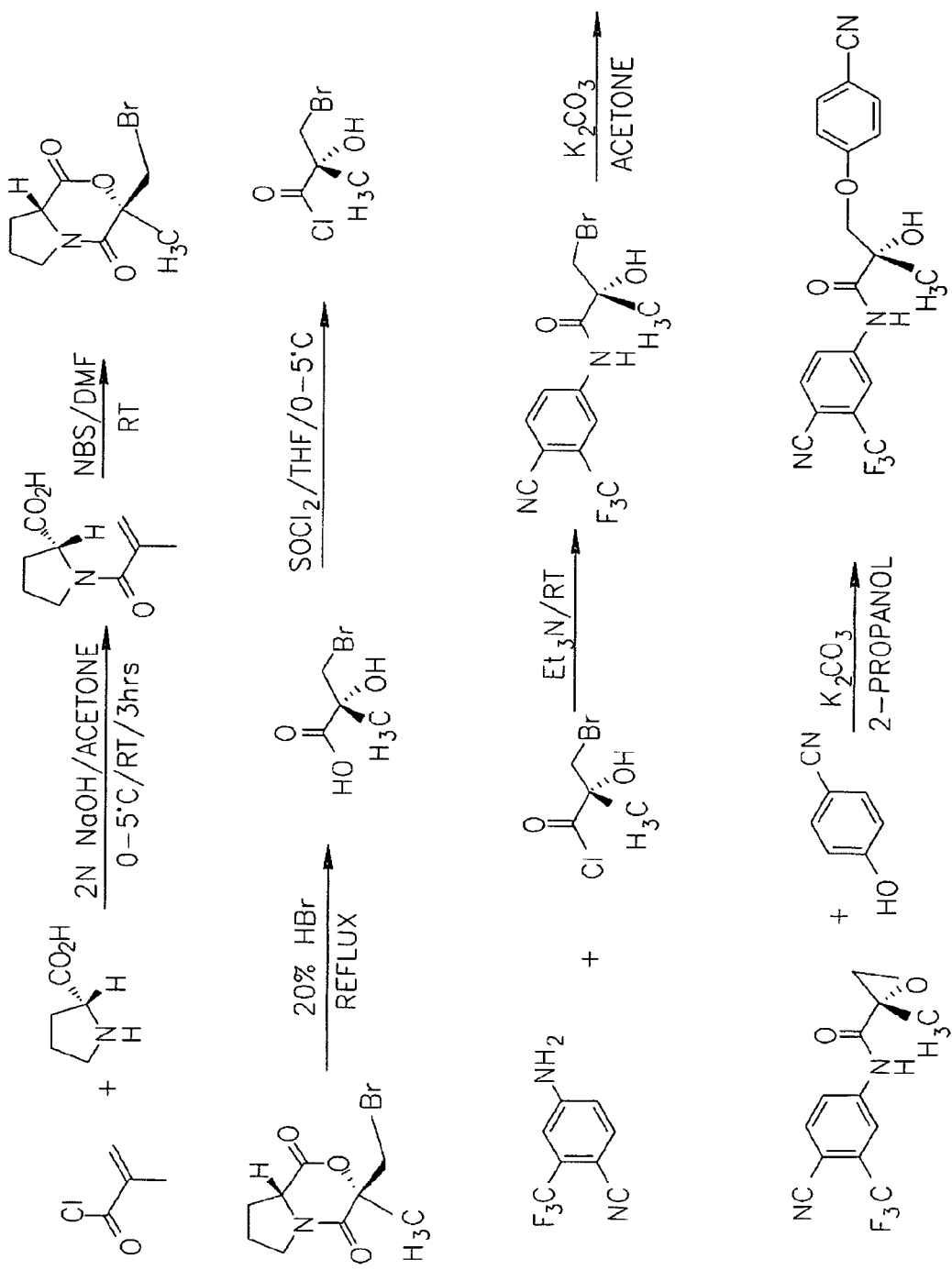
FIG. 28C is a synthetic scheme for the preparation of an (S) enantiomer of a compound of formula III (S-III) including an oxirane intermediate.
Figure 28D:
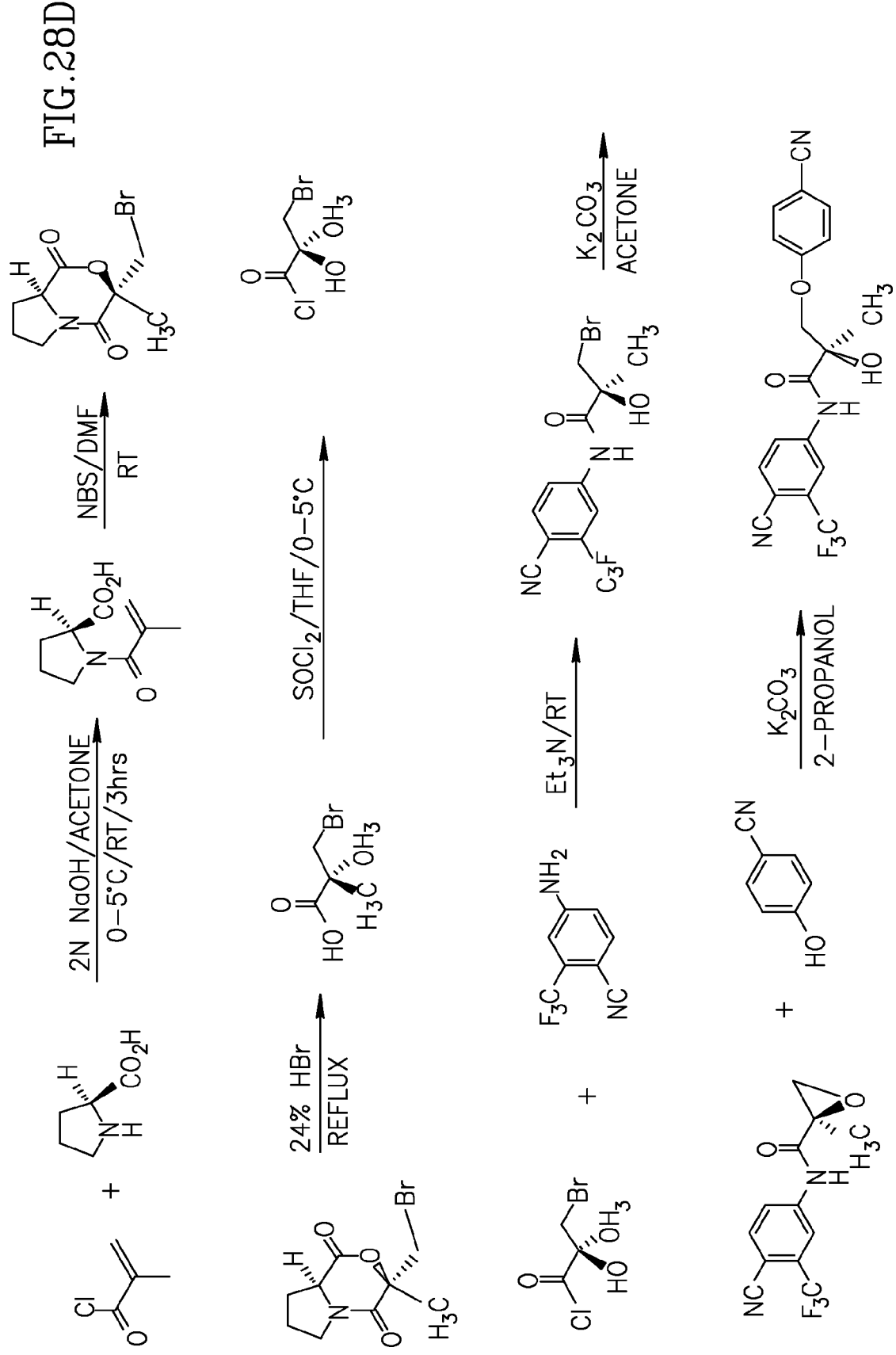
FIG. 28D is a synthetic scheme for the preparation of an (R) enantiomer of a compound of formula III (R-III) including an oxirane intermediate.
Figure 28E:
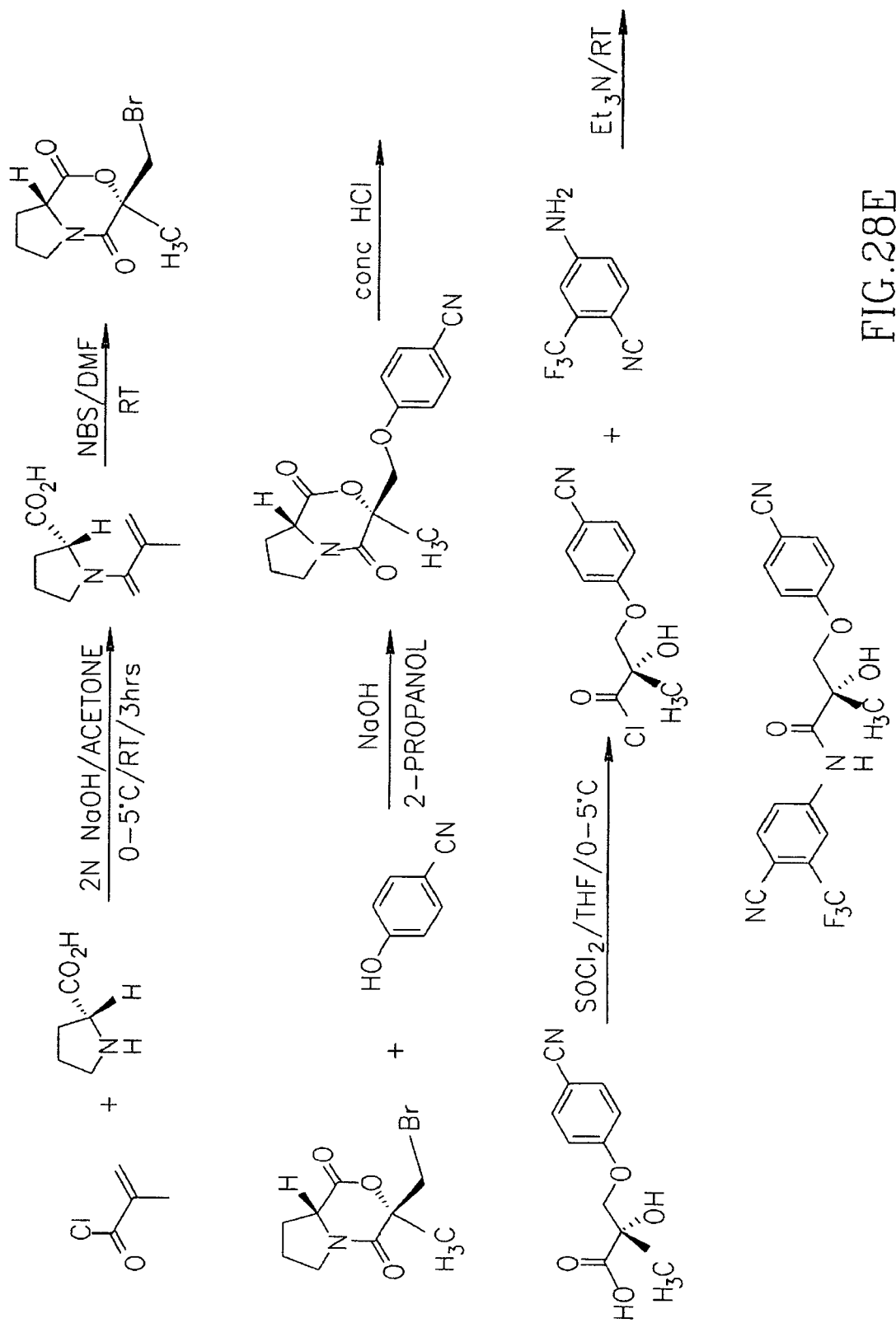
FIG. 28E is a synthetic scheme for the preparation of an (S) enantiomer of a compound of formula III (S-III) involving B-ring addition prior to A-ring addition.
Figure 28F:
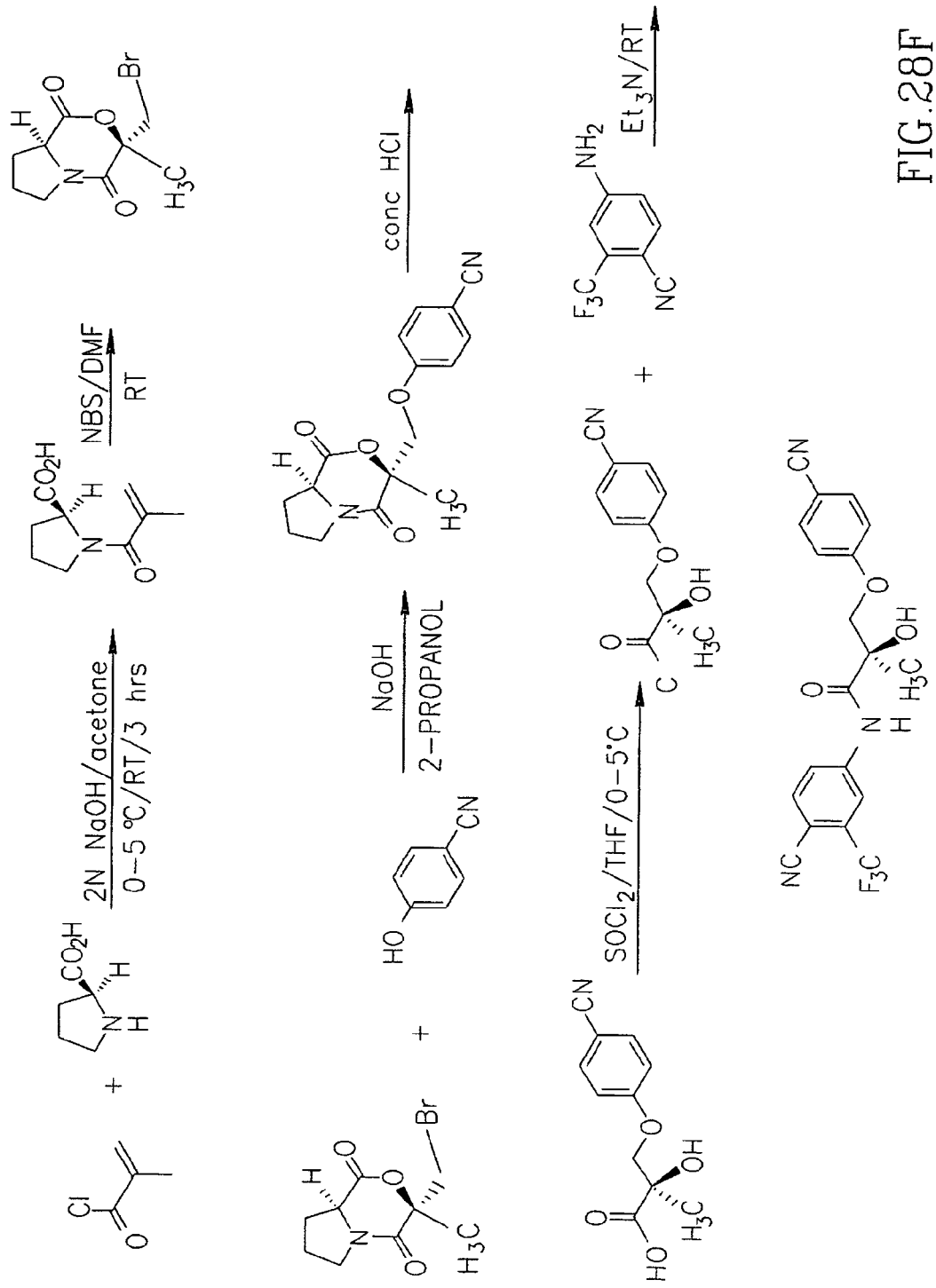
FIG. 28F is a synthetic scheme for the preparation of an (R) enantiomer of a compound of formula III (R-III) involving B-ring addition prior to A-ring addition.
Figure 28G:
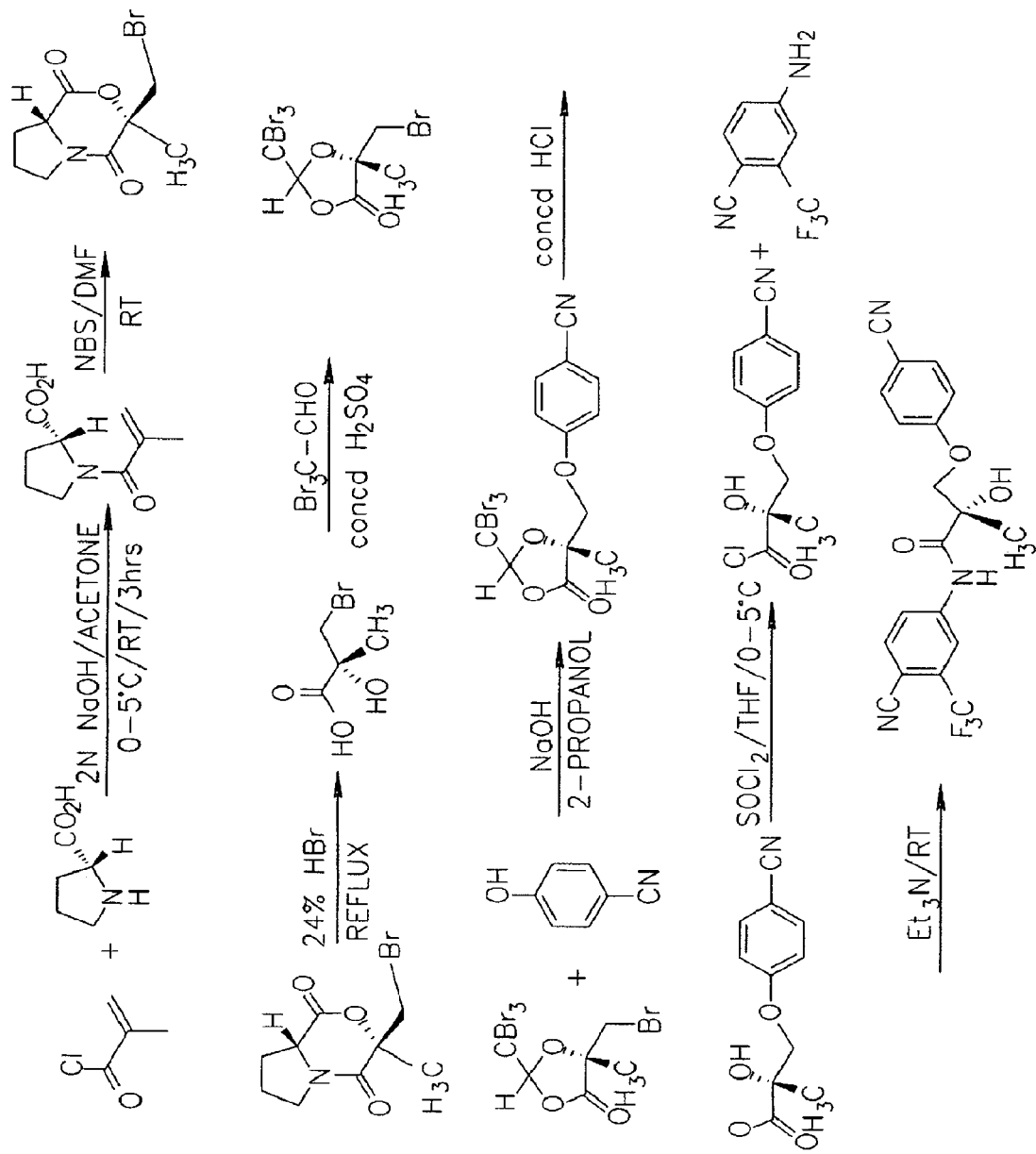
FIG. 28G is a synthetic scheme for the preparation of an (S) enantiomer of a compound of formula III (S-III) using 2-tribromomethyl-[1,3]dioxolan-4-one intermediate and involving B-ring addition prior to A-ring addition.
Figure 28H:
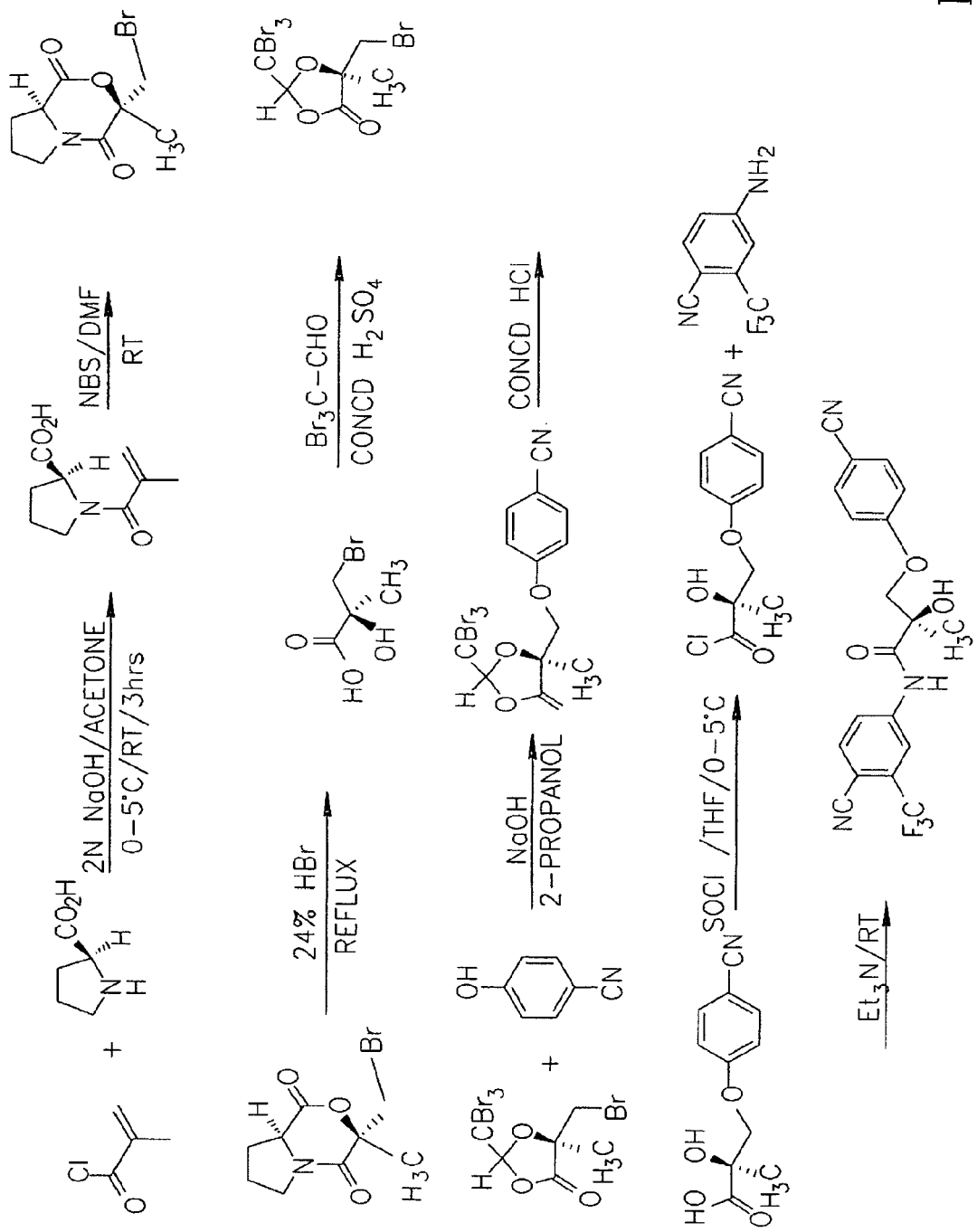
FIG. 28H is a synthetic scheme for the preparation of an (R) enantiomer of a compound of formula III (R-III) using 2-tribromomethyl-[1,3]dioxolan-4-one intermediate and involving B-ring addition prior to A-ring addition.
Figure 28I:
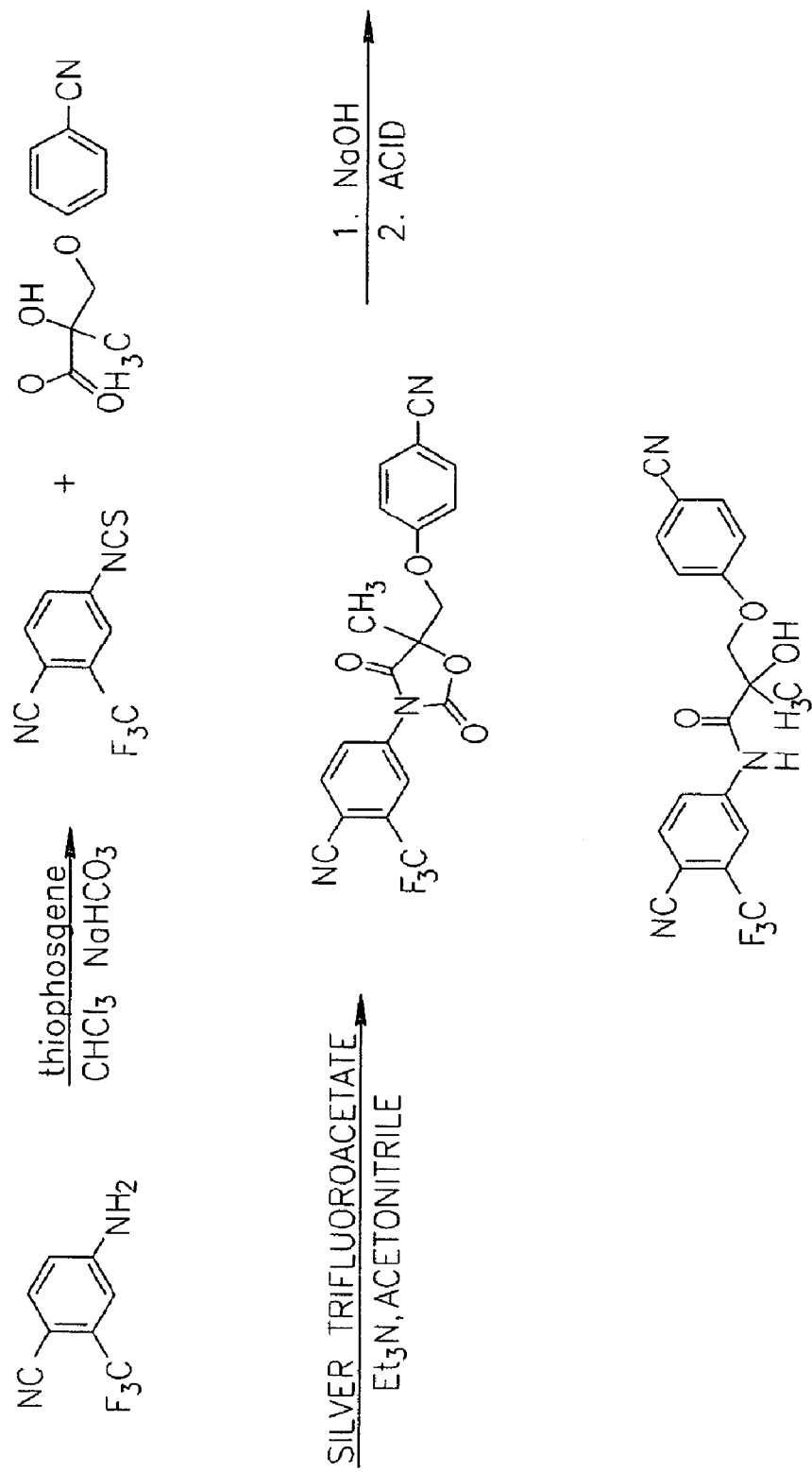
FIG. 28I is a synthetic scheme for preparation of a racemic mixture of a compound of formula III, involving oxazolidinedione intermediate and B ring addition prior to A ring.
Figure 28J:
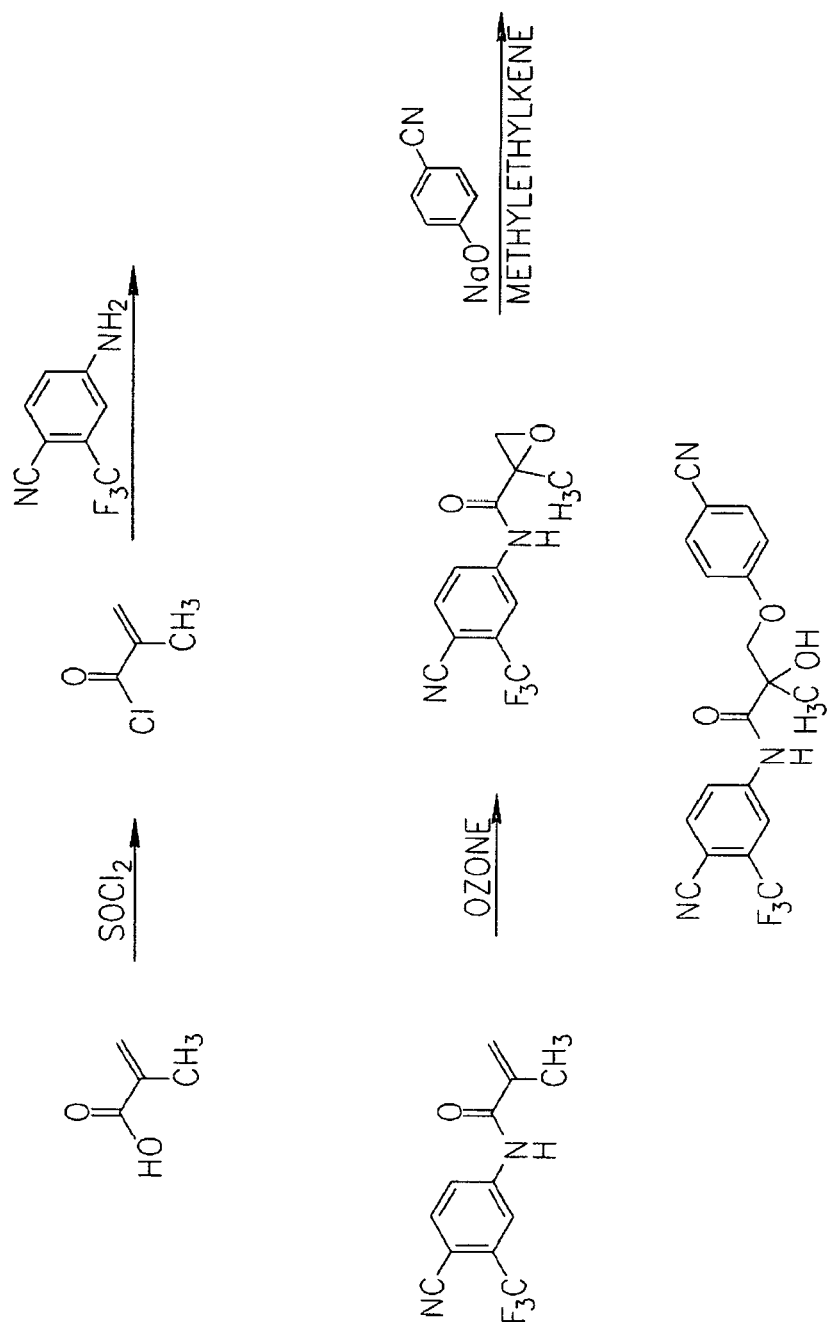
FIG. 28J is a synthetic scheme for preparation of a racemic mixture of a compound of formula III, involving an oxirane intermediate and A ring addition prior to B ring.
Figure 28K:
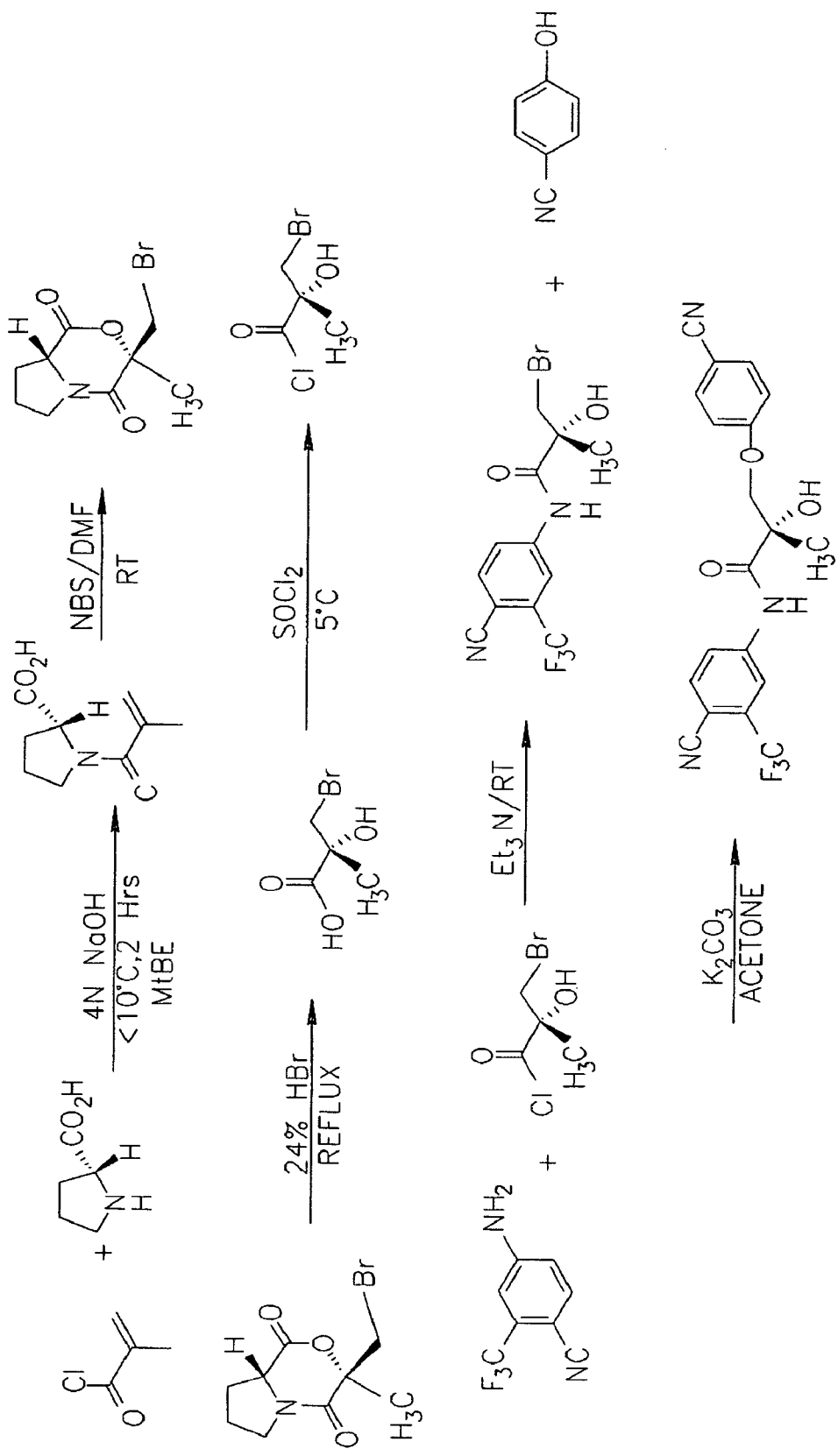
FIG. 28K is a synthetic scheme for preparation of a large scale or commercial scale of an (S) enantiomer of a compound of formula III (S-III).

Example 8 and FIG. 28K provide one embodiment of a large scale process for the preparation of a large scale synthesis of compounds of formulas V and III.

In one embodiment, the present invention provides a process for preparing a selective androgen modulator compound of formula I wherein is X is O. In another embodiment, the present invention provides a process for preparing a selective androgen modulator compound of formula I wherein is T is OH. In another embodiment, the present invention provides a process for preparing a selective androgen modulator compound of formula I wherein is $R_1$ is $CH_3$. In another embodiment, the present invention provides a process for preparing a selective androgen modulator compound of formula I wherein Z is $NO_2$. In another embodiment, the present invention provides a process for preparing a selective androgen modulator compound of formula I wherein Z is CN. In another embodiment, the present invention provides a process for preparing a selective androgen modulator compound of formula I wherein Y is $CF_3$. In another embodiment, the present invention provides a process for preparing a selective androgen modulator compound of formula I wherein Q is $NHCOCH_3$. In another embodiment, the present invention provides a process for preparing a selective androgen modulator compound of formula I wherein Q is F. In another embodiment, the present invention provides a process for preparing a selective androgen modulator compound of formula I wherein Q is CN.

In another embodiment, the present invention provides a process for preparing a selective androgen modulator compound represented by the structure of formula (IV):

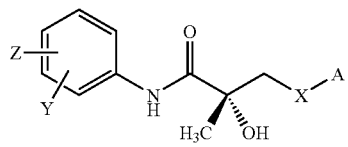

(IV)

In one embodiment, the SARM compound of formula IV may be produced by processes as exemplified herein, and as will be known to one skilled in the art. The process may comprise the step of coupling an amide of formula (XXII):

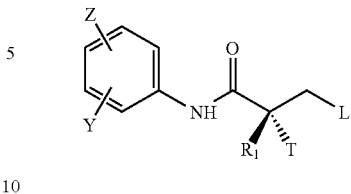

(XXII)

with a compound of formula XXVII:

HX-A                    XXVII wherein Z, Y, X, $R_1$, T and A of the compound of formula IV are as defined herein and L is a leaving group.

Figure 27:
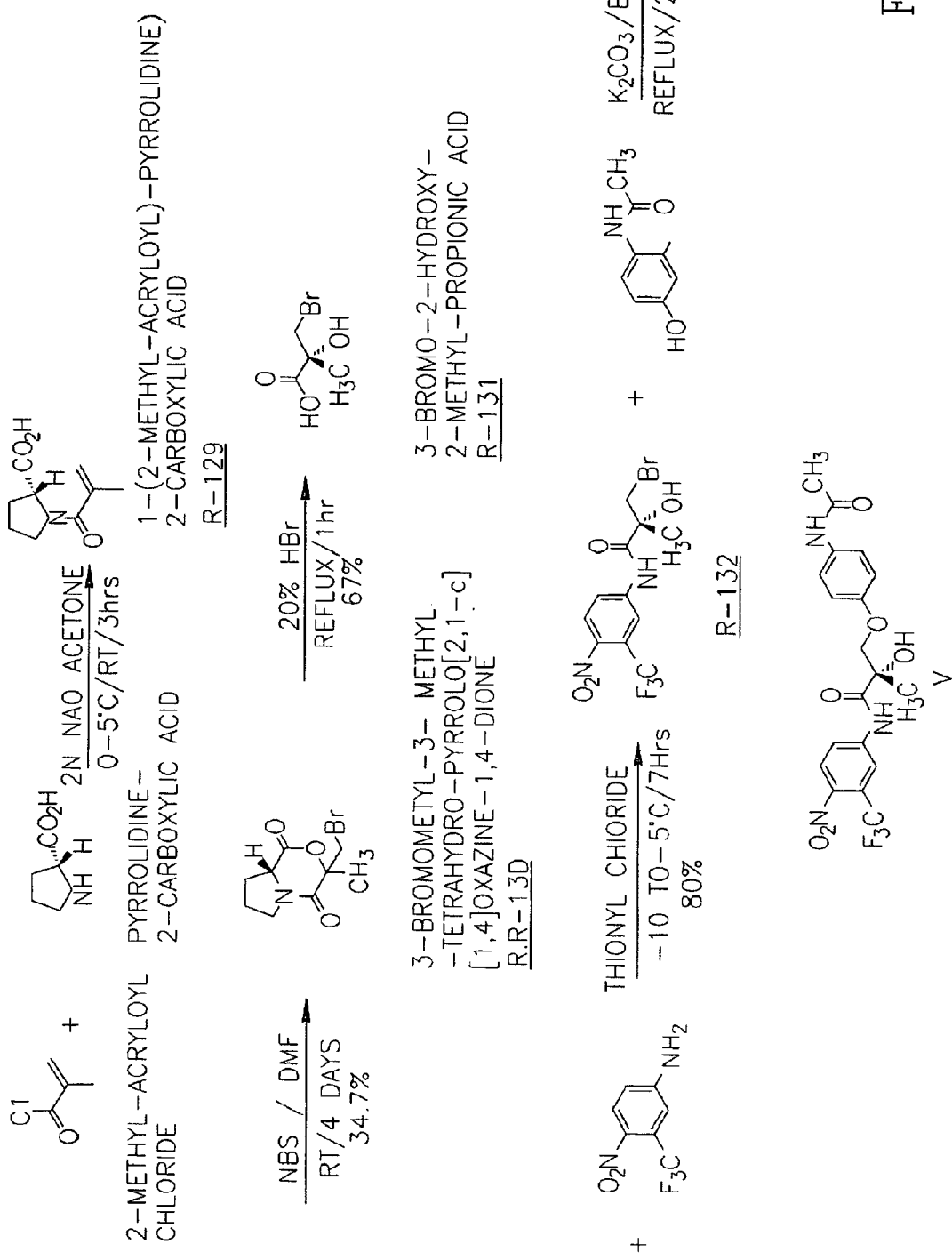
FIG. 27: Synthetic scheme of compound of formula V.

In another embodiment, the present invention provides a process for preparing a selective androgen modulator compound represented by the structure of formula V, as depicted in FIG. 27 and Examples 7 and 8:

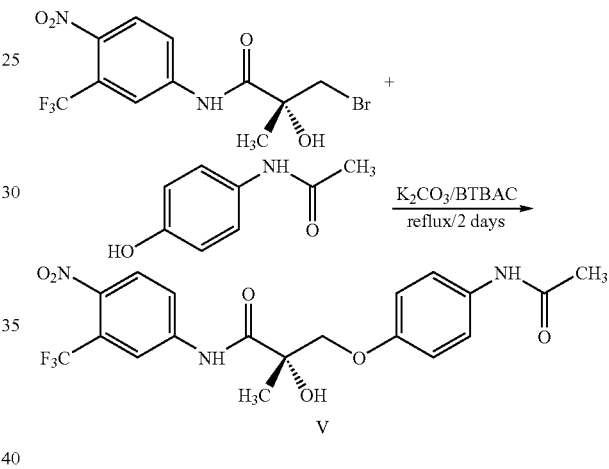

In another embodiment, the present invention provides a process for preparing a selective androgen modulator compound represented by the structure of formula VI:

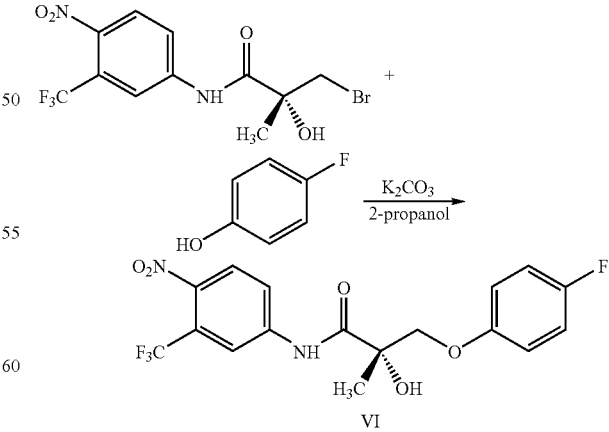

In another embodiment, the present invention provides a process for preparing a selective androgen modulator compound represented by the structure of formula X:

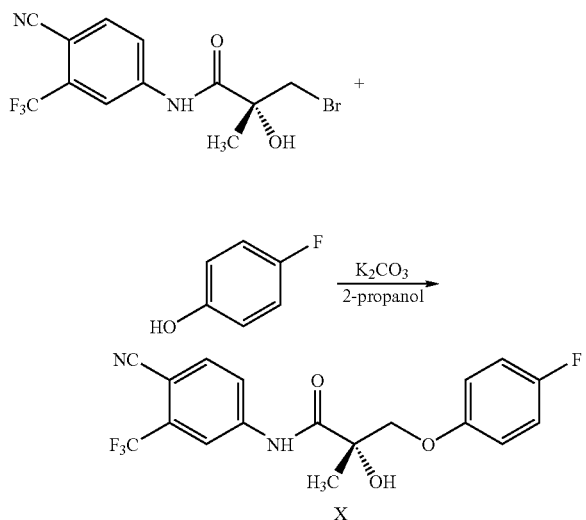

In another embodiment, the present invention provides a process for preparing a selective androgen modulator compound represented by the structure of formula XI:

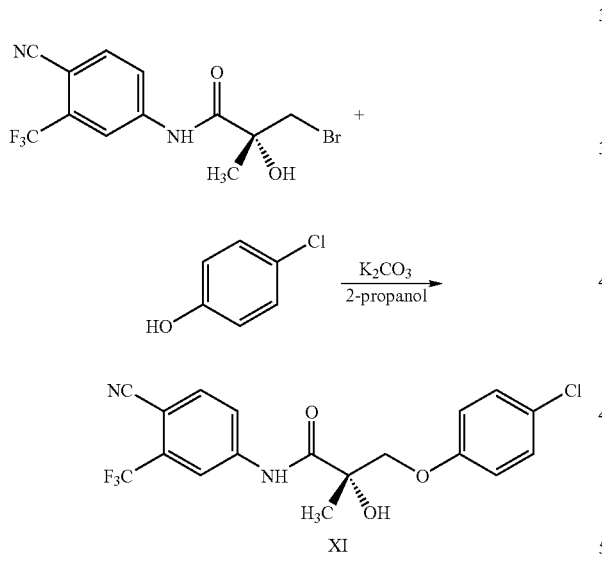

In another embodiment, the present invention provides a process for preparing an (S) enantiomer of SARM compound represented by the structure of formula S-III:

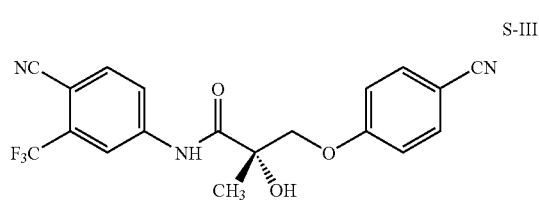

said process comprising the steps of:
a) coupling an amine of formula XXVIa:

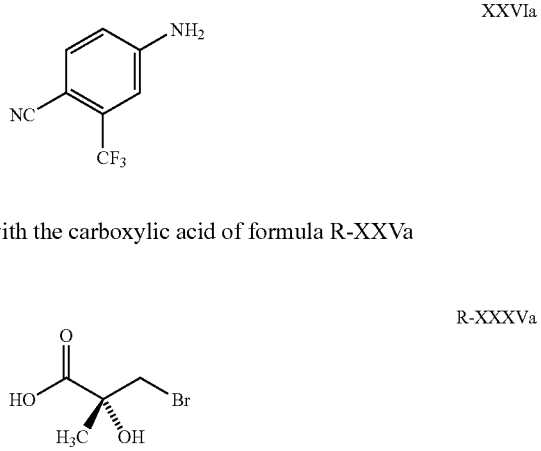

with the carboxylic acid of formula R-XXVa

R-XXXVa

HO—C(=O)—C(CH$_3$)(OH)—CH$_2$Br in the presence of a coupling reagent, to produce an amide of formula R-XXIIa

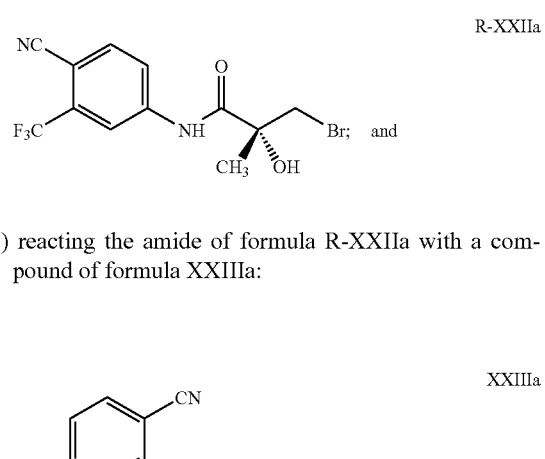

b) reacting the amide of formula R-XXIIa with a compound of formula XXIIIa:

XXIIIa

HO—C$_6$H$_4$—CN to produce a compound of S-III.

In one embodiment, whereby compound R-XXVa of step (a) is reacted with a coupling agent prior to step (b).

FIG. 28A and Example 19 provide one embodiment of a process for the preparation of a compound of formula S-III.

In another embodiment, the conditions of step (b) of the process outlined hereinabove may comprise potassium carbonate, sodium carbonate, or cesium carbonate, or another base appropriate for this reaction, using 2-propanol, THF or methylethylketone as a solvent, optionally with a transition catalyst, BTBAC (benzyltributylammonium chloride) or other suitable agent.

In another embodiment, the present invention provides a process for preparing an (R) enantiomer of SARM compound represented by the structure of formula R-III:

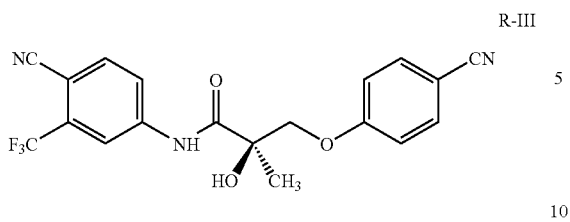

said process comprising the steps of:
a) coupling an amine of formula XXVIa:

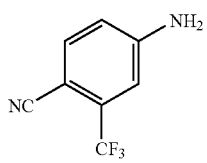

with the carboxylic acid of formula S-XXVa

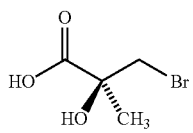

in the presence of a coupling reagent, to produce an amide of formula S-XXIIa

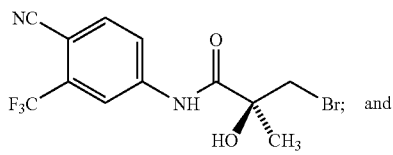

b) reacting the amide of formula S-XXIIa with a compound of formula XXIIIa

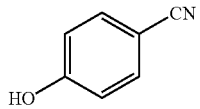

to produce a compound of R-III.

In one embodiment, whereby compound S-XXVa of step (a) is reacted with a coupling agent prior to step (b).

FIG. 28B depicts one embodiment of such a process for the preparation of compound of formula R-III.

In another embodiment, the conditions of step (b) of the process outlined hereinabove may comprise potassium carbonate, sodium carbonate, or cesium carbonate, or another base appropriate for this reaction, using 2-propanol, THF or methylethylketone as a solvent, optionally with a transition catalyst, BTBAC (benzyltributylammonium chloride) or other suitable agent.

In another embodiment, the present invention provides a process for preparing a SARM compound represented by the structure of formula I:

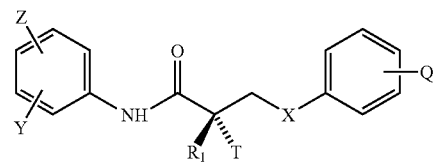

wherein
X is O, NH, Se, PR, or NR;
T is OH or OR;
Z is a hydrogen bond acceptor, hydrogen, alkyl, $NO_2$, CN, COOH, COR, NHCOR or CONHR;
Y is a lipid soluble group, hydrogen, alkyl, hydroxyalkyl, alkylaldehyde, $CF_3$, F, I, Br, Cl, CN, $C(R)_3$ or $Sn(R)_3$;
Q is alkyl, halogen, $CF_3$, CN, $C(R)_3$, $Sn(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR; or Q together with the benzene ring to which it is attached is a fused ring system represented by structure A, B or C:

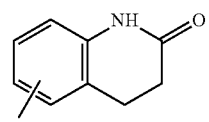

A

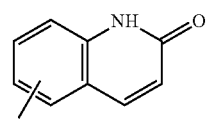

B

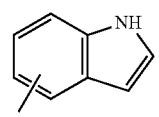

C

R is alkyl, haloalkyl, dihaloalkyl, trihaloalkyl, $CH_2F$, $CHF_2$, $CF_3$, $CF_2CF_3$, aryl, phenyl, halogen, alkenyl or OH; and
$R_1$ is $CH_3$, $CH_2F$, $CHF_2$, $CF_3$, $CH_2CH_3$, or $CF_2CF_3$;
said process comprising the steps of:
a) preparing a carboxylic acid of formula XXV by ring opening of a cyclic compound of formula XXIV

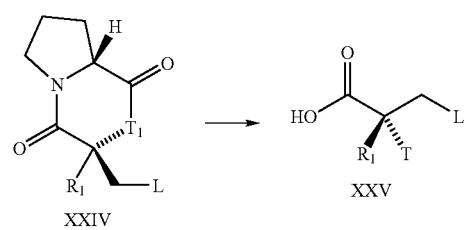

wherein L, $R_1$ and T are as defined above, and $T_1$ is O or NH;

b) reacting an amine of formula XXVI:

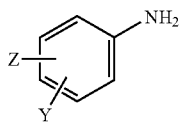
XXVI wherein Z and Y are as defined above, with the carboxylic acid of formula XXV in the presence of a coupling reagent, to produce an amide of formula XXII

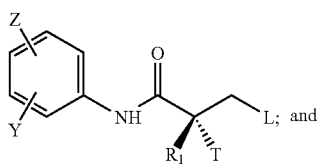
XXII e) reacting the amide of formula XXII, with a base to form an oxirane XXVIII;

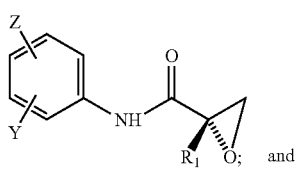
XXVIII d) reacting the oxirane of formula XXVIII with a compound of formula XXIII;

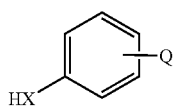
XXIII wherein Q and X are as defined above, to produce the compound of formula I.

In one embodiment, the amide of formula XXII has a structure as follows:

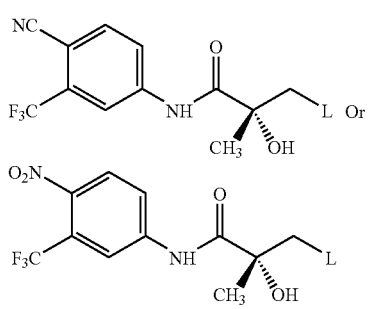

In one embodiment, the oxirane of formula XXVIII has a structure as follows:

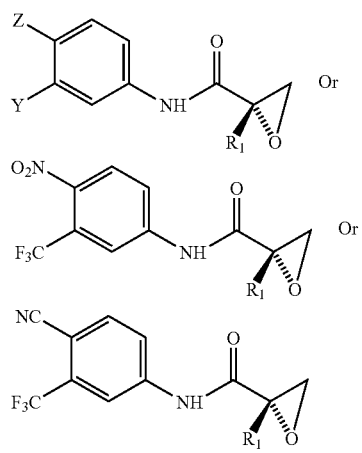

In one embodiment, the oxiranes described hereinabove can be used in accordance with any process as herein described, as appropriate.

In one embodiment, step (a) is carried out in the presence of HBr.

In one embodiment, whereby compound XXV of step (a) is reacted with a coupling agent prior to step (b).

In another embodiment, this invention provides a large scale process for the preparation of compound of formula I, wherein the process comprise the same steps as described herein above, wherein compound of formula XXIV is prepared according to the following scheme, in the presence of 4N NaOH:

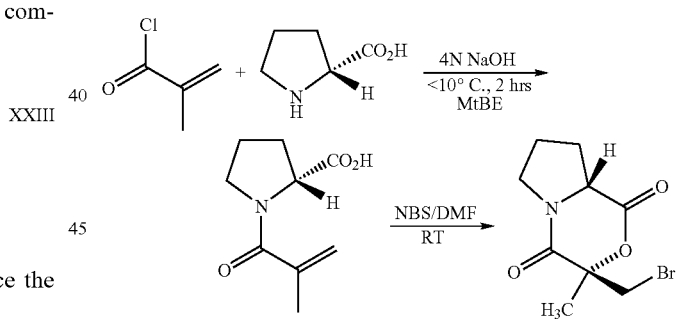

Figure 28L:
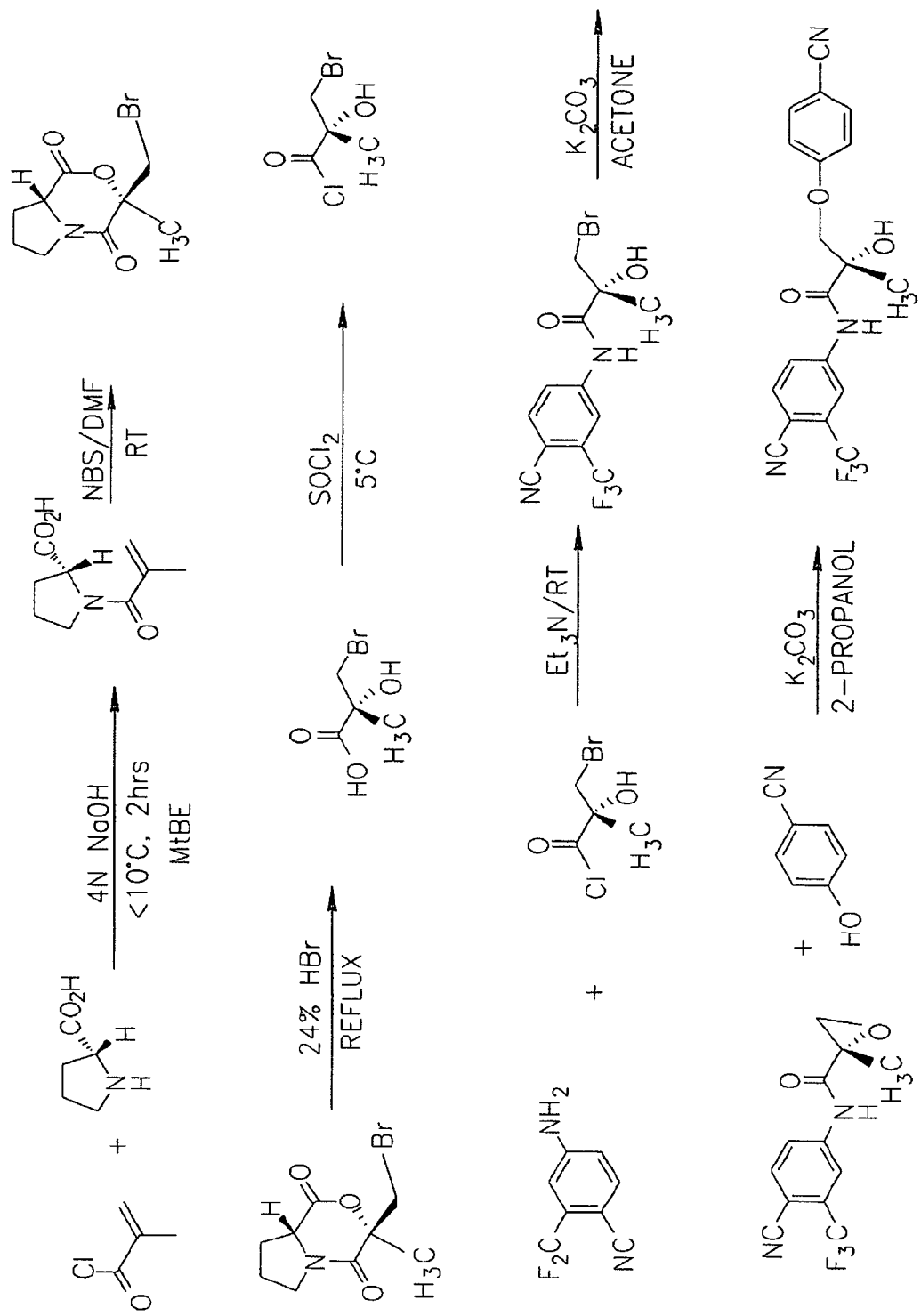
FIG. 28L is a synthetic scheme for preparation of a large scale or commercial scale of an (S) enantiomer of a compound of formula III (S-III), including an oxirane intermediate.

FIG. 28L provide one embodiment of a large scale process for the preparation of a large scale synthesis of compound III.

In another embodiment, the present invention provides a process for preparing an (S) enantiomer of a SARM compound represented by the structure of formula S-III:

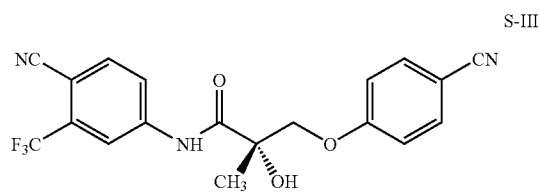
S-III said process comprising the steps of:
a) coupling an amine of formula XXVIa:

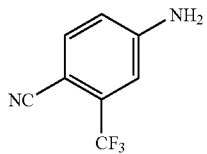  XXVIa with the carboxylic acid of formula R-XXVa

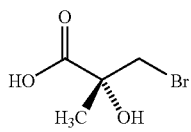  R-XXXVa in the presence of a coupling reagent, to produce an amide of formula R-XXIIa

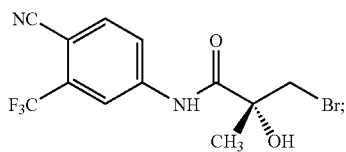  R-XXIIa b) reacting the amide of formula R-XXIIa, with a base to form an oxirane S-XXVIIIa

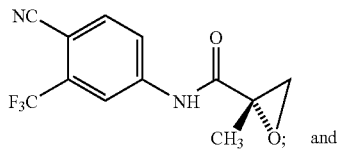  S-XXVIIIa c) reacting the oxirane of formula S-XXVIIIa with a compound of formula XXIIIa:

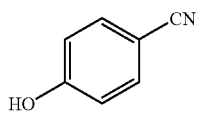  XXIIIa to produce a compound of S-III.

In one embodiment, whereby compound R-XXVa of step (a) is reacted with a coupling agent prior to step (b).

FIG. 28C depicts an embodiment of such a process for the preparation of compound of formula S-III.

In another embodiment, the present invention provides a process for preparing an (R) enantiomer of SARM compound represented by the structure of formula R-III:

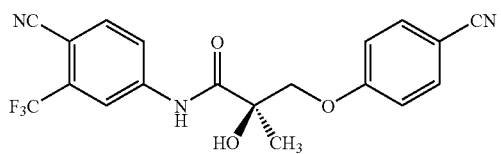  R-III said process comprising the steps of:
a) coupling an amine of formula XXVIa:

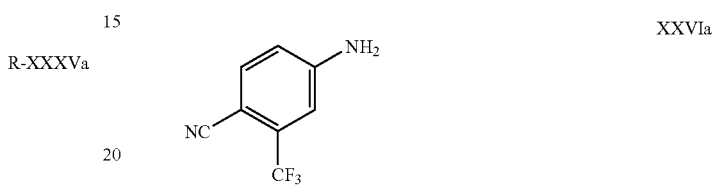  XXVIa with the carboxylic acid of formula S-XXVa

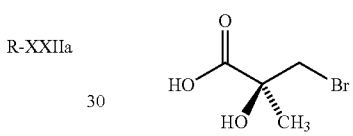  S-XXXVa in the presence of a coupling reagent, to produce an amide of formula S-XXIIa

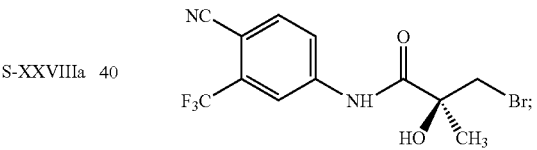  S-XXIIa b) reacting the amide of formula S-XXIIa, with a base to form an oxirane R-XXVIIIa

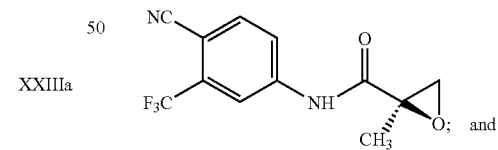  R-XXVIIIa c) reacting the oxirane of formula R-XXVIIIa with a compound of formula XXIIIa:

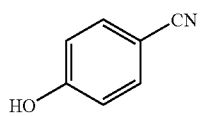  XXIIIa to produce a compound of R-III.

In one embodiment, whereby compound S-XXVa of step (a) is reacted with a coupling agent prior to step (b).

FIG. 28D depicts an embodiment of such a process for the preparation of compound of formula R-III.

In another embodiment, the present invention provides a process for preparing a SARM compound, represented by the structure of formula I:

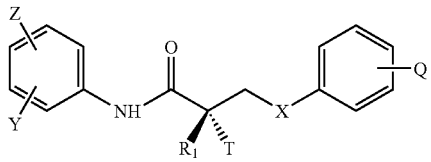

I wherein
X is O, NH, Se, PR, or NR;
T is OH or OR;
Z is a hydrogen bond acceptor, hydrogen, alkyl, $NO_2$, CN, COOH, COR, NHCOR or CONHR;
Y is a lipid soluble group, hydrogen, alkyl, hydroxylalkyl, alkylaldehyde, $CF_3$, F, I, Br, Cl, CN, $C(R)_3$ or $Sn(R)_3$;
Q is alkyl, halogen, $CF_3$, CN, $C(R)_3$, $Sn(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR; or Q together with the benzene ring to which it is attached is a fused ring system represented by structure A, B or C:

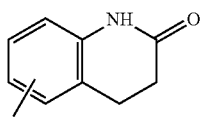

A

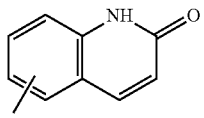

B

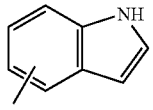

C

R is alkyl, haloalkyl, dihaloalkyl, trihaloalkyl, $CH_2F$, $CHF_2$, $CF_3$, $CF_2CF_3$, aryl, phenyl, halogen, alkenyl or OH; and
$R_1$ is $CH_3$, $CH_2F$, $CHF_2$, $CF_3$, $CH_2CH_3$, or $CF_2CF_3$;
said process comprising the steps of:
a) reacting a ring of formula XXIV

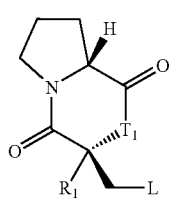

XXIV wherein L, $R_1$ are as defined above, and $T_1$ is O or NH with a compound of XXIII

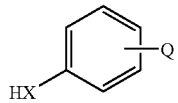

XXIII to produce a compound of formula XXIX;

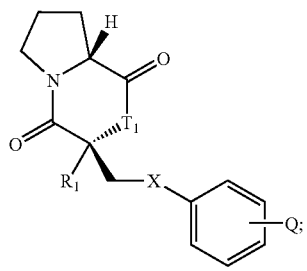

XXIX b) ring opening of compound of formula XXIX to produce a compound of formula XXX

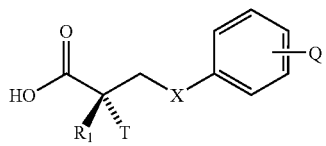

XXX wherein $R_1$, T, X and Q are as defined above; and
c) coupling the carboxylic acid of compound of formula XXX with the amine of formula XXVI

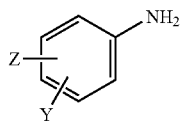

XXVI wherein Z and Y are as defined above, in the presence of a coupling reagent, to produce the compound of formula I.

In another embodiment, the present invention provides a process for preparing an (S) enantiomer of a SARM compound represented by the structure of formula S-III:

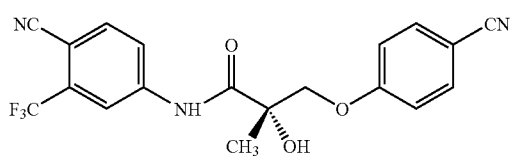

S-III said process comprising the steps of:
a) reacting a ring of formula R-XXIVa R-XXIVa with a compound of XXIIIa XXIIIa to produce a compound of formula S-XXIXa;

S-XXIXa d) ring opening of compound of formula S-XXIXa to produce a compound of formula S-XXXa S-XXXa coupling the carboxylic acid of compound of formula S-XXXa with the amine of formula XXVIa XXVIa to produce the compound of formula S-III.

FIG. 28E depicts an embodiment of such a process for the preparation of compound of formula S-Ill.

In another embodiment, the invention provides a SARM compound represented by the structure of formula S-I, and a process for the preparation of the SARM of compound S-1:

S-I wherein

X is O, $CH_2$, NH, Se, PR, or NR;

Z is a hydrogen bond acceptor, $NO_2$, CN, COR, CONHR;

Y is a lipid soluble group, I, $CF_3$, $CH_3$, H, Br, Cl, $Sn(R)_3$;

R is an alkyl, aryl, phenyl, alkenyl, haloalkyl, haloalkenyl, halogen or OH;

and Q is CN, halogen, acetamido-, trifluroacetamido-, alkylamines, ether, alkyl, N-sulfonyl, O-sulfonyl, alkylsulfonyl, carbonyl, ketone, Q is alkyl, halogen, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR $NHSO_2CH_3$, $NHSO_2R$, OR, COR, OCOR, $OSO_2R$, $SO_2R$ or SR;

or Q together with the benzene ring to which it is attached is a fused ring system represented by structure A, B or C:

$R_1$ is $CH_3$, $CF_3$, $CH_2CH_3$, or $CF_2CF_3$; and

T is OH, OR, —$NHCOCH_3$, or NHCOR;

wherein R is a $C_1$-$C_4$ alkyl, aryl, phenyl, alkenyl, hydroxyl, a $C_1$-$C_4$ haloalkyl, halogen, or haloalkenyl.

In one embodiment, the process comprises the steps of:
a) reacting a ring of formula:

with a compound of:

to produce a compound of formula:

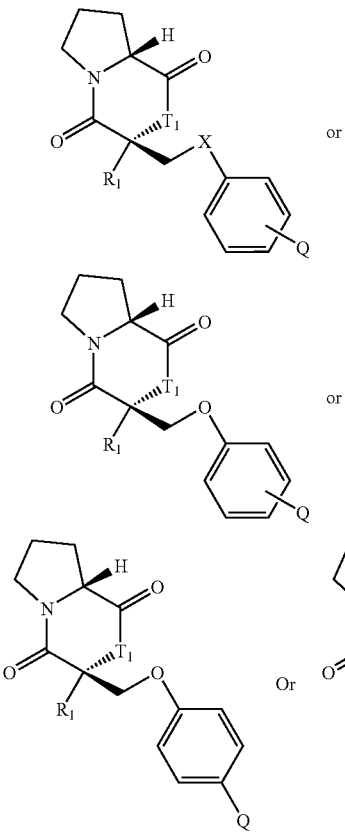

e) ring opening of compound of formula S-XXIX to produce a compound of formula S-XXX

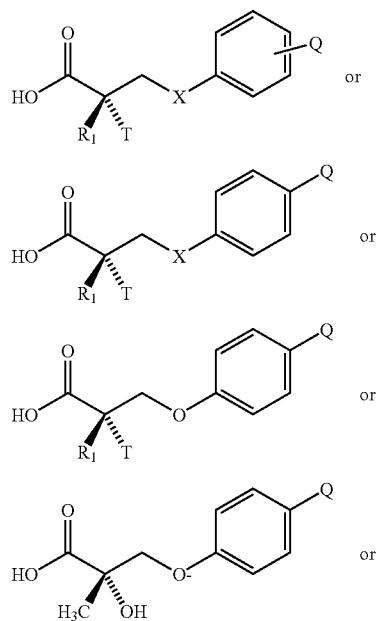

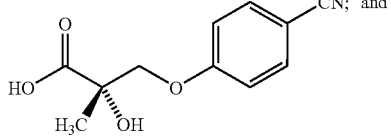

coupling the carboxylic acid of compound of formula S-XXX with the amine of formula XXVI

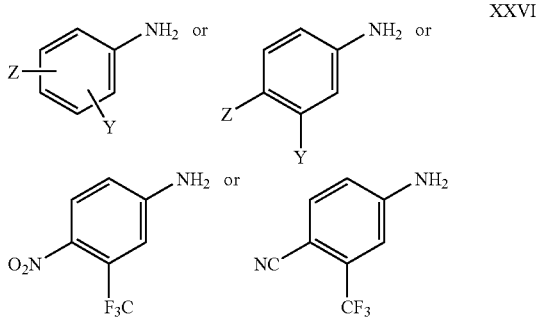

to produce the compound of formula S-III.

In another embodiment, the present invention provides a process for preparing an (R) enantiomer of a SARM compound represented by the structure of formula R-III:

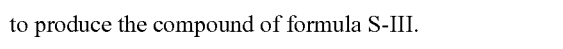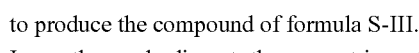

said process comprising the steps of:

a) reacting a ring of formula S-XXIVa

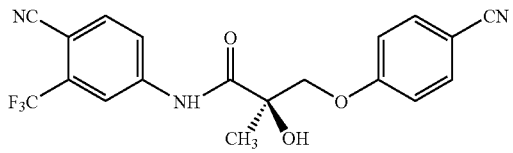

with a compound of XXIIIa

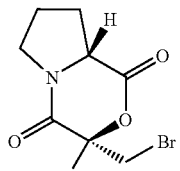

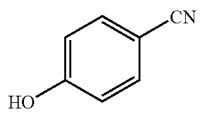

to produce a compound of formula R-XXIXa;

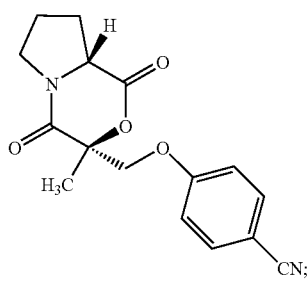

R-XXIXa f) ring opening of compound of formula R-XXIXa to produce a compound of formula R-XXXa

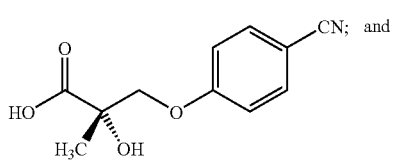

R-XXXa coupling the carboxylic acid of compound of formula R-XXXa with the amine of formula XXVIa

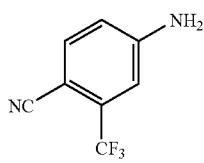

XXVIa to produce the compound of formula R-III.

FIG. 28F depicts an embodiment of such a process for the preparation of compound of formula R-III.

In one embodiment, the present invention provides a process for preparing a SARM compound having in vivo androgenic and anabolic activity of a nonsteroidal ligand for the androgen receptor, the compound represented by the structure of formula I:

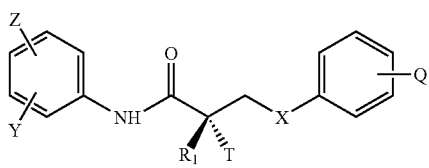

I wherein
X is O, NH, Se, PR, or NR;
T is OH or OR;
Z is a hydrogen bond acceptor, hydrogen, alkyl, $NO_2$, CN, COOH, COR, NHCOR or CONHR;
Y is a lipid soluble group, hydrogen, alkyl, hydroxylalkyl, alkylaldehyde, $CF_3$, F, I, Br, Cl, CN, $C(R)_3$ or $Sn(R)_3$;
Q is alkyl, halogen, $CF_3$, CN, $C(R)_3$, $Sn(R)_3$, $N(R)_2$, $NHCOCH_3$, $NHCOCF_3$, NHCOR, NHCONHR, NHCOOR, OCONHR, CONHR, $NHCSCH_3$, NHCSCF_3, NHCSR, $NHSO_2CH_3$, $NHSO_2R$, OR, COR, OCOR, $OSO_2R$, $SO_2R$, SR; or Q together with the benzene ring to which it is attached is a fused ring system represented by structure A, B or C:

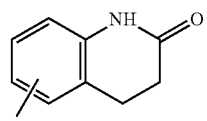

A

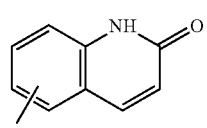

B

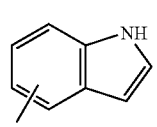

C

R is alkyl, haloalkyl, dihaloalkyl, trihaloalkyl, $CH_2F$, $CHF_2$, $CF_3$, $CF_2CF_3$, aryl, phenyl, halogen, alkenyl or OH; and
$R_1$ is $CH_3$, $CH_2F$, $CHF_2$, $CF_3$, $CH_2CH_3$, or $CF_2CF_3$;
said process comprising the steps of:
a) preparing a carboxylic acid of formula XXV by ring opening of a cyclic compound of formula XXIV

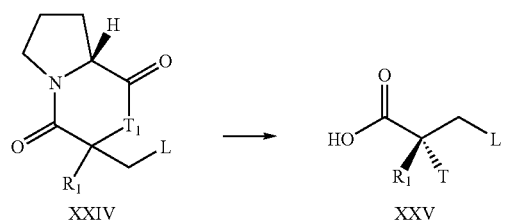

XXIV    XXV wherein L, $R_1$ and T are as defined above, and $T_1$ is O or NH; and
b) reacting the carboxylic acid of formula XXV with tribromoacetaldehyde to produce a compound of formula XXXI:

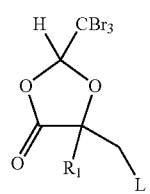

XXXI c) reacting the dioxalane derivative with a compound of formula XXIII

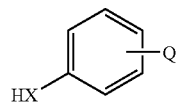

XXIII wherein X and Q are as defined above, in the presence of a base to produce a compound of formula XXXII

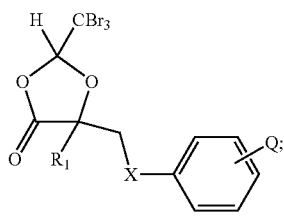

(XXXII)

d) ring opening of compound of formula XXXII, in the presence of an acid to produce a compound of formula XXX

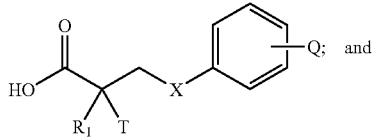

XXX wherein R₁, T, X and Q are as defined above; and
e) coupling the carboxylic acid of compound of formula XXX with the amine of formula XXVI

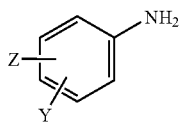

XXVI wherein Z and Y are as defined above, in the presence of a coupling reagent, to produce the compound of formula I.

In another embodiment, the present invention provides a process for preparing an (S) enantiomer of a SARM compound represented by the structure of formula S-III:

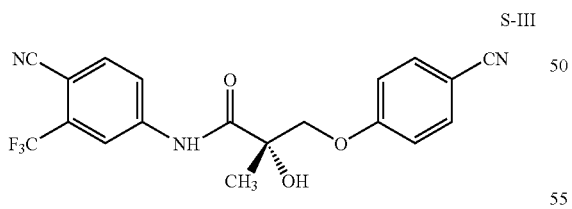

S-III said process comprising the steps of:
a) reacting the carboxylic acid of formula R-XXVa

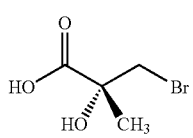

R-XXVa with tribromoacetaldehyde to produce a compound of formula R-XXXIa:

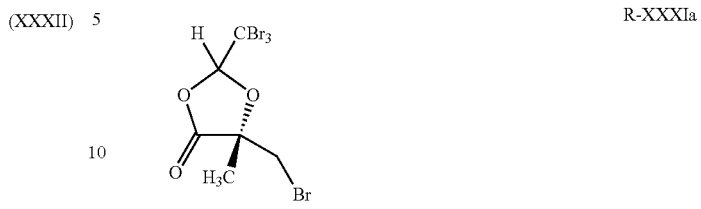

R-XXXIa b) reacting the dioxalane derivative R-XXXIIa with a compound of formula XXIIIa

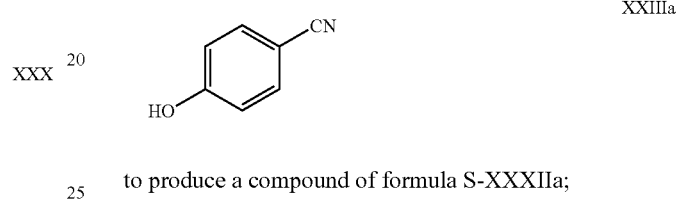

XXIIIa to produce a compound of formula S-XXXIIa;

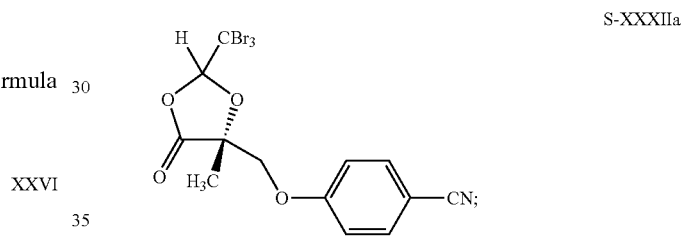

S-XXXIIa c) ring opening of compound of formula S-XXXIIa to produce a compound of formula S-XXXa

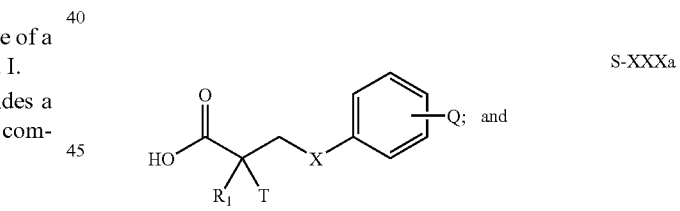

S-XXXa coupling the carboxylic acid of compound of formula S-XXXa with the amine of formula XXVIa:

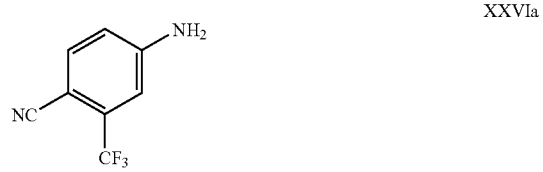

XXVIa to produce the compound of formula S-III.

FIG. 28G depicts an embodiment of such a process for the preparation of compound of formula S-III.

In another embodiment, the present invention provides a process for preparing an (R) enantiomer of a SARM compound represented by the structure of formula R-III:

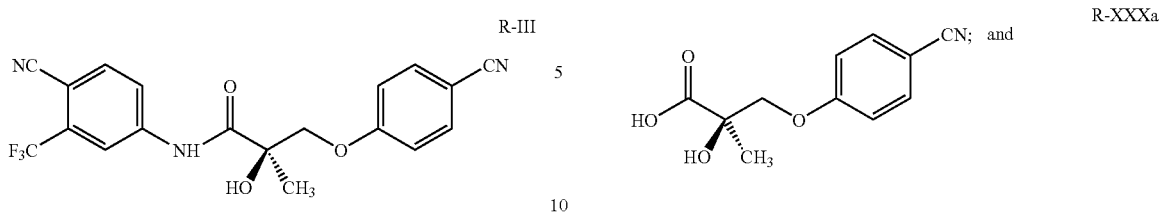
R-III said process comprising the steps of:
a) reacting the carboxylic acid of formula S-XXVa

S-XXXVa with tribromoacetaldehyde to produce a compound of formula S-XXXIa:

S-XXXIa d) reacting the dioxalane derivative S-XXXIa with a compound of formula XXIIIa

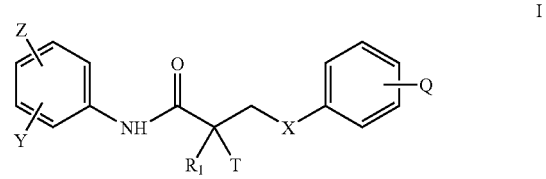
XXIIIa to produce a compound of formula R-XXXIIa;

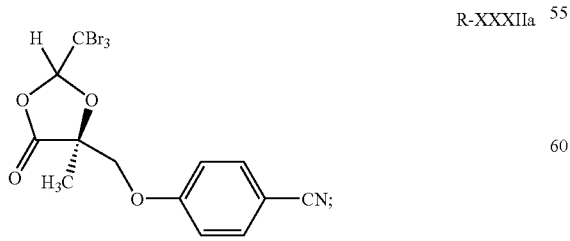
R-XXXIIa e) ring opening of compound of formula R-XXXIIa to produce a compound of formula R-XXXa

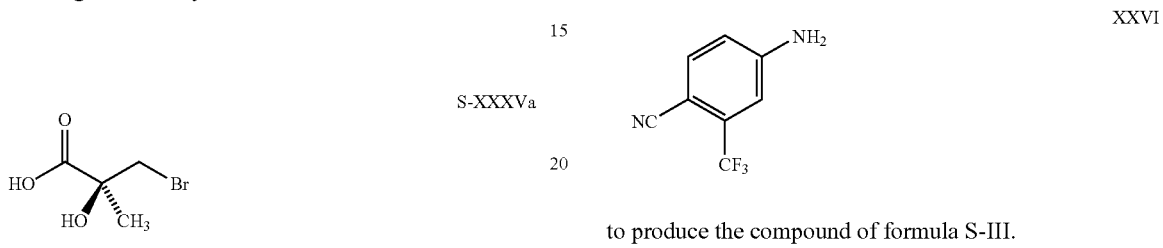
R-XXXa coupling the carboxylic acid of compound of formula R-XXXa with the amine of formula XXVI:

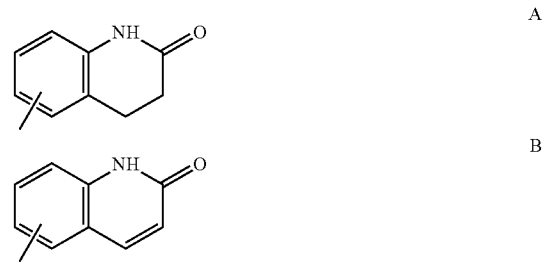
XXVI to produce the compound of formula S-III.

FIG. 28H depicts an embodiment of such a process for the preparation of compound of formula R-III.

In one embodiment, the present invention provides a process for preparing a racemic SARM compound having in vivo androgenic and anabolic activity of a nonsteroidal ligand for the androgen receptor, the compound represented by the structure of formula I:

I wherein
X is O, NH, Se, PR, or NR;
T is OH or OR;
Z is a hydrogen bond acceptor, hydrogen, alkyl, $NO_2$, CN, COOH, COR, NHCOR or CONHR;
Y is a lipid soluble group, hydrogen, alkyl, hydroxylalkyl, alkylaldehyde, $CF_3$, F, I, Br, Cl, CN, $C(R)_3$ or $Sn(R)_3$;
Q is alkyl, halogen, $CF_3$, CN, $C(R)_3$, $Sn(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR; or Q together with the benzene ring to which it is attached is a fused ring system represented by structure A, B or C:

A

B

-continued

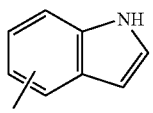

C

R is alkyl, haloalkyl, dihaloalkyl, trihaloalkyl, $CH_2F$, $CHF_2$, $CF_3$, $CF_2CF_3$, aryl, phenyl, halogen, alkenyl or OH; and
$R_1$ is $CH_3$, $CH_2F$, $CHF_2$, $CF_3$, $CH_2CH_3$, or $CF_2CF_3$;
said process comprising the steps of:
a) reacting a compound of formula XXX:

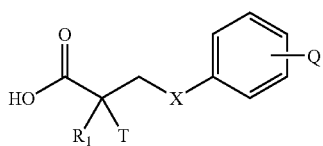

XXX wherein T is OH, $R_1$, Q and X are as defined above, with a compound of formula XXVIc

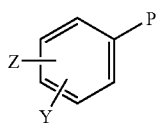

XXVIc wherein Z and Y are as defined above and P is selected from isocyanate (NCO) or isothiocyanate (NCS) to produce a compound of formula XXXIVa or XXXIVa, respectively:

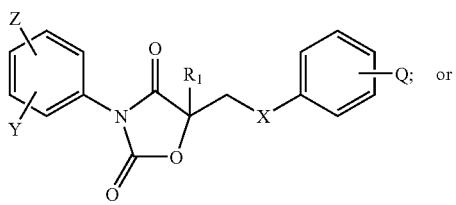

XXXIVa

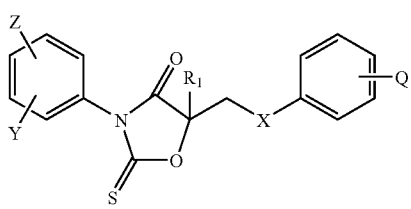

XXXIVb b) ring opening of the oxazolidinedione or 2-thioxooxazolid-4-one ring of formula XXXIVa or XXXIVb in the presence of a base to produce a compound of formula I.

In another embodiment, the carboxylic acid (XXX) of step (a) is in an activated form, such as an acylhalide, ester, or anhydride.

In another embodiment the SARM compound of formula I is partial or full enantiomeric pure depending on the chirality of the acid of formula XXX used in step (a).

In another embodiment, the present invention provides a process for preparing a racemic mixture of a SARM compound represented by the structure of formula III:

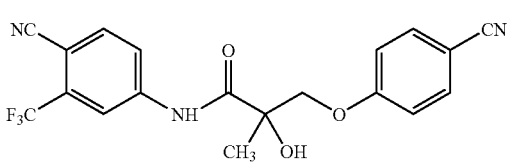

III said process comprising the steps of:
a) reacting a compound of formula XXX

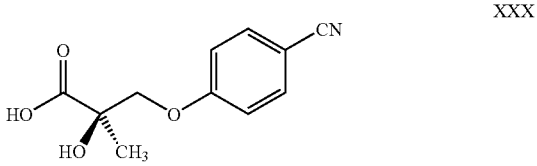

XXX with a compound of formula XXVIc

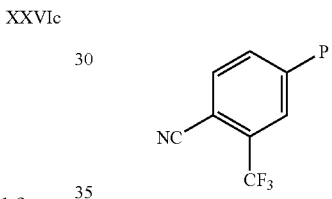

XXVIc wherein P is selected from isocyanate (NCO) or isothiocyanate (NCS) to produce a compound of formula XXXIVc or XXXIVd, respectively

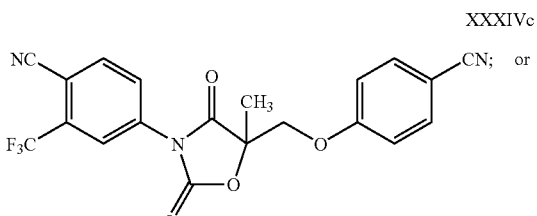

XXXIVc

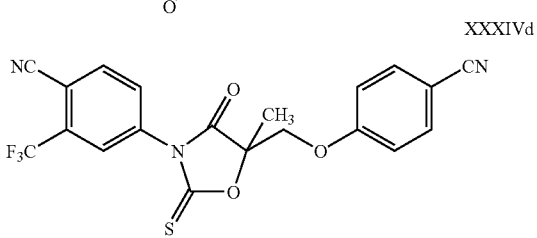

XXXIVd b) ring opening of the oxazolidinedione or 2-thioxooxazolid-4-one ring of formula XXXIVc or XXXIVd in a presence of a base to produce a compound of formula III.

FIG. 28I depicts an embodiment of such a process for the preparation of racemic compound of formula III.

In one embodiment, the present invention provides a process for preparing a racemic SARM compound having in vivo androgenic and anabolic activity of a nonsteroidal ligand for the androgen receptor, the compound represented by the structure of formula I:

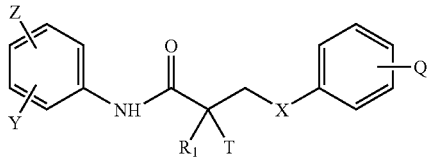

I wherein

X is O, NH, Se, PR, or NR;

T is OH or OR;

Z is a hydrogen bond acceptor, hydrogen, alkyl, $NO_2$, CN, COOH, COR, NHCOR or CONHR;

Y is a lipid soluble group, hydrogen, alkyl, hydroxylalkyl, alkylaldehyde, $CF_3$, F, I, Br, Cl, CN, $C(R)_3$ or $Sn(R)_3$;

Q is alkyl, halogen, $CF_3$, CN, $C(R)_3$, $Sn(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR; or Q together with the benzene ring to which it is attached is a fused ring system represented by structure A, B or C:

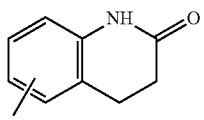

A

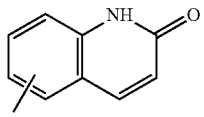

B

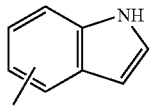

C

R is alkyl, haloalkyl, dihaloalkyl, trihaloalkyl, $CH_2F$, $CHF_2$, $CF_3$, $CF_2CF_3$, aryl, phenyl, halogen, alkenyl or OH; and $R_1$ is $CH_3$, $CH_2F$, $CHF_2$, $CF_3$, $CH_2CH_3$, or $CF_2CF_3$;

said process comprising the steps of:

a) chlorinating substituted acrylic acid

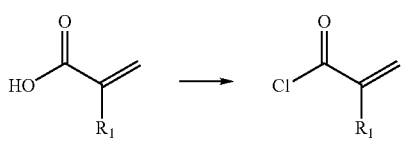

XXXV wherein $R_1$ is as defined above, and b) coupling an amine of formula XXVI:

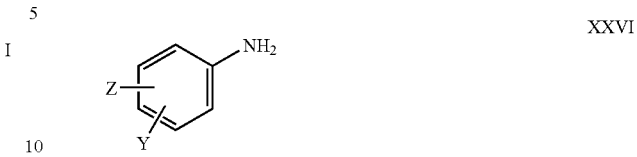

XXVI wherein Z and Y, are as defined above, with the chlorinated formula XXXV to produce the amide of formula XXXVI.

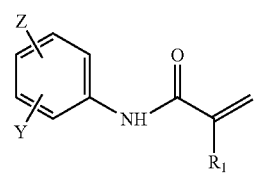

XXXVI c) oxidizing an amide of formula XXXVI, to produce the oxirane of formula XXVIII

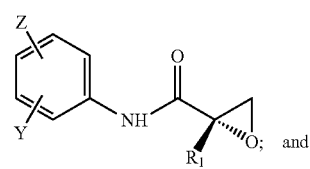

XXVIII d) reacting the oxirane of formula XXVIII with a compound of formula XXIII;

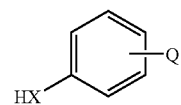

XXIII wherein Q and X are as defined above, to produce the compound of formula I.

In another embodiment, the present invention provides a process for preparing a racemic mixture of a SARM compound represented by the structure of formula III:

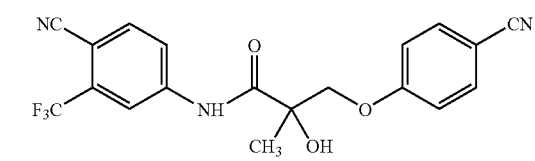

III said process comprising the steps of:

a) chlorinating methacrylic acid

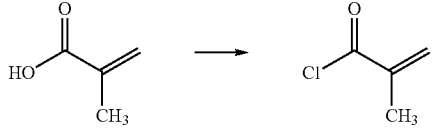

b) coupling an 3-cyano 4-trifluoromethyl aniline of formula XXVIa with methacryloyl chloride:

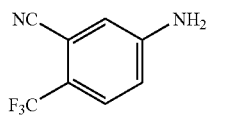

XXVIa to produce the amide of formula XXXVIa.

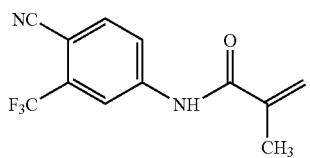

XXXVIa c) oxidizing an amide of formula XXXVIa, to produce the oxirane of formula XXVIIIa

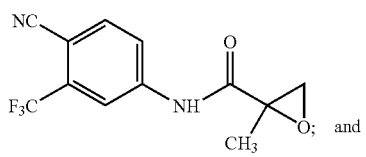

XXVIIIa d) reacting the oxirane of formula XXVIIIa with a compound of formula XXIIIa

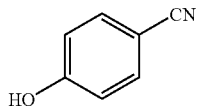

XXIIIa to produce the compound of formula I.

FIG. 28J depicts an embodiment of a process for the preparation of racemic compound of formula III.

In another embodiment, the present invention provides a process for preparing a SARM compound, represented by the structure of formula I:

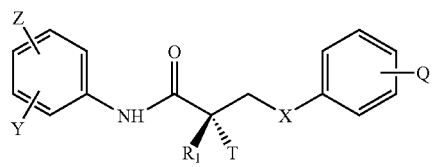

I wherein

X is a bond or $CH_2$;

T is OH, OR, $NHCOCH_3$, or NHCOR;

Z is a hydrogen bond acceptor, hydrogen, alkyl, $NO_2$, CN, COOH, COR, NHCOR or CONHR;

Y is a lipid soluble group, hydrogen, alkyl, hydroxylalkyl, alkylaldehyde, $CF_3$, F, I, Br, Cl, CN, $C(R)_3$ or $Sn(R)_3$;

Q is alkyl, halogen, $CF_3$, CN, $C(R)_3$, $Sn(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR; or Q together with the benzene ring to which it is attached is a fused ring system represented by structure A, B or C:

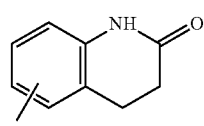

A

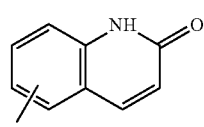

B

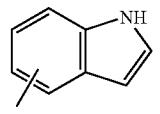

C

R is alkyl, haloalkyl, dihaloalkyl, trihaloalkyl, $CH_2F$, $CHF_2$, $CF_3$, $CF_2CF_3$, aryl, phenyl, halogen, alkenyl or OH; and $R_1$ is $CH_3$, $CH_2F$, $CHF_2$, $CF_3$, $CH_2CH_3$, or $CF_2CF_3$;

said process comprising the steps of:

a) reacting a ring of formula XXXVII

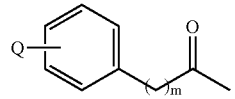

XXXVII wherein Q is as defined above, and m is 1 or 2 with $Me_3SiCN$ catalyst and a Lewis acid to produce a compound of formula

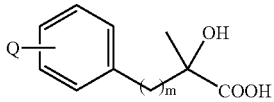

XXXVIII b) coupling the carboxylic acid of formula XXXVIII with the aniline of formula XXVI

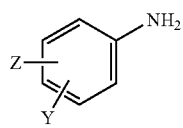

XXVI wherein Z and Y are as defined above, in the presence of a coupling reagent, to produce the compound of formula I.

In another embodiment the Lewis Acid of step (a) is $ZnI_2$.

In another embodiment, the present invention provides a process for preparing a selective androgen modulator compound represented by the structure of formula XIX:

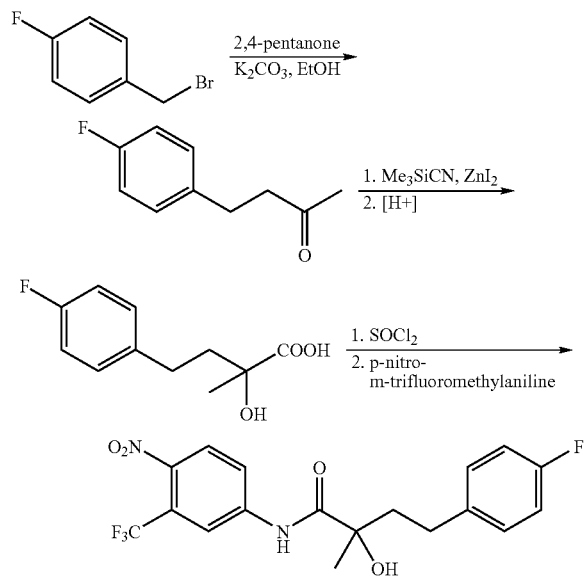

In another embodiment, the present invention provides a process for preparing a SARM compound represented by the structure of formula XVIII:

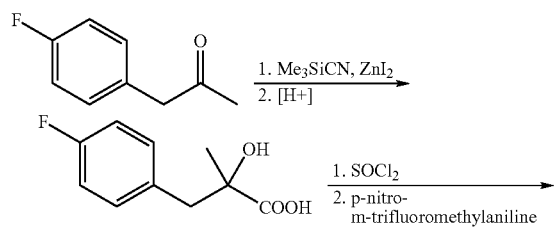

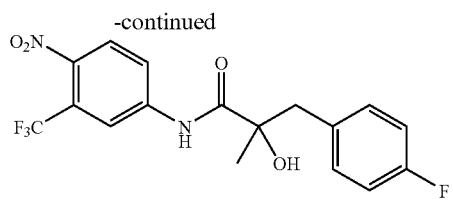

-continued

In another embodiment, the oxidizing an amide of formula XXX of step (c) comprises ozone. In another embodiment, the oxidizing agent is a peroxyacid, for example, peracetic acid, ($CH_3COOOH$). In another embodiment, the oxidizing agent meta-chloroperbenzoic acid (m-CPBA). In another embodiment, the oxidizing agent is Magnesium MonoPeroxyPthalic Acid (MMPP). In another embodiment, the oxidizing agent is hydrogen peroxide together with catalytic amounts (1.0-0.1 mol %) of manganese ($2^+$) salts.

In one embodiment, this invention provides a process for preparing pure enantiomers of SARMs compounds of this invention, comprising the steps of a) preparing a racemic SARM compound of this invention; and b) separating pure SARM compound of this invention from its racemic mixture.

In one embodiment, separation of the optically-active (R) isomer or (S) enantiomer, from the racemic SARM compounds of this invention comprises crystallization techniques. In another embodiment, the crystallization techniques include differential crystallization of enantiomers. In another embodiment, the crystallization techniques include differential crystallization of diasteriomeric salts (tartaric salts or quinine salts). In another embodiment, the crystallization techniques include differential crystallization of chiral auxiliary derivatives (menthol esters, etc). In another embodiment, separation of the optically-active (R) isomer or (S) enantiomer, from the racemic SARM compounds of this invention comprises reacting the racemate mixture with another chiral group, forming of a diasteriomeric mixture followed by separation of the diasteriomers and removing the additional chiral group to obtain pure enantiomers. In another embodiment, separation of the optically-active (R) isomer or (S) enantiomer, from the racemic SARM compounds of this invention comprises chiral synthesis. In another embodiment, separation of the optically-active (R) isomer or (S) enantiomer, from the racemic SARM compounds of this invention comprises biological resolution. In another embodiment, separation of the optically-active (R) isomer or (S) enantiomer, from the racemic SARM compounds of this invention comprises enzymatic resolution. In another embodiment, separation of the optically-active (R) isomer or (S) enantiomer, from the racemic SARM compounds of this invention comprises chromatographic separation using a chiral stationary phase. In another embodiment, separation of the optically-active (R) isomer or (S) enantiomer, from the racemic SARM compounds of this invention comprises affinity chromatography. In another embodiment, separation of the optically-active (R) isomer or (S) enantiomer, from the racemic SARM compounds of this invention comprises capillary electrophoresis. In another embodiment, separation of the optically-active (R) isomer or (S) enantiomer, from the racemic SARM compounds of this invention comprises forming an ester group of the hydroxyl group of the chiral carbon with an optically-active acid, for example (−)-camphanic acid, separating the diastereomers esters, thus obtained, by fractional crystallization or preferably, by flash-chromatography, and then hydrolyzing each separate ester to the alcohol.

In another embodiment, the purity, and selectivity of an enantiomer obtained by the process of this invention, or by chiral separation of a racemic mixture of this invention can be determined by HPLC analysis.

Figure 30:
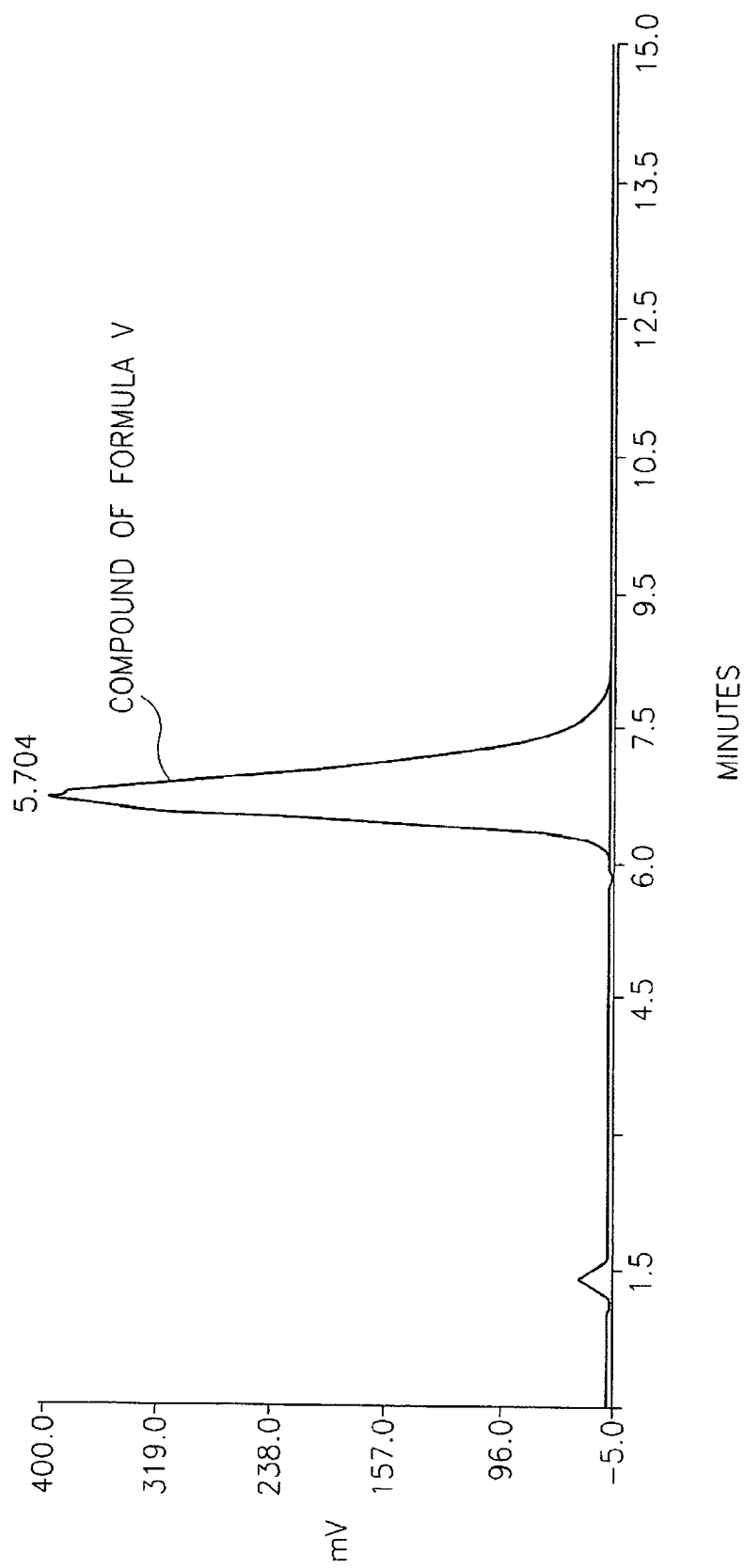
FIG. 30: HPLC chromatogram of enantiomer R of compound of formula V.

FIG. 30 depicts in one embodiment, an HPLC chromatogram of the R enantiomer of compound of formula V.

In another embodiment, the process further comprises the step of converting the SARM compound to its analog, isomer, metabolite, derivative, pharmaceutically acceptable salt, pharmaceutical product, N-oxide, hydrate or any combination thereof.

According to this aspect of the invention, and in one embodiment, the reagent used for reacting the amide derivative, for example compound of formula XXII and the phenyl derivative such as for example XXIII, is carried out in the presence of a base. Any suitable base that will deprotonate the hydrogen of the —XH moiety (for example, a phenol moiety when X is O) and allow the coupling may be used. Nonlimiting examples of bases are carbonates such as alkali carbonates, for example sodium carbonate ($Na_2CO_3$), potassium carbonate ($K_2CO_3$) and cesium carbonate ($Cs_2CO_3$); bicarbonates such as alkali metal bicarbonates, for example sodium bicarbonate ($NaHCO_3$), potassium bicarbonate ($KHCO_3$), alkali metal hydrides such as sodium hydride (NaH), potassium hydride (KH) and lithium hydride (LiH), and the like.

The leaving group L, according to this aspect, and in one embodiment, may comprise any removable group customarily considered for chemical reactions, as will be known to the person skilled in the art. Suitable leaving groups are halogens, for example F, Cl, Br and I; alkyl sulfonate esters (—$OSO_2R$) wherein R is an alkyl group, for example methanesulfonate (mesylate), trifluoromethanesulfonate, ethanesulfonate, 2,2, 2-trifluoroethanesulfonate, perfluoro butanesulfonate; aryl sulfonate esters (—$OSO_2Ar$) wherein Ar is an aryl group, for example p-toluoylsulfonate (tosylate), benzenesulphonate which may be unsubstituted or substituted by methyl, chlorine, bromine, nitro and the like; $NO_3$, $NO_2$, or sulfate, sulfite, phosphate, phosphite, carboxylate, imino ester, $N_2$ or carbamate.

According to this aspect of the invention and in one embodiment, the reaction is carried out in a suitable inert solvent or diluent such as, for example, tetrahydrofuran, diethyl ether, aromatic amines such as pyridine; aliphatic and aromatic hydrocarbons such as benzene, toluene, and xylene; dimethylsulfoxide (DMSO), dimethylformamide (DMF), and dimethylacetamide (DMAC). In one embodiment, the reaction may be carried out at an appropriate temperature, as will be known to one skilled in the art, for example, in the range, of −20 to 120 C., or for example at or near ambient temperature.

According to this aspect of the invention and in one embodiment, the coupling reagent is a reagent capable of turning the carboxylic acid into a reactive derivative thereof, thus enabling coupling with amine to form an amide bond. A suitable reactive derivative of a carboxylic acid is, for example, an acyl halide, for example an acyl chloride formed by the reaction of the acid and an inorganic acid chloride, for example thionyl chloride; a mixed anhydride, for example an anhydride formed by the reaction of the acid and a chloroformate such as isobutyl chloroformate; an active ester, for example an ester formed by the reaction of the acid and a phenol such as pentafluorophenol, an ester such as pentafluorophenyl trifluoroacetate or an alcohol such as methanol, ethanol, isopropanol, butanol or N-hydroxybenzotriazole; an acyl azide, for example an azide formed by the reaction of the acid and azide such as diphenylphosphoryl azide; an acyl cyanide, for example a cyanide formed by the reaction of an acid and a cyanide such as diethylphosphoryl cyanide; or the product of the reaction of the acid and a carbodiimide such as dicyclohexylcarbodiimide.

It is to be understood that the process may comprise any embodiment described herein, as will be appropriate to produce a SARM of a corresponding formula, as will be appreciated by one skilled in the art.

In one embodiment, the process for preparing a SARM of this invention may comprise modifying known methods in the art (see for example, Tucker et al (1988); U.S. Pat. No. 4,636,505; Kirkovsky et al (2000); U.S. Pat. No. 6,160,011; and U.S. Pat. No. 6,071,957), which in one embodiment, may involve ring opening in the presence of less acidic conditions, which in another embodiment, diminish the likelihood of obtaining SARM compound mixtures, and provide higher yield and purity of a SARM of interest. In one embodiment, the ring opening of a process as described herein, to produce a carboxylic acid of formula XXV, is carried out in the presence of HBr, which, in one embodiment, is at a concentration of up to 30%, or in another embodiment, of up to 40%, or in another embodiment, is of up to 25%, or in another embodiment, of up to 23%, or in another embodiment, of up to between 20-25%. In one embodiment, the SARMs of this invention may be produced via large-scale synthesis, providing highly pure products in high yields.

It is understood to a person skilled in the art that, in reference to the processes to produce the SARMs of this invention, when $T_1$ is O or NH, T in compound XXV is OH or $NH_2$. Thus, when T in compound I is OR, the reaction will involve a further step of converting the OH to OR by a reaction with, for example, an alkyl halide R—X. When T in compound of the formula I is NHCOR, $NHCOCH_3$, the reaction will involve a further step of converting the $NH_2$ to NHCOR or $NHCOCH_3$, by a reaction with, for example, the corresponding acyl chloride ClCOR or $ClCOCH_3$.

In one embodiment, the reaction may be carried out in a suitable inert solvent or diluent as described hereinabove, suitably in the presence of a base such as triethylamine, and at a temperature in the range, as described above.

Selective Androgen Receptor Modulators (SARMS)

Selective androgen receptor modulators (SARMs) are, in some embodiments, androgen receptor targeting agents (ARTA), which are nonsteroidal ligands for the androgen receptor and may demonstrate tissue-selective androgenic and/or anabolic activity. These novel agents are useful in males for the treatment of a variety of hormone-related conditions such as sexual dysfunction, decreased sexual libido, erectile dysfunction, hypogonadism, sarcopenia, osteopenia, osteoporosis, alterations in cognition and mood, depression, anemia, hair loss, obesity, benign prostate hyperplasia and/or prostate cancer. Further, SARMs are useful for oral testosterone replacement therapy, and treating prostate cancer. In other embodiments, the SARMs are useful for the treatment of a variety of hormone-related conditions in females including, sexual dysfunction, decreased sexual libido, hypogonadism, sarcopenia, osteopenia, osteoporosis, alterations in cognition and mood, depression, anemia, hair loss, obesity, endometriosis, infertility, breast cancer, uterine cancer and ovarian cancer.

In some embodiments, the SARM compounds of this invention are useful in preventing and treating muscle wasting disorders and bone related disorders.

In some embodiments, the SARM compounds stimulate cell signaling events via binding the androgen or other cell signaling receptors. In some embodiments, receptors for extracellular signaling molecules are referred to as "cell signaling receptors", which are transmembrane proteins on a cell surface. The receptors may bind an extracellular signaling molecule (i.e., a ligand), and become activated so as to generate a cascade of intracellular signals that alter the behavior of the cell. In contrast, in some cases, the receptors are inside the cell and the signaling ligand has to enter the cell to activate them; these signaling molecules therefore must be sufficiently small and hydrophobic to diffuse across the plasma membrane of the cell.

Steroid hormones are one example of small hydrophobic molecules that diffuse directly across the plasma membrane of target cells and bind to intracellular cell signaling receptors. These receptors are structurally related and constitute the intracellular receptor superfamily (or steroid-hormone receptor superfamily). Steroid hormone receptors include progesterone receptors, estrogen receptors, androgen receptors, glueocorticoid receptors, and mineralocorticoid receptors. The present invention is particularly directed to androgen receptors.

A receptor agonist is a substance which binds receptors and activates them. A receptor partial agonist is a substance which binds receptor and partially activates them. A receptor antagonist is a substance which binds receptors and inactivates them. The SARM compounds of the present invention may, in some embodiments, have a tissue-selective effect, wherein, for example, a single agent is an agonist, partial agonist and/or antagonist, depending on the tissue in which the receptor is expressed. For example, the SARM compound may stimulate muscle tissue and concurrently inhibit prostate tissue. In one embodiment, the SARMs which are useful in treating and preventing muscle wasting disorders are AR agonists, and are, therefore, useful in binding to and activating the AR. In another embodiment, the SARMs are AR antagonists, and are, therefore, useful in binding to and inactivating the AR. Assays to determine whether the compounds of the present invention are AR agonists or antagonists are well known to a person skilled in the art. For example, AR agonistic activity can be determined by monitoring the ability of the SARM compounds to maintain and/or stimulate the growth of AR containing tissue such as prostate and seminal vesicles, as measured by weight. AR antagonistic activity can be determined by monitoring the ability of the SARM compounds inhibit the growth of AR containing tissue.

In another embodiment, the SARM compounds of the present invention can be classified as partial AR agonist/antagonists. The SARMs are AR agonists in some tissues, to cause increased transcription of AR-responsive genes (e.g. muscle anabolic effect). In other tissues, these compounds serve as competitive inhibitors of testosterone/DHT on the AR to prevent agonistic effects of the native androgens. The term SARM or SARM refers, in one embodiment, to a compound which modulates androgen receptor activity. In one embodiment, the SARM is an agonist, or in another embodiment, an antagonist.

Figure 8:
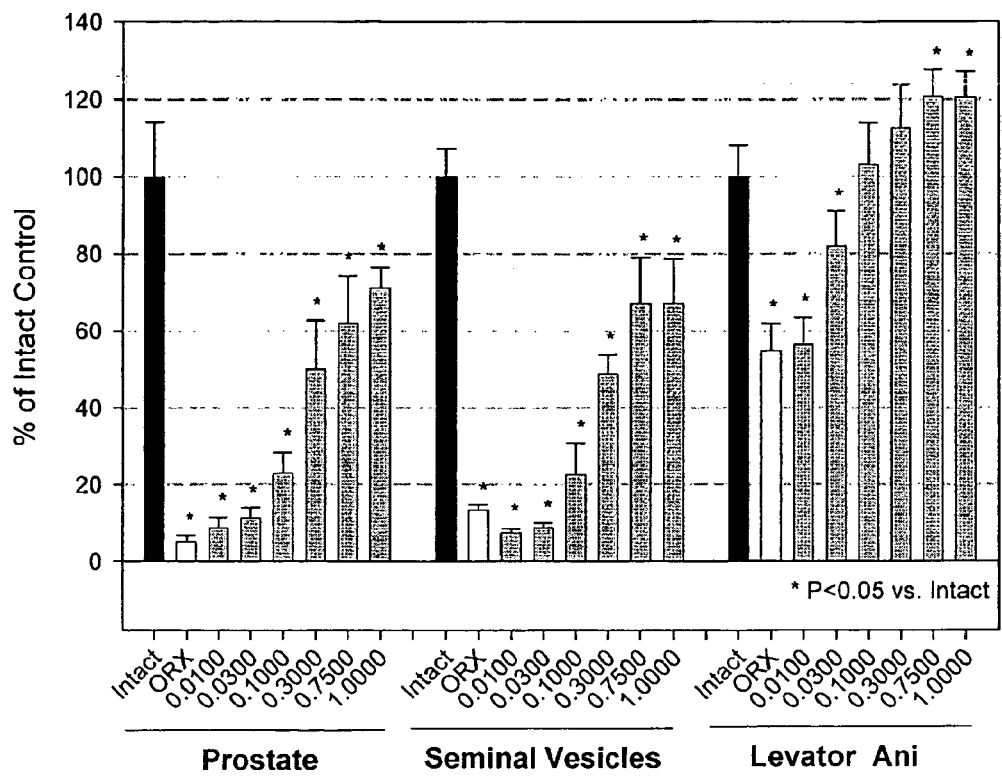
FIG. 8: Organ weights from castrated, compound of formula III-treated rats presented as a percentage of intact control. * P-value <0.05 versus intact controls.
Figure 9:
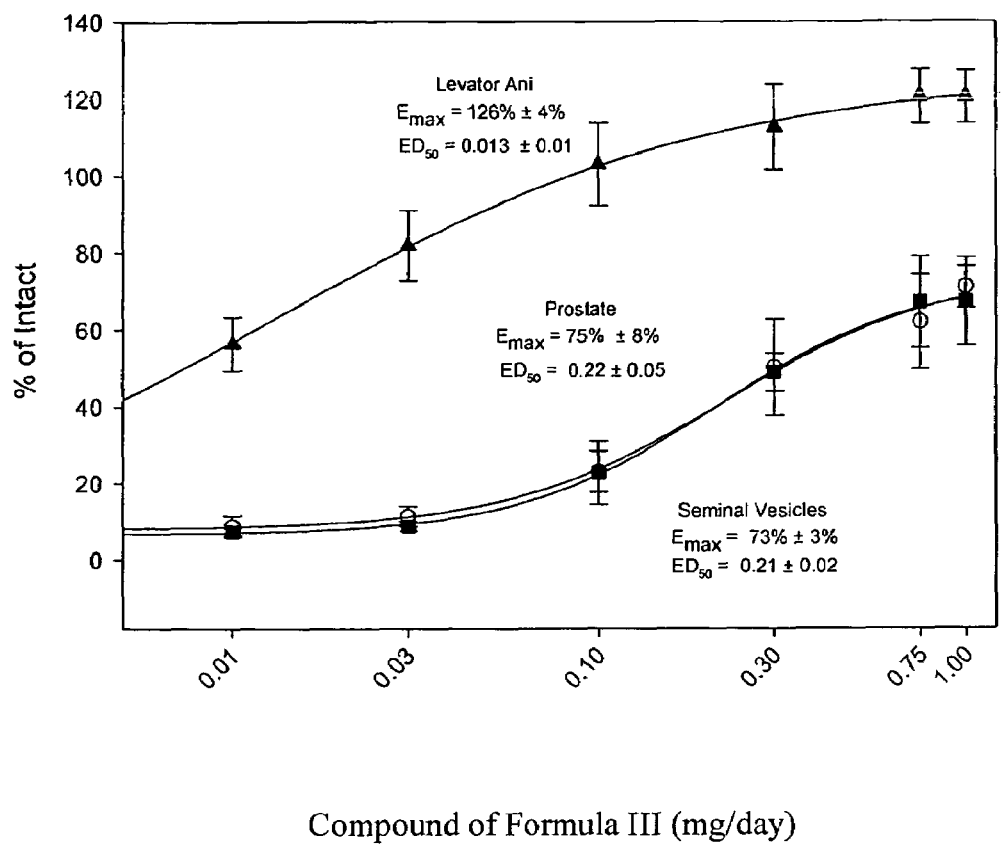
FIG. 9: Organ weight regrowth dose-response curves for compound of formula III in castrated rats. $E_{max}$ and $ED_{50}$ values for the levator ani (closed triangles), prostate (open circles), and seminal vesicles (closed squares) were obtained by nonlinear regression analysis using the sigmoid $E_{max}$ model in WinNonlin®.

In one embodiment, the SARM will have antagonist activity in a gonad of a subject, and agonist activity peripherally, such as, for example, in muscle. Such activity was demonstrated herein, in terms of effects on prostate tissue versus that of levator ani muscle tissue, as exemplified in FIG. 5, 6, or 8. In one embodiment, the SARM compounds of the present invention bind reversibly or, in another embodiment, irreversibly to the androgen receptor. In one embodiment, the SARM compounds bind reversibly to the androgen receptor. In another embodiment, the SARM compounds bind irreversibly to the androgen receptor. The compounds of the present invention may contain a functional group (affinity label) that allows alkylation of the androgen receptor (i.e. covalent bond formation). Thus, in this case, the compounds bind irreversibly to the receptor and, accordingly, cannot be displaced by a steroid, such as the endogenous ligands DHT and testosterone.

Assays to determine whether the compounds of the present invention are AR agonists or antagonists are well known to a person skilled in the art. For example, AR agonistic activity can be determined by monitoring the ability of the SARM compounds to maintain and/or stimulate the growth of AR containing tissue such as prostate and seminal vesicles, as measured by weight. AR antagonistic activity can be determined by monitoring the ability of the SARM compounds to inhibit the growth of AR containing tissue.

In addition to ligand binding to the receptors, the receptors can be blocked to prevent ligand binding. When a substance binds to a receptor, the three-dimensional structure of the substance fits into a space created by the three-dimensional structure of the receptor in a ball and socket configuration. The better the ball fits into the socket, the more tightly it is held. This phenomenon is called affinity. If the affinity of a substance is greater than the original hormone, it will compete with the hormone and bind the binding site more frequently. Once bound, signals may be sent through the receptor into the cells, causing the cell to respond in some fashion. This is called activation. On activation, the activated receptor then directly regulates the transcription of specific genes. But the substance and the receptor may have certain attributes, other than affinity, in order to activate the cell. Chemical bonds between atoms of the substance and the atoms of the receptors may form. In some cases, this leads to a change in the configuration of the receptor, which is enough to begin the activation process (called signal transduction).

The compounds of the present invention bind either reversibly or irreversibly to an androgen receptor. In one embodiment, the androgen receptor is an androgen receptor of a mammal. In another embodiment, the androgen receptor is an androgen receptor of a human. In one embodiment, the SARM compounds bind reversibly to the androgen receptor of a mammal, for example a human. Reversible binding of a compound to a receptor means that a compound can detach from the receptor after binding.

In another embodiment, the SARM compounds bind irreversibly to the androgen receptor of a mammal, for example a human. Thus, in one embodiment, the compounds of the present invention may contain a functional group (e.g. affinity label) that allows alkylation of the androgen receptor (i.e. covalent bond formation). Thus, in this case, the compounds are alkylating agents which bind irreversibly to the receptor and, accordingly, cannot be displaced by a steroid, such as the endogenous ligands DHT and testosterone. An "alkylating agent" is defined herein as an agent which alkylates (forms a covalent bond) with a cellular component, such as DNA, RNA or enzyme. It is a highly reactive chemical that introduces alkyl radicals into biologically active molecules and thereby prevents their proper functioning. The alkylating moiety is an electrophilic group that interacts with nucleophilic moieties in cellular components.

According to one embodiment of the present invention, a method is provided for binding the SARM compounds of the present invention to an androgen receptor by contacting the receptor with a SARM compound and/or its analog, derivative, isomer, metabolite, pharmaceutically acceptable salt, pharmaceutical product, polymorph, crystal, impurity, hydrate, N-oxide or any combination thereof, under conditions effective to cause the SARM compound to bind the androgen receptor. The binding of the SARM compounds to the androgen receptor enables the compounds of the present invention to be useful as a male contraceptive and in a number of hormone therapies. The agonist compounds bind to and activate the androgen receptor. The antagonist compounds bind to and inactivate the androgen receptor. Binding of the agonist or antagonist compounds is either reversible or irreversible.

The present invention also relates to a method of binding a SARM compound to an androgen receptor, which includes contacting the androgen receptor with the SARM compound of this invention under conditions effective to bind the SARM compound to the androgen receptor.

The novel SARM compounds and the non-steroidal agonist compounds of the present invention, either alone or as a composition, are useful in males and females for the treatment of a variety of hormone-related conditions, such as hypogonadism, sarcopenia, erythropoiesis, erectile function, lack of libido, osteoporosis and fertility. Further, the SARM compounds and the non-steroidal agonist compounds are useful for oral testosterone replacement therapy, treating prostate cancer, imaging prostate cancer, and maintaining sexual desire in women. The agents may be used alone or in combination with a progestin or estrogen.

In one embodiment, modulation of the androgen receptor refers to the ability of the compound to stimulate or enhance signaling through the receptor, and any or, in another embodiment, all, downstream effects of receptor signal transduction.

In another embodiment, a SARM of this invention may interact with a homologue of an androgen receptor. In one embodiment, the term "homologue of an androgen receptor" refers to structurally or, in another embodiment, functionally related receptors, whose regulation is desired. In one embodiment, the SARMs of this invention may interact with estrogen receptors, or, in another embodiment, other cell surface molecules which are involved in anabolic pathways, or in another embodiment, steroidogenic pathways, or in another embodiment, metabolic pathways.

The present invention further relates to a method of determining the presence of a selective androgen modulator compound and/or a non-steroidal agonist compound of the present invention in a sample. The method comprises the steps of obtaining the sample, and detecting the compound in the sample, thereby determining the presence of the compound in the sample. In one embodiment, the sample is a blood serum, plasma, urine, or saliva sample. In another embodiment, the detection step comprises measuring the absorbance of the compound.

In one embodiment, the sample is a blood serum sample. In another embodiment, the sample is a plasma sample. In another embodiment, the sample is a urine sample. In another embodiment, the sample is a saliva sample. In another embodiment, the sample is any other tissue sample.

In one embodiment, the detection step comprises measuring the absorbance of the compound at a predetermined wavelength. For example, the compounds of the present invention absorb in the ultraviolet region of the spectrum, with an absorbency peak at 270 nm. Thus, in one embodiment of the present invention, the compound is detected by monitoring the UV absorbance of the sample at 270 nm. It should be noted that the present invention is not limited to UV absorption, and that any other spectrometric methods of identification are applicable. For example, compounds can be detected by measuring their infra-red or visible absorbance.

In another embodiment, the present invention further provides a method of determining the concentration of a SARM compound and/or a non-steroidal agonist compound of the present invention in a sample. The method comprises the steps of obtaining a sample; determining the level of the compound in the sample, and calculating the concentration of the compound in the sample by comparing the level with a standard sample containing a known concentration of the compound. Calibration curves of known concentrations of the compound in the sample, can be obtained, and the concentration of the compound in the test sample is calculated therefrom. By "level" it is meant the absorption level of the compound at the measured wavelength.

In another embodiment, the compound is detected in the sample by contacting the sample with a binding protein which specifically binds to the compound, and determining the amount of binding protein bound to the compound. The concentration of the compound can be determined by measuring the amount of binding protein bound to the compound, and comparing that amount to a standard sample containing a known concentration of the compound—binding protein complex.

Protein levels can be determined according to standard techniques, as described in Sambrook et al. Briefly, a sample obtained from a subject is contacted with a binding protein which specifically binds to a specific compound of the present invention, and the amount of complex formed between the binding protein and the compound is determined. In one embodiment, the binding protein is an antibody which specifically binds to one or more compounds of the present invention. In another embodiment, the binding protein has a detectable label bound thereto, and the complex between the binding protein-label compound is determined by visualizing the complex As defined herein, "contacting" means that the binding protein is introduced into the sample in a test tube, flask, tissue culture, chip, array, plate, microplate, capillary, or the like, and incubated at a temperature and time sufficient to permit the binding component to bind to a cell or a fraction thereof or plasma/serum or a fraction thereof containing the target. Methods for contacting the samples with the binding proteins, or other specific binding components are known to those skilled in the art and may be selected depending on the type of assay protocol to be run. Incubation methods are also standard and are known to those skilled in the art.

"Visualizing" the complex may be carried out by any means known in the art, including, but not limited to, ELISA, radioimmunoassay, flow cytometry, dot blots, western immunoblotting combined with gel electrophoresis, immunohistochemistry at light and electron pe levels, HPLC and mass spectrometry.

Either monoclonal or polyclonal antibodies (as well as any recombinant antibodies) specific for the selective androgen modulator compounds or the non-steroidal agonist compounds of the present invention can be used in the various immunoassays. The antibodies may be delectably labeled, utilizing conventional labeling techniques well-known to the art. As used herein, the term "label" refers to a molecule, which may be conjugated or otherwise attached (i.e., covalently or non-covalently) to a binding protein as defined herein. Labels are known to those skilled in the art. Thus, the antibodies may be labeled with radioactive isotopes, non-radioactive isotopic labels, fluorescent labels, enzyme labels, chemiluminescent labels, bioluminescent labels, free radical labels, or bacteriophage labels, using techniques known in the art. Examples of radioisotopic labels are $^3H$, $^{125}I$, $^{131}I$, $^{35}S$, $^{14}C$, etc. Examples of non-radioactive isotopic labels are $^{55}Mn$, $^{56}Fe$, etc. Examples of fluorescence labels are fluorescent labels which are directly labeled with the preferred fluorescence label, or fluorescent labels which are indirectly labeled with the preferred fluorescence label. In the last case, the preferred fluorescence label is conjugated to a secondary antibody, which is directed against the first antibody, such as an anti species Ig antibody. Typical fluorescent labels include, but are not limited to a fluorescein label, an isothiocyanate label, a rhodamine label, a phycoerythrin label, etc., for example fluorescein isothiocyanate (FITC, International Biological Supplies, Melbourne, Fla.), rhodamine, phycoerythrin (P.E., Coulter Corp., Hialeah, Fla.), phycocyanin, allophycocyanin, phycoerythrin-cyanin dye 5 (PECy5, Coulter), label, a phycocyanin label, an allophycocyanin label, an O-phthaldehyde label, a fluorescamine and Texas Red.

Examples of enzyme labels include alkaline phosphatase, beta-galactosidase, glucose-6-phosphate dehydrogenase, maleate dehydrogenase, and peroxidase. Two principal types of enzyme immunoassay are the enzyme-linked immunosorbent assay (ELISA), and the homogeneous enzyme immunoassay, also known as enzyme-multiplied immunoassay (EMIT, Syva Corporation, Palo Alto, Calif.). In the ELISA system, separation may be achieved, for example, by the use of antibodies coupled to a solid phase. The EMIT system depends on deactivation of the enzyme in the tracer-antibody complex; the activity can thus be measured without the need for a separation step.

Particularly suitable labels include those, which permit analysis by flow cytometry, e.g., fluorochromes. Other suitable detectable labels include those useful in colorimetric enzyme systems, e.g., horseradish peroxidase (HRP) and alkaline phosphatase (AP). Other proximal enzyme systems are known to those of skill in the art, including hexokinase in conjunction with glucose-6-phosphate dehydrogenase.

Additionally, chemiluminescent compounds may be used as labels. Chemiluminescent labels, such as green fluorescent proteins, blue fluorescent proteins, and variants thereof are known. Also bioluminescence or chemiluminescence can be detected using, respectively, NAD oxidoreductase with luciferase and substrates NADH and FNIN or peroxidase with luminol and substrate peroxide. Typical chemiluminescent compounds include luminol, isoluminol, aromatic acridinium esters, imidazoles, acridinium salts, and oxalate esters. Similarly, bioluminescent compounds may be utilized for labelling, the bioluminescent compounds including luciferin, luciferase, and aequorin. Once labeled, the antibody may be employed to identify and quantify immunologic counterparts (antibody or antigenic polypeptide) utilizing techniques well-known to the art.

Pharmaceutical Compositions

As used herein, "pharmaceutical composition" means a "therapeutically effective amount" of the active ingredient, i.e. the SARM compound, together with a pharmaceutically acceptable carrier or diluent. A "therapeutically effective amount" as used herein refers to that amount which provides a therapeutic effect for a given condition and administration regimen.

As used herein, the term "administering" refers to bringing a subject in contact with a SARM compound of the present invention. As used herein, administration can be accomplished in vitro, i.e. in a test tube, or in vivo, i.e. in cells or tissues of living organisms, for example humans. In one embodiment, the present invention encompasses administering the compounds of the present invention to a subject.

The pharmaceutical compositions containing the SARM agent can be administered to a subject by any method known to a person skilled in the art, such as orally, parenterally, intravascularly, paracancerally, transmucosally, transdermally, intramuscularly, intranasally, intravenously, intradermally, subcutaneously, sublingually, intraperitonealy, intraventricularly, intracranially, intravaginally, by inhalation, rectally, intratumorally, or by any means in which the recombinant virus/composition can be delivered to tissue (e.g., needle or catheter). Alternatively, topical administration may be desired for application to mucosal cells, for skin or ocular application. Another method of administration is via aspiration or aerosol formulation.

In one embodiment, the pharmaceutical compositions are administered orally, and are thus formulated in a form suitable for oral administration, i.e. as a solid or a liquid preparation. Suitable solid oral formulations include tablets, capsules, pills, granules, pellets, powders, and the like. Suitable liquid oral formulations include solutions, suspensions, dispersions, emulsions, oils and the like. In one embodiment of the present invention, the SARM compounds are formulated in a capsule. In accordance with this embodiment, the compositions of the present invention comprise in addition to the SARM active compound and the inert carrier or diluent, a hard gelatin capsule.

In one embodiment, the micronized capsules comprise particles containing a SARM of this invention, wherein the term "micronized" used herein refers to particles having a particle size is of less than 100 microns, or in another embodiment, less than 50 microns, or in another embodiment, less than 35 microns, or in another embodiment, less than 15 microns, or in another embodiment, less than 10 microns, or in another embodiment, less than 5 microns.

Further, in another embodiment, the pharmaceutical compositions are administered by intravenous, intraarterial, or intramuscular injection of a liquid preparation. Suitable liquid formulations include solutions, suspensions, dispersions, emulsions, oils and the like. In one embodiment, the pharmaceutical compositions are administered intravenously, and are thus formulated in a form suitable for intravenous administration. In another embodiment, the pharmaceutical compositions are administered intraarterially, and are thus formulated in a form suitable for intraarterial administration. In another embodiment, the pharmaceutical compositions are administered intramuscularly, and are thus formulated in a form suitable for intramuscular administration.

Further, in another embodiment, the pharmaceutical compositions are administered topically to body surfaces, and are thus formulated in a form suitable for topical administration. Suitable topical formulations include gels, ointments, creams, lotions, drops and the like. For topical administration, the SARM agents or their physiologically tolerated derivatives such as salts, esters, N-oxides, and the like are prepared and applied as solutions, suspensions, or emulsions in a physiologically acceptable diluent with or without a pharmaceutical carrier.

Further, in another embodiment, the pharmaceutical compositions are administered as a suppository, for example a rectal suppository or a urethral suppository. Further, in another embodiment, the pharmaceutical compositions are administered by subcutaneous implantation of a pellet. In a further embodiment, the pellet provides for controlled release of SARM agent over a period of time. In a further embodiment, the pharmaceutical compositions are administered intravaginally.

In another embodiment, the active compound can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid).

As used herein "pharmaceutically acceptable carriers or diluents" are well known to those skilled in the art. The carrier or diluent may be a solid carrier or diluent for solid formulations, a liquid carrier or diluent for liquid formulations, or mixtures thereof.

Solid carriers/diluents include, but are not limited to, a gum, a starch (e.g. corn starch, pregeletanized starch), a sugar (e.g., lactose, mannitol, sucrose, dextrose), a cellulosic material (e.g. microcrystalline cellulose), an acrylate (e.g. polymethylacrylate), calcium carbonate, magnesium oxide, talc, or mixtures thereof.

In one embodiment, the compositions of this invention may include, a SARM of this invention or any combination thereof, together with one or more pharmaceutically acceptable excipients.

Suitable excipients and carriers may be, according to embodiments of the invention, solid or liquid and the type is generally chosen based on the type of administration being used. Liposomes may also be used to deliver the composition. Examples of suitable solid carriers include lactose, sucrose, gelatin and agar. Oral dosage forms may contain suitable binders, lubricants, diluents, disintegrating agents, coloring agents, flavoring agents, flow-inducing agents, and melting agents. Liquid dosage forms may contain, for example, suitable solvents, preservatives, emulsifying agents, suspending agents, diluents, sweeteners, thickeners, and melting agents. Parenteral and intravenous forms should also include minerals and other materials to make them compatible with the type of injection or delivery system chosen. Of course, other excipients may also be used.

For liquid formulations, pharmaceutically acceptable carriers may be aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, cyclodextrins, emulsions or suspensions, including saline and buffered media. Examples of oils are those of petroleum, animal, vegetable, or synthetic origin, for example, peanut oil, soybean oil, mineral oil, olive oil, sunflower oil, and fish-liver oil.

Parenteral vehicles (for subcutaneous, intravenous, intraarterial, or intramuscular injection) include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions. Examples of oils are those of petroleum, animal, vegetable, or synthetic origin, for example, peanut oil, soybean oil, mineral oil, olive oil, sunflower oil, and fish-liver oil.

In addition, the compositions may further comprise binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmelose sodium, crospovidone, guar gum, sodium starch glycolate), buffers (e.g., Tris-HCl., acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., cremophor, glycerol, polyethylene glycerol, benzlkonium chloride, benzyl benzoate, cyclodextrins, sobitan esters, stearic acids), anti-oxidants (e.g., ascorbic acid, sodium metabisulfite, butylated hydroxyanisole), stabilizers (e.g. hydroxypropyl cellulose, hyroxypropylmethyl cellulose), viscosity increasing agents (e.g. carbomer, colloidal silicon dioxide, ethyl cellulose, guar gum), sweetners (e.g. aspartame, citric acid), preservatives (e.g., Thimerosal, benzyl alcohol, parabens), coloring agents, lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g., poloxamers or poloxamines), coating and film forming agents (e.g. ethyl cellulose, acrylates, polymethacrylates), and/or adjuvants.

In one embodiment, the pharmaceutical compositions provided herein are controlled release compositions, i.e. compositions in which the SARM compound is released over a period of time after administration. Controlled or sustained release compositions include formulation in lipophilic depots (e.g. fatty acids, waxes, oils). In another embodiment, the composition is an immediate release composition, i.e. a composition in which all of the SARM compound is released immediately after administration.

In yet another embodiment, the pharmaceutical composition can be delivered in a controlled release system. For example, the agent may be administered using intravenous infusion, an implantable osmotic pump, a transdermal patch, liposomes, or other modes of administration. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989). In another embodiment, polymeric materials can be used. In yet another embodiment, a controlled release system can be placed in proximity to the therapeutic target, i.e., the brain, thus requiring only a fraction of the systemic dose (see, e.g., Goodson, in Medical Applications of Controlled Release, supra, vol. 2, pp. 115-138 (1984). Other controlled release systems are discussed in the review by Langer (Science 249:1527-1533 (1990).

The compositions may also include incorporation of the active material into or onto particulate preparations of polymeric compounds such as polylactic acid, polglycolic acid, hydrogels, etc, or onto liposomes, microemulsions, micelles, unilamellar or multilamellar vesicles, erythrocyte ghosts, or spheroplasts.) Such compositions will influence the physical state, solubility, stability, rate of in vivo release, and rate of in vivo clearance.

Also comprehended by the invention are particulate compositions coated with polymers (e.g. poloxamers or poloxamines) and the compound coupled to antibodies directed against tissue-specific receptors, ligands or antigens or coupled to ligands of tissue-specific receptors.

Also comprehended by the invention are compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline. The modified compounds are known to exhibit substantially longer half-lives in blood following intravenous injection than do the corresponding unmodified compounds (Abuchowski et al., 1981; Newmark et al., 1982; and Katre et al., 1987). Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound abducts less frequently or in lower doses than with the unmodified compound.

The preparation of pharmaceutical compositions which contain an active component is well understood in the art, for example by mixing, granulating, or tablet-forming processes. The active therapeutic ingredient is often mixed with excipients which are pharmaceutically acceptable and compatible with the active ingredient. For oral administration, the SARM agents or their physiologically tolerated derivatives such as salts, esters, N-oxides, and the like are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions. For parenteral administration, the SARM agents or their physiologically tolerated derivatives such as salts, esters, N-oxides, and the like are converted into a solution, suspension, or emulsion, if desired with the substances customary and suitable for this purpose, for example, solubilizers or other.

An active component can be formulated into the composition as neutralized pharmaceutically acceptable salt forms. Pharmaceutically acceptable salts include the acid addition salts (formed with the free amino groups of the polypeptide or antibody molecule), which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

For use in medicine, the salts of the SARM will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic: acid, oxalic acid, citric acid, tartaric acid, carbonic acid or phosphoric acid.

In one embodiment, this invention provides pharmaceutical compositions comprising a SARM of this invention. In one embodiment, such compositions are useful for oral testosterone replacement therapy.

In one embodiment, this invention also provides a composition comprising two or more SARMs of this invention, or polymorphs, isomers, hydrates, salts, N-oxides, etc., thereof. The present invention also relates to compositions and a pharmaceutical compositions which comprises a SARM alone or in combination with a progestin or estrogen, or in another embodiment, chemotherapeutic compound, osteogenic or myogenic compound, or other agents suitable for the applications as herein described. In one embodiment, the compositions of this invention will comprise a suitable carrier, diluent or salt.

The SARMs of this invention may be administered at various dosages. In one embodiment, the SARM is administered at a dosage of 0.1-200 mg per day. In one embodiment, the SARM is administered at a dose of 0.1-10 mg, or in another embodiment, 0.1-25 mg, or in another embodiment, 0.1-50 mg, or in another embodiment, 0.3-15 mg, or in another embodiment, 0.3-30 mg, or in another embodiment, 0.5-25 mg, or in another embodiment, 0.5-50 mg, or in another embodiment, 0.75-15 mg, or in another embodiment, 0.75-60 mg, or in another embodiment, 1-5 mg, or in another embodiment, 1-20 mg, or in another embodiment, 3-15 mg, or in another embodiment, 30-50 mg, or in another embodiment, 30-75 mg, or in another embodiment, 100-2000 mg.

The SARMs of this invention may be administered at various dosages. In one embodiment, the SARM is administered at a dosage of 1 mg. In another embodiment the SARM is administered at a dosage of 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg or 100 mg.

In one embodiment, the present invention provides a pharmaceutical composition comprising a) a SARM compound; and b) a pharmaceutically acceptable carrier or diluent; wherein the compound represented by the structure formula I, or its analog, isomer, metabolite, derivative, pharmaceutically acceptable salt, N-oxide, hydrate or any combination thereof;

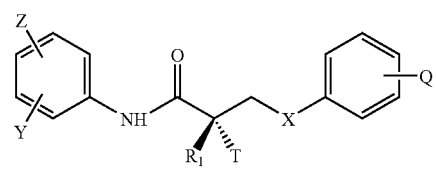

I wherein
X is a bond, O, $CH_2$, NH, Se, PR, or NR;
T is OH, OR, $NHCOCH_3$, or NHCOR;
Z is a hydrogen bond acceptor, hydrogen, alkyl, $NO_2$, CN, COOH, COR, NHCOR or CONHR;
Y is a lipid soluble group, hydrogen, alkyl, hydroxylalkyl, alkylaldehyde, $CF_3$, F, I, Br, Cl, CN, $C(R)_3$ or $Sn(R)_3$;
Q is alkyl, halogen, $CF_3$, CN, $C(R)_3$, $Sn(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR; or Q together with the benzene ring to which it is attached is a fused ring system represented by structure A, B or C:

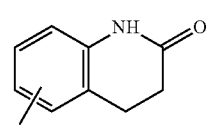

A

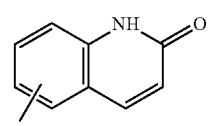

B

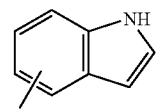

C

R is alkyl, haloalkyl, dihaloalkyl, trihaloalkyl, $CH_2F$, $CHF_2$, $CF_3$, $CF_2CF_3$, aryl, phenyl, halogen, alkenyl or OH; and $R_1$ is $CH_3$, $CH_2F$, $CHF_2$, $CF_3$, $CH_2CH_3$, or $CF_2CF_3$.

In one embodiment, X is O. In another embodiment, Z is CN. In another embodiment, Y is CF₃. In another embodiment, Q is CN.

In one embodiment, the present invention provides a pharmaceutical composition comprising a) a SARM compound; and b) a pharmaceutically acceptable carrier or diluent; wherein the compound represented by the compound of formula II, or its analog, isomer, metabolite, derivative, pharmaceutically acceptable salt, N-oxide, hydrate or any combination thereof;

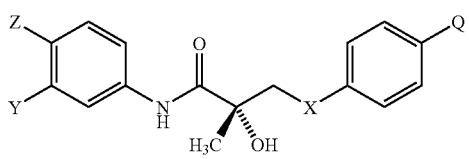
II wherein the substituents X, Q, Z and Y are as defined above for the compound of formula I.

In one embodiment, the present invention provides a pharmaceutical composition comprising a) a SARM compound; and b) a pharmaceutically acceptable carrier or diluent; wherein the compound represented by the compound of formula III, or its analog, isomer, metabolite, derivative, pharmaceutically acceptable salt, N-oxide, hydrate or any combination thereof;

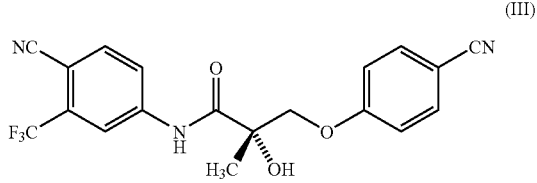
(III)

In one embodiment, the present invention provides a pharmaceutical composition comprising a) a SARM compound; and b) a pharmaceutically acceptable carrier or diluent; wherein the compound represented by the compound of formula IV, or its analog, isomer, metabolite, derivative, pharmaceutically acceptable salt, N-oxide, hydrate or any combination thereof;

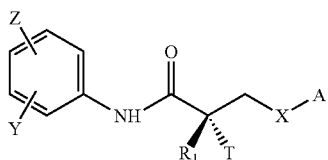
IV wherein
X is O or NH;
T is OH, OR, NHCOCH₃, NHCOR or OC(O)R;
Z is hydrogen, alkyl, NO₂, CN, COOH, COR, NHCOR or CONHR;
Y is hydrogen, alkyl, CF₃, halogen, hydroxy-alkyl or alkyl aldehyde;
R is alkyl, haloalkyl, dihaloalkyl, trihaloalkyl, CH₂F, CHF₂, CF₃, CF₂CF₃, aryl, phenyl, halogen, haloalkenyl, alkenyl or OH; and R₁ is CH₃, CH₂F, CHF₂, CF₃, CH₂CH₃, or CF₂CF₃.

A is a group selected from:

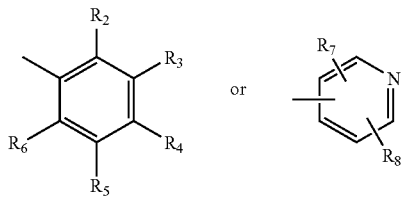

wherein

R₂, R₃, R₄, R₅, R₆ are independently is H, halogen, NO₂, CN, NHCOR₉, N(COR₉)₂, COR₁₀, OR₁₁, OSO₂R₁₂, SO₂R₁₃, NHSO₂R₁₂, SR₁₄, an imide ring, alkyl or substituted alkyl with at least one substituent of halogen, CN, NH₂, OH, alkoxy; or R₂ and R₃; R₃ and R₄; or R₄ and R₅, or R₅ and R₆ form, together with any of the ring atom(s) to which they are attached, a condensed 5 to 7 membered aliphatic or aromatic carbocyclic ring or a condensed 5 to 7 membered heterocyclic ring containing 1 to 3 heteroatom(s) selected from N, O, S; or represented by structures A, B or C:

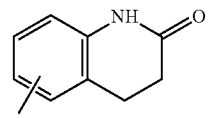
A

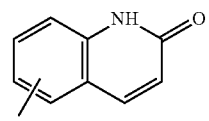
B

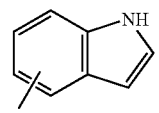
C

R₇ and R₈ are independently H, halogen, alkyl or alkenyl

R₉ and R₁₀ are independently alkyl, alkenyl, haloalkyl, aminoalkyl, mono- or di alkylaminoalkyl, aryl, N(R₁₅)₂ or —OR₁₆;

R₁₁ and R₁₄ independently H, alkyl, alkenyl, haloalkyl, aminoalkyl, mono- or di alkylaminoalkyl, aryl, —COR₁₇;

R₁₂ and R₁₃ are independently alkyl or alkenyl, haloalkyl or aryl;

R₁₅ and R₁₆ are independently H, alkyl, alkenyl, haloalkyl, aminoalkyl or aryl;

R₁₇ is alkyl, alkenyl, haloalkyl or aryl.

In one embodiment, the present invention provides a pharmaceutical composition comprising a) a SARM compound; and b) a pharmaceutically acceptable carrier or diluent; wherein the compound represented by the compound of formula XVI, or its analog, isomer, metabolite, derivative, pharmaceutically acceptable salt, N-oxide, hydrate or any combination thereof;

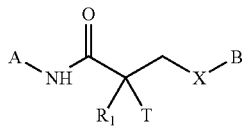

wherein

X is O, CH$_2$, NH, Se, PR, or NR;

R$_1$ is CH$_3$, CF$_3$, CH$_2$CH$_3$, or CF$_2$ CF$_3$;

T is OH, OR, NHCOCH$_3$, or NHCOR;

wherein R is a C$_1$-C$_4$ alkyl, a C$_1$-C$_4$ haloalkyl, aryl, phenyl, halogen, alkenyl, haloalkenyl, or hydroxyl;

A is a 5 or 6 membered saturated, unsaturated or aromatic carbocyclic or heterocyclic ring represented by the structure:

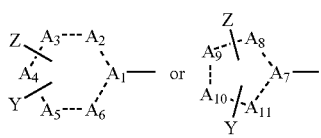

B is a 5 or 6 membered saturated, unsaturated or aromatic carbocyclic or heterocyclic ring represented by the structure:

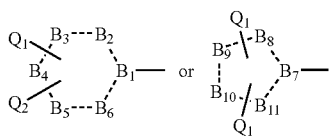

wherein

A$_1$-A$_{11}$ are each C, O, S or N;

B$_1$-B$_{11}$ are each C, O, S or N;

Z is NO$_2$, CN, COOH, COR, or CONHR;

Y is I, CF$_3$, Br, Cl, or Sn(R)$_3$; and

Q1 and Q2 are independently of each other alkyl, halogen, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R or SR;

wherein R is a C$_1$-C$_4$ alkyl, a C$_1$-C$_4$ haloalkyl, aryl, phenyl, halogen, alkenyl, haloalkenyl, or hydroxyl.

Thus, in one embodiment, the present invention provides a pharmaceutical composition comprising a) a SARM compound; and b) a pharmaceutically acceptable carrier or diluent; wherein the compound represented by the compound of formula V, or its analog, isomer, metabolite, derivative, pharmaceutically acceptable salt, N-oxide, hydrate or any combination thereof;

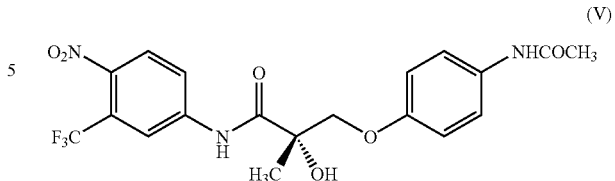

Further, in one embodiment, the present invention provides a pharmaceutical composition comprising a) a SARM compound, of this invention or its analog, isomer, metabolite, derivative, pharmaceutically acceptable salt, pharmaceutical product, N-oxide, hydrate or any combination thereof; b) a pharmaceutically acceptable carrier or diluent; c) a flow-aid; and d) a lubricant.

Further, in another embodiment, the present invention provides a pharmaceutical composition comprising a) a SARM compound, of this invention or its analog, isomer, metabolite, derivative, pharmaceutically acceptable salt, pharmaceutical product, N-oxide, hydrate or any combination thereof; b) lactose monohydrate; c) microcrystalline cellulose; d) magnesium stearate; and e) colloidal silicon dioxide.

In some embodiments, the compositions comprising the SARM compounds of the present invention offer the advantage that the compounds are nonsteroidal ligands for the androgen receptor, and exhibit anabolic activity in vivo. According to this aspect, such compounds are unaccompanied by serious side effects, provide convenient modes of administration, and lower production costs and are orally bioavailable, lack significant cross-reactivity with other undesired steroid receptors, and may possess long biological half-lives.

For administration to mammals, and particularly humans, it is expected that the physician will determine the actual dosage and duration of treatment, which will be most suitable for an individual and can vary with the age, weight and response of the particular individual.

In one embodiment, the compositions for administration may be sterile solutions, or in other embodiments, aqueous or non-aqueous, suspensions or emulsions. In one embodiment, the compositions may comprise propylene glycol, polyethylene glycol, injectable organic esters, for example ethyl oleate, or cyclodextrins. In another embodiment, compositions may also comprise wetting, emulsifying and/or dispersing agents. In another embodiment, the compositions may also comprise sterile water or any other sterile injectable medium.

In one embodiment, the compounds and compositions of this invention may be used for any of the methods of this invention, as described herein. In one embodiment, use of a SARM or a composition comprising the same, will have utility in inhibiting, suppressing, enhancing or stimulating a desired response in a subject, as will be understood by one skilled in the art. In another embodiment, the compositions may further comprise additional active ingredients, whose activity is useful for the particular application for which the SARM compound is being administered.

Biological Activity of Selective Androgen Modulator Compounds

The SARMs of this invention may be useful, in some embodiments, for oral testosterone replacement therapy. In other embodiments, appropriately substituted compounds are useful for a) male contraception; b) treatment of a variety of hormone-related conditions, for example conditions associated with ADAM, such as fatigue, depression, decreased libido, sexual dysfunction, erectile dysfunction, hypogonadism, osteoporosis, hair loss, obesity, sarcopenia, osteopenia, benign prostate hyperplasia, and alterations in mood and cognition; c) treatment of conditions associated with ADIF, such as sexual dysfunction, decreased sexual libido, hypogonadism, sarcopenia, osteopenia, osteoporosis, alterations in cognition and mood, depression, anemia, hair loss, obesity, endometriosis, breast cancer, uterine cancer and ovarian cancer; d) treatment and/or prevention of chronic muscular wasting; e) treatment of prostate cancer, imaging of prostate cancer; decreasing the incidence of, halting or causing a regression of prostate cancer; f) oral androgen replacement and/or other clinical therpauetic and/or diagnostic areas. In some embodiments, the SARM compounds possess in vivo tissue selective androgenic and anabolic activity, which is accordingly utilized for particular applications, as will be appreciated by one skilled in the art.

In some embodiments, the SARMs of this invention and/or compositions comprising the same may be used for applications and treating diseases in which the improvement of cognition, reduction or treatment of depression, or other neuroportective effects are desired.

In one embodiment, "Cognition" refers to the process of knowing, specifically the process of being aware, knowing, thinking, learning and judging. Cognition is related to the fields of psychology, linguistics, computer science, neuroscience, mathematics, ethology and philosophy. In one embodiment, "mood" refers to a temper or state of the mind. As contemplated herein, alterations mean any change for the positive or negative, in cognition and/or mood.

In one embodiment, "depression" refers to an illness that involves the body, mood and thoughts, that affects the way a person eats, sleeps and the way one feels about oneself, and thinks about things. The signs and symptoms of depression include loss of interest in activities, loss of appetite or overeating, loss of emotional expression, an empty mood, feelings of hopelessness, pessimism, guilt or helplessness, social withdrawal, fatigue, sleep disturbances, trouble concentrating, remembering, or making decisions, restlessness, irritability, headaches, digestive disorders or chronic pain.

In some embodiments, the SARMs of this invention and/or compositions comprising the same may be used for applications in or treating hair loss. In one embodiment, "hair loss", medically known as alopecia, refers to baldness as in the very common type of male-pattern baldness. Baldness typically begins with patch hair loss on the scalp and sometimes progresses to complete baldness and even loss of body hair. Hair loss affects both males and females.

In some embodiments, the SARMs of this invention and/or compositions comprising the same may be used for applications in, or treating diseases or conditions associated with a subject having anemia. In one embodiment, "Anemia" refers to the condition of having less than the normal number of red blood cells or less than the normal quantity of hemoglobin in the blood. The oxygen-carrying capacity of the blood is, therefore, decreased. Persons with anemia may feel tired and fatigue easily, appear pale, develop palpitations and become usually short of breath. Anemia is caused by four basic factors: a) hemorrhage (bleeding); b) hemolysis (excessive destruction of red blood cells); c) underproduction of red blood cells; and d) not enough normal hemoglobin. There are many forms of anemia, including aplastic anemia, benzene poisoning, Fanconi anemia, hemolytic disease of the newborn, hereditary spherocytosis, iron deficiency anemia, osteopetrosis, pernicious anemia, sickle cell disease, thalassemia, myelodysplastic syndrome, and a variety of bone marrow diseases. As contemplated herein, the SARM compounds of the present invention are useful in preventing and/or treating any one or more of the above-listed forms of anemia.

In some embodiments, the SARMs of this invention and/or compositions comprising the same may be used for applications in and/or treating diseases and/or conditions associated with problems with a subject's libido, or erectile dysfunction in a subject. In one embodiment, "libido, as used herein, means sexual desire.

In one embodiment, "erectile", as used herein, means capable of being erected. An erectile tissue is a tissue, which is capable of being greatly dilated and made rigid by the distension of the numerous blood vessels, which it contains.

According to one embodiment of the present invention relates to a method of modulating spermatogenesis in a subject, which includes contacting an androgen receptor of the subject with a SARM compound of the present invention and/or its analog, derivative, isomer, metabolite, pharmaceutically acceptable salt, pharmaceutical product, polymorph, crystal, impurity, hydrate, N-oxide or any combination thereof, under conditions effective to increase or decrease sperm production.

In another embodiment, this invention provides for the use of a SARM of this invention, or a composition comprising the same, in promoting or suppressing spermatogenesis in a male subject. Some of the SARMs of the present invention exhibit, inter-alia, androgenic activity, which in turn stimulates spermatogenesis. In other embodiments, the SARMs of this invention exhibit antagonist activity in the gonads of a subject, which in turn, may suppress spermatogenesis. In one embodiment, the SARMs may therefore be used as a contraceptive.

In another embodiment of the present invention, a method is provided for contraception in a male subject, comprising the step of administering to the subject a SARM compound and/or a non steroidal agonist of the present invention and/or its analog, derivative, isomer, metabolite, pharmaceutically acceptable salt, pharmaceutical product, polymorph, crystal, impurity, hydrate, N-oxide or any combination thereof, in an amount effective to suppress sperm production in the subject, thereby effecting contraception in the subject.

In another embodiment of the present invention, a method is provided for hormonal therapy in a patient (i.e., one suffering from an androgen-dependent condition) which includes contacting an androgen receptor of a patient with a SARM compound and/or a non steroidal agonist of the present invention and/or its analog, derivative, isomer, metabolite, pharmaceutically acceptable salt, pharmaceutical product, polymorph, crystal, impurity, hydrate, N-oxide or any combination thereof, in an amount effective to bind the SARM compound to the androgen receptor and effect a change in an androgen-dependent condition.

In another embodiment of the present invention, a method is provided for hormone replacement therapy in a patient (i.e., one suffering from an androgen-dependent condition) which includes contacting an androgen receptor of a patient with a SARM compound of the present invention and/or its analog, derivative, isomer, metabolite, pharmaceutically acceptable salt, pharmaceutical product, polymorph, crystal, impurity, hydrate, N-oxide or any combination thereof, in an amount effective to bind the SARM compound to the androgen receptor and effect a change in an androgen-dependent condition.

According to another embodiment of the present invention, a method is provided for treating a subject having a hormone related condition, which includes administering to the subject a SARM compound of the present invention and/or its analog, derivative, isomer, metabolite, pharmaceutically acceptable salt, pharmaceutical product, polymorph, crystal, impurity, hydrate, N-oxide or any combination thereof, in an amount effective to bind the SARM compound to the androgen receptor and effect a change in an androgen-dependent condition.

Androgen-dependent conditions which may be treated with the compounds, compositions and/or methods of the present invention include those conditions which are associated with aging, such as hypogonadism, sarcopenia, erythropoiesis, osteoporosis, and any other conditions later determined to be dependent upon low androgen (e.g., testosterone) levels.

In one embodiment, "Hypogonadism" is a condition resulting from or characterised by abnormally decreased functional activity of the gonads, with retardation of growth and sexual development.

In another embodiment of the present invention, a method is provided for treating a subject suffering from prostate cancer, comprising the step of administering to the subject a SARM compound of the present invention and/or its analog, derivative, isomer, metabolite, pharmaceutically acceptable salt, pharmaceutical product, polymorph, crystal, impurity, hydrate, N-oxide or any combination thereof, in an amount effective to treat prostate cancer in the subject.

In one embodiment, "Prostate cancer" is one of the most frequently occurring cancers among men in the United States, with hundreds of thousands of new cases diagnosed each year. Over sixty percent of newly diagnosed cases of prostate cancer are found to be pathologically advanced, with no cure and a dismal prognosis. One third of all men over 50 years of age have a latent form of prostate cancer that may be activated into the life-threatening clinical prostate cancer form. The frequency of latent prostatic tumors has been shown to increase substantially with each decade of life from the 50s (5.3-14%) to the 90s (40-80%). The number of people with latent prostate cancer is the same across all cultures, ethnic groups, and races, yet the frequency of clinically aggressive cancer is markedly different. This suggests that environmental factors may play a role in activating latent prostate cancer.

In another embodiment of the present invention, a method is provided for preventing prostate cancer in a subject, comprising the step of administering to the subject a SARM compound of the present invention and/or its analog, derivative, isomer, metabolite, pharmaceutically acceptable salt, pharmaceutical product, polymorph, crystal, impurity, hydrate, N-oxide or any combination thereof, in an amount effective to treat prevent prostate cancer in the subject.

In another embodiment of the present invention, a method is provided for delaying the progression of prostate cancer in a subject suffering from prostate cancer, comprising the step of administering to the subject a SARM compound of the present invention and/or its analog, derivative, isomer, metabolite, pharmaceutically acceptable salt, pharmaceutical product, polymorph, crystal, impurity, hydrate, N-oxide or any combination thereof, in an amount effective to delay the progression of prostate cancer in the subject.

In another embodiment of the present invention, a method is provided for preventing the recurrence of prostate cancer in a subject suffering from prostate cancer, comprising the step of administering to the subject a SARM compound of the present invention and/or its analog, derivative, isomer, metabolite, pharmaceutically acceptable salt, pharmaceutical product, polymorph, crystal, impurity, hydrate, N-oxide or any combination thereof, in an amount effective to prevent the recurrence of prostate cancer in the subject.

In one embodiment, this invention provides compounds, compositions and/or methods of use thereof in treating benign prostate hyperplasia (BPH). "BPH (benign prostate hyperplasia)" is a nonmalignant enlargement of the prostate gland, and is the most common non-malignant proliferative abnormality found in any internal organ and the major cause of morbidity in the adult male. BPH occurs in over 75% of men over 50 years of age, reaching 88% prevalence by the ninth decade. BPH frequently results in a gradual squeezing of the portion of the urethra which traverses the prostate (prostatic urethra). This causes patients to experience a frequent urge to urinate because of incomplete emptying of the bladder and urgency of urination. The obstruction of urinary flow can also lead to a general lack of control over urination, including difficulty initiating urination when desired, as well as difficulty in preventing urinary flow because of the inability to empty urine from the bladder, a condition known as overflow urinary incontinence, which can lead to urinary obstruction and to urinary failure.

In another embodiment of the present invention, the method for treating benign prostate hyperplasia (BPH) in a subject, comprises the step of administering to the subject a SARM compound of the present invention and/or its analog, derivative, isomer, metabolite, pharmaceutically acceptable salt, pharmaceutical product, polymorph, crystal, impurity, hydrate, N-oxide or any combination thereof, in an amount effective to treat BPH in the subject.

Stimulation of the androgen receptor stimulates the production of tears, and thus the SARM compounds of the present invention may be used to treat dry eye conditions. In one embodiment, this invention provides compounds, compositions and/or methods of use thereof in treating a dry eye condition in a subject suffering from dry eyes, comprising the step of administering to said subject the SARM compound of the present invention and/or its analog, derivative, isomer, metabolite, pharmaceutically acceptable salt, pharmaceutical product, polymorph, crystal, impurity, hydrate, N-oxide or any combination thereof, in an amount effective to treat dry eyes in the subject.

In another embodiment of the present invention, this invention provides compounds, compositions and/or methods of use thereof in preventing a dry eye condition in a subject, comprising the step of administering to said subject the SARM compound of the present invention and/or its analog, derivative, isomer, metabolite, pharmaceutically acceptable salt, pharmaceutical product, polymorph, crystal, impurity, hydrate, N-oxide or any combination thereof, in an amount effective to prevent dry eyes in the subject.

In one embodiment, "contacting" or "administering" refers to direct or indirect exposure of the indicated compound to the stated source. In one embodiment, direct contact or administration may comprise introducing the indicated compound into the desired source, for example a cell, via direct injection, or in another embodiment, into a media surrounding the cell, or in another embodiment, into a blood or lymph supply which in turn brings the compound in proximity with desired cells, or in another embodiment, oral delivery, which in turn exposes the desired cell or tissue to the compound, following its metabolism, etc., as will be appreciated by one skilled in the art.

In another embodiment, the term "contacting" means that the SARM compound of the present invention is introduced into a subject receiving treatment, and the SARM compound is allowed to come in contact with the androgen receptor in vivo.

In one embodiment, the term "treating" includes preventative as well as disorder remitative treatment. In one embodiment, the terms "reducing", "suppressing" and "inhibiting" have their commonly understood meaning of lessening or decreasing. In one embodiment, the term "progression" means increasing in scope or severity, advancing, growing or becoming worse. In one embodiment, the term "recurrence" means the return of a disease after a remission.

In one embodiment, the term "administering" refers to bringing a subject in contact with a SARM compound of the present invention. In one embodiment, administration can be accomplished in vitro, i.e. in a test tube, or in vivo, i.e. in cells or tissues of living organisms, for example humans. In one embodiment, the present invention encompasses administering the compounds of the present invention to a subject.

In one embodiment, this invention provides for the use of a SARM compound of this invention, or its prodrug, analog, isomer, metabolite, derivative, pharmaceutically acceptable salt, pharmaceutical product, polymorph, crystal, impurity, N-oxide, hydrate or any combination thereof, for 1) treating a bone related disorder; 2) preventing a bone related disorder; 3) suppressing a bone related disorder; 4) inhibiting a bone related disorder; 5) increasing a strength of a bone of a subject; 5) increasing a bone mass in a subject; 6) use for osteoclastogenesis inhibition.

In one embodiment, the bone related disorder is a genetic disorder, or in another embodiment, is induced as a result of a treatment regimen for a given disease. For example, and in one embodiment, the SARMs of this invention are useful in treating a bone-related disorder that arises as a result of androgen-deprivation therapy, given in response to prostate carcinogenesis in a subject.

In one embodiment, the present invention provides a use of SARM compound of the present invention for preventing a bone-related disorder in a subject. In another embodiment, the present invention provides a use of SARM compound of the present invention for suppressing a bone-related disorder in a subject. In another embodiment, the present invention provides a use of SARM compound of the present invention for inhibiting a bone-related disorder in a subject.

In one embodiment, the bone-related disorder is osteoporosis. In another embodiment, the bone-related disorder is osteopenia. In another embodiment, the bone-related disorder is increased bone resorption. In another embodiment, the bone-related disorder is bone fracture. In another embodiment, the bone-related disorder is bone frailty. In another embodiment, the bone-related disorder is a loss of BMD. In another embodiment, the bone-related disorder is any combination of osteoporosis, osteopenia, increased bone resorption, bone fracture, bone frailty and loss of BMD. Each disorder represents a separate embodiment of the present invention.

"Osteoporosis" refers, in one embodiment, to a thinning of the bones with reduction in bone mass due to depletion of calcium and bone protein. In another embodiment, osteoporosis is a systemic skeletal disease, characterized by low bone mass and deterioration of bone tissue, with a consequent increase in bone fragility and susceptibility to fracture. In osteoporotic patients, bone strength is abnormal, in one embodiment, with a resulting increase in the risk of fracture. In another embodiment, osteoporosis depletes both the calcium and the protein collagen normally found in the bone, in one embodiment, resulting in either abnormal bone quality or decreased bone density. In another embodiment, bones that are affected by osteoporosis can fracture with only a minor fall or injury that normally would not cause a bone fracture. The fracture can be, in one embodiment, either in the form of cracking (as in a hip fracture) or collapsing (as in a compression fracture of the spine). The spine, hips, and wrists are common areas of osteoporosis-induced bone fractures, although fractures can also occur in other skeletal areas. Unchecked osteoporosis can lead, in another embodiment, to changes in posture, physical abnormality, and decreased mobility.

In one embodiment, the osteoporosis results from androgen deprivation. In another embodiment, the osteoporosis follows androgen deprivation. In another embodiment, the osteoporosis is primary osteoporosis. In another embodiment, the osteoporosis is secondary osteoporosis. In another embodiment, the osteoporosis is postmenopausal osteoporosis. In another embodiment, the osteoporosis is juvenile osteoporosis. In another embodiment, the osteoporosis is idiopathic osteoporosis. In another embodiment, the osteoporosis is senile osteoporosis.

In another embodiment, the primary osteoporosis is Type I primary osteoporosis. In another embodiment, the primary osteoporosis is Type II primary osteoporosis. Each type of osteoporosis represents a separate embodiment of the present invention.

Osteoporosis and osteopenia are, in another embodiment, systemic skeletal diseases characterized by low bone mass and microarchitectural deterioration of bone tissue. "Microarchitectural deterioration" refers, in one embodiment, to thinning of the trabeculae (defined below) and the loss of inter-trabecular connections in bone. In another embodiment, "osteoporosis" is defined as having a BMD 2.5 standard deviations (SD) or more below the young adult mean. In another embodiment, "osteoporosis" is defined as having a BMC 2.5 SD or more below the young adult mean. In another embodiment, "osteoporosis" is defined as having a BMD 2.0 SD or more below the young adult mean. In another embodiment, "osteoporosis" is defined as having a BMC 2.0 SD or more below the young adult mean. In another embodiment, "osteoporosis" is defined as having a BMD 3.0 SD or more below the young adult mean. In another embodiment, "osteoporosis" is defined as having a BMC 3.0 SD or more below the young adult mean. Each definition of osteoporosis or osteopenia represents a separate embodiment of the present invention.

In another embodiment, "osteoporosis" is defined as having a BMD 2.5 SD below the young adult mean. In another embodiment, "osteoporosis" is defined as having a BMC 2.5 SD below the young adult mean. In another embodiment, "osteoporosis" is defined as having a BMD 2.0 SD below the young adult mean. In another embodiment, "osteoporosis" is defined as having a BMC 2.0 SD below the young adult mean. In another embodiment, "osteoporosis" is defined as having a BMD 3.0 SD below the young adult mean. In another embodiment, "osteoporosis" is defined as having a BMC 3.0 SD below the young adult mean. Each definition of osteoporosis represents a separate embodiment of the present invention.

Methods for assessing osteoporosis and osteopenia are well known in the art. For example, in one embodiment, a patient's BMD, measured by densitometry and expressed in $g/cm^2$, is compared with a "normal value," which is the mean BMD of sex-matched young adults at their peak bone mass, yielding a "T score." In another embodiment, Z-score, the amount of bone loss in a patient is compared with the expected loss for individuals of the same age and sex. In another embodiment, "osteoporosis" is defined as having a T score 2.5 SD or more below the young adult mean. In another embodiment, "osteoporosis" is defined as having a Z score 2.5 SD or more below the young adult mean. In another embodiment, "osteoporosis" is defined as having a T score 2.0 SD or more below the young adult mean. In another embodiment, "osteoporosis" is defined as having a Z score 2.0 SD or more below the young adult mean. In another embodiment, "osteoporosis" is defined as having a T score 3.0 SD or more below the young adult mean. In another embodiment, "osteoporosis" is defined as having a Z score 3.0 SD or more below the young adult mean.

In another embodiment, "osteoporosis" is defined as having a T score 2.5 SD below the young adult mean. In another embodiment, "osteoporosis" is defined as having a Z score 2.5 SD below the young adult mean. In another embodiment, "osteoporosis" is defined as having a T score 2.0 SD below the young adult mean. In another embodiment, "osteoporosis" is defined as having a Z score 2.0 SD below the young adult mean. In another embodiment, "osteoporosis" is defined as having a T score 3.0 SD below the young adult mean. In another embodiment, "osteoporosis" is defined as having a Z score 3.0 SD below the young adult mean. Each definition of osteoporosis represents a separate embodiment of the present invention.

The term "BMD" is, in one embodiment, a measured calculation of the true mass of bone. The absolute amount of bone as measured by BMD generally correlates with bone strength and its ability to bear weight. By measuring BMD, it is possible to predict fracture risk in the same manner that measuring blood pressure can help predict the risk of stroke.

BMD, in one embodiment, can be measured by known BMD mapping techniques. In one embodiment, bone density of the hip, spine, wrist, or calcaneus may be measured by a variety of techniques. The preferred method of BMD measurement is dual-energy x-ray densitometry (DEXA). BMD of the hip, antero-posterior (AP) spine, lateral spine, and wrist can be measured using this technology. Measurement at any site predicts overall risk of fracture, but information from a specific site is the best predictor of fracture at that site. Quantitative computerized tomography (QCT) is also used to measure BMD of the spine. See for example, "Nuclear Medicine: "Quantitative Procedures" by Wahner H W, et al, published by Toronto Little, Brown & Co., 1983, pages 107-132; "Assessment of Bone Mineral Part 1," J Nucl Medicine, pp 1134-1141 (1984); and "Bone Mineral Density of The Radius" J Nucl Medicine 26: 13-39 (1985). Each method of measuring BMD represents a separate embodiment of the present invention.

"Osteopenia" refers, in one embodiment, to having a BMD or BMC between 1 and 2.5 SD below the young adult mean. In another embodiment, "osteopenia" refers to decreased calcification or density of bone. This term encompasses, in one embodiment, all skeletal systems in which such a condition is noted. Each definition or means of diagnosis of the disorders disclosed in the present invention represents a separate embodiment of the present invention.

In one embodiment, the term "bone fracture" refers to a breaking of bones, and encompasses both vertebral and non-vertebral bone fractures. The term "bone frailty" refers, in one embodiment, to a weakened state of the bones that predisposes them to fractures.

In one embodiment, the bone-related disorder is treated with a SARM compound of this invention, or a combination thereof. In another embodiment, other bone-stimulating compounds can be provided to a subject, prior to, concurrent with or following administration of a SARM or SARMs of this invention. In one embodiment, such a bone stimulating compound may comprise natural or synthetic materials.

In one embodiment, the bone stimulating compound may comprise a bone morphogenetic protein (BMP), a growth factor, such as epidermal growth factor (EGF), a fibroblast growth factor (FGF), a transforming growth factor (TGF, an insulin growth factor (IGF), a platelet-derived growth factor (PDGF) hedgehog proteins such as sonic, indian and desert hedgehog, a hormone such as follicle stimulating hormone, parathyroid hormone, parathyroid hormone related peptide, activins, inhibins, follistatin, frizzled, frzb or frazzled proteins, BMP binding proteins such as chordin and fetuin, a cytokine such as IL-3, IL-7, GM-CSF, a chemokine, such as eotaxin, a collagen, osteocalcin, osteonectin and others, as will be appreciated by one skilled in the art.

In another embodiment, the compositions for use in treating a bone disorder of this invention may comprise a SARM or SARMs of this invention, an additional bone stimulating compound, or compounds, and osteogenic cells. In one embodiment, an osteogenic cell may be a stem cell or progenitor cell, which may be induced to differentiate into an osteoblast. In another embodiment, the cell may be an osteoblastIn another embodiment, nucleic acids which encode bone-stimulating compounds may be administered to the subject, which is to be considered as part of this invention.

In one embodiment, the osteoporosis, osteopenia, increased bone resorption, bone fracture, bone frailty, loss of BMD, and other diseases or disorders of the present invention are caused by a hormonal disorder, disruption or imbalance. In another embodiment, these conditions occur independently of a hormonal disorder, disruption or imbalance. Each possibility represents a separate embodiment of the present invention.

In one embodiment, the hormonal disorder, disruption or imbalance comprises an excess of a hormone. In another embodiment, the hormonal disorder, disruption or imbalance comprises a deficiency of a hormone. In one embodiment, the hormone is a steroid hormone. In another embodiment, the hormone is an estrogen. In another embodiment, the hormone is an androgen. In another embodiment, the hormone is a glucocorticoid. In another embodiment, the hormone is a cortico-steroid. In another embodiment, the hormone is Luteinizing Hormone (LH). In another embodiment, the hormone is Follicle Stimulating Hormone (FSH). In another embodiment, the hormone is any other hormone known in the art. In another embodiment, the hormonal disorder, disruption or imbalance is associated with menopause. In another embodiment, hormone deficiency is a result of specific manipulation, as a byproduct of treating a disease or disorder in the subject. For example, the hormone deficiency may be a result of androgen depletion in a subject, as a therapy for prostate cancer in the subject. Each possibility represents a separate embodiment of the present invention.

In one embodiment, this invention provides compounds, compositions and/or methods of use thereof in increasing the strength of a bone of a subject. In one embodiment the SARM compound or its prodrug, analog, isomer, metabolite, derivative, pharmaceutically acceptable salt, pharmaceutical product, polymorph, crystal, impurity, N-oxide, hydrate or any combination thereof may be thus utilized.

In another embodiment, the subject has osteoporosis. In another embodiment the osteoporosis is hormonally induced.

In one embodiment, for the compounds and/or compositions and/or methods of utilizing the same are for applications in increasing a bone mass of a subject. In one embodiment the SARM compound or its prodrug, analog, isomer, metabolite, derivative, pharmaceutically acceptable salt, pharmaceutical product, polymorph, crystal, impurity, N-oxide, hydrate or any combination thereof, or a composition comprising the same, may be thus utilized.

In another embodiment the subject has sarcopenia or cachexia. In another embodiment the methods of this invention provide for increasing a bone mass in the subject. In one embodiment, the compounds and/or compositions and/or methods of use thereof are directed to promoting bone formation in a subject. In one embodiment, such applications are directed to promoting or increasing which cortical bone mass. In another embodiment the bone mass is trabecular bone mass. In another embodiment the bone mass is a cancellous bone mass.

In another embodiment, the SARM compound stimulates or enhances osteoblastogenesis. In another embodiment, the said SARM compound inhibits osteoclast proliferation.

In one embodiment, the invention provides for bone formation via osteoblast stimulation or enhanced proliferation. In one embodiment, the term "osteoblast" refers to cell which participates in bone-formation. In one embodiment, osteoblast involvement in bone formation may form the tissue and deposit minerals therein, giving bone its strength. In another embodiment, the invention provides for bone formation via suppression of osteoclast induction, or in another embodiment, activity. In one embodiment, the term "osteoclast" refers to a cell which participates in bone remodeling, and in particular in bone resorption.

In one embodiment, bone diseases or disorders are treated by the methods of this invention via stimulation of bone formation. In another embodiment, the treatments of this invention provide for maintenance of bone mass. Bone mass is maintained by a balance between the activity of osteoblasts that form bone and osteoclasts that break it down. In one embodiment, the compounds and methods of this invention provide a means whereby such a balance is maintained.

Figure 2:
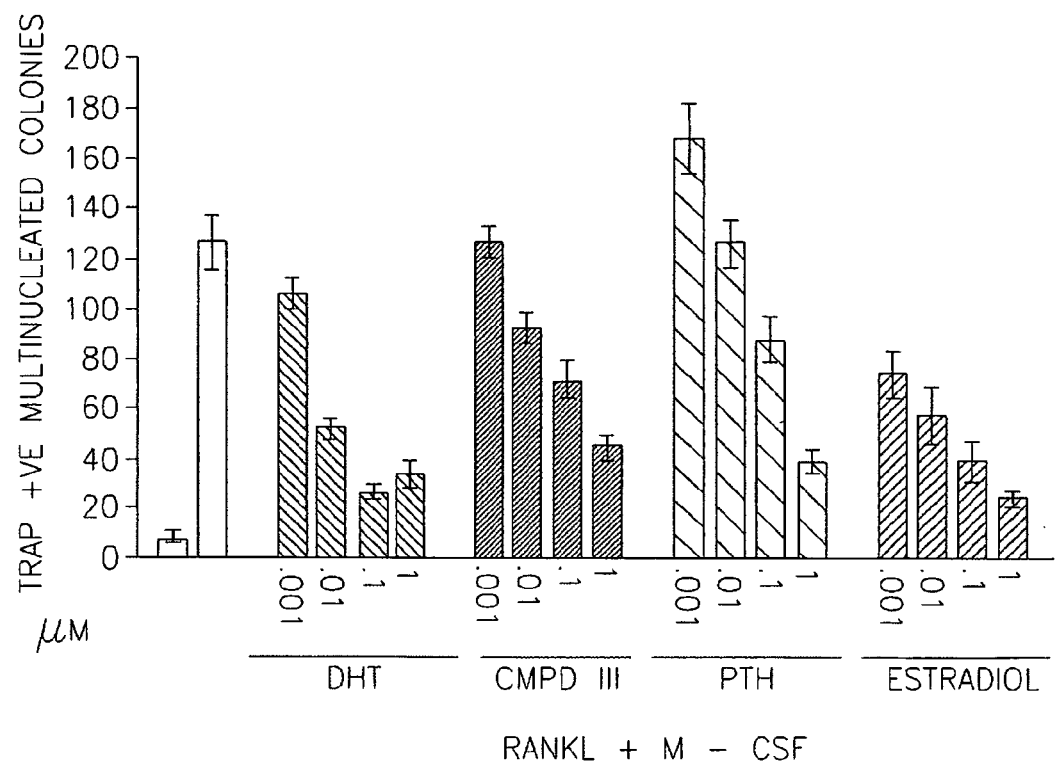
FIG. 2: Effect of SARMs, DHT and PTH on TRAP Positive Multinucleated Osteoclasts.

FIGS. 1-2 demonstrate that SARM compound of formula III induced differentiation of bone marrow cells to osteoblasts yet inhibited osteoclast induction, indicating direct effects of SARMs on both osteoblasts and osteoclasts, which would be useful in increasing bone mass in osteoporotic patients.

In one embodiment, this invention provides use of a SARM compound of this invention, or its prodrug, analog, isomer, metabolite, derivative, pharmaceutically acceptable salt, pharmaceutical product, polymorph, crystal, impurity, N-oxide, hydrate or any combination thereof, for 1) treating a muscle wasting disorder; 2) preventing a muscle wasting disorder; 3) treating, preventing, suppressing, inhibiting or reducing muscle loss due to a muscle wasting disorder; 4) treating, preventing, inhibiting, reducing or suppressing muscle wasting due to a muscle wasting disorder; and/or 5) treating, preventing, inhibiting, reducing or suppressing muscle protein catabolism due to a muscle wasting disorder. In another embodiment, the invention provides a composition comprising a SARM of this invention for use in the methods as described herein.

In one embodiment, the invention provides a use of SARM compound of the present invention for treating a subject suffering from a muscle wasting disorder. In another embodiment the use of a SARM compound of the present invention or its prodrug, analog, isomer, metabolite, derivative, pharmaceutically acceptable salt, pharmaceutical product, polymorph, crystal, impurity, N-oxide, hydrate or any combination thereof, or a composition comprising the same. Thus, treating a subject suffering from a muscle wasting disorder.

In another embodiment, the use of a SARM compound for treating a subject suffering from a muscle wasting disorder includes administering a pharmaceutical composition including the SARM compound of the present invention. In another embodiment, the administering step includes intravenously, intraarterially, or intramuscularly injecting to said subject said pharmaceutical composition in liquid form; subcutaneously implanting in said subject a pellet containing said pharmaceutical composition; orally administering to said subject said pharmaceutical composition in a liquid or solid form; or topically applying to the skin surface of said subject said pharmaceutical composition.

A muscle is a tissue of the body that primarily functions as a source of power. There are three types of muscles in the body: a) skeletal muscle—the muscle responsible for moving extremities and external areas of the bodies; b) cardiac muscle—the heart muscle; and c) smooth muscle—the muscle that is in the walls of arteries and bowel.

A wasting condition or disorder is defined herein as a condition or disorder that is characterized, at least in part, by an abnormal, progressive loss of body, organ or tissue mass. A wasting condition can occur as a result of a pathology such as, for example, cancer, or an infection, or it can be due to a physiologic or metabolic state, such as disuse deconditioning that can occur, for example, due to prolonged bed rest or when a limb is immobilized, such as in a cast. A wasting condition can also be age associated. The loss of body mass that occurs during a wasting condition can be characterized by a loss of total body weight, or a loss of organ weight such as a loss of bone or muscle mass due to a decrease in tissue protein.

In one embodiment, "muscle wasting" or "muscular wasting", used herein interchangeably, refer to the progressive loss of muscle mass and/or to the progressive weakening and degeneration of muscles, including the skeletal or voluntary muscles which control movement, cardiac muscles which control the heart, and smooth muscles. In one embodiment, the muscle wasting condition or disorder is a chronic muscle wasting condition or disorder. "Chronic muscle wasting" is defined herein as the chronic (i.e. persisting over a long period of time) progressive loss of muscle mass and/or to the chronic progressive weakening and degeneration of muscle.

The loss of muscle mass that occurs during muscle wasting can be characterized by a muscle protein breakdown or degradation, by muscle protein catabolism. Protein catabolism occurs because of an unusually high rate of protein degradation, an unusually low rate of protein synthesis, or a combination of both. Protein catabolism or depletion, whether caused by a high degree of protein degradation or a low degree of protein synthesis, leads to a decrease in muscle mass and to muscle wasting. The term "catabolism" has its commonly known meaning in the art, specifically an energy burning form of metabolism.

Muscle wasting can occur as a result of a pathology, disease, condition or disorder. In one embodiment, the pathology, illness, disease or condition is chronic. In another embodiment, the pathology, illness, disease or condition is genetic. In another embodiment, the pathology, illness, disease or condition is neurological. In another embodiment, the pathology, illness, disease or condition is infectious. As described herein, the pathologies, diseases, conditions or disorders for which the compounds and compositions of the present invention are administered are those that directly or indirectly produce a wasting (i.e. loss) of muscle mass, that is a muscle wasting disorder.

In one embodiment, muscle wasting in a subject is a result of the subject having a muscular dystrophie; muscle atrophy; X-linked spinal-bulbar muscular atrophy (SBMA), cachexia; malnutrition, tuberculosis, leprosy, diabetes, renal disease, chronic obstructive pulmonary disease (COPD), cancer, end stage renal failure, sarcopenia, emphysema, osteomalacia, or cardiomyopathy.

In another embodiment, the muscle wasting disorder is due to infection with enterovirus, Epstein-Barr virus, herpes zoster, HIV, trypanosomes, influenze, coxsackie, rickettsia, trichinella, schistosoma or mycobacteria.

The muscular dystrophies are genetic diseases characterized by progressive weakness and degeneration of the skeletal or voluntary muscles that control movement. The muscles of the heart and some other involuntary muscles are also affected in some forms of muscular dystrophy. The major forms of muscular dystrophy (MD) are: duchenne muscular dystrophy, myotonic dystrophy, duchenne muscular dystrophy, becker muscular dystrophy, limb-girdle muscular dystrophy, facioscapulhumeral muscular dystrophy, congenital muscular dystrophy, oculopharyngeal muscular dystrophy, distal muscular dystrophy and emery-dreifuss muscular dystrophy.

Muscular dystrophy can affect people of all ages. Although some forms first become apparent in infancy or childhood, others may not appear until middle age or later. Duchenne MD is the most common form, typically affecting children. Myotonic dystrophy is the most common of these diseases in adults.

Muscle atrophy (MA) is characterized by wasting away or diminution of muscle and a decrease in muscle mass. For example, Post-Polio MA is a muscle wasting that occurs as part of the post-polio syndrome (PPS). The atrophy includes weakness, muscle fatigue, and pain.

Another type of MA is X-linked spinal-bulbar muscular atrophy (SBMA—also known as Kennedy's Disease). This disease arises from a defect in the androgen receptor gene on the X chromosome, affects only males, and its onset is in adulthood. Because the primary disease cause is an androgen receptor mutation, androgen replacement is not a current therapeutic strategy. There are some investigational studies where exogenous testosterone propionate is being given to boost the levels of androgen with hopes of overcoming androgen insensitivity and perhaps provide an anabolic effect. Still, use of supraphysiological levels of testosterone for supplementation will have limitations and other potentially serious complications.

Cachexia is weakness and a loss of weight caused by a disease or as a side effect of illness. Cardiac cachexia, i.e. a muscle protein wasting of both the cardiac and skeletal muscle, is a characteristic of congestive heart failure. Cancer cachexia is a syndrome that occurs in patients with solid tumors and hematological malignancies and is manifested by weight loss with massive depletion of both adipose tissue and lean muscle mass.

Cachexia is also seen in acquired immunodeficiency syndrome (AIDS), human immunodeficiency virus (HIV)-associated myopathy and/or muscle weakness/wasting is a relatively common clinical manifestation of AIDS. Individuals with HIV-associated myopathy or muscle weakness or wasting typically experience significant weight loss, generalized or proximal muscle weakness, tenderness, and muscle atrophy.

Sarcopenia is a debilitating disease that afflicts the elderly and chronically ill patients and is characterized by loss of muscle mass and function. Further, increased lean body mass is associated with decreased morbidity and mortality for certain muscle-wasting disorders. In addition, other circumstances and conditions are linked to, and can cause muscle wasting disorders. For example, studies have shown that in severe cases of chronic lower back pain, there is paraspinal muscle wasting.

Muscle wasting is also associated with advanced age. It is believed that general weakness in old age is due to muscle wasting. As the body ages, an increasing proportion of skeletal muscle is replaced by fibrous tissue. The result is a significant reduction in muscle power, performance and endurance.

Long term hospitalization due to illness or injury, or disuse deconditioning that occurs, for example, when a limb is immobilized, can also lead to muscle wasting. Studies have shown that in patients suffering injuries, chronic illnesses, burns, trauma or cancer, who are hospitalized for long periods of time, there is a long-lasting unilateral muscle wasting, with a consequent decrease in body mass.

Injuries or damage to the central nervous system (CNS) are also associated with muscle wasting disorders. Injuries or damage to the CNS can be, for example, caused by diseases, trauma or chemicals. Examples are central nerve injury or damage, peripheral nerve injury or damage and spinal cord injury or damage.

In another embodiment, muscle wasting may be a result of alcoholism, and may be treated with the compounds and compositions of the invention, representing embodiments thereof.

In one embodiment, the invention provides a use of SARM compound of the present invention for preventing a muscle wasting disorder in a subject. In another embodiment the use of a SARM compound of the present invention or its prodrug, analog, isomer, metabolite, derivative, pharmaceutically acceptable salt, pharmaceutical product, polymorph, crystal, impurity, N-oxide, hydrate or any combination thereof. In another embodiment, the administering comprises administering a pharmaceutical composition comprising said SARM and/or its prodrug, analog, isomer, metabolite, derivative, pharmaceutically acceptable salt, pharmaceutical product, hydrate, N-oxide, or any combination thereof; and a pharmaceutically acceptable carrier. Thus, preventing a muscle wasting disorder in a subject.

In one embodiment, the invention provides a use of SARM compound of this invention for treating a muscle-wasting conditions associated with chronic illness. In another embodiment the use of a SARM compound or its prodrug, analog, isomer, metabolite, derivative, pharmaceutically acceptable salt, pharmaceutical product, polymorph, crystal, impurity, N-oxide, hydrate or any combination thereof, or a composition comprising the same. In another embodiment, the use of the SARM compounds is orally administered to said subject.

In one embodiment, the present invention provides a use of a SARM compound of the present invention for preventing a muscle wasting disorder in a subject, in another embodiment, suppressing a muscle wasting disorder in a subject, in another embodiment inhibiting a muscle wasting disorder in a subject, in another embodiment reducing the incidence of a muscle wasting in a subject. In another embodiment the use of a SARM or its prodrug, analog, isomer, metabolite, derivative, pharmaceutically acceptable salt, pharmaceutical product, polymorph, crystal, impurity, N-oxide, hydrate or any combination thereof, or a composition comprising the same.

In another embodiment, this invention provides for the use of a SARM compound of this invention, or its prodrug, analog, isomer, metabolite, derivative, pharmaceutically acceptable salt, pharmaceutical product, polymorph, crystal, impurity, N-oxide, hydrate or any combination thereof, or a composition comprising the same, in treating, preventing, suppressing, inhibiting or reducing the incidence of a muscle wasting disorder in a subject.

In another embodiment, this invention provides for the use of a SARM of this invention, or its prodrug, analog, isomer, metabolite, derivative, pharmaceutically acceptable salt, pharmaceutical product, polymorph, crystal, impurity, N-oxide, hydrate or any combination thereof, or a composition comprising the same, in increasing muscle performance, muscle size, muscle strength, or any combination thereof in a subject.

In another embodiment, the SARMs and compositions of this invention are useful in promoting or speeding recovery following a surgical procedure.

In one embodiment, the present invention provides a use of a SARM compound of the present invention for reducing a fat mass in a subject. In another embodiment the use of a SARM compound of the present invention or its prodrug, analog, isomer, metabolite, derivative, pharmaceutically acceptable salt, pharmaceutical product, polymorph, crystal, impurity, N-oxide, hydrate or any combination thereof, or a composition comprising the same.

In another embodiment, this invention provides for the use of a SARM compound of the present invention, or its prodrug, analog, isomer, metabolite, derivative, pharmaceutically acceptable salt, pharmaceutical product, polymorph, crystal, impurity, N-oxide, hydrate or any combination thereof, or a composition comprising the same, in treating obesity or diabetes associated with a metabolic syndrome in a subject In another embodiment, the subject has a hormonal imbalance, disorder, or disease. In another embodiment the subject has menopause.

In one embodiment, the present invention provides a use of a SARM compound of the present invention for increasing a lean mass in a subject. In another embodiment the use of a SARM compound of the present invention or its prodrug, analog, isomer, metabolite, derivative, pharmaceutically acceptable salt, pharmaceutical product, polymorph, crystal, impurity, N-oxide, hydrate or any combination thereof. Thus, increasing a lean mass in a subject.

In another embodiment the subject has a hormonal imbalance, disorder, or disease. In another embodiment the subject has menopause.

FIGS. 3-9 demonstrate that compound of formula III is anabolic yet minimally androgenic, thus such compounds may be useful in treating patient groups in which androgens were contraindicated in the past. Compound of formula III was shown to stimulate muscle growth, whether in the presence or absence of testosterone while exerting anti-proliferative effects on the prostate, thus, in one embodiment, the SARMs of this invention restore lost muscle mass in patients with sarcopenia or cachexia.

The present invention provides, in one embodiment, a safe and effective method for treating, preventing, suppressing, inhibiting or reducing loss of muscle and/or muscle protein catabolism due to muscle wasting. The invention is useful, in another embodiment, in treating a subject suffering from a muscle wasting disorder, or in another embodiment in treating a bone related disorder. In one embodiment, the subject is a mammalian subject.

In another embodiment, this invention relates to a method of preventing, suppressing, inhibiting or reducing the incidence of obesity in a subject, comprising the step of administering to the subject a SARM of this invention and/or its analog, derivative, isomer, metabolite, pharmaceutically acceptable salt, pharmaceutical product, hydrate, N-oxide, prodrug, polymorph, crystal, or any combination thereof, in an amount effective to prevent, suppress, inhibit or reduce the incidence of obesity in the subject.

In one embodiment, the SARM compounds of the present invention alter the levels of leptin in a subject. In another embodiment, the SARM compound of the present invention decreases the levels of leptin. In another embodiment, the SARM compound of the present invention increases the levels of leptin in a subject. Leptin is known to have an effect on appetite on weight loss in obese mice, and thus has been implicated in obesity.

The SARMs of this invention, in one embodiment, affect circulating, or in another embodiment, tissue levels of leptin. In one embodiment, the term 'level/s of leptin' refers to the serum level of leptin. As contemplated herein, the SARM compounds of the present invention have an effect on leptin in-vitro and in-vivo. Leptin levels can be measured by methods known to one skilled in the art, for example by commercially available ELISA kits. In addition, Leptin levels may be determined in in-vitro assays, or in in-vivo assays, by any method known to a person skilled in the art.

Since leptin is implicated in controlling appetite, weight loss, food intake, and energy expenditure, modulating and/or controlling the levels of leptin is a useful therapeutic approach in treating preventing, inhibiting or reducing the incidence of obesity in subjects suffering from obesity. Modulating the level of leptin can result in a loss of appetite, a reduction of food intake, and an increase in energy expenditure in the subject, and thus may contribute to the control and treatment of obesity.

The term "obesity" is defined, in one embodiment, as an increase in body weight beyond the limitation of skeletal and physical requirement, as the result of excessive accumulation of fat in the body.

The term "obesity-associated metabolic disorder" refers, in one embodiment, to a disorder which results from, is a consequence of, is exacerbated by or is secondary to obesity. Non-limiting examples of such a disorder are osteoarthritis, Type II diabetes mellitus, increased blood pressure, stroke, and heart disease.

The term "osteoarthritis" refers, in another embodiment, to a non-inflammatory degenerative joint disease occurring chiefly in older people, characterized by degeneration of the articular cartilage, hypertrophy of bones and the margins and changes in the synovial membrane. It is accompanied, in other embodiments, by pain and stiffness, particularly after prolonged activity.

The term "diabetes", in one embodiment, refers to a relative or absolute lack of insulin leading to uncontrolled carbohydrate metabolism. Most patients can be clinically classified as having either insulin-dependent diabetes mellitus (IDDM or Type-I diabetes) or non-insulin-dependent diabetes mellitus (NIDDM or Type-II diabetes).

The term "increased blood pressure" or "hypertension" refers, in other embodiments, to a repeatedly high blood pressure above 140 over 90 mmHg. Chronically-elevated blood pressure can cause blood vessel changes in the back of the eye, thickening of the heart muscle, kidney failure, and brain damage.

The term "stroke" refers, in other embodiments, to damage to nerve cells in the brain due to insufficient blood supply often caused by a bursting blood vessel or a blood clot. The term "heart disease", in other embodiments, refers to a malfunction in the heart normal function and activity, including heart failure.

In addition, androgens have recently been shown to be involved in commitment of mesenchymal pluripotent cells into myogenic lineage and to block differentiation into adipogenic lineage (Singh et al., Endocrinology, 2003, Jul. 24). Accordingly, SARM compounds can be useful in methods of blocking adipogenesis, and/or altering stem cell differentiation, as described herein.

In another embodiment, this invention relates to a method of promoting, increasing or facilitating weight loss in a subject, comprising the step of administering to the subject a SARM of this invention and/or its analog, derivative, isomer, metabolite, pharmaceutically acceptable salt, pharmaceutical product, hydrate, N-oxide, prodrug, polymorph, crystal, or any combination thereof, in an amount effective to promote, increase or facilitate weight loss in the subject.

In another embodiment, this invention relates to a method of decreasing, suppressing, inhibiting or reducing appetite of a subject, comprising the step of administering to the subject a SARM of this invention and/or its analog, derivative, isomer, metabolite, pharmaceutically acceptable salt, pharmaceutical product, hydrate, N-oxide, prodrug, polymorph, crystal, or any combination thereof, in an amount effective to decrease, suppress, inhibit or reduce the appetite of the subject.

In another embodiment, this invention relates to a method of altering the body composition of a subject, comprising the step of administering to the subject a SARM of this invention and/or its analog, derivative, isomer, metabolite, pharmaceutically acceptable salt, pharmaceutical product, hydrate, N-oxide, prodrug, polymorph, crystal, or any combination thereof, in an amount effective to alter the body composition of the subject. In one embodiment, altering the body composition comprises altering the lean body mass, the fat free body mass of the subject, or a combination thereof.

In another embodiment, this invention relates to a method of altering lean body mass or fat free body mass of a subject, comprising the step of administering to the subject a SARM of this invention and/or its analog, derivative, isomer, metabolite, pharmaceutically acceptable salt, pharmaceutical product, hydrate, N-oxide, prodrug, polymorph, crystal, or any combination thereof, in an amount effective to alter the lean body mass or fat free body mass of the subject.

In another embodiment, this invention relates to a method of converting fat to lean muscle in a subject, comprising the step of administering to the subject a SARM of this invention and/or its analog, derivative, isomer, metabolite, pharmaceutically acceptable salt, pharmaceutical product, hydrate, N-oxide, prodrug, polymorph, crystal, or any combination thereof, in an amount effective to convert fat to lean muscle in the subject.

In another embodiment, this invention relates to a method of treating an obesity-associated metabolic disorder in a subject, comprising the step of administering to the subject a SARM of this invention and/or its analog, derivative, isomer, metabolite, pharmaceutically acceptable salt, pharmaceutical product, hydrate, N-oxide, prodrug, polymorph, crystal, or any combination thereof, in an amount effective to treat the obesity-associated metabolic disorder in the subject.

In another embodiment, this invention relates to a method of preventing, suppressing, inhibiting or reducing an obesity-associated metabolic disorder in a subject, comprising the step of administering to the subject a SARM of this invention and/or its analog, derivative, isomer, metabolite, pharmaceutically acceptable salt, pharmaceutical product, hydrate, N-oxide, prodrug, polymorph, crystal, or any combination thereof, in an amount effective to prevent, suppress, inhibit or reduce the obesity-associated metabolic disorder in the subject.

In one embodiment, the obesity-associated metabolic disorder is hypertension. In another embodiment, the disorder is osteoarthritis. In another embodiment, the disorder is Type II diabetes mellitus. In another embodiment, the disorder is increased blood pressure. In another embodiment, the disorder is stroke. In another embodiment, the disorder is heart disease.

In another embodiment, this invention relates to a method of decreasing, suppressing, inhibiting or reducing adipogenesis in a subject, comprising the step of administering to the subject a SARM of this invention and/or its analog, derivative, isomer, metabolite, pharmaceutically acceptable salt, pharmaceutical product, hydrate, N-oxide, prodrug, polymorph, crystal, or any combination thereof, in an amount effective to decrease, suppress, inhibit or reduce adipogenesis in the subject.

In another embodiment, this invention relates to a method of altering stem cell differentiation in a subject, comprising the step of administering to the subject a SARM of this invention and/or its analog, derivative, isomer, metabolite, pharmaceutically acceptable salt, pharmaceutical product, hydrate, N-oxide, prodrug, polymorph, crystal, or any combination thereof, in an amount effective to alter stem cell differentiation in the subject.

In another embodiment, this invention relates to a method of altering the level of leptin in a subject, comprising the step of administering to the subject a SARM of this invention and/or its analog, derivative, isomer, metabolite, pharmaceutically acceptable salt, pharmaceutical product, hydrate, N-oxide, prodrug, polymorph, crystal, or any combination thereof, in an amount effective to alter the level of leptin in the subject. In one embodiment, altering the level of leptin comprises decreasing the level of leptin in the subject.

In another embodiment, this invention relates to a method of decreasing, suppressing, inhibiting or reducing the level of leptin in a subject, comprising the step of administering to the subject a SARM of this invention and/or its analog, derivative, isomer, metabolite, pharmaceutically acceptable salt, pharmaceutical product, hydrate, N-oxide, prodrug, polymorph, crystal, or any combination thereof, in an amount effective to decrease, suppress, inhibit or reduce the level of leptin in the subject.

In one embodiment, the SARM that is useful in a) treating, preventing, suppressing, inhibiting, or reducing obesity; b) promoting, increasing or facilitating weight loss; c) decreasing, suppressing, inhibiting or reducing appetite; d) altering the body composition; e) altering lean body mass or fat free body mass; f) converting fat to lean muscle; g) treating, preventing, suppressing, inhibiting, or reducing an obesity-associated metabolic disorder, for example hypertension, osteoarthritis, Type II diabetes mellitus, increased blood pressure, stroke, or heart disease; h) decreasing, suppressing, inhibiting or reducing adipogenesis; i) altering stem cell differentiation; and/or j) altering the level of leptin, is a compound represented by the compounds of this invention In one embodiment, the SARMs of this invention find utility in treating or halting the progression of, or treating symptoms of diabetes. In another embodiment, the SARMs of this invention are useful in treating co-morbidities related to diabetes. These conditions include: hypertension, cerebrovascular disease, atherosclerotic coronary artery disease, macular degeneration, diabetic retinopathy (eye disease) and blindness, cataracts—systemic inflammation (characterized by elevation of inflammatory markers such as erythrocyte sedimentation rate or C-reactive protein), birth defects, pregnancy related diabetes, pre-eclampsia and hypertension in pregnancy, kidney disease (renal insufficiency, renal failure etc.), nerve disease (diabetic neuropathy), superficial and systemic fungal infections, congestive heart failure, gout/hyperuricemia, obesity, hypertriglyceridemia, hypercholesterolemia, fatty liver disease (non-alcoholic steatohepatitis, or NASH), and diabetes-related skin diseases such as Necrobiosis Lipoidica Diabeticorum (NLD), Blisters of diabetes (Bullosis Diabeticorum), Eruptive Xanthomatosis, Digital Sclerosis, Disseminated Granuloma Annulare, and Acanthosis Nigricans.

In one embodiment this invention provides a method for a) treating, preventing, suppressing inhibiting atherosclerosis b) treating, preventing, suppressing inhibiting liver damage due to fat deposits comprising the step of administering to the subject a SARM of this invention and/or its analog, derivative, isomer, metabolite, pharmaceutically acceptable salt, pharmaceutical product, hydrate, N-oxide, prodrug, polymorph, crystal, or any combination thereof, or a composition comprising the same, in an amount effective to treat, prevent or inhibit atherosclerosis and liver damage due to fat deposit.

In one embodiment, the SARM of this invention is useful in a) treating, preventing, suppressing, inhibiting, or reducing atherosclerosis; b) treating, preventing, suppressing inhibiting liver damage due to fat deposits.

In one embodiment atherosclerosis refers to a slow, complex disease that may begin with damage to the innermost layer of the artery. In another embodiment the causes of damage to the arterial wall may include a) elevated levels of cholesterol and in the blood; b) high blood pressure; c) tobacco smoke d) diabetes. In another embodiment, the condition is treatable in a smoker, despite the fact that tobacco smoke may greatly worsen atherosclerosis and speed its growth in the coronary arteries, the aorta and arteries in the legs. Similarly, in another embodiment, the methods of this invention may be useful in treating subjects with a family history of premature cardiovascular disease who have an increased risk of atherosclerosis.

In one embodiment, liver damage due to fat deposits refer to the build-up of fat in the liver cells forming a Fatty Liver which may be associated with or may lead to inflammation of the liver. This can cause scarring and hardening of the liver. When scarring becomes extensive, it is called cirrhosis.

In another embodiment the fat accumulates in the liver as obesity. In another embodiment fatty liver is also associated with diabetes mellitus, high blood triglycerides, and the heavy use of alcohol. In another embodiment fatty Liver may occur with certain illnesses such as tuberculosis and malnutrition, intestinal bypass surgery for obesity, excess vitamin A in the body, or the use of certain drugs such as valproic acid (trade names: Depakene/Depakote) and corticosteroids (cortisone, prednisone). Sometimes fatty liver occurs as a complication of pregnancy.

In one embodiment, the compounds and/or compositions and/or methods of use thereof are for the treatment of human subjects, wherein, in one embodiment, the subject is male, or in another embodiment, the subject is female.

In one embodiment, the methods of the present invention comprise administering a SARM compound as the sole active ingredient. However, also encompassed within the scope of the present invention are methods for hormone therapy, dry eye, obesity, treating prostate cancer, delaying the progression of prostate cancer, and for preventing and/or treating the recurrence of prostate cancer, male contraception; treatment of osteoporosis, treatment of conditions associated with ADIF and for treatment and/or prevention of chronic muscular wasting which comprise administering the SARM compounds in combination with one or more therapeutic agents. These agents include, but are not limited to: LHRH analogs, reversible antiandrogens, antiestrogens, anticancer drugs, 5-alpha reductase inhibitors, aromatase inhibitors, progestins, agents acting through other nuclear hormone receptors, selective estrogen receptor modulators (SERM), progesterone, estrogen, PDE5 inhibitors, apomorphine, bisphosphonate, and one or more additional SARMS.

Thus, in one embodiment, the methods of the present invention comprise administering the SARM compound, in combination with an LHRH analog. In another embodiment, the methods of the present invention comprise administering a SARM compound, in combination with a reversible antiandrogen. In another embodiment, the methods of the present invention comprise administering a SARM compound, in combination with an antiestrogen. In another embodiment, the methods of the present invention comprise administering a SARM compound, in combination with an anticancer drug. In another embodiment, the methods of the present invention comprise administering a SARM compound, in combination with a 5-alpha reductase inhibitor. In another embodiment, the methods of the present invention comprise administering a SARM compound, in combination with an aromatase inhibitor. In another embodiment, the methods of the present invention comprise administering a SARM compound, in combination with a progestin. In another embodiment, the methods of the present invention comprise administering a SARM compound, in combination with an agent acting through other nuclear hormone receptors. In another embodiment, the methods of the present invention comprise administering a SARM compound, in combination with a selective estrogen receptor modulators (SERM). In another embodiment, the methods of the present invention comprise administering a SARM compound, in combination with a progesterone. In another embodiment, the methods of the present invention comprise administering a SARM compound, in combination with an estrogen. In another embodiment, the methods of the present invention comprise administering a SARM compound, in combination with a PDE5 inhibitor. In another embodiment, the methods of the present invention comprise administering a SARM compound, in combination with apomorphine. In another embodiment, the methods of the present invention comprise administering a SARM compound, in combination with a bisphosphonate. In another embodiment, the methods of the present invention comprise administering a SARM compound, in combination with one or more additional SARMS.

It is to be understood that any use of the SARMs of this invention, including, inter-alia, uses in applications regarding diseases or conditions which pertain to prostate cancer, dry eye, contraception, muscle, fat, cardiac, liver, gonadal or bone tissue, whereby administration of the SARM compounds of this invention, or a composition comprising the same, alter the course of such diseases or conditions favorably for a subject, are to be considered as part of this invention.

The following examples are presented in order to more fully illustrate the preferred embodiments of the invention. They should in no way, however, be construed as limiting the broad scope of the invention.

EXAMPLES

Example 1

Effects of SARM Compound of Formula II on Progenitor Cell Differentiation to Osteoblasts and Osteoclasts Materials and Methods Chemicals A mixture comprising the compound of formula III, DHT and PTH were prepared at concentrations ranging from 1 nM-1 μM.

Animals

Four month old female rats were sacrificed by euthanasia and the femurs were excised from the animals. The femurs were cleaned off any muscle and connective tissues and were stored on ice in Minimum Essential Medium (MEM) with penicillin, Streptomycin and Fungizone until the cells were cultured.

Bone Marrow Cell Culture

All cell culture materials were obtained from Invitrogen (Carlsbad, Calif.). The femurs were first rinsed in 70% ethanol and were washed three times with 5 ml each of penicillin and streptomycin. Both the ends of the femurs were snapped and the bone marrow cells were flushed with 15 ml of MEM with penicillin, Streptomycin and Fungizone into a 50 ml conical tube and stored on ice. The same procedure was performed with all the femurs. The bone marrow cells and were pooled were centrifuged at 1000 rpm for 5 min in a clinical centrifuge. The cells were resuspended in MEM without phenol red supplemented with 10% charcoal stripped serum, penicillin, streptomycin and fungizone. The cells were triturated through a 22 g needle, counted under microscope and were plated at 1.5 million cells per well of a 6 well plate in MEM without phenol red supplemented with 15% charcoal stripped serum, penicillin streptomycin, 300 ng/ml fungizone, 0.28 mM Ascorbic acid and 10 mM β-glycerophosphate to differentiate towards fibroblast/osteoblast lineage and at 2.5 million cells per well of a 24 well plate in MEM without phenol red supplemented with 10% charcoal stripped serum, penicillin streptomycin and 300 ng/ml fungizone to differentiate towards osteoclast lineage. The medium was changed on day 2 and the cells were treated with the indicated hormone. Osteoclast cultures were carried out in the presence of 50 ng RANK Ligand and 10 ng GM-CSF to induce osteoclastogenesis. Medium was completely changed every third day for osteoclast cultures. For fibroblast cultures, half the culture medium was changed every third day to leave the growth factors secreted by the cells.

Staining of Cells

At the end of 12 days, the cells were fixed in 10% buffered formalin for fibroblast cultured and in 4% formaldehyde in PBS for osteoclast cultures. The fibroblasts were stained for alkaline phosphatase activity and the O.D. at 405 nm was measured using a spectrophotometer as described earlier. Osteoclasts were stained for Tartarate Resistant Acid Phosphatase Activity (TRAP) and cells having 2 or more nuclei were counted under the microscope and plotted as indicated earlier.

Results

SARMs are Potent Inducers of Differentiation of Bone Marrow Cells Towards the Osteoblast and Osteoclast Lineage Androgens exert anabolic effects on bone and lack of androgens under conditions such as androgen deprivation therapy in prostate cancer and in old age have clearly indicated the benefits of androgens as a bone protective hormone. However, the use of ectopic androgen is limited due to its side effects and also due to the risk of conversion of androgens to estrogens.

In order to determine whether a SARM could be therapeutic yet obviate the above side-effects, various SARMs were evaluated in terms of their ability to have bone protective effects, with fewer side effects, as seen with the parent hormone. The efficacy of dihydrotestosterone (DHT) and Parathyroid hormone (PTH) were compared to a SARM, the compound of formula III, in terms of their ability to differentiate primary rat bone marrow cells towards the osteoblast and the osteoclast lineage (FIGS. 1 and 2). Bone marrow cells from rats were cultured in the presence or absence of the above indicated hormones for 12 days in culture medium and were evaluated in terms of their differentiation towards osteoblast or osteoclast lineage.

DHT and the compound of formula III all increased differentiation of primary bone marrow cells toward the osteoblast lineage as measured by alkaline phosphatase (ALP) activity of the cells (FIG. 1). At 1 μM concentration, DHT and the SARM induced the ALP activity comparably whereas at lower concentrations of 100 nM and 10 nM Compound III showed better induction than the DHT. PTH, another bone anabolic hormone induced the ALP staining only at higher concentration but not at lower concentrations.

FIG. 2 shows a clear increase in the number of TRAP positive multinucleated osteoclasts, when cells were incubated in the presence of RANK ligand and GM-CSF. Treatment of cells with DHT or SARM significantly inhibited RANK ligand and GM-CSF- induced TRAP positive multinucleated osteoclast proliferation. PTH inhibited induction at higher concentrations, however, at lower concentrations, PTH increased the number of TRAP positive osteoclasts. Estradiol inhibited osteoclastogenesis, at all dosages evaluated.

Example 2

SARM Bone Effects Alone and in Combination with the Anti-Resorptive Agent, Alendronate Materials and Methods Sixty female, virgin, intact Sprague-Dawley rats were obtained from Charles River Laboratories (Wilmington, Mass.) and aged to 23 wks. The animals were housed 2-3 per cage and acclimated to a 12-h light/dark cycle. Food (7012C L-485 Mouse/Rat Sterilizable Diet, Harlan Teklad, Madison, Wis.) and water were provided ad libitum. The Institutional Animal Care and Use Committee of the University of Tennessee reviewed and approved the animal protocol for this study.

Sham surgeries or ovariectomies were performed on Day 0. The study was comprised of six treatment groups as follows: (1) intact+vehicle, (2) intact+COMPOUND III, (3) OVX+ vehicle, (4) OVX+COMPOUND III, (5) OVX+alendronate (6) OVX+alendronate+COMPOUND III. Doses were administered daily via oral gavage in a vehicle of DMSO:PEG300 (10:90) beginning on Day 1. Animals were sacrificed on Day 45 of the study. Femurs were removed, cleared of soft tissue, and stored in saline soaked gauze at −20° C. until analysis. Nine animals died during the course of the study. These deaths were attributed to surgical complications arising from the ovariectomies and technical errors during oral dosing (i.e., dosing solution delivered into the lungs). Dose groups are listed in Table 1.

TABLE 1

| Group | Gonadal Status | Treatment | Dose | Animals/group |
|---|---|---|---|---|
| 1 | Intact | Vehicle | N/A | 9 |
| 2 | Intact | COMPOUND III | 3 mg/day | 9 |
| 3 | OVX | Vehicle | N/A | 7 |
| 4 | OVX | COMPOUND III | 3 mg/day | 8 |
| 5 | OVX | Alendronate | 1 mg/day | 10 |
| 6 | OVX | Alendronate/ COMPOUND III | 1 and 3 mg/day | 8 |

The left femurs were sent to SkeleTech Inc. (Bothell, Wash.) for biomechanical strength (three point bending) and pQCT analysis. A Stratec XCT RM and associated software (Stratec Medizintechnik GmbH, Pforzheim, Germany. Software version 5.40 C) were used for the pQCT analysis. The femur was analyzed at both the mid-shaft and distal regions. The mid-shaft analysis was performed on the region at 50% of the length of the femur. The distal analysis was performed on the region at 20% of the length of the femur starting at the distal end. One 0.5 mm slice perpendicular to the long axis of the femur was used for analysis. Total bone mineral content, total bone area, total bone mineral density, cortical bone mineral content, cortical bone area, cortical bone mineral density, cortical thickness, periosteal perimeter (circumference) and endosteal perimeter were determined at the mid-shaft of the femur. At the distal femur, total bone mineral content, total bone area, total bone mineral density, trabecular bone mineral content, trabecular bone area and trabecular bone mineral density were determined. Following pQCT analysis, the femoral strength was determined by a three-point bending test. The anterior to posterior diameter (APD) (unit:mm) at the midpoint of the femoral shaft was measured with an electronic caliper. The femur was placed on the lower supports of a three-point bending fixture with the anterior side of the femur facing downward in an Instron Mechanical Testing Machine (Instron 4465 retrofitted to 5500)(Canton, MA). The length (L) between the lower supports was set to 14 mm. The upper loading device was aligned to the center of the femoral shaft. The load was applied at a constant displacement rate of 6 mm/min until the femur broke. The mechanical testing machine directly measured the maximum load ($F_u$) (unit:N), stiffness (S) (units:N/mm), and energy absorbed (W) (unit:mJ). The axial area moment of inertia (I) (unit: $mm^4$) was calculated by the software during the pQCT analysis of the femoral mid-shaft. Stress ($\sigma$) (units:N/$mm^2$), elastic modulus (E) (unit:Mpa), and toughness (T) (units:mJ/$m^3$) were calculated by the following formulas: stress: $\sigma=(F_u*L*(a/2))/(4*I)$; elastic modulus: $E=S*L^3/(48*I)$; and toughness: $T=3*W*(APD/2)^2/(L*I)$.

Statistical analysis was performed by Student's T-test. P-values of less than 0.05 were considered as statistically significant differences.

Results

Figure 3:
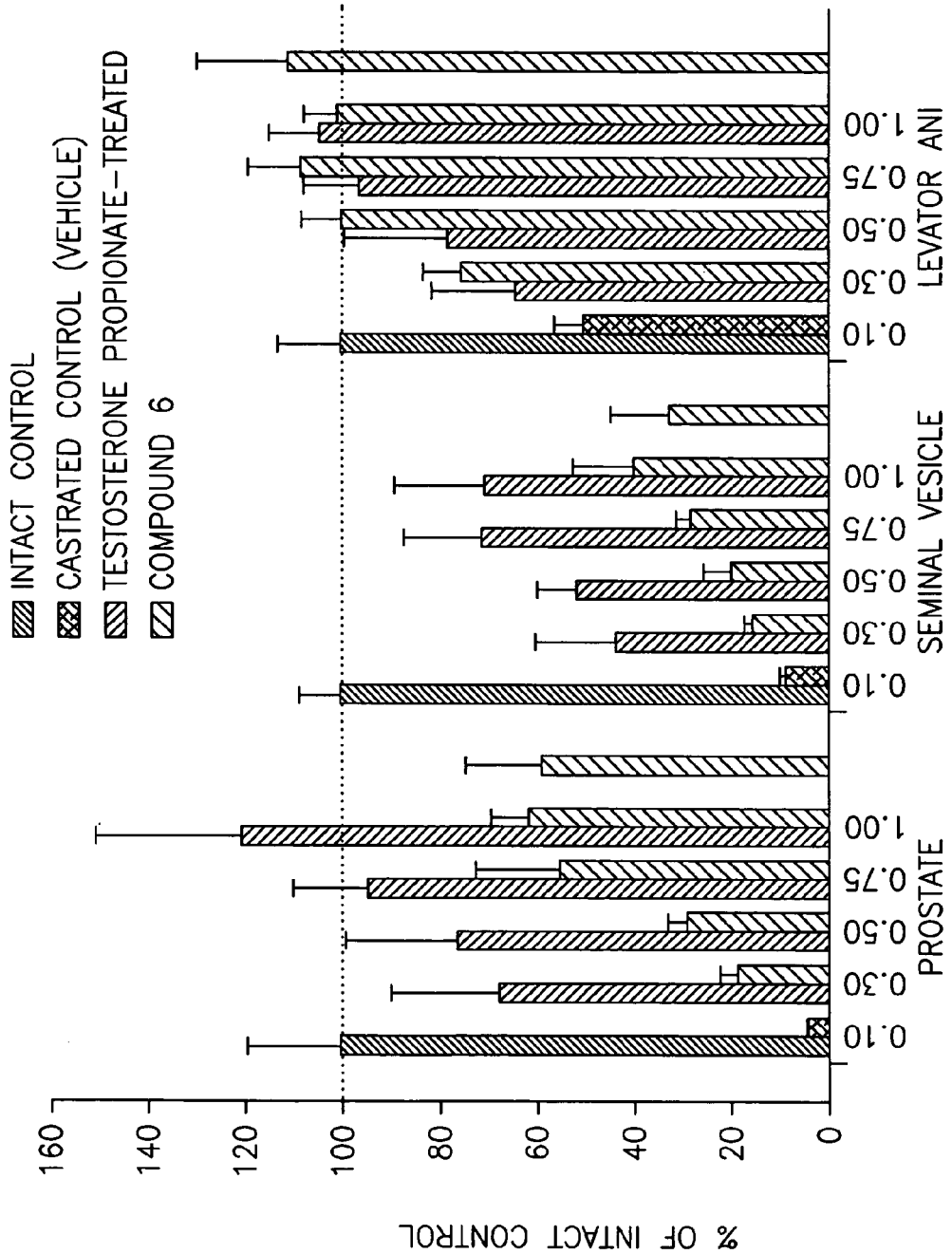
FIG. 3: Femoral maximum load determined by 3-point bending of the femur.

Femoral maximum load was determined by 3-point bending of the femur. Results are shown in FIG. 3. No differences were observed between the intact vehicle (210 N) and the OVX vehicle (212 N) control groups. We observed trends in the COMPOUND III treated groups with maximum load increasing to 224 and 233 newtons in the intact and OVX groups, respectively. The alendronate (213 N) and alendronate+COMPOUND III (207N) groups were not different from controls.

Figure 4:
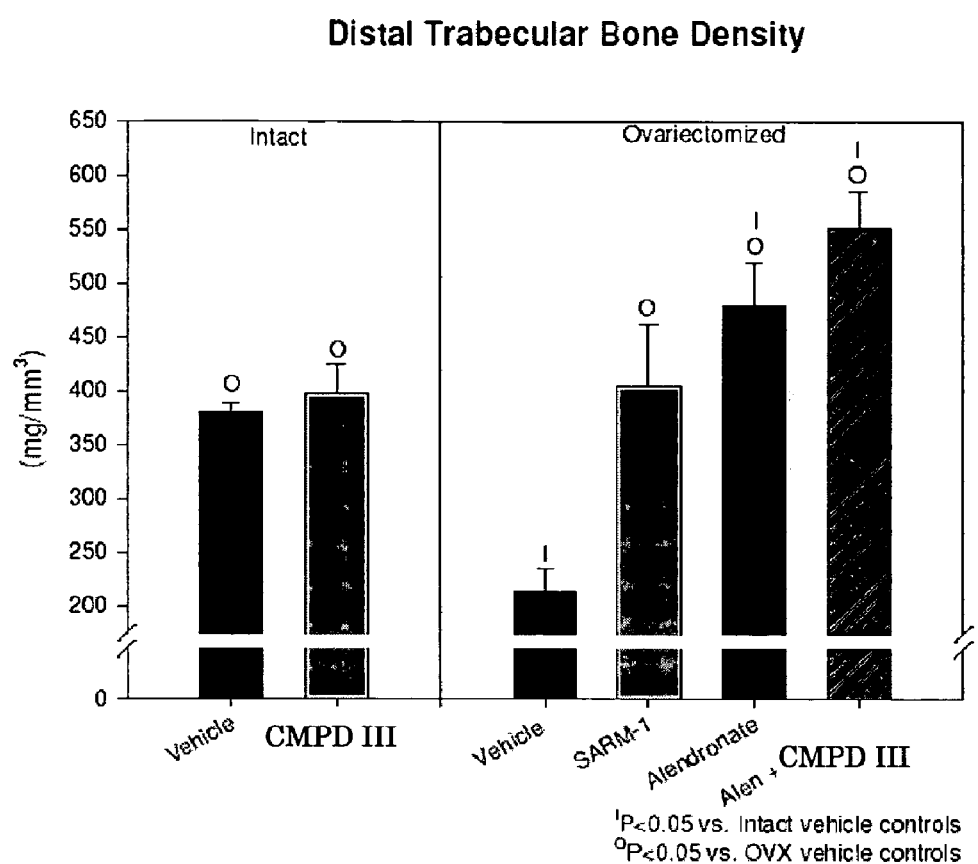
FIG. 4: Trabecular bone mineral density determined by pQCT analysis of the distal femur.

Trabecular bone mineral density was analyzed by pQCT at the distal femur. Results are shown in FIG. 4. We observed significant trabecular bone loss following OVX. Trabecular bone density decreased from 379 to 215 mg/$mm^3$ in the intact and OVX vehicle control groups, respectively. In intact animals treated with COMPOUND III, we observed a slight increase in trabecular bone density to 398 mg/$mm^3$. In OVX animals treated with COMPOUND III, we observed a significant increase over the OVX vehicle control group to 406 mg/$mm^3$. Alendronate increased trabecular bone density to 480 mg/$mm^3$. The combination therapy of Alendronate and COMPOUND III showed additive effects increasing trabecular bone density to 552 mg/$mm^3$.

Example 3

Androgenic & Anabolic Activity in Intact and ORX Rats of Compound III

Materials and Methods

Male Sprague-Dawley rats weighing approximately 200 g were purchased from Harlan Bioproducts for Science (Indianapolis, Ind.). The animals were maintained on a 12-h light/dark cycle with food (7012C L-485 Mouse/Rat Sterilizable Diet, Harlan Teklad, Madison, Wis.) and water available ad libitum. The animal protocol was reviewed and approved by the Institutional Animal Care and Use Committee of the University of Tennessee. Anabolic and androgenic activity of Compound III in intact animals was evaluated, and the dose response in acutely orchidectomized (ORX) animals was evaluated as well. Regenerative effects of Compound III in chronically (9 days) ORX rats were also assessed.

The compound was weighed and dissolved in 10% DMSO (Fisher) diluted with PEG 300 (Acros Organics, NJ) for preparation of the appropriate dosage concentrations. The animals were housed in groups of 2 to 3 animals per cage. Intact and ORX animals were randomly assigned to one of seven groups consisting of 4 to 5 animals per group. Control groups (intact and ORX) were administered vehicle daily. Compound III was administered via oral gavage at doses of 0.01, 0.03, 0.1, 0.3, 0.75, and 1 mg/day to both intact and ORX groups.

Castrated animals (on day one of the study) were randomly assigned to dose groups (4-5 animals/group) of 0.01, 0.03, 0.1, 0.3, 0.75, and 1 mg/day, for dose-response evaluation. Dosing began nine days post ORX and was administered daily via oral gavage for fourteen days. The animals were sacrificed under anesthesia (ketamine/xyalzine, 87:13 mg/kg) after a 14-day dosing regimen, and body weights were recorded. In addition, ventral prostate, seminal vesicles, and levator ani muscle were removed, individually weighed, normalized to body weight, and expressed as a percentage of intact control. Student's T-test was used to compare individual dose groups to the intact control group. Significance was defined a priori as a P-value <0.05. As a measure of androgenic activity, ventral prostate and seminal vesicle weights were evaluated, whereas levator ani muscle weight was evaluated as a measure of anabolic activity. Blood was collected from the abdominal aorta, centrifuged, and sera were frozen at −80° C. prior to determination of serum hormone levels. Serum lutenizing hormone (LH) and follicle stimulating hormone (FSH) concentrations were determined.

Results

Figure 5:
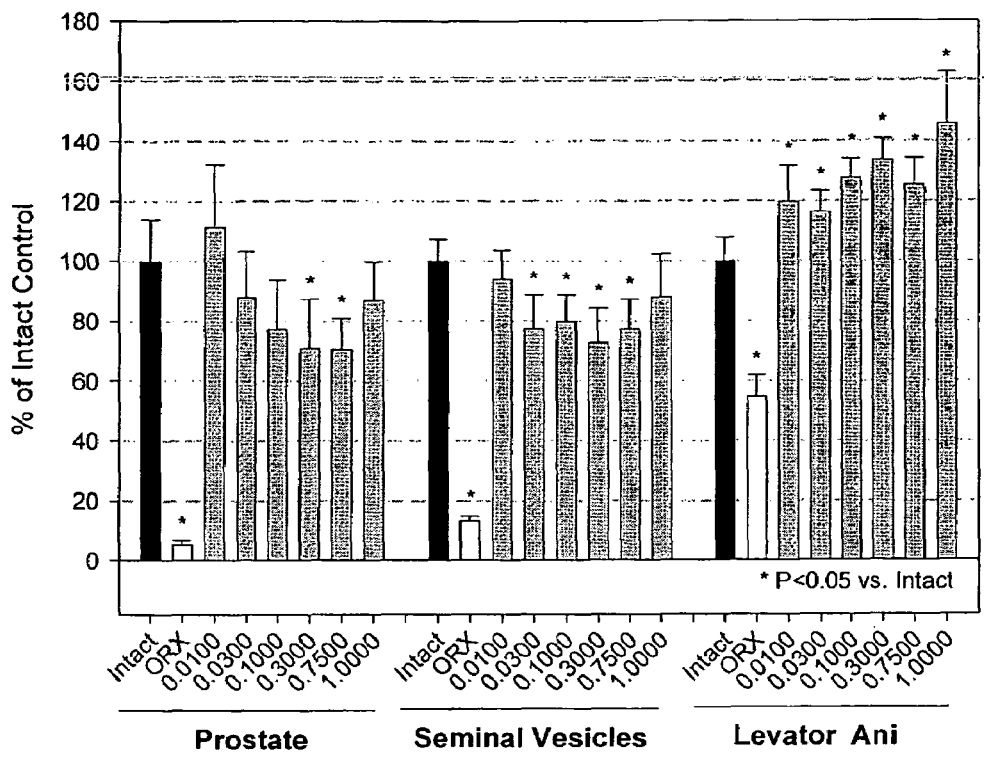
FIG. 5: Pharmacology of compound of formula III in intact rats.
Figure 6:
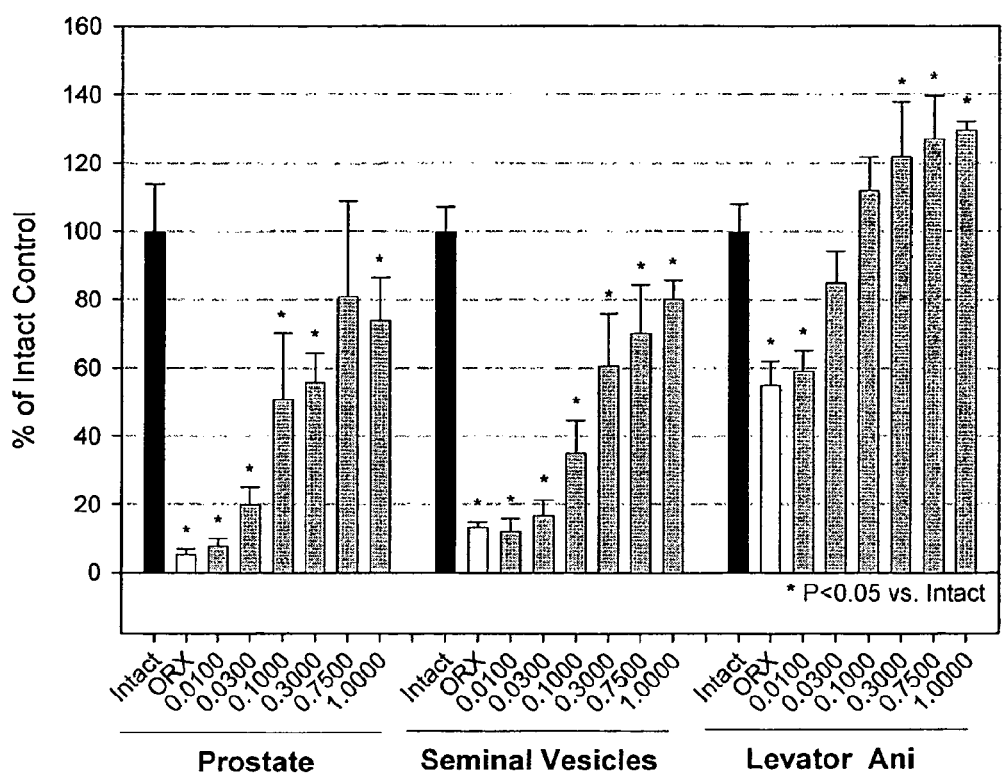
FIG. 6: Organ weights from castrated, compound of formula III-treated rats presented as a percentage of intact control. * P-value <0.05 versus intact controls.
Figure 7:
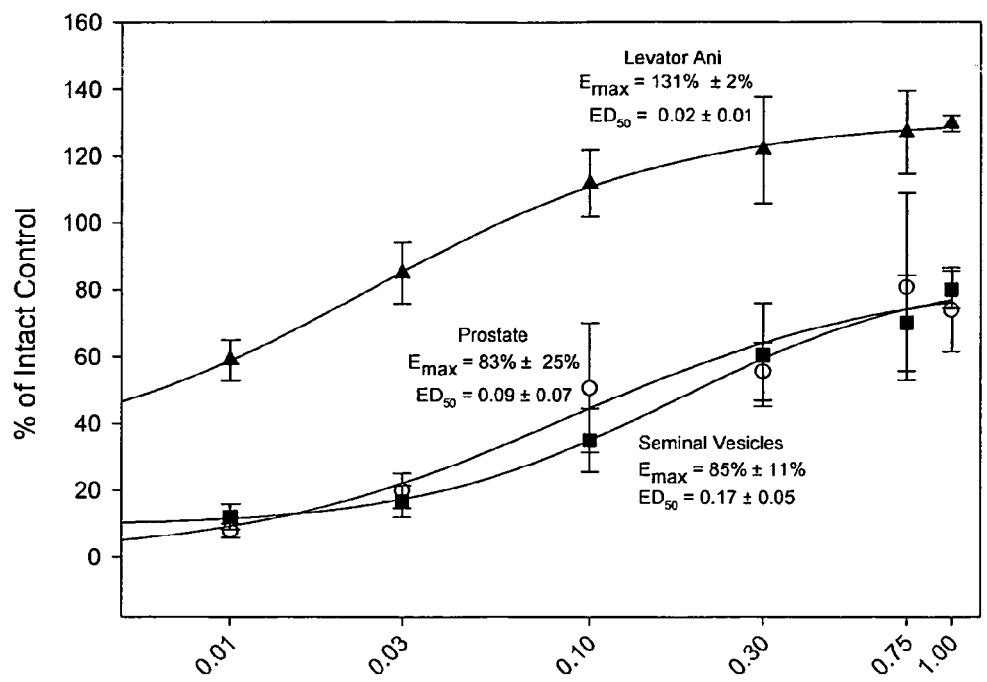
FIG. 7: Organ weight maintenance dose-response curves for compound of formula III in castrated rats. $E_{max}$ and $ED_{50}$ values for the levator ani (closed triangles), prostate (open circles), and seminal vesicles (closed squares) were obtained by nonlinear regression analysis using the sigmoid $E_{max}$ model in WinNonlin®.

Prostate weights following Compound III treatment were 111% ±21%, 88% ±15%, 77% ±17%, 71% ±16%, 71% ±10%, and 87% ±13% of intact controls following doses of 0.01, 0.03, 0.1, 0.3, 0.75, and 1 mg/day, respectively (FIG. 5). Similarly, seminal vesicle weights decreased to 94% 9%, 77% ±11%, 80% ±9%, 73% ±12%, 77% ±10%, and 88% ±14% of intact controls following doses of 0.01, 0.03, 0.1, 0.3, 0.75, and 1 mg/day, respectively. Significant increases were seen in levator ani muscle weights of sham animals, however, in all dose groups, when compared to intact controls. The levator ani muscle weights were 120% ±12%, 116% ±7%, 128% ±7%, 134% ±7%, 125% ±9%, and 146%

±17% of intact controls corresponding to 0.01, 0.03, 0.1, 0.3, 0.75, and 1.0 mg/day dose groups, respectively. The results are presented graphically in FIG. 5.

Compound III partially maintained prostate weight following orchidectomy. Prostate weight in vehicle treated ORX controls decreased to 5% ±1% of intact controls. At doses of 0.01, 0.03, 0.1, 0.3, 0.75, and 1.0 mg/day, Compound III maintained prostate weights at 8% ±2%, 20% ±5%, 51%±19%, 56% ±9%, 80% ±28%, and 74±12.5% of intact controls, respectively. In castrated controls, seminal vesicle weight decreased to 13% ±2% of intact controls. Compound III partially maintained seminal vesicle weights in ORX animals. Seminal vesicle weights from drug treated animals were 12%±4%, 17% ±5%, 35% ±10%, 61% ±15%, 70% ±14%, and 80% ±6% of intact controls, following doses of 0.01, 0.03, 0.1, 0.3, 0.75, and 1.0 mg/day, respectively. In ORX controls the levator ani muscle weight decreased to 55% ±7% of intact controls. We observed an anabolic effect in the levator ani muscle of Compound III treated animals. Compound III fully maintained levator ani muscle weights at doses >0.1 mg/day. Doses >0.1 mg/day resulted in significant increases in levator ani weight compared to that observed in intact controls. Levator ani muscle weights as a percentage of intact controls were 59%±6%, 85% ±9%, 112% ±10%, 122% ±16%, 127±12%, and 129.66±2% for the 0.01, 0.03, 0.1, 0.3, 0.75, and 1.0 mg/day dose groups, respectively. Results are graphically presented in FIG. 6. $E_{max}$ and $ED_{50}$ values were determined in each tissue by nonlinear regression analysis in WinNonlin® and presented in FIG. 7. $E_{max}$ values were 83% ±25%, 85% ±11%, and 131% ±2% for prostate, seminal vesicles, and levator ani, respectively. The $ED_{50}$ in prostate, seminal vesicles, and levator ani was 0.09±0.07, 0.17±0.05, and 0.02±0.01 mg/day, respectively.

Serum Hormone Analysis

Serum LH and FSH data for the animals are presented in Table 2. LH decreased in a dose-dependent manner in both intact and castrated animals. Following doses >0.1 mg/day, LH levels were below the limit of quantitation (0.07 ng/mL). The 0.1 mg/day dose in ORX animals returned LH levels back to those seen in intact controls. Similar effects were observed with FSH. In intact animals, a significant decrease in FSH levels was observed with the 0.75 and 1 mg/day doses. In ORX animals, a dose-dependent decrease in FSH levels was observed. Doses of Compound III >0.1 mg/day in ORX animals returned FSH levels to those of intact controls.

Androgenic & Anabolic Activity Following Delayed Dosing

Compound III partially restored both prostate and seminal vesicle weight in ORX animals. Prostates were restored to 9% ±3%, 11% ±3%, 23% ±5%, 50% ±13%, 62% ±12%, and 71% ±5%, while seminal vesicles were restored 7% ±1%, 9% ±1%, 23% ±8%, 49% ±5%, 67% ±12%, and 67% ±11% of intact controls for the 0.01, 0.03, 0.1, 0.3, 0.75, and 1.0 mg/day dose groups, respectively. Compound III fully restored levator ani muscle weight at doses >0.1 mg/day. Levator ani muscle weights were restored to 56% ±7%, 82% ±9%, 103% ±11%, 113% ±11%, 121% ±7%, and 120%±7% corresponding to doses of 0.01, 0.03, 0.1, 0.3, 0.75, and 1.0 mg/day, respectively. Results are presented graphically in FIG. 8. $E_{max}$ and $ED_{50}$ values were determined in each tissue by nonlinear regression analysis in WinNonlin® and presented in FIG. 9. $E_{max}$ values were 75% ±8%, 73% ±3%, and 126% ±4% for prostate, seminal vesicles, and levator ani, respectively. The $ED_{50}$ in prostate, seminal vesicles, and levator ani was 0.22±0.05, 0.21±0.02, and 0.013±0.01 mg/day, respectively.

Example 4

Pharmacokinetic Characterization of the Novel Oral Anabolic SARM Compound III in Humans Pharmacokinetic after 72 hours Materials and Methods Cohorts of a maximum of 12 healthy male volunteers were dosed at each dose level (9 active, 3 placebo) in a randomized, double-blind study design. Eight cohorts were recruited (aged 18-45 years) and each cohort received one single oral dose corresponding to either 1, 3, 10, 30 or 100 mg compound III (or placebo of equal volume of PEG300) in solution, or 3 or 30 mg in experimental capsules. The effect of micronization (i.e. particle size reduction) was investigated on the pharmacokinetics of compound III in the 30 mg solid oral dosage form. Samples for pharmacokinetic assessment of parent drug were taken for up to 72 hours following dosing.

Results

Figure 10:
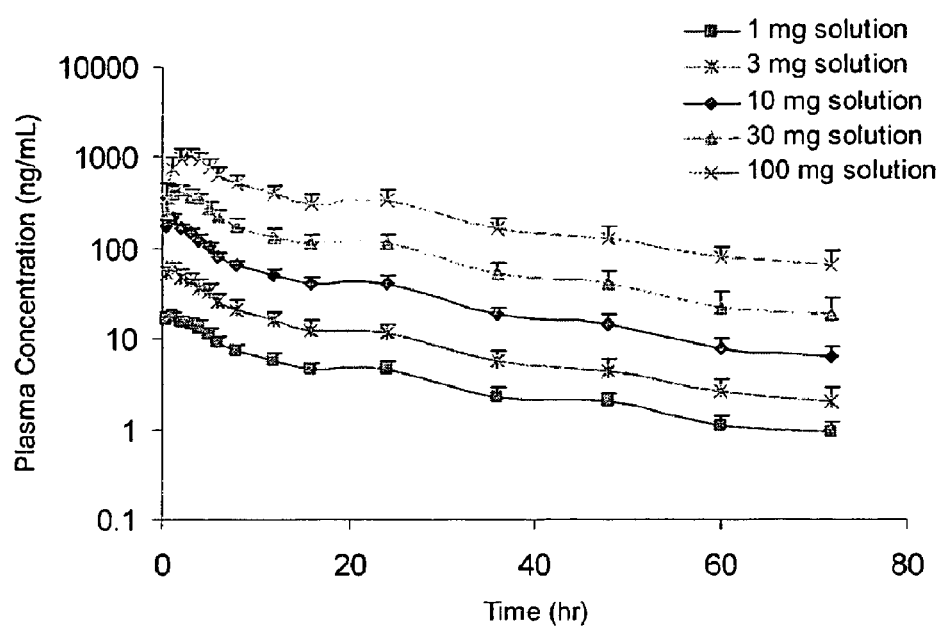
FIG. 10: Plasma concentration-time profile for compound of formula III in healthy human volunteers with oral dose in PEG300.
Figure 11:
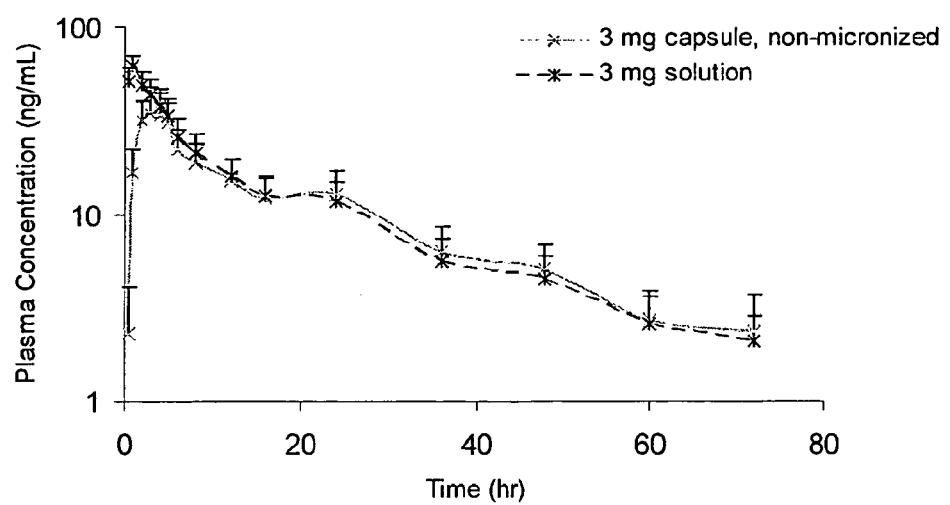
FIG. 11: Plasma-concentration-time profiles of compound of formula III solution vs. solid oral dosage forms.
Figure 12:
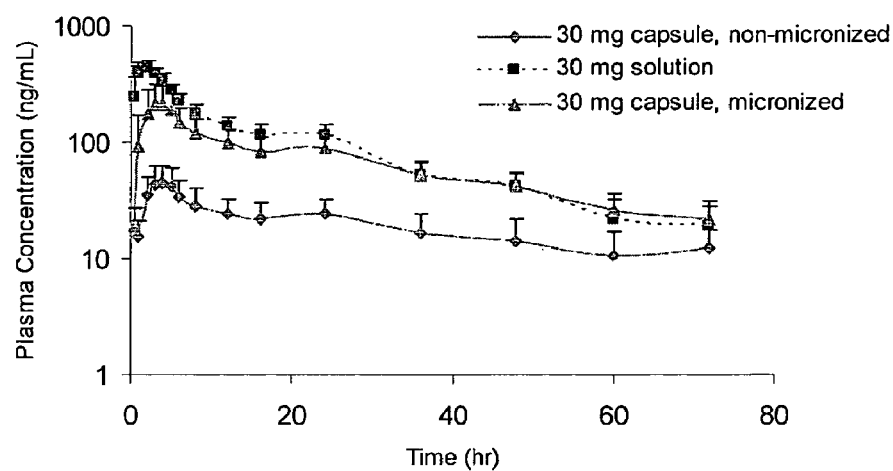
FIG. 12: Plasma-concentration-time profiles of various compound of formula III dosage forms at 30 mg.

Doses of compound III in PEG300-based solutions at 1, 3, 10, 30 and 100 mg were rapidly absorbed from the gastrointestinal tract. All dose levels resulted in plasma compound III concentrations that were quantifiable through the last time point collected (72 hours) (FIGS. 10-12). Exposure

TABLE 2

Serum LH and FSH levels from animals in Arm 1 and Arm2.

| Compound III | Lutenizing Hormone | | Follicle Stimulating Hormone | |
|---|---|---|---|---|
| (mg/day) | Intact (ng/ml) | ORX (ng/ml) | Intact (ng/ml) | ORX (ng/ml) |
| Vehicle | 0.281 ± 0.126[b] | 9.66 ± 1.13[a] | 6.40 ± 1.58[b] | 43.45 ± 4.97[a] |
| 0.01 | 0.195 ± 0.106[b] | 8.45 ± 2.44[a] | 5.81 ± 0.31[b] | 36.23 ± 7.75[a] |
| 0.03 | 0.176 ± 0.092[b] | 4.71 ± 1.72[a,b] | 5.74 ± 0.78[b] | 40.15 ± 3.33[a] |
| 0.1 | 0.177 ± 0.058[b] | 0.778 ± 0.479[b] | 6.60 ± 1.06[b] | 20.69 ± 3.52[a,b] |
| 0.3 | <LOQ | <LOQ | 5.32 ± 1.80[b] | 8.73 ± 2.25[b] |
| 0.75 | <LOQ | <LOQ | 4.30 ± 0.62[a,b] | 7.19 ± 1.11[b] |
| 1 | <LOQ | <LOQ | 4.38 ± 0.42[a,b] | 6.33 ± 0.70[b] |

[a] $P < 0.05$ vs. Intact Controls.
[b] $P < 0.05$ vs. ORX Controls.

Figure 13:
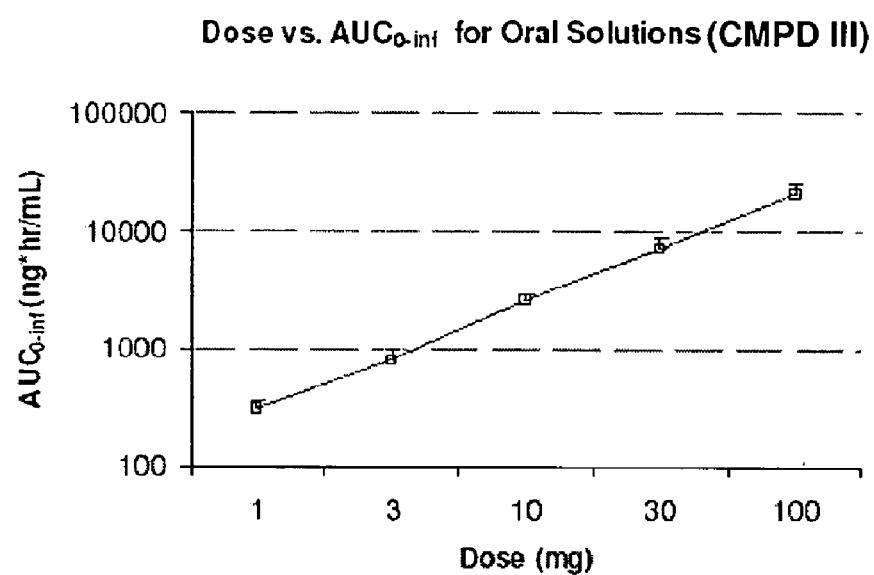
FIG. 13: Dose versus $AUC_{0-inf}$ for oral solutions (G100401).
Figure 14:
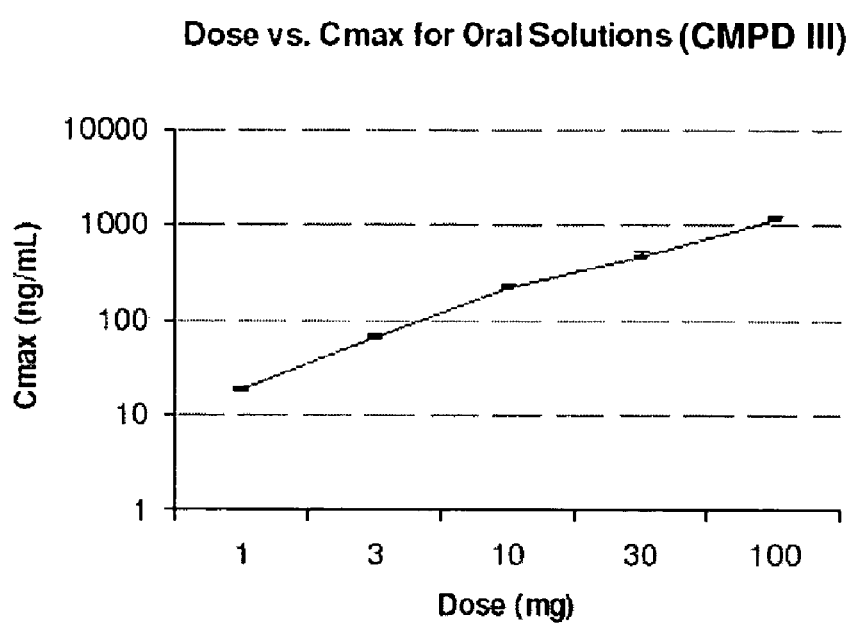
FIG. 14: Dose versus $C_{max}$ for oral solutions.

($C_{max}$ and AUC) to compound III increased with increasing dose and was linear for solutions over the dose range 1 to 100 mg. $T_{max}$ was achieved between 0.8 and 2.3 hours (median value=1.0 hours) for compound III in solution, and between 3.2 and 3.9 hours following the solid oral formulations (FIGS. 13 and 14). The terminal elimination half-life ranged from 19 to 22 hours (median value=20 hours) for 1-100 mg solutions and the 3 mg capsule, and was increased with the 30 mg capsules to 27 and 31 hours for micronized and non-micronized, although not significantly (p>0.1). Oral clearance was inversely associated with half-life, with the 30 mg non-micronized capsule exhibiting the longest half-life and the lowest clearance compared to the other dosage forms and amounts. The 3 mg non-micronized capsule and solution were equally bioavailable, but at the higher dose (30 mg) micronization improved oral bioavailability (p<0.05) (FIG. 12). As suggested by a consistent second peak over the elimination phase of the drug, it is possible that enterohepatic recirculation through the hepatobiliary system plays a role in redistribution of parent drug.

Pharmacokinetic After 14 Days

Materials and Methods 1, 3, 10 and 30 mg of compound of formula III (or matching placebo) were administered daily by mouth for 14 days to 48 healthy young males and 23 males with truncal obesity.

Results

The results are summarized in the Table 3.

according to their most recent body weight with doses of either 0, 3, 10, 30 or 100 mg/kg. During the study period, rats had access to water and a standard laboratory diet of Harlan Taklad Rodent Chow ad libitum. After 28 consecutive days of dosing, animals were fasted overnight, blood samples were collected and processed to yield serum. Serum levels of total cholesterol were determined using an automated laboratory assay method.

Results

Figure 15:
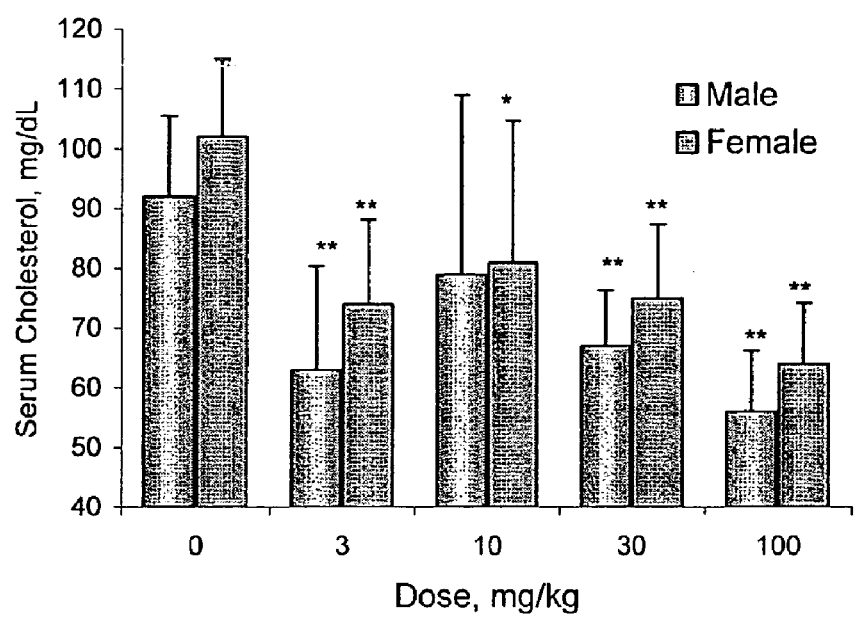
FIG. 15: Cholesterol reduction by compound of formula III in rats.

The male and female rats in the vehicle only group (0 mg/kg) had serum total cholesterol values of 92±13.5 and 102±13 mg/dL respectively. These values are considered within the normal historical range for the testing laboratory. Daily oral doses of Compound III at or above 3 mg/kg caused a significant reduction in total cholesterol levels in both male and female rats. At 3 mg/kg, compared to vehicle control animals, an approximate 30% reduction in total cholesterol was noted where males and females had 63±17.4 and 74±14.2 mg/dL respectively. Although a slightly greater effect was noted at the highest dose group (100 mg/kg per day), in general, a dose-response relationship was not observed in the reduction of total cholesterol levels in the Sprague Dawley rat. Results are presented graphically in FIG. 15.

Example 6

Synthesis of Compound V

Compound V was synthesized as described below, and as depicted in Scheme 1.

TABLE 3

| Parameter | Change From Screening Statistic | Treatment | | | | | | |
|---|---|---|---|---|---|---|---|---|
| | | | Compound III | | | | | |
| | | All Placebo N = 17 | 1 mg, Young N = 9 | 3 mg, Young N = 9 | 10 mg, Young N = 9 | 3 mg, Elderly N = 9 | 30 mg, Young N = 8 | 30 mg, Elderly N = 7 |
| Tissue (% fat) | Mean | 0.69 | 0.26 | −0.24 | 0.10 | −0.96 | 1.01 | −0.13 |
| | Median | 0.80 | 0.20 | 0.10 | 0.00 | −0.90 | 0.65 | −0.90 |
| Region (% fat) | Mean | 0.64 | 0.23 | −0.22 | 0.11 | −0.90 | 0.95 | −0.90 |
| | Median | 0.80 | 0.10 | 0.00 | −0.10 | −0.80 | 0.55 | −0.70 |
| Tissue (g) | Mean | −8.24 | 52.78 | 728.89 | 566.22 | 1101.22 | 140.38 | 196.57 |
| | Median | −132.00 | −652.00 | 508.00 | 608.00 | 1002.00 | 745.00 | 207.00 |
| Fat (g) | Mean | 436.47 | 197.89 | −22.67 | 197.44 | −467.89 | 801.13 | −64.14 |
| | Median | 590.00 | 112.00 | 277.00 | 48.00 | −171.00 | 641.50 | −151.00 |
| Lean (g) | Mean | −444.94 | −145.44 | 752.11 | 368.67 | 1569.44 | −660.88 | 261.00 |
| | Median | −115.00 | −668.00 | 513.00 | −29.00 | 1284.00 | −60.50 | 2.00 |
| BMC[1] (g) | Mean | 36.47 | −13.00 | −32.22 | 17.33 | −3.44 | 35.00 | −18.57 |
| | Median | 36.00 | −12.00 | −36.00 | 25.00 | 55.00 | 20.50 | −3.00 |

[1]BMC (bone mineral content)

Example 5

SARM Reduction of Cholesterol Levels

Materials and Methods

One hundred Sprague Dawley rats (50 male and 50 female) were divided into five groups (n=10 per gender per group), representing vehicle only (PEG300:40% Cavasol® [75/25 (v/v)]), and four dose groups of Compound III. Animals were administered Compound III once daily by oral gavage

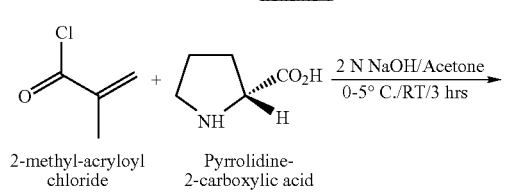

Scheme 1

2-methyl-acryloyl chloride + Pyrrolidine-2-carboxylic acid → (2 N NaOH/Acetone, 0-5° C./RT/3 hrs)

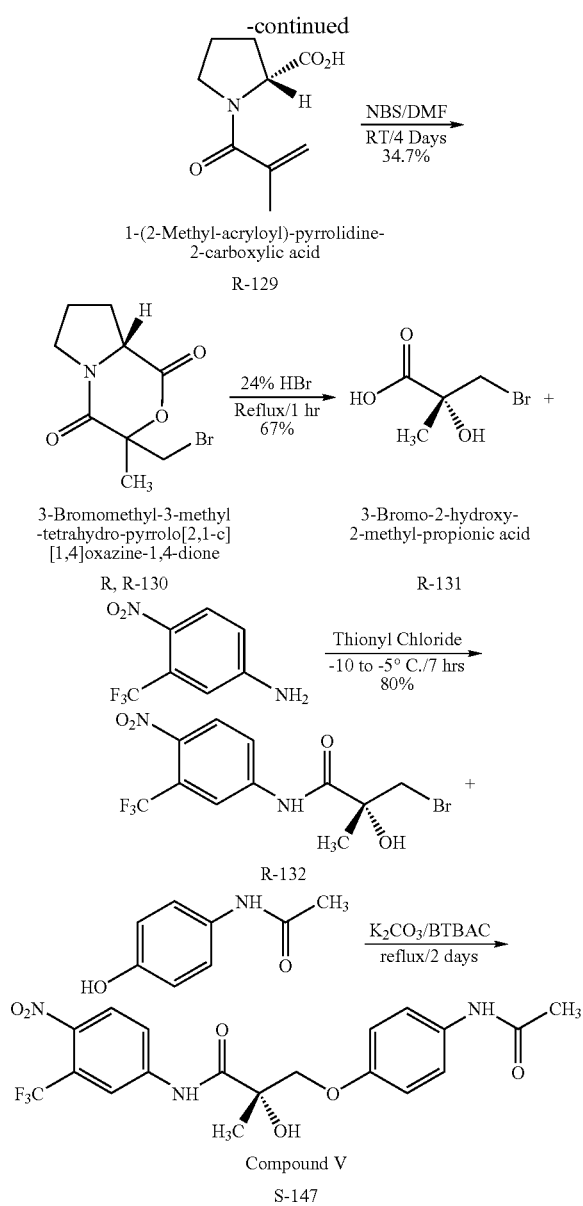

(2R)-1-Methacryloylpyrrolidin-2-carboxylic Acid (R-129). D-Proline (R-128, 14.93 g, 0.13 mol) was dissolved in 71 mL of 2 N NaOH and cooled in an ice bath; the resulting alkaline solution was diluted with acetone (71 mL). An acetone solution (71 mL) of metacryloly chloride 127 (13.56 g, 0.13 mol) and 2N NaOH solution (71 mL) were simultaneously added over 40 min to the aqueous solution of D-proline in an ice bath. The pH of the mixture was kept at 10-11° C. during the addition of the metacryloly chloride. After stirring (3 h, room temperature), the mixture was evaporated in vacuo at a temperature at 35-45° C. to remove acetone. The resulting solution was washed with ethyl ether and was acidified to pH 2 with concentrated HCl. The acidic mixture was saturated with NaCl and was extracted with EtOAc (100 mL×3). The combined extracts were dried over $Na_2SO_4$, filtered through Celite, and evaporated in vacuo to give the crude product as a colorless oil. Recrystallization of the oil from ethyl ether and hexanes afforded 16.2 (68%) of the desired compound as colorless crystals: mp 102-103° C. (lit. [214] mp 102.5-103.5° C.); the NMR spectrum of this compound demonstrated the existence of two rotamers of the title compound. $^1$H NMR (300 MHz, DMSO-$d_6$) δ 5.28 (s) and 5.15 (s) for the first rotamer, 5.15 (s) and 5.03 (s) for the second rotamer (totally 2H for both rotamers, vinyl $CH_2$), 4.48-4.44 for the first rotamer, 4.24-4.20 (m) for the second rotamer (totally 1H for both rotamers, CH at the chiral canter), 3.57-3.38 (m, 2H, $CH_2$), 2.27-2.12 (1H, CH), 1.97-1.72 (m, 6H, $CH_2$, CH, Me); $^{13}$C NMR (75 MHz, DMSO-$d_6$) δ for major rotamer 173.3, 169.1, 140.9, 116.4, 58.3, 48.7, 28.9, 24.7, 19.5: for minor rotamer 174.0, 170.0, 141.6, 115.2, 60.3, 45.9, 31.0, 22.3, 19.7; IR (KBr) 3437 (OH), 1737 (C=O), 1647 (CO, COOH), 1584, 1508, 1459, 1369, 1348, 1178 cm$^{-1}$; $[\alpha]_D^{26}$+80.8° (c=1, MeOH); Anal. Calcd. for $C_9H_{13}NO_3$: C, 59.00; H, 7.15; N, 7.65. Found: C 59.13, H 7.19, N 7.61.

(3R,8aR)-3-Bromomethyl-3-methyl-tetrahydro-pyrrolo[2,1-c][1,4]oxazine-1,4-dione (R, R-130). A solution of NBS (23.5 g, 0.132 mol) in 100 mL of DMF was added dropwise to a stirred solution of compound R-129 (16.1 g, 88 mmol) in 70 mL of DMF under argon at room temperature, and the resulting mixture was stirred 3 days. The solvent was removed in vacuo, and a yellow solid was precipitated. The solid was suspended in water, stirred overnight at room temperature, filtered, and dried to give 18.6 (81%) (smaller weight when dried ~34%) of the title compound as a yellow solid: mp 152-154° C. (lit. [214] mp 107-109° C. for the S-isomer); $^1$H NMR (300 MHz, DMSO-$d_6$) δ 4.69 (dd, J=9.6 Hz, J=6.7 Hz, 1H, CH at the chiral center), 4.02 (d, J=11.4 Hz, 1H, CHH$_a$), 3.86 (d, J=11.4 Hz, 1H, CHH$_b$), 3.53-3.24 (m, 4H, $CH_2$), 2.30-2.20 (m, 1H, CH), 2.04-1.72 (m, 3H, $CH_2$ and CH), 1.56 (s, 2H, Me); $^{13}$C NMR (75 MHz, DMSO-$d_6$) δ 167.3, 163.1, 83.9, 57.2, 45.4, 37.8, 29.0, 22.9, 21.6; IR (KBr) 3474, 1745 (C=O), 1687 (C=O), 1448, 1377, 1360, 1308, 1227, 1159, 1062 cm$^{-1}$; $[\alpha]_D^{26}$+124.5° (c=1.3, chloroform); Anal. Calcd. for $C_9H_{12}BrNO_3$: C, 41.24; H, 4.61; N, 5.34. Found: C 41.46, H 4.64, N 5.32.

(2R)-3-Bromo-2-hydroxy-2-methylpropanoic Acid (R-131). A mixture of bromolactone R-130 (18.5 g, 71 mmol) in 300 mL of 24% HBr was heated at reflux for 1 h. The resulting solution was diluted with brine (200 mL), and was extracted with ethyl acetate (100 mL×4). The combined extracts were washed with saturated $NaHCO_3$ (100 mL×4). The aqueous solution was acidified with concentrated HCl to pH=1, which, in turn, was extracted with ethyl acetate (100 mL×4). The combined organic solution was dried over $Na_2SO_4$, filtered through Celite, and evaporated in vacuo to dryness. Recrystallization from toluene afforded 10.2 g (86%) of the desired compound as colorless crystals: mp 107-109° C. (lit. [214] mp 109-113° C. for the S-isomer); $^1$H NMR (300 MHz, DMSO-$d_6$) δ 3.63 (d, J=10.1 Hz, 1H, CHH$_a$), 3.52 (d, J=10.1 Hz, 1H, CHH$_b$), 1.35 (s, 3H, Me); IR (KBr) 3434 (OH), 3300-2500 (COOH), 1730 (C=O), 1449, 1421, 1380, 1292, 1193, 1085 cm$^{-1}$; $[\alpha]_D^{26}$ +10.5° (c=2.6, MeOH); Anal. Calcd. for $C_4H_7BrO_3$: C 26.25, H 3.86. Found: C 26.28, H 3.75.

N-[4-Nitro-3-(trifluoromethyl)phenyl]-(2R)-3-bromo-2-hydroxy-2-methylpropanamide (R-132). Thionyl chloride (8.6 g, 72 mmol) was added dropwise under argon to a solution of bromoacid R-131 (11.0 g, 60 mmol) in 70 mL of DMA at −5 to −10° C. The resulting mixture was stirred for 2 h under the same conditions. A solution of 4-nitro-3-trifluoromethyl-aniline (12.4 g, 60 mmol) in 80 mL of DMA was added dropwise to the above solution, and the resulting mixture was stirred overnight at room temperature. The solvent was removed on Rotavapor using high vacuum oil pump; the residue was diluted with saturated $NaHCO_3$ solution, and extracted with ethyl ether (100 mL×3). Combined extracts were dried over anhydrous Na$_2$SO$_4$, filtered through Celite, and purified by flash chromatography on silica gel, using methylene chloride as eluent to afford 18.0 g (80%) of the desired compound: mp 98-100° C. (R$_f$=0.2, silica gel, CH$_2$Cl$_2$); $^1$H NMR (300 MHz, DMSO-d$_6$) δ 10.54 (s, 1H, NH), 8.54 (d, J=2.1 Hz, 1H, ArH), 8.34 (dd, J=9.0 Hz, J=2.1 Hz, 1H, ArH), 8.18 (d, J=9.0 Hz, 1H, ArH), 6.37 (s, 1H, OH), 3.82 (d, J=10.4 Hz, 1H, CHH$_a$), 3.58 (d, J=10.4 Hz, 1H, CHH$_b$), 1.48 (s, 3H, Me); $^{13}$C NMR (75 MHz, DMSO-d$_6$) δ 173.6 (C=O), 143.0, 127.2, 123.2, 122.6 (q, J=33.0 Hz), 122.0 (q, J=271.5 Hz), 118.3 (q, J=6.0 Hz), 74.4, 41.4, 24.9; IR (KBr) 3344 (OH), 1680 (C=O), 1599, 1548 (C=C, Ar), 1427, 1363, 1161 cm$^{-1}$; MS (ESI): m/z 370.8 (M)$^+$; Anal. Calcd. for C$_{11}$H$_{10}$BrN$_2$O$_4$: C, 35.60; H, 2.72; N, 7.55. Found: C, 35.68; H, 2.72; N, 7.49.

N-[4-nitro-3-trifluoromethyl)phenyl]-(2S)-3-[4-(acetylamino)phenoxy]-2-hydroxy-2-methylpropanamide (S-147). The title compound was prepared from compound R-132 (0.37 g, 1.0 mmol), 4-acetamidophenol (0.23 g, 1.5 mmol) K$_2$CO$_3$ (0.28 g, 2.0 mmol), and 10% of benzyltributylammonium chloride as a phase transfer catalyst in 20 mL of methyl ethyl ketone was heated at reflux overnight under argon. The reaction was followed by TLC, the resulting mixture was filtered through Celite, and concentrated in vacuo to dryness. Purification by flash column chromatography on silica gel (hexanes-ethyl acetate, 3:1) yielded 0.38 g (86%) (R$_f$=0.18 hexanes-ethyl acetate, 3:1) of the desired compound as a light yellow powder: mp 70-74° C.; The solid can be recrystalized from ethyl acetate and hexane); $^1$H NMR (300 MHz, DMSO-d$_6$) δ 10.62 (s, 1H, NH), 9.75 (s, 1H, NH), 8.56 (d, J=1.9 Hz, 1H, ArH), 8.36 (dd, J=9.1 Hz, J=1.9 Hz, 1H, ArH), 8.18 (d, J=9.1 Hz, 1H, ArH), 7.45-7.42 (m, 2H, ArH), 6.85-6.82 (m, 2H, ArH), 6.25 (s, 1H, OH), 4.17 (d, J=9.5 Hz, 1H, CHH$_a$), 3.94 (d, J=9.5 Hz, 1H, CHH$_b$), 1.98 (s, 3H, Me), 1.43 (s, 3H, Me); $^{13}$C NMR (75 MHz, DMSO-d$_6$) δ 174.6 (C=O), 167.7, 154.2, 143.3, 141.6, 132.8, 127.4, 123.0, 122.7 (q, J=33.0 Hz), 122.1 (q, J=271.5 Hz), 120.1, 118.3 (q, J=6.0 Hz), 114.6, 74.9, 73.8, 23.8, 23.0; IR (KBr) 3364 (OH), 1668 (C=O), 1599, 1512 (C=C, Ar), 1457, 1415, 1351, 1323, 1239, 1150 1046 cm$^{-1}$; MS (ESI): m/z 464.1 (M+Na)$^+$; Anal. Calcd. for C$_{19}$H$_{18}$F$_3$N$_3$O$_6$: C 51.71; H 4.11, N 9.52. Found: C 52.33, H 4.40, N 9.01.

The synthesis of the various ether analogs of compound V utilizes the common intermediate that is the final reaction step. Bromo-intermediates are used which allow various phenolic compounds to displace the bromide to give the desired ether product. Bromohydrin was converted to an epoxide and to open the epoxide to give the same desired ether product.

Melting points were determined on a Thomas-Hoover capillary melting point apparatus and are uncorrected. Infrared spectra were recorded on a Perkin Elmer System 2000 FT-IR. Optical rotations were determined on an Autopol® III Automatic Polarimeter (Rudolph Research Model III-589-10, Fairfield, N.J.). Proton and carbon-13 magnetic resonance spectra were obtained on a Bruker AX 300 spectrometer (300 and 75 MHz for $^1$H and $^{13}$C, respectively). Chemical shift values were reported as parts per million (δ) relative to tetramethylsilane (TMS). Spectral data were consistent with assigned structures. Mass spectra were determined on a Bruker-HP Esquire LC System. Elemental analyses were performed by Atlantic Microlab Inc. (Norcross, Ga.), and found values were within 0.4% of the theoretical values. Routine thin-layer chromatography (TLC) was performed on silica gel on aluminum plates (silica gel 60 F 254, 20×20 cm, Aldrich Chemical Company Inc., Milwaukee, Wis.). Flash chromatography was performed on silica gel (Merck, grade 60, 230-400 mesh, 60). Tetrahydrofuran (THF) was dried by distillation over sodium metal. Acetonitrile (MeCN) and methylene chloride (CH$_2$Cl$_2$) were dried by distillation from P$_2$O$_5$.

Example 7

Large Scale Synthesis of Compound V

Compound V (3-[4-(acetylamino)phenoxy]-2-hydroxy-2-methyl-N-[3-trifluoromethyl-4-nitrophenyl)-propanamide) is a member of the oxolutamide family of androgen receptor agonists, and is a nonsteroidal SARM. It binds the androgen receptor in vitro with high affinity (Ki=7.5±0.5 nM). In vivo it acts as a partial agonist at the androgen receptor and results in strong anabolic and weakly androgenic effects. Compound V has no other known endocrine activities.

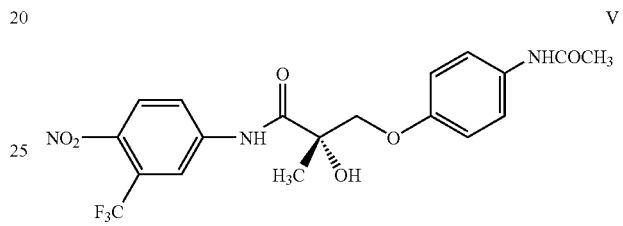

V

Compound V was synthesized according to the following synthetic Steps:

Step 1—Synthesis of (2R)-1-Methacryloylpyrrolidin-2-carboxylic acid (R-129)

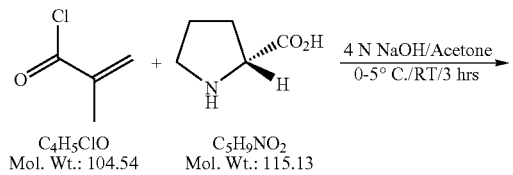

C$_4$H$_5$ClO
Mol. Wt.: 104.54

C$_5$H$_9$NO$_2$
Mol. Wt.: 115.13

C$_9$H$_{13}$NO$_3$
Mol. Wt.: 183.20

A 72 L flask with a mechanical stirrer and inlet for inert atmosphere was set up in a cooling bath. The flask was placed under argon and charged with 5000 g (43.4 moles) of D-proline [ICN lot# 7150E, >99%], 11.9 L of 4N NaOH, and 12 L acetone. The mixture was cooled to 5° C. on an ice bath. A solution of 4548.8 g (43.5 moles) of methacryloyl chloride [Aldrich lot#12706HO, 98+%] in 12.0 L of acetone was prepared. The solution of methacryloyl chloride and 11.9 L of 4N NaOH were added simultaneously to the reaction mixture in the 72 L flask. During the addition, the temperature was maintained less than 10° C. and the pH of the reaction mixture was maintained at greater than or equal to 10. The pH was maintained by adding the 4N NaOH more slowly or more quickly depending on the pH of the solution. The addition time was approximately 2 hours and 40 minutes. After the addition was complete, the reaction mixture was stirred overnight and allowed to warm to room temperature.

The acetone was removed on a rotary evaporator, and the aqueous mixture was extracted with methyl t-butyl ether or MtBE (28.0 L). The mixture was then acidified with concentrated HCl (6568.1 g) to a pH of less than 2. The product was isolated by extraction into methylene chloride (3×20 L). The extracts were concentrated on a rotary evaporator. MtBE (10 L) was added and concentrated on the rotary evaporator to perform a solvent exchange. Additional MtBE (10 L) was added to precipitate the product. Ice was charged to the rotary evaporator bath and the product was allowed to crystallize. The crystalline product was collected and isolated by filtration. The weight after drying in a vacuum oven at 50° C. was 4422.2 g (55.6% yield).

Step 2—Synthesis of (3R,8R)-3-Bromomethyl-3-methyl-tetrahydropyrolo-[2,1-c][1,4]oxazine-1,4-dione (R,R-130)

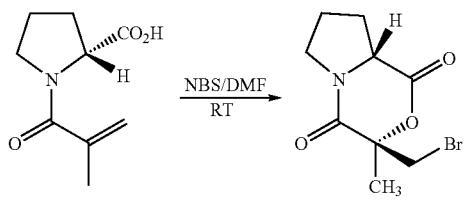

A 50 L flask was set up with a mechanical stirrer, inlet for inert atmosphere, and cooling capacity. The flask was placed under an argon atmosphere and was charged with 4410.0 g (24.1 moles) of R-129 and 8.8 L of DMF. Then NBS (6409.6 g, 36.0 moles) was added slowly over a period of 2 hours and 7 minutes. The reaction mixture was agitated for at least 8 hours. Water (20.0 L) was added to precipitate the product. The product was allowed to stir for at least 4 hours to crystallize. The crystalline product was collected and isolated by filtration. The weight after drying in a vacuum oven at 50° C. was 5532.1 g (87.7% yield).

Step 3—Synthesis of (2R)-3-Bromo-2-hydroxy-2-methylpropanoic acid (R-131)

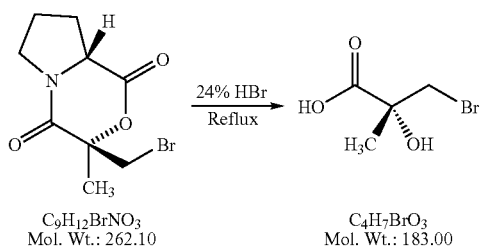

A 50 L flask was set up with a mechanical stirrer, inlet for inert atmosphere, and heating capacity. The flask was placed under an argon atmosphere and was charged with 5472.3 g (20.8 moles) of R,R-130 and 14.175 L of deionized water and 14,118.4 g of 48% HBr. The reaction mixture was heated to 102° C. for 6 hours, and allowed to cool 31° C. Brine (20 L) was added to the reaction mixture and the product was extracted with 6×20.4 L of t-Butyl methyl ether. The organic layers were combined and concentrated with the rotary evaporator. Toluene (4.0 L) was charged to the rotary evaporator. The product was dried by toluene distillation. The mixture was concentrated with the rotary evaporator. The product was recrystallized from toluene (45.0 L) by heating to 100° C. to dissolve the product. The flask was cooled on ice and the product was allowed to crystallize. The crystalline product was collected by filtration and washed with toluene (3.4 L). The weight after drying in a vacuum oven at 50° C. was 3107.0 g (81.3% yield).

Step 4—Synthesis of N-[4-Nitro-3-(trifluoromethyl) phenyl]-(2R)-3-bromo-2-hydroxy-2-methylpropanamide (R-132)

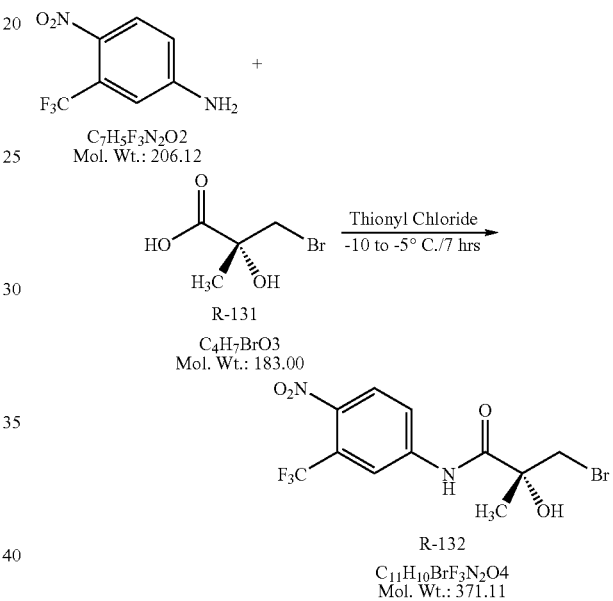

A 50 L flask was set up with a mechanical stirrer, inlet for inert atmosphere, and cooling capacity. The flask was placed under an argon atmosphere and was charged with 2961.5 g (16.2 moles) of R-131 and 9.0 L of THF. The flask was cooled on ice to less than 5° C. Thionyl chloride (1200 mL, 16.4 moles) dissolved in 6.0 L of THF was added slowly via an addition funnel to the reaction flask. The temperature of the reaction flask was maintained less than or equal to 10° C. The addition time was 1 hour 10 minutes. The reaction mixture was allowed to agitate for an additional 2 hours 50 minutes. Then a solution of 2359.4 g of (11.4 moles) of 4-nitro-3-trifluoromethylaniline (Aldrich, 98%) and 3.83 L of triethylamine in 6.0 L THF was added over a period of 3 hours 5 minutes. The temperature of the reaction flask was maintained less than or equal to 10° C. The ice bath was removed, and the reaction mixture was allowed to stir for 30 minutes. With a heating mantle, the reaction mixture was heated to 50° C. for 15 hours and 10 minutes. After the reaction was complete as analyzed by TLC, the reaction mixture was cooled to less than 30° C. and 7.5 L of deionized water was added. The aqueous layer was removed and a second water wash (7.5 L) was performed. The organic layer was then washed three times with 10% bicarbonate (8.1 L) until the pH was greater than 7.

The solvent was removed on a rotary evaporator. Toluene (3.0 L) was added and then removed on the rotary evaporator to dry the crude product. The product was dissolved in 2.0 L of toluene at 65° C. Upon cooling the product crystallized. The crystalline product was collected and isolated by filtration. The wet cake was washed with 1.0 L of toluene. The weight after drying in a vacuum oven at 50° C. was 3751.0 g (70.3% yield).

Step 5—Synthesis of Compound V

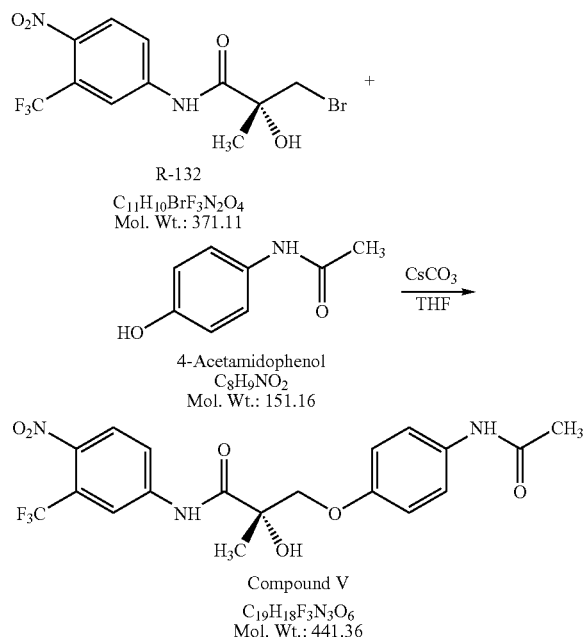

A 22 L flask was set up with a mechanical stirrer, inlet for inert atmosphere, and cooling capacity. The flask was placed under an argon atmosphere and was charged with 1002.8 g (2.70 moles) of R-132, 4.0 L of THF, and 454.2 g (3.00 moles) of 4-acetamidophenol (Aldrich, 98%). While stirring, the flask was then charged with 1769.9 g of cesium carbonate (Aldrich, 99%). The flask was heated to reflux for at least 8 hours, and the reaction monitored by TLC [silica gel, dichloromethane/hexane 3:1, Epoxide $R_f$=0.5]. When the reaction was complete, the flask was allowed to cool to room temperature.

Water was added to dissolve the carbonate and ethyl acetate was added to help with the phase separations. The aqueous phase was separated as waste. The organic phase was washed with a second portion of water. The organic layer was transferred to a rotary evaporator and the solvent was removed. The solvent was exchanged into ethanol by charging ethanol into the rotovap flask and removing some of the ethanol to remove all of the ethyl acetate. The ethanol solution was added to water to precipitate the product. The crude product was collected by filtration and washed with water. The product was transferred back to the rotary evaporator for crystallization. Ethyl acetate was charged to the rotovap flask to exchange the solvent into ethyl acetate. The ethyl acetate was removed under vacuum which dried the product. A minimum amount of ethyl acetate was added to dissolve the product at 60° C. T-Butyl methyl ether was added to crystallize the product. After cooling, the product was collected by filtration and washed with t-Butyl methyl ether. The wet cake was added back to the rotary evaporator and ethanol was charged.

A solvent exchange into ethanol removed the residual t-Butyl methyl ether. Filtering the ethanol solution into water recrystallized the product. After stirring, the product was collected by filtration and washed with water. The weight after drying in a vacuum oven oat 50° C. was 52%.

Example 8

Binding Activity of Compound V

The in vitro activity of the SARM compounds, specifically compound V, demonstrated high androgen receptor binding affinity (Ki=7.5 nM). Animal studies with the SARM compounds, specifically compound V, demonstrated that it is a potent androgenic and anabolic nonsteroidal agent. Four groups of rats were used for these studies: (1) intact controls, (2) castrated controls, (3) castrated animals treated with testosterone propionate (100 μg/day), and (4) castrated animals treated with compound V (1000 μug/day). Testosterone and compound V were delivered at a constant rate for 14 days via subcutaneous osmotic pumps.

Figure 16:
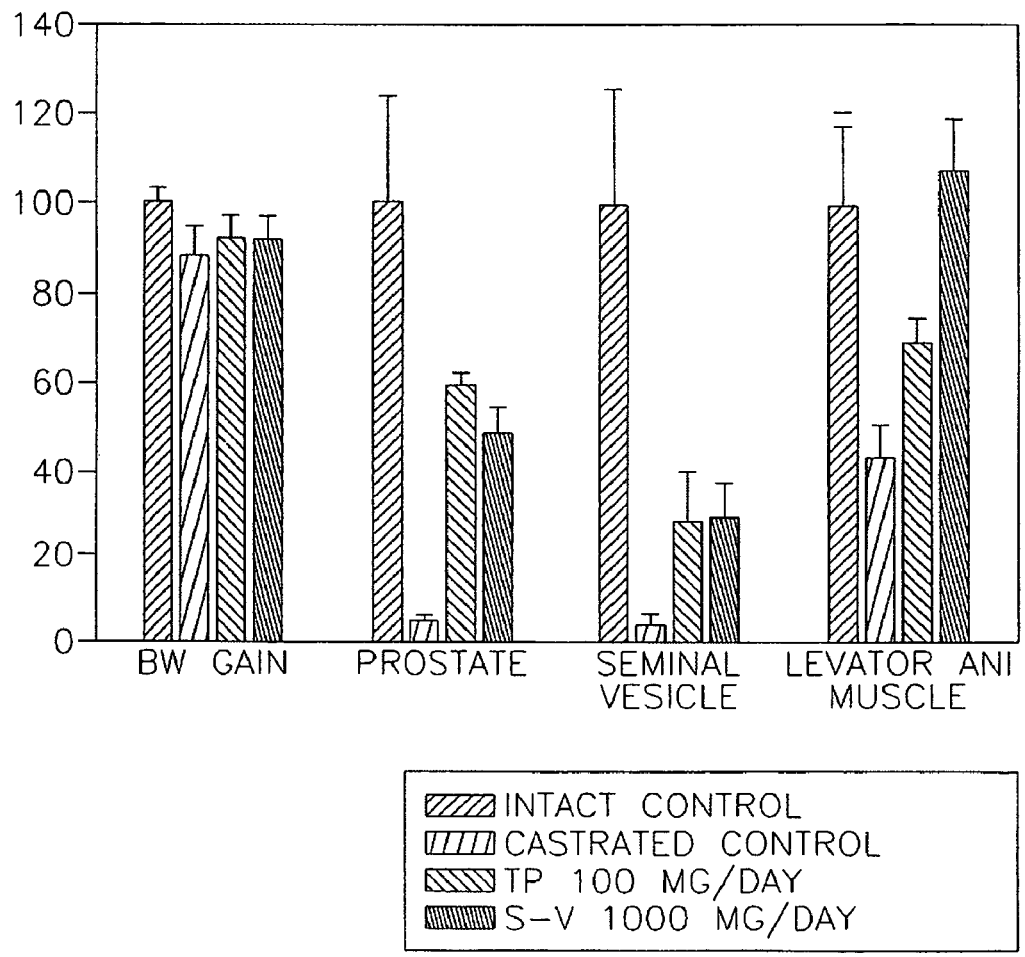
FIG. 16: Androgenic and Anabolic activity of the (S) enantiomer of compound of formula V (S-V) in rats. Rats were left untreated (intact control), castrated (castrated control), treated with testosterone propionate (TP), or treated with S-V, and the body weight gain as well as the weight of androgen-responsive tissues (prostate, seminal vesicles and levator ani muscle) was determined.

The results of these studies are shown in FIG. 16. Castration significantly reduced the weight of androgenic (e.g., prostate and seminal vesicles) and anabolic (e.g., levator ani muscle) tissues, but had little effect on animal body weight (BW). Treatment of castrated animals with testosterone propionate or compound V maintained the weight of androgenic tissues to the same degree. Compound V had similar androgenic activity as testosterone propionate (i.e., the prostate and seminal vesicle weights were the same), but much greater efficacy as an anabolic agent. Compound V showed greater anabolic activity than testosterone propionate at the doses tested (i.e., the levator ani muscle maintained the same weight as intact control animals and was greater than that observed for testosterone). The experiments presented herein are the first in vivo results which demonstrate tissue-selective androgenic and anabolic activity (i.e., differing androgenic and anabolic potency) of a nonsteroidal ligand for the androgen receptor.

Example 9

Nonsteroidal Ligands with Androgenic and Anabolic Activity

The in vivo efficacy and acute toxicity of four novel nonsteroidal androgens (compounds V, VI, XIV, XV) in rats was examined. In vitro assays established that these compounds bind the androgen receptor with very high affinity. The structures and names of the four compounds are presented below:

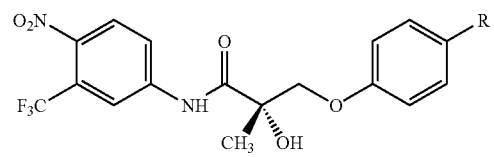

Compound V: R=NHCOCH$_3$
Compound VI: R=F
Compound XIV: R=COCH$_3$
Compound XV: R=COCH$_2$CH$_3$ Methods Materials. The S-isomers of compounds VI, XIV, XV, and V and the R-isomer of VI were synthesized in accordance with the scheme as set forth in FIG. 24. Testosterone propionate (TP), polyethylene glycol 300 (PEG300, reagent grade) and neutral buffered formalin (10% w/v) were purchased from Sigma Chemical Company (St Louis, Mo.). Alzet osmotic pumps (model 2002) were purchased from Alza Corp. (Palo Alto, Calif.).

Animals. Immature male Sprague-Dawley rats, weighing 90 to 100 g, were purchased from Harlan Biosciences (Indianapolis, Ind.). The animals were maintained on a 12-hour light-dark cycle with food and water available ad libitum. The animal protocol was reviewed and approved by the Institutional Laboratory Animal Care and Use Committee.

Study Design. Rats were randomly distributed into twenty-nine (29) groups, with 5 animals per group. Treatment groups are described in Table 4. One day prior to the start of drug treatment, animals in groups 2 through 29 were individually removed from the cage, weighed and anesthetized with an intraperitoneal dose of ketamine/xylazine (87/13 mg/kg; approximately 1 mL per kg). When appropriately anesthetized (i.e., no response to toe pinch), the animals' ears were marked for identification purposes. Animals were then placed on a sterile pad and their abdomen and scrotum washed with betadine and 70% alcohol. The testes were removed via a midline scrotal incision, with sterile suture being used to ligate supra-testicular tissue prior to surgical removal of each testis. The surgical wound site was closed with sterile stainless steel wound clips, and the site cleaned with betadine. The animals were allowed to recover on a sterile pad (until able to stand) and then returned to their cage.

Twenty-four hours later, animals in groups 2 through 29 were re-anesthetized with ketamine/xylazine, and an Alzet osmotic pump(s) (model 2002) was placed subcutaneouly in the scapular region. In this instance, the scapular region was shaved and cleaned (betadine and alcohol) and a small incision (1 cm) made using a sterile scalpel. The osmotic pump was inserted and the wound closed with a sterile stainless steel wound clip. Animals were allowed to recover and were returned to their cage. Osmotic pumps contained the appropriate treatment (designated in Table 1) dissolved in polyethylene glycol 300 (PEG300). Osmotic pumps were filled with the appropriate solution one day prior to implantation. Animals were monitored daily for signs of acute toxicity to drug treatment (e.g., lethargy, rough coat).

After 14 days of drug treatment, rats were anesthetized with ketamine/xylazine. Animals were then sacrificed by exsanguinations under anesthesia. A blood sample was collected by venipuncture of the abdominal aorta, and submitted for complete blood cell analysis. A portion of the blood was placed in a separate tube, centrifuged at 12,000 g for 1 minute, and the plasma layer removed and frozen at −20.degree.C. The ventral prostates, seminal vesicles, levator ani muscle, liver, kidneys, spleen, lungs, and heart were removed, cleared of extraneous tissue, weighed, and placed in vials containing 10% neutral buffered formalin. Preserved tissues were sent to GTx, Inc. for histopathological analysis.

For data analysis, the weights of all organs were normalized to body weight, and analyzed for any statistical significant difference by single-factor ANOVA. The weights of prostate and seminal vesicle were used as indexes for evaluation of androgenic activity, and the levator ani muscle weight was used to evaluate the anabolic activity.

Results

The androgenic and anabolic activities the S isomers of compounds V, VI, XIV and XV, and the R isomer of VI were examined in a castrated rat model after 14 days of administration. Testosterone propionate, at increasing doses, was used as the positive control of anabolic and androgenic effects.

Figure 17:
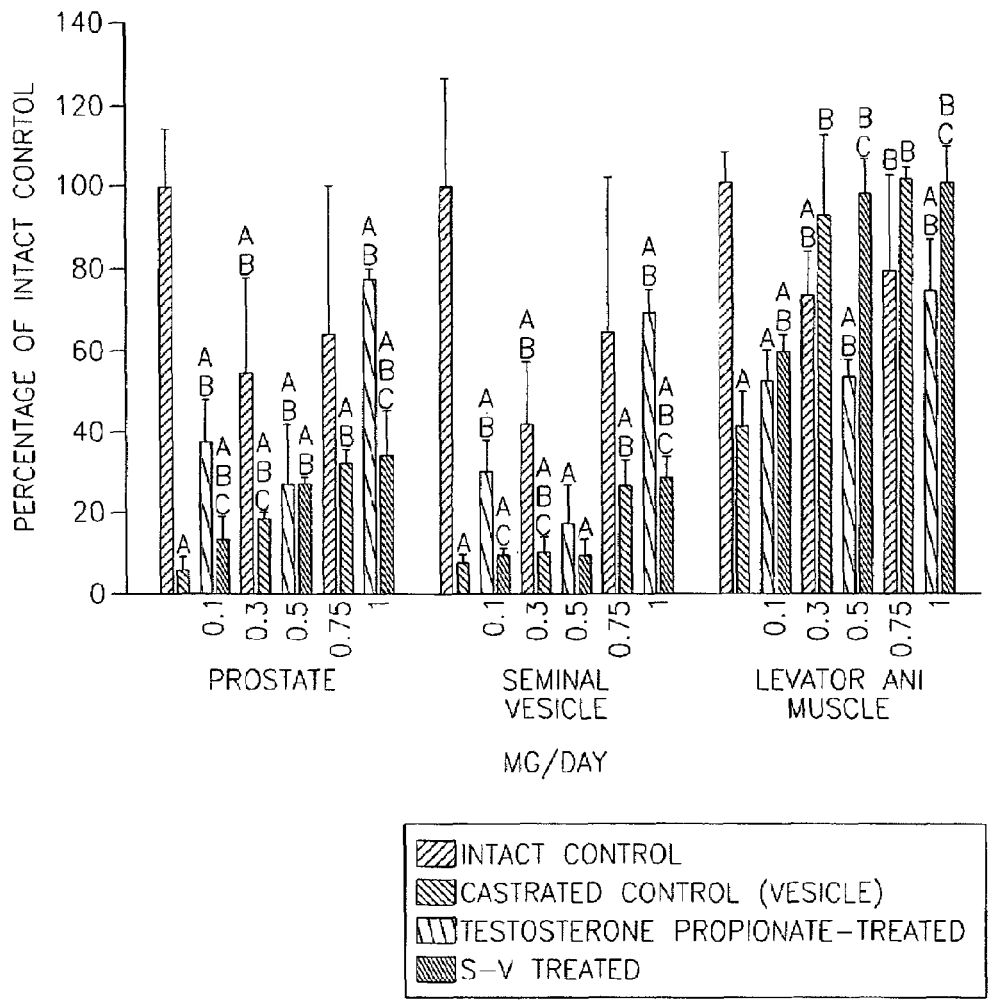
FIG. 17: Androgenic and Anabolic activity of compound S-V in rats. Rats were left untreated (intact control), castrated (castrated control), treated with 0.1, 0.3, 0.5, 0.75 and 1.0 mg/day testosterone propionate (TP), or treated with 0.1, 0.3, 0.5, 0.75 and 1.0 mg/day compound S-V, and the weight of androgen-responsive tissues (prostate, semimal vesicles and levator ani muscle) was determined.
Figure 18:
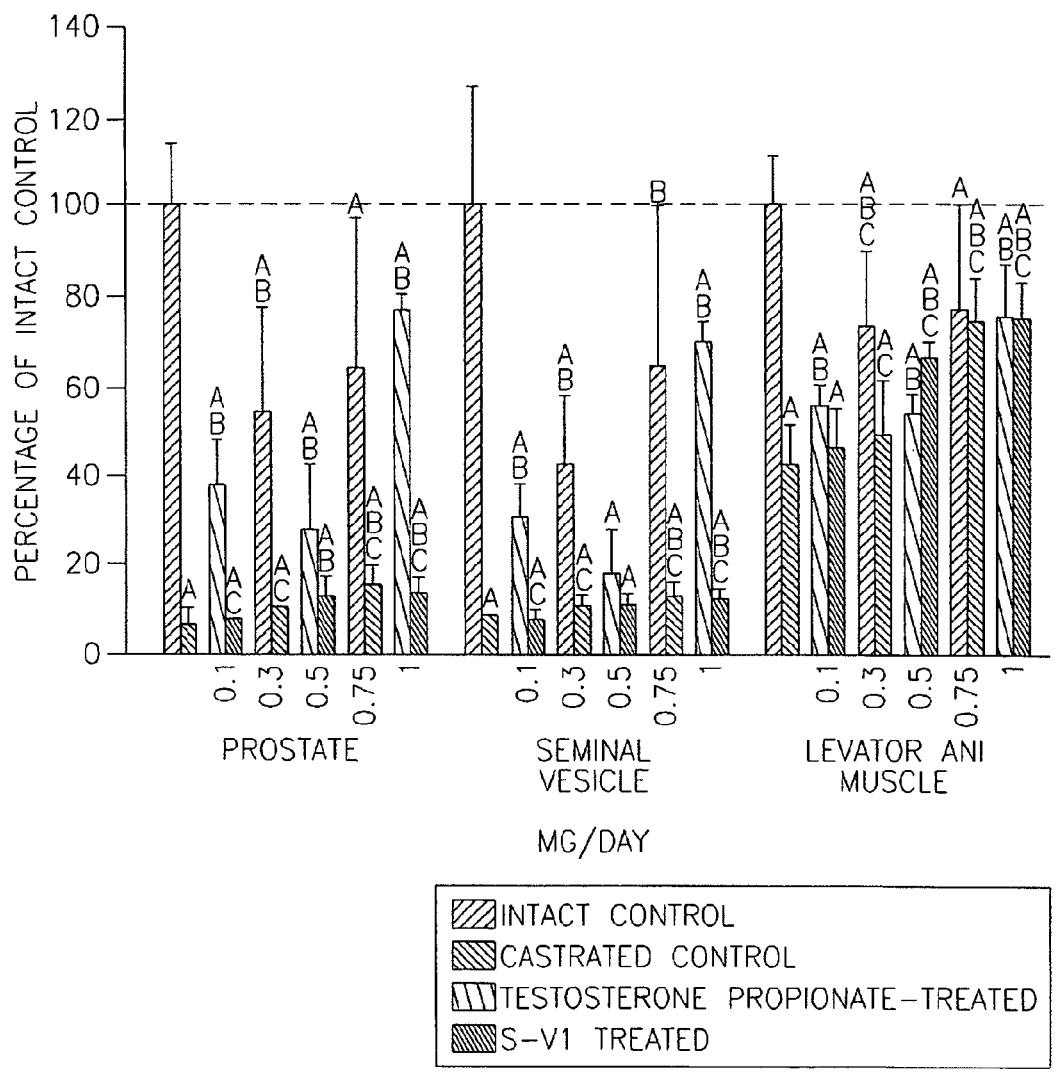
FIG. 18: Androgenic and Anabolic activity of the S enantiomer of compound of formula VI (S-VI) in rats. Rats were left untreated (intact control), castrated (castrated control), treated with 0.1, 0.3, 0.5, 0.75 and 1.0 mg/day testosterone propionate (TP), or treated with 0.1, 0.3, 0.5, 0.75 an d 1.0 mg/day compound S-VI, and the weight of androgen-responsive tissues (prostate, semimal vesicles and levator ani muscle) was determined.

As shown in FIGS. 17 and 18 the weights of prostate, seminal vesicle, and levator ani muscle in castrated, vehicle-treated rats decreased significantly, due to the ablation of endogenous androgen production. Exogenous administration of testosterone propionate, an androgenic and anabolic steroid, increased the weights of prostate, seminal vesicle, and levator and muscle in castrated rats in a dose-dependent manner The R-isomer of compound VI, and S-isomers of compound XIV and compound XV showed no effect on the weights of prostate, seminal vesicle, and levator ani muscle in castrated animals (data not shown). The S-isomers of compound V (FIG. 17: S-V) and compound VI (FIG. 18: S-VI) resulted in dose-dependent increases in prostate, seminal vesicle and levator ani muscle weights. Compared with testosterone propionate, S-V showed lower potency and intrinsic activity in increasing the weights of prostate and seminal vesicle, but a greater potency and intrinsic activity in increasing the weight of levator ani muscle. Particularly, compound S-V, at a dose as low as 0.3 mg/day, was able to maintain the levator ani muscle weight of castrated animals in the same level as that of intact animals. Thus, S-V is a potent nonsteroidal anabolic agent with less androgenic activity but more anabolic activity than testosterone propionate. This is a significant improvement over previous claims, in that this compound selectively stimulates muscle growth and other anabolic effects while having less effect on the prostate and seminal vesicles. This may be particularly relevant in aging men with concerns related to the development or progression of prostate cancer.

Compound VI was less potent than compound V, but showed greater tissue selectivity (compare effects on the prostate and seminal vesicles in FIGS. 17 and 18). Compound VI significantly increased levator ani muscle weights, but showed little to no ability to stimulate prostate and seminal vesicle growth (i.e., the prostate and seminal vesicle weights were less than 20% of that observed in intact animals or in animals treated with testosterone propionate).

Results showed that none of the examined compounds produced significant effect on body weight or the weights of other organs (i.e., liver, kidneys, spleen, lungs and heart). Nor did any compound produce any signs of acute toxicity, as gauged by diagnostic hematology tests and visual examination of animals receiving treatments. Importantly, compound V did not suppress the production of luteinizing hormone (LH) or follicle stimulating hormone (FSH) at a dose of 0.3 mg/day (i.e., a dose that exhibited maximal anabolic effects).

In summary, compound S-V exhibited exceptional anabolic activity in animals by maintaining the weight of levator ani muscle after removal of endogenous androgen. This discovery represents major progress towards the development of therapeutically useful nonsteroidal androgens, and a major improvement (i.e., tissue selectivity and potency) over previous drugs in this class. Compounds S-VI and S-V showed selective anabolic activity in comparison with testosterone propionate, an androgenic and anabolic steroid. The tissue-selective activity is actually one of the advantages of nonsteroidal androgens in terms of anabolic-related applications.

Despite similarities in structure and in vitro functional activity, the S-isomers of compounds V, VI, XIV, XV exhibited profound differences in terms of their in vivo activity compound V the most efficacious androgenic and anabolic activity in animals, with the anabolic activity greater than that of testosterone propionate. Compound VI showed a small degree of androgenic activity, but an anabolic activity comparable to testosterone propionate. In contrast, compounds XIV and XV failed to produce any androgenic or anabolic activity in vivo.

These studies show the discovery of two members (compounds VI and V), of a new class of SARMs (SARMS) that demonstrate potent anabolic effects (e.g., muscle growth) with less androgenic activity (e.g., prostatic growth). This new class of drugs has several advantages over nonselective androgens, including potential therapeutic applications in males and females for modulation of fertility, erythropoiesis, osteoporosis, sexual libido and in men with or at high risk for prostate cancer.

Figure 22:
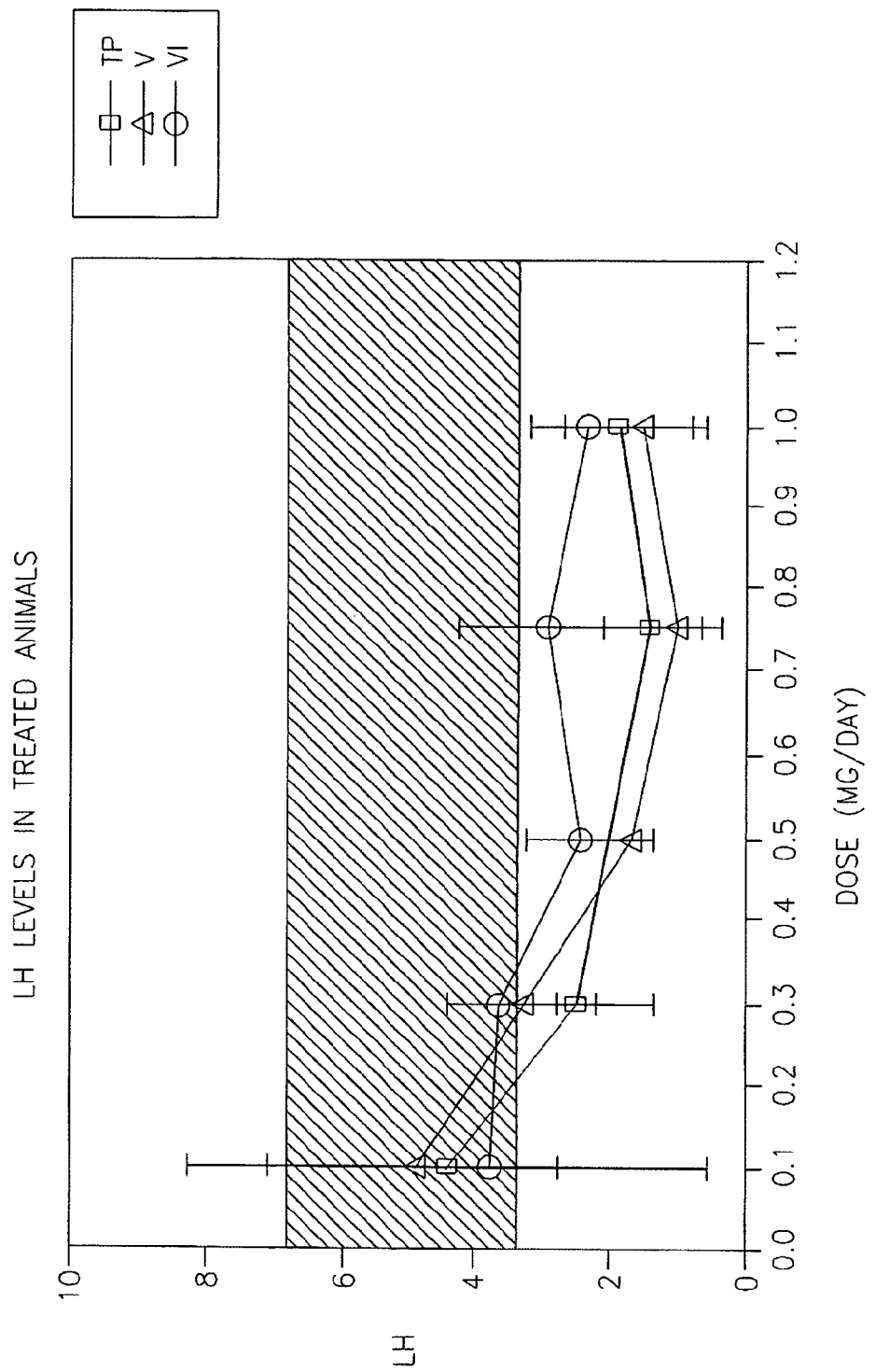
FIG. 22: Effects of compound of formula V and compound of formula VI on LH Levels.
Figure 23:
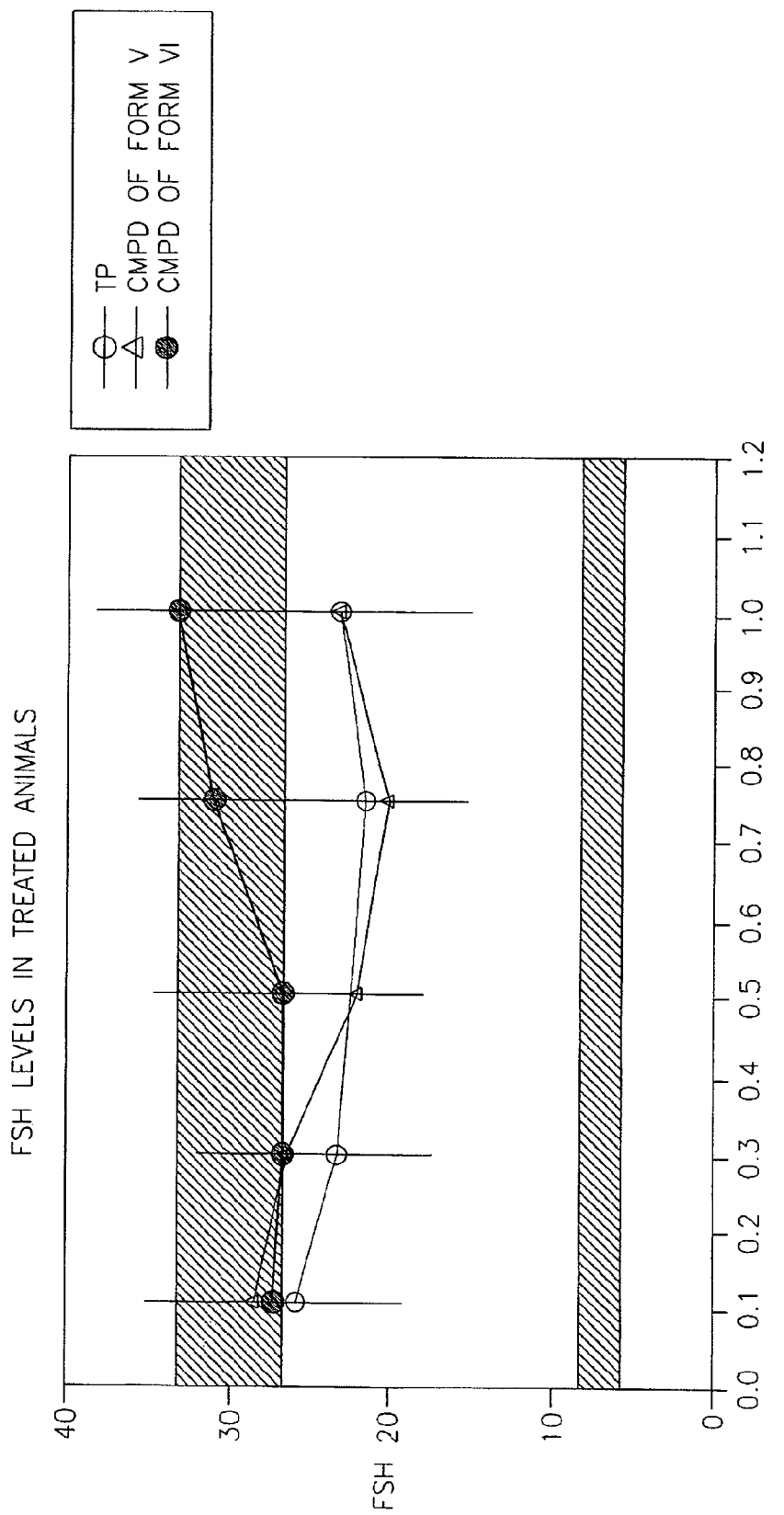
FIG. 23: Effects of compound of formula VI and compound of formula V on FSH Levels.

Further, FIGS. 22 and 23 demonstrate the effects of compounds V and VI and compound V on LH and FSH levels in rats. These results further demonstrate the novelty of these SARM, due to their differential effects on these reproductive hormones, thus demonstrating the tissue-specific pharmacologic activity. In FIG. 22, LH levels in castrated animals treated with TP and compound VI were significantly lower than those of untreated animals (i.e., castrated controls) at doses greater than or equal to 0.3 mg/day. However, higher doses (i.e., 0.5 mg/day or higher) of compound V were required before significant decreases in LH levels were observed. Thus, compound V does not suppress LH levels at doses that are capable of eliciting maximal stimulation of levator ani muscle growth. In FIG. 23, FSH levels in castrated animals treated with compound VI were significantly lower than hose of untreated animals (i.e., castrated controls) at doses of 0.5 mg/day or higher. Similarly, lower FSH levels were observed in animals treated with TP. However, only this difference was only significant at a dose of 0.75 mg/day. FSH levels in animals treated with compound V were not significantly different from those of untreated animals at any dose level tested. Thus, compound V does not suppress FSH levels at doses that are capable of eliciting maximal stimulation of levator ani muscle growth.

TABLE 4

Animals Groups and Experimental Design

| Group # | Castrated | Drug | Dose | # of animals |
|---|---|---|---|---|
| 1 | No | None | None | 5 |
| 2 | Yes | None | Vehicle only | 5 |
| 3 | Yes | Testosterone | 0.1 mg/day | 5 |
| 4 | Yes | Testosterone | 0.3 mg/day | 5 |
| 5 | Yes | Testosterone | 0.5 mg/day | 5 |
| 6 | Yes | Testosterone | 0.75 mg/day | 5 |
| 7 | Yes | Testosterone | 1.0 mg/day | 5 |
| 8 | Yes | R-III | 1.0 mg/day | 5 |
| 9 | Yes | S-III | 0.1 mg/day | 5 |
| 10 | Yes | S-III | 0.3 mg/day | 5 |
| 11 | Yes | S-III | 0.5 mg/day | 5 |
| 12 | Yes | S-III | 0.75 mg/day | 5 |
| 13 | Yes | S-III | 1.0 mg/day | 5 |
| 14 | Yes | S-VI | 0.1 mg/day | 5 |
| 15 | Yes | S-VI | 0.3 mg/day | 5 |
| 16 | Yes | S-VI | 0.5 mg/day | 5 |
| 17 | Yes | S-VI | 0.75 mg/day | 5 |
| 18 | Yes | S-VI | 1.0 mg/day | 5 |
| 19 | Yes | S-VII | 0.1 mg/day | 5 |
| 20 | Yes | S-VII | 0.3 mg/day | 5 |
| 21 | Yes | S-VII | 0.5 mg/day | 5 |
| 22 | Yes | S-VII | 0.75 mg/day | 5 |
| 23 | Yes | S-VII | 1.0 mg/day | 5 |
| 24 | Yes | S-V | 0.1 mg/day | 5 |
| 25 | Yes | S-V | 0.3 mg/day | 5 |
| 26 | Yes | S-V | 0.5 mg/day | 5 |
| 27 | Yes | S-V | 0.75 mg/day | 5 |
| 28 | Yes | S-V | 1.0 mg/day | 5 |
| 29 | Yes | None | Vehicle only | 5 |

Example 10

Pharmacokinetics of Compound V in Dogs

Figure 19:
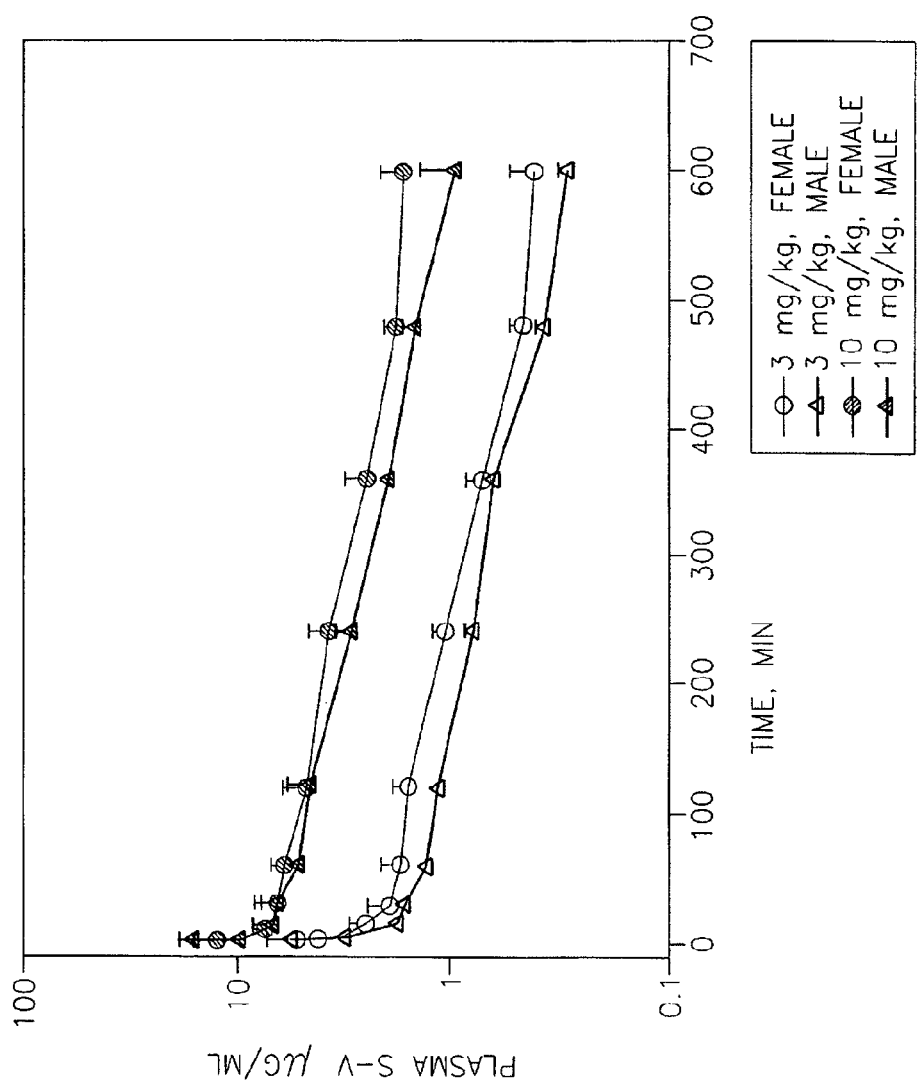
FIG. 19: Average plasma concentration-time profiles of compound S-V in beagle dogs after i.v. administration at 3 and 10 mg/kg.
Figure 20:
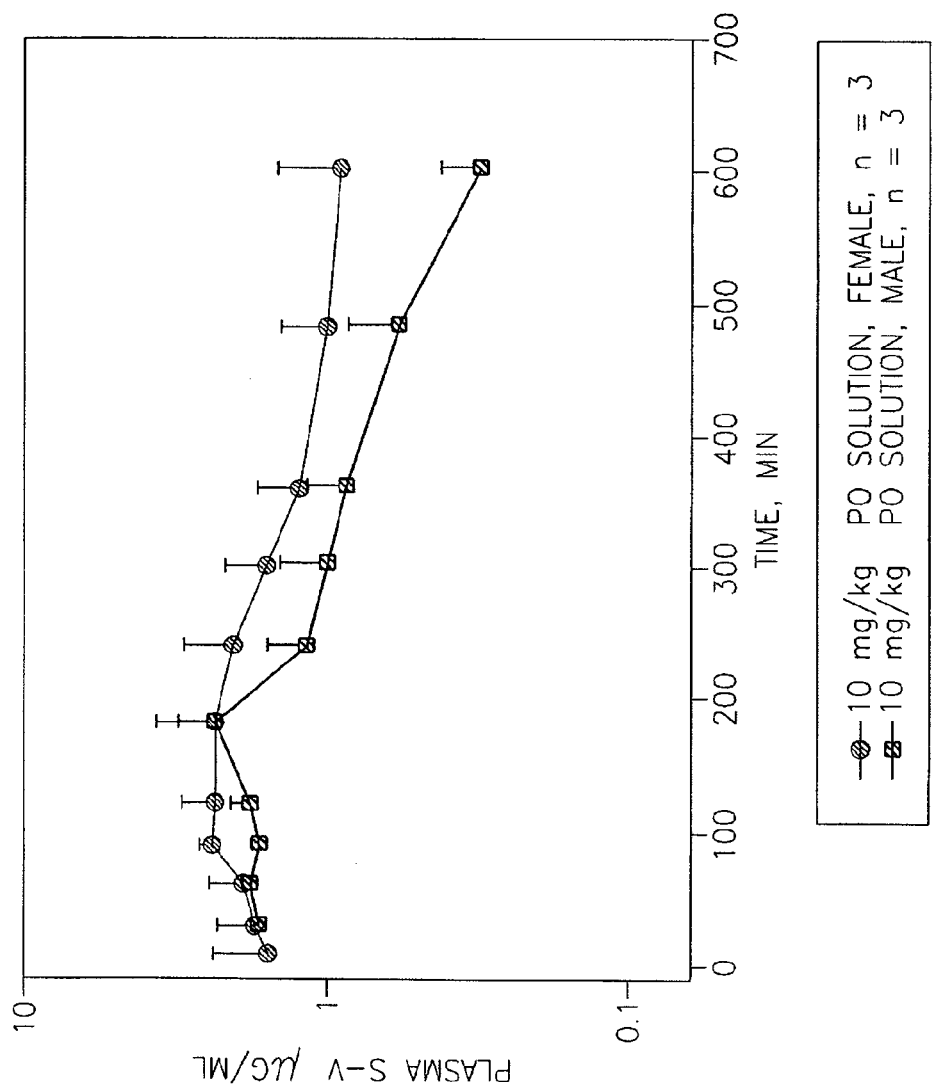
FIG. 20: Average plasma concentration-time profiles of compound S-V in beagle dogs after p.o. administration as solution at 10 mg/kg.
Figure 21:
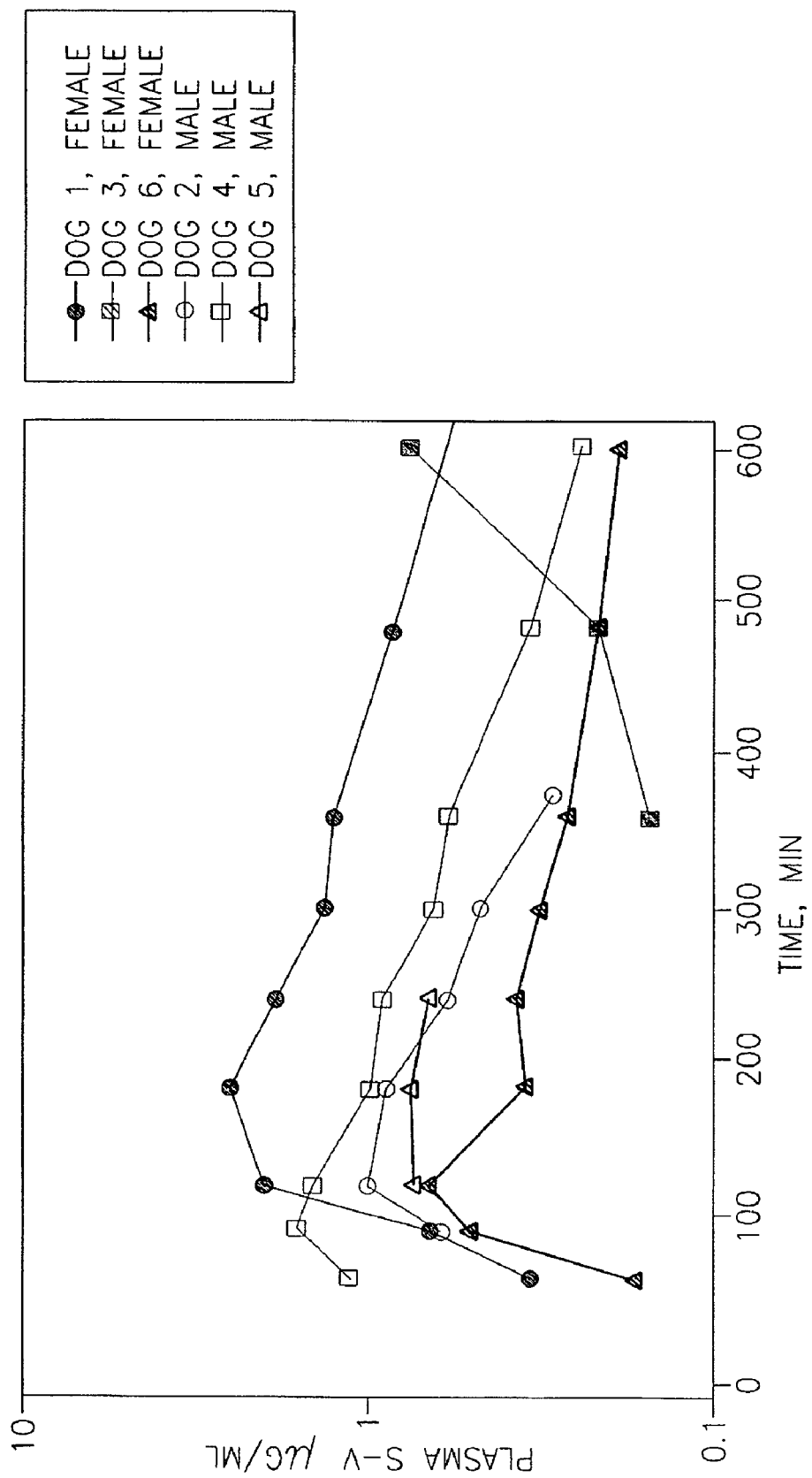
FIG. 21: Average plasma concentration-time profiles of compound S-V in beagle dogs after i.v. administration as capsules at mg/kg.

The pharmacokinetics of compound S-V, a novel SARM, were characterized in beagle dogs. A four-treatment, four-period crossover design was utilized in the study, which involved a total of six beagle dogs, three of each gender. Each animal received a 3 mg/kg I.V. dose, a 10 mg/kg I.V. dose, a 10 mg/kg P.O. dose in solution, and a 10 mg/kg P.O. dose in capsule, in a randomly assigned order. There was an one-week washout period between treatments Plasma samples were collected for up to 72 hr after drug administration. Plasma S-V concentrations were analyzed by a validated HPLC method. The clearance (CL), volume of distribution (Vss), half-life ($T_{1/2}$), and other pharmacokinetic parameters were determined by noncompartmental methods. Results showed that compound S-V was cleared from dog plasma with a terminal $T_{1/2}$ of about 4 hr and a CL of 4.4 mL/min/kg after I.V. administration. FIGS. 19-21 show the plasma concentration-time profiles of compound S-V after administration of an intravenous solution, oral solution, and oral capsule, respectively. The Pharmacokinetics were dose- and gender-independent. The oral bioavailability of compound S-V varied with the dosage form, and averaged 38% and 19% for solution and capsule, respectively. Thus, compound S-V demonstrated moderate half-life, slow clearance and moderate bioavailability in beagle dogs, identifying it as the first of a new class of orally bioavailable tissue-SARMs.

Example 11

Detection of Compound V in Dog Plasma

A reversed phase high pressure liquid chromatograph (HPLC) assay was developed to quantitate S-V concentrations in dog plasma. Dog blood samples were obtained by venipuncture and centrifuged at 1000 g for 15 minutes. Samples were stored frozen at −20° C. until analysis. Individual samples were rapidly thawed and an aliquot (0.5 ml) was spiked with internal standard (20 μl of a 200 μg/ml aqueous solution of CM-II-87). An aliquot of 1 ml of acetonitrile was added to the samples to precipitate plasma proteins. The samples were vortexed and then centrifuged at 1000 g for 15 minutes. The supernatant was decanted into glass extraction tubes and 7.5 ml of ethyl acetate was added. The extraction mixture was left at room temperature for 20 minutes, and vortexed several times during this interval. The samples were then centrifuged at 1000 g for 10 minutes, and the organic phase was removed and placed in conical-bottomed glass tubes. The organic phase was evaporated under nitrogen. The samples were reconstituted in 200 μl of mobile phase (35:65 acetonitrile:water) and transferred to an autosampler vial for HPLC injection (Waters 717 plus autosampler, Waters Corp., Milford, Mass.). The isocratic mobile phase of 35% (v/v) acetonitrile in water was pumped at a flow rate of 1 ml/min (Model 510, Waters Corp.). The stationary phase was a C18 reversed phase column (Novapac C18, 3.9.times.150 mm). Analytes were monitored with UV detection at 270 nm (Model 486 absorbance detector, Waters Corp.). Retention times for S-V and CM-II-87 were 11.1 and 16.9 minutes, respectively. Chromatography data was collected and analyzed using Millennium software. Plasma concentrations of S-V in each sample were determined by comparison to calibration curves. Calibration curves were constructed by adding known amounts of compound V to dog plasma. Final compound V concentrations in dog plasma samples used in the calibration curves were 0.08, 0.2, 0.4, 2, 4, 10, and 20 μg/ml. Calibration curves were linear over this concentration range and exhibited correlation coefficients ($r^2$) of 0.9935 or greater. Intra- and inter-day coefficients of variation for the standards ranged from 6.4% for 0.08 μg/ml to 7.9% for 20 μg/ml.

Melting points were determined on a Thomas-Hoover capillary melting point apparatus and are uncorrected. Infrared spectra were recorded on a Perkin Elmer System 2000 FT-IR. Optical rotations were determined on an Autopol™ III Automatic Polarimeter (Rudolph Research Model III-589-10, Fairfield, N.J.). Proton and carbon-13 magnetic resonance spectra were obtained on a Bruker AX 300 spectrometer (300 and 75 MHz for $^1$H and $^{13}$C, respectively). Chemical shift values were reported as parts per million (δ) relative to tetramethylsilane (TMS). Spectral data were consistent with assigned structures. Mass spectra were determined on a Bruker-HP Esquire LC System. Elemental analyses were performed by Atlantic Microlab Inc. (Norcross, Ga.), and found values were within 0.4% of the theoretical values. Routine thin-layer chromatography (TLC) was performed on silica gel on aluminum plates (silica gel 60 F 254, 20.times.20 cm, Aldrich Chemical Company Inc., Milwaukee, Wis.). Flash chromatography was performed on silica gel (Merck, grade 60, 230-400 mesh, 60). Tetrahydrofuran (THF) was dried by distillation over sodium metal. Acetonitrile (MeCN) and methylene chloride ($CH_2Cl_2$) were dried by distillation from $P_2O_5$.

Example 12

Pharmaceutical Compositions Comprising Compound V

The active ingredient is Compound V (>99.9% pure S-isomer). The inactive ingredients are lactose monohydrate, lactose fast-flo 316, Avicel PH102 (microcrystalline cellulose), magnesium stearate and colloidal silicon dioxide. The blended active and inactive ingredients are filled into white opaque hard gelatin capsules (size one).

(V)

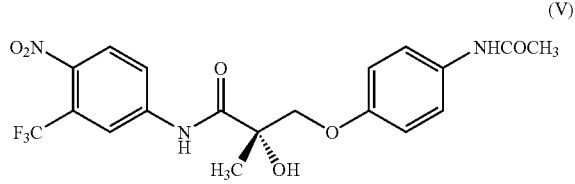

Quantitative Composition

TABLE 5

| Ingredient: | Excipient Purpose: | Weight/Count Per dosage unit: | Weight/Count Per Batch*: |
|---|---|---|---|
| Compound V | Active | 1.00 mg | 0.500 g |
| Lactose Monohydrate, NF (#310 Regular) | Diluent/Filler | 80.00 mg | 40.000 g |
| Lactose Monohydrate, NF (#316 Fast-Flo Modified, Spray-Dried) | Filler/Flow-Aid | 196.45 mg | 98.225 g |
| Microcrystalline Cellulose, NF (Avicel PH102) | Filler/Disintegrant | 30.00 mg | 15.000 g |
| Silicon Dioxide, Colloidal, USP/NF (Cab-O-Sil M-5P) | Flow-Aid | 1.00 mg | 0.500 g |
| Magnesium Stearate, NF HyQual | Lubricant | 1.55 mg | 0.775 g |

TABLE 5-continued

| Ingredient: | Excipient Purpose: | Weight/Count Per dosage unit: | Weight/Count Per Batch*: |
|---|---|---|---|
| Capsule, Hard Gelatin Size 1, White Opaque | Capsule | 1 (Count) | 500 (Count) |
| Compound III | Active | 0.10 mg | 0.050 g |
| Lactose Monohydrate, NF (#310 Regular) | Diluent/Filler | 80.00 mg | 40.000 g |
| Lactose Monohydrate, NF (#316 Fast-Flo Modified, Spray-Dried) | Filler/Flow-Aid | 197.35 mg | 98.675 g |
| Microcrystalline Cellulose, NF (Avicel PH102) | Filler/Disintegrant | 30.00 mg | 15.000 g |
| Silicon Dioxide, Colloidal, USP/NF (Cab-O-Sil M-5P) | Flow-Aid | 1.00 mg | 0.500 g |
| Magnesium Stearate, NF HyQual | Lubricant | 1.55 mg | 0.775 g |
| Capsule, Hard Gelatin Size 1, White Opaque | Capsule | 1 (Count) | 500 (Count) |

*Batch size based on 500 capsules but may change depending on requirements

Specifications and Analytical Methods for Inactive Compounds

All active ingredients included in the formulation have monographs that denote full compendial testing per Standard Operating Procedure of the manufacturer.

Method of Manufacturing

Figure 29:
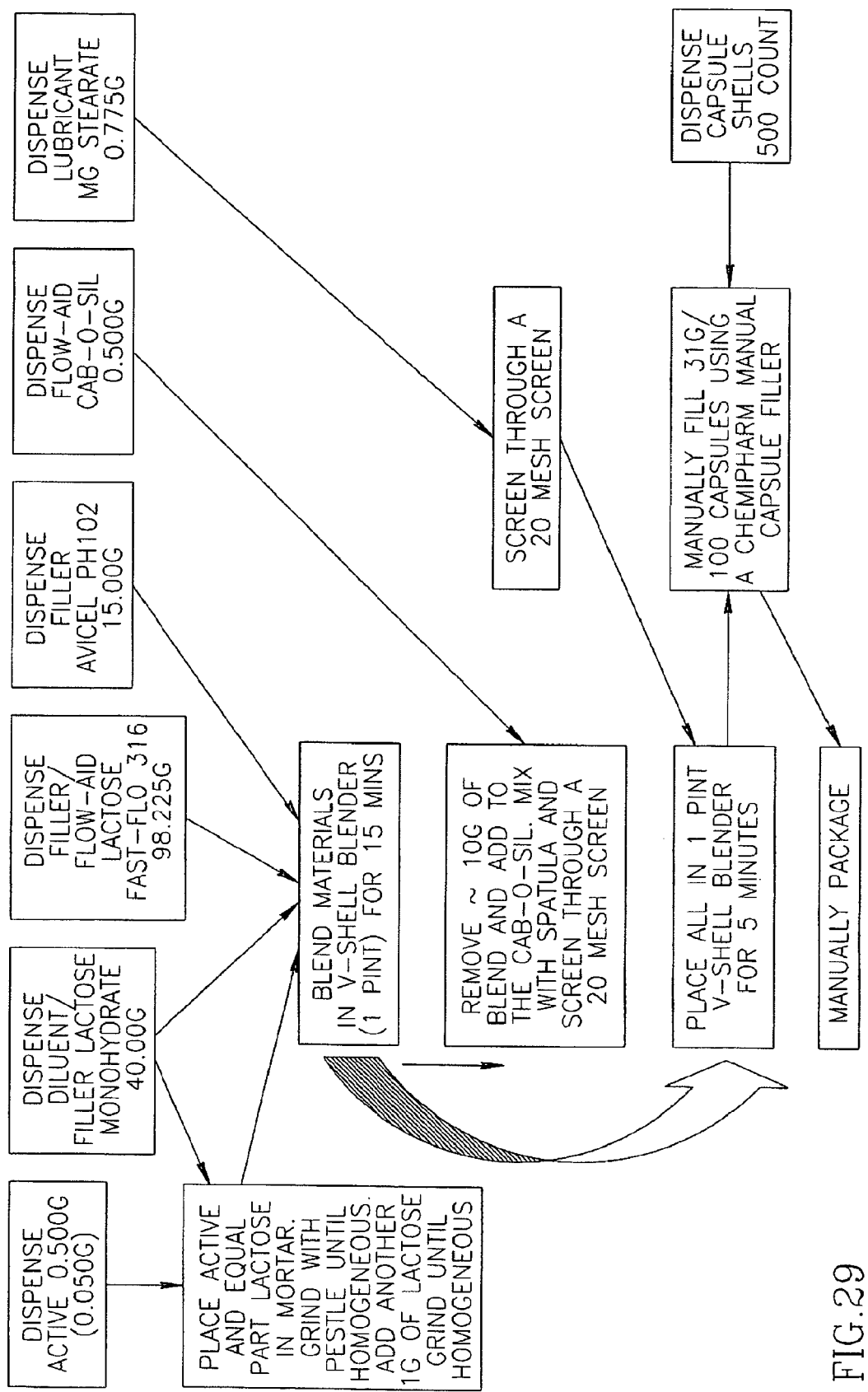
FIG. 29: a flow diagram illustrating the manufacturing process of the pharmaceutical compositions of the present invention.

Capsules of Compound V are manufactured in accordance with the flow chart depicted in FIG. 29, using the formulations as set forth in Table 5 (1 mg formulation) and Table 6 (0.1 mg formulation).

For 1 mg Compound V capsules: the indicated amount of active and inactive ingredients are dispensed. 0.5 grams of Compound V (active pharmaceutical ingredient, API) are diluted by placing API and an equal part of lactose monohydrate (0.5 grams) in mortar. The mixture is ground with a pestle until homogenous. The mixture is diluted again by adding one additional gram of lactose monohydrate to the mixture and grinding until homogenous. The diluted active:lactose monohydrate mixture is blended with 38.5 grams of lactose monohydrate, 98.225 grams of lactose fast-flo, and 15 grams of Avicel PH102 in a one pint V-shell blender for 15 minutes. Approximately 10 grams of the blend is removed and added to 0.5 grams of Cab-O-Sil. The mixture is mixed with a spatula and screened through a 20-mesh screen. 0.775 grams of magnesium stearate are independently screened through a 20-mesh screen. The screened ingredients (10 grams of initial blend with Cab-O-Sil, and magnesium stearate) are added to the remainder of the initial blend in the one pint V-shell blender. All ingredients are blended together in a V-shell blender for five minutes. Capsule shells (500 count) are dispensed into a Chemipharm Manual Capsule Filler. 31 grams of blended mixture are manually filled into 100 capsules using the Chemipharm Manual Capsule Filler. The capsules are manually packaged and labeled. Each capsule contains 1 milligram of active and 309 milligrams of inactive ingredients.

Figure 26:
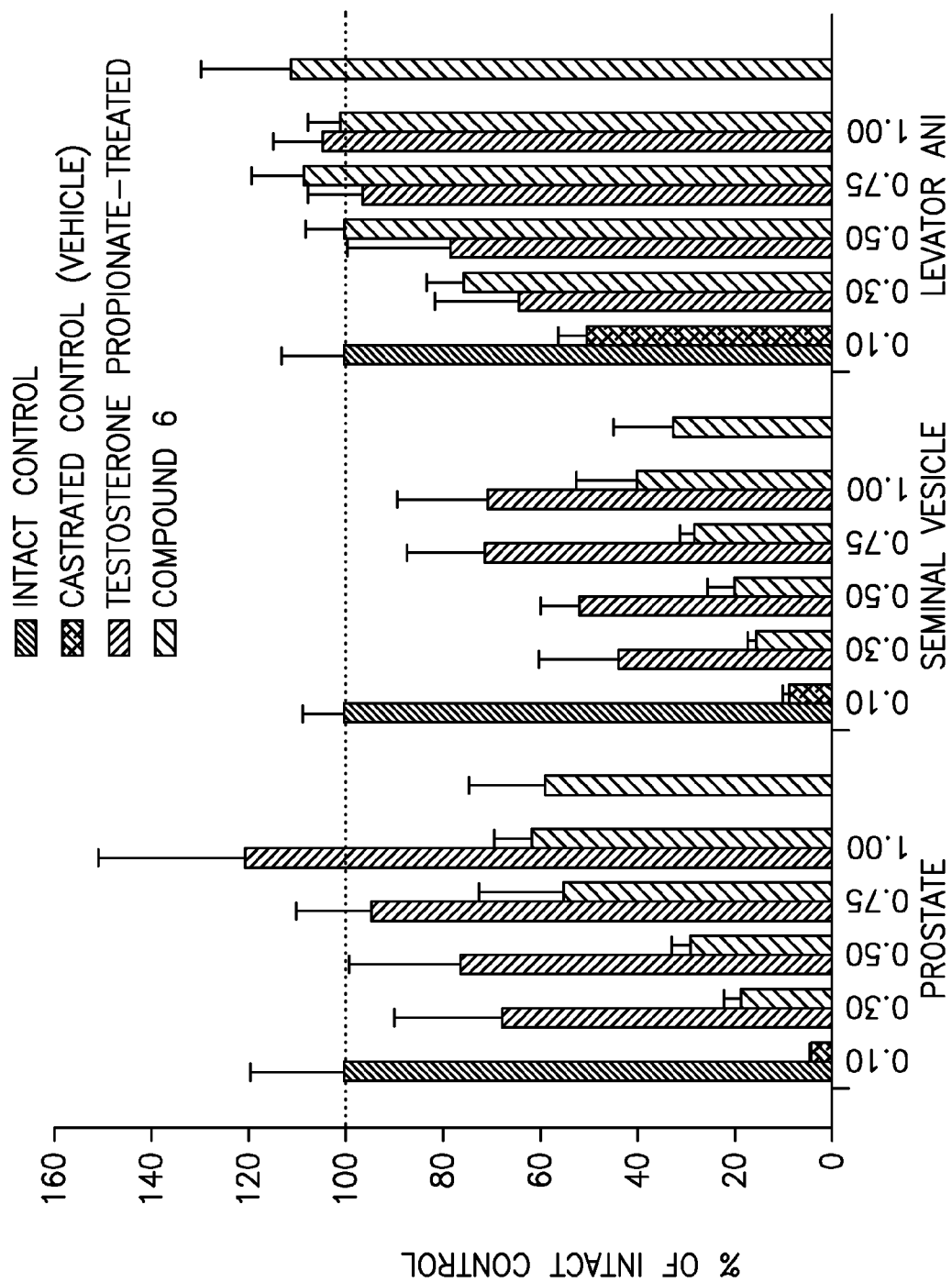
FIG. 26: Androgenic and Anabolic activity of Compound 6 (see Table 9) in rats. Rats were left untreated (intact control), castrated (castrated control), treated with 0.1, 0.3, 0.5, 0.75 and 1.0 mg/day testosterone propionate (TP), or treated with 0.1, 0.3, 0.5, 0.75 and 1.0 mg/day Compound 6, and the weight of androgen-responsive tissues (prostate, semimal vesicles and levator ani muscle) was determined.

For 0.1 mg Compound V capsules: the same Method of Manufacturing is used, the amounts of Compound V API and inactive ingredients are adjusted accordingly (Table 3 and flow diagram in FIG. 26).

Example 13

Androgenic and Anabolic Activity of Compounds 1-4

Binding affinities of select B-ring halogenated SARMS were determined and are represented in Table 6:

TABLE 6

| Name | Structure | MW | RBA (%) | Ki (nM) |
|---|---|---|---|---|
| 1 | $O_2N$-C$_6$H$_3$(CF$_3$)-NH-C(O)-C(CH$_3$)(OH)-CH$_2$-O-C$_6$H$_4$-F | 402.3 | 26.4 | 2.3 ± 0.0.06 |
| 2 | $O_2N$-C$_6$H$_3$(CF$_3$)-NH-C(O)-C(CH$_3$)(OH)-CH$_2$-O-C$_6$H$_4$-Cl | 419 | 7.6 | 8.6 ± 1.2 |
| 3 | $O_2N$-C$_6$H$_3$(CF$_3$)-NH-C(O)-C(CH$_3$)(OH)-CH$_2$-O-C$_6$H$_4$-Br | 462 | 5.3 | 12.6 ± 1.8 |
| 4 | $O_2N$-C$_6$H$_3$(CF$_3$)-NH-C(O)-C(CH$_3$)(OH)-CH$_2$-O-C$_6$H$_4$-I | 510 | 2.7 | 23 ± 1.6 | site cleaned with betadine. The animals were allowed to recover on a sterile pad (until able to stand) and then returned to their cage.

Twenty-four hours later, animals were re-anesthetized with ketamine/xylazine, and an Alzet osmotic pump(s) (model 2002) was placed subcutaneouly in the scapular region. In this instance, the scapular region was shaved and cleaned (betadine and alcohol) and a small incision (1 cm) made using a sterile scalpel. The osmotic pump was inserted and the wound closed with a sterile stainless steel wound clip. Animals were allowed to recover and were returned to their cage. Osmotic pumps contained the appropriate treatment dissolved in polyethylene glycol 300 (PEG300). Osmotic pumps were filled with the appropriate solution one day prior to implantation. Animals were monitored daily for signs of acute toxicity to drug treatment (e.g., lethargy, rough coat).

After 14 days of drug treatment, rats were anesthetized with ketamine/xylazine. Animals were then sacrificed by exsanguinations under anesthesia. A blood sample was collected by venipuncture of the abdominal aorta, and submitted for complete blood cell analysis. A portion of the blood was placed in a separate tube, centrifuged at 12,000 g for 1 minute, and the plasma layer removed and frozen at −20° C. The ventral prostates, seminal vesicles, levator ani muscle, liver, kidneys, spleen, lungs, and heart were removed, cleared of extraneous tissue, weighed, and placed in vials containing 10% neutral buffered formalin. Preserved tissues were sent to GTx, Inc. for histopathological analysis.

For data analysis, the weights of all organs were normalized to body weight, and analyzed for any statistical significant difference by single-factor ANOVA. The weights of prostate and seminal vesicle were used as indexes for evaluation of androgenic activity, and the levator ani muscle weight was used to evaluate the anabolic activity.

Methods

Animals. Immature male Sprague-Dawley rats, weighing 90 to 100 g, were purchased from Harlan Biosciences (Indianapolis, Ind.). The animals were maintained on a 12-hour light-dark cycle with food and water available ad libitum. The animal protocol was reviewed and approved by the Institutional Laboratory Animal Care and Use Committee.

Study Design. Rats were randomly distributed into treatment groups groups. One day prior to the start of drug treatment, animals were individually removed from the cage, weighed and anesthetized with an intraperitoneal dose of ketamine/xylazine (87/13 mg/kg; approximately 1 mL per kg). When appropriately anesthetized (i.e., no response to toe pinch), the animals' ears were marked for identification purposes. Animals were then placed on a sterile pad and their abdomen and scrotum washed with betadine and 70% alcohol. The testes were removed via a midline scrotal incision, with sterile suture being used to ligate supra-testicular tissue prior to surgical removal of each testis. The surgical wound site was closed with sterile stainless steel wound clips, and the

Results

The androgenic and anabolic activities of compounds 1-4 were examined in a castrated rat model after 14 days of administration. The results are shown in FIG. 24 A-D as a percent of the Intact Control (not castrated, untreated). 0 mg/day denotes Castrated Controls (castrated, untreated).

As shown in FIG. 24, the weights of prostate, seminal vesicle, and levator ani muscle in castrated rats decreased significantly, due to the ablation of endogenous androgen production. Treatment with increasing dosages of compounds 1-4 (FIG. 24 A-D respectively) resulted in a tissue-selective increase in leyator ani muscle weights, with little or no stimulation of prostate and seminal vesicle growth (i.e. the prostate and seminal vesicle weights were less than 40% of that observed in intact animals for compound 2, and less than 20% for compounds 1, 3 and 4). Thus these compounds showed little potency and intrinsic activity in increasing the weights of prostate and seminal vesicle, but a great potency and intrinsic activity in increasing the weight of levator ani muscle. Particularly, compound 2 was able to maintain the levator ani muscle weight of castrated animals in the same level as that of intact animals. Thus, compounds 1-4 are potent nonsteroidal anabolic agents. This is a significant improvement over previous compounds, in that these compound selectively stimulate muscle growth and other anabolic effects while having less effect on the prostate and seminal vesicles. This may be particularly relevant in aging men with concerns related to the development or progression of prostate cancer.

Example 14

Androgenic and Anabolic Activity of Compound 5

The binding affinity of select compound 5 is represented in Table 7:

TABLE 7

| Name | Structure | MW | Ki (nM) |
|---|---|---|---|
| 5 | NC–, CF₃–phenyl–NH–C(=O)–C(CH₃)(OH)–CH₂–O–phenyl–F | 382.3 | 3.3 ± 0.08 |

The androgenic and anabolic activities of compound 5 were examined in a castrated rat model after 14 days of administration, using the method outlined in Example 1 above.

Figure 25:
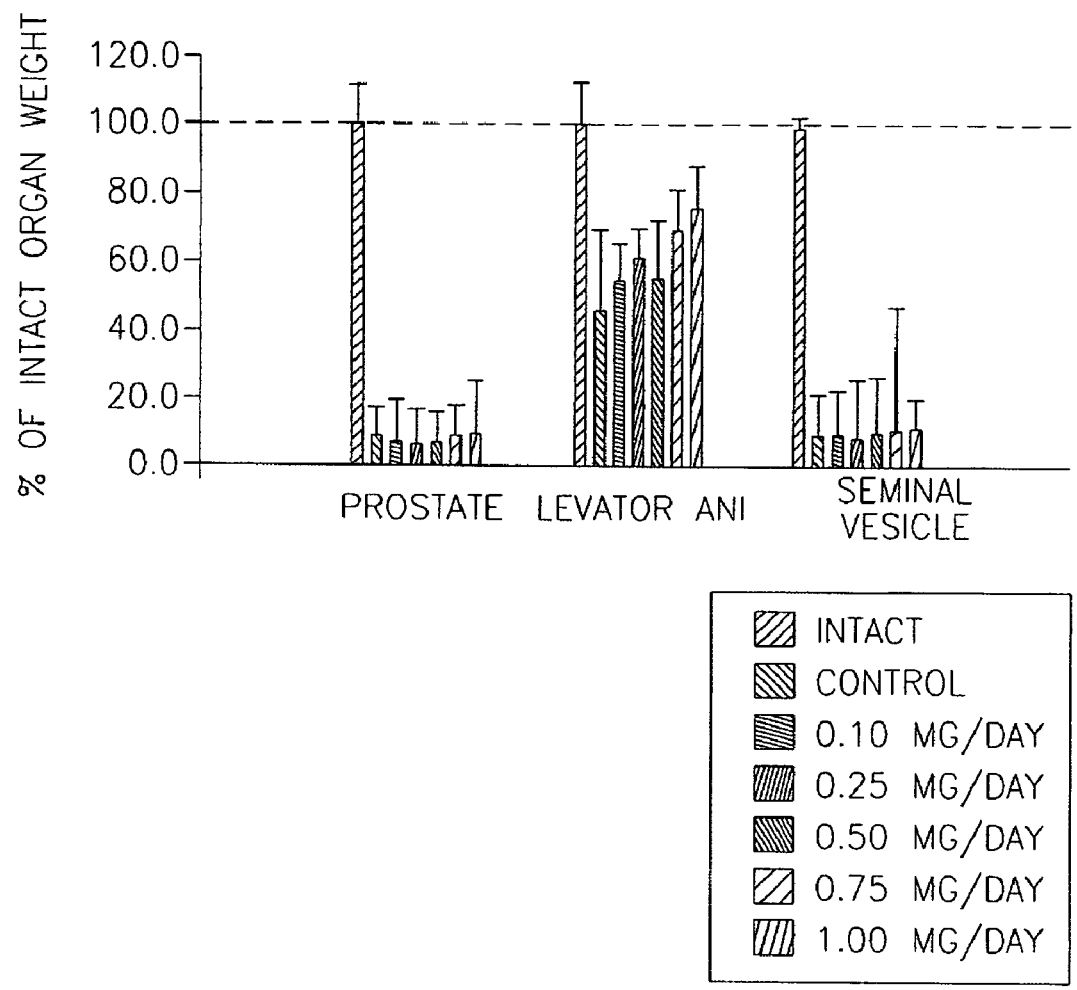
FIG. 25: Androgenic and Anabolic activity of compound 5 (see Table 7). Rats were left untreated (intact control), castrated (0 mg/day control), or treated with 0.1, 0.25, 0.5, 0.75 and 1.0 mg/day of compound 5, and the weight of androgen-responsive tissues (prostate, semimal vesicles and levator ani muscle) was determined.

As shown in Table 8 and in FIG. 25, compound 5 demonstrated tissue-selective pharmacological effects in castrated male rats, with higher efficacy in anabolic tissues (i.e. levator ani) as compared to androgenic tissues (i.e. prostate and seminal vesicles). Compound 5 demonstrated little pharmacologic activity in the prostate (8.7±1.39% of intact at 1.0 mg/day dose) and seminal vesicles (10.7±0.91% of intact at 1.0 mg/day dose), suggesting that it acts as a weak partial agonist in these tissues. Importantly, compound 5 demonstrates highly efficacious anabolic activity at 1.0 mg/day dose, returning the levator ani muscle to 75.2±9.51% of that observed in intact animals.

TABLE 8

| | Average (Mean ± S.D.) Organ Weights | | |
|---|---|---|---|
| | Prostate (g) | Levator Ani (g) | Seminal Vesicles (g) |
| Intact Control | 100 ± 11.28 | 100 ± 12.12 | 100 ± 2.48 |
| Castrated Control | 7.6 ± 0.68 | 45.9 ± 10.84 | 8.4 ± 1.05 |
| 0.10 mg/day | 6.4 ± 0.82 | 54.9 ± 5.77 | 8.8 ± 1.18 |
| 0.25 mg/day | 5.7 ± 0.61 | 61.0 ± 5.23 | 7.6 ± 1.37 |
| 0.50 mg/day | 6.2 ± 0.56 | 55.0 ± 9.23 | 9.3 ± 1.57 |
| 0.75 mg/day | 7.6 ± 0.74 | 68.9 ± 8.46 | 9.8 ± 3.65 |
| 1.00 mg/day | 8.7 ± 1.39 | 75.2 ± 9.51 | 10.7 ± 0.91 |

Example 15

Androgenic and Anabolic Activity of compound 6

The binding affinity of select compound 6 is represented in Table 9:

TABLE 9

| Name | Structure | MW | Ki (nM) |
|---|---|---|---|
| 6 | NC–, CF₃–phenyl–NH–C(=O)–C(CH₃)(OH)–CH₂–O–phenyl–Cl | 398.8 | 3.4 ± 0.08 |

The androgenic and anabolic activities of compound 6 was examined in a castrated rat model after 14 days of administration, using the method outlined in Example 1 above.

As shown in FIG. 26, the weights of prostate, seminal vesicle, and levator ani muscle in castrated, vehicle-treated rats decreased significantly, due to the ablation of endogenous androgen production. Exogenous administration of testosterone propionate, an androgenic and anabolic steroid, increased the weights of prostate, seminal vesicle, and levator ani muscle in castrated rats in a dose-dependent manner. Treatment with compound 6 resulted in dose-dependent increases in prostate, seminal vesicle and levator ani muscle weights. Compared with testosterone propionate, compound 6 showed lower potency and intrinsic activity in increasing the weights of prostate and seminal vesicle, but a greater potency and intrinsic activity in increasing the weight of levator ani muscle. Particularly, compound V, at a dose as low as 0.3 mg/day, was able to maintain the levator ani muscle weight of castrated animals in the same level as that of intact animals. Thus, compound 6 is a potent nonsteroidal anabolic agent with less androgenic activity but more anabolic activity than testosterone propionate. As in compounds 1-5 above, this is a significant improvement in that this compound selectively stimulates muscle growth and other anabolic effects while having less effect on the prostate and seminal vesicles.

Example 16

Binding Affinities of SARMs

The in vitro androgen receptor binding affinity of other SARM compounds was studied and the results are presented in Table 10.

TABLE 10

| Name | Structure | MW | Ki (nM) |
|---|---|---|---|
| 7 | [structure] | 348.1 | 4.5 ± 0.11 |
| 8 | [structure] | 421.4 | 12.7 ± 0.03 |
| 9 | [structure] | 360.6 | 22.2 ± 0.17 |
| 10 | [structure] | 391.7 | 14.5 ± 0.18 |
| 11 | [structure] | 375.3 | 32.6 ± 0.1 |
| 12 | [structure] | 483.2 | 15.6 ± 0.19 |

TABLE 10-continued

| Name | Structure | MW | Ki (nM) |
|---|---|---|---|
| 13 | 4-Br, 3-CF3-phenyl-NH-C(O)-C(CH3)(OH)-CH2-O-4-Cl-phenyl | 452.7 | 52.0 ± 0.13 |
| 14 | 4-Br, 3-CF3-phenyl-NH-C(O)-C(CH3)(OH)-CH2-O-4-Br-phenyl | 436.2 | 25.9 ± 0.04 |
| 15 | 3-CF3-phenyl-NH-C(O)-C(CH3)(OH)-CH2-O-4-F-phenyl | 357.3 | 62.0 ± 0.05 |
| 16 | 4-NC, 3-I-phenyl-NH-C(O)-C(CH3)(OH)-CH2-O-4-F-phenyl | 440.2 | 3.5 ± 0.13 |
| 17 | 7-nitro-benzofurazan-4-yl-NH-C(O)-C(CH3)(OH)-CH2-O-4-F-phenyl | 376.3 | >1800 |
| 18 | 4-Br, 3-CF3-phenyl-NH-C(O)-C(CH3)(OH)-CH2-O-4-F-phenyl | 436.2 | ND |
| 19 | 4-O2N, 3-CF3-phenyl-NH-C(O)-C(CH3)(OH)-CH2-O-4-(thiourea)-phenyl | 458.41 | ND |
| 20 | 4-O2N, 3-CF3-phenyl-NH-C(O)-C(CH3)(OH)-CH2-O-indol-5-yl | | 17.0 ± 0.64 |

ND—Not Determined

Average DHT Ki value: 0.36 ± 0.15

Example 17

4-Cyano and 4-Nitro Substitution on the Pharmacologic Activity and Pharmacokinetics of SARMs

Purpose

The purpose of this study was to examine the in vitro and in vivo pharmacologic activities of four compounds (N-1 through N-4) incorporating 4-nitro and/or 4-cyano substituents in the A- and B-ring.

TABLE 11

| Compound | Structure |
|---|---|
| N-1 | O₂N–[ring(F₃C)]–NH–C(O)–C(CH₃)(OH)–CH₂–O–[ring]–NO₂ |
| N-2 | O₂N–[ring(F₃C)]–NH–C(O)–C(CH₃)(OH)–CH₂–O–[ring]–CN |
| N-3 | NC–[ring(F₃C)]–NH–C(O)–C(CH₃)(OH)–CH₂–O–[ring]–NO₂ |
| N-4 | NC–[ring(F₃C)]–NH–C(O)–C(CH₃)(OH)–CH₂–O–[ring]–CN |

Methods

Relative binding affinity (RBA) was calculated as: RBA (%)=(Ki of DHT/Ki of compound of interest) and determined using $^3$H-mibolerone and androgen receptor (AR) isolated from rat ventral prostate. In vivo pharmacologic activities were determined by weight increase (% of intact control) of anabolic (levator ani muscle) and androgenic (prostate, seminal vesicle) target tissues of castrated that received 1 mg/day of tested compounds for 14 days.

Results

The RBA of N-1, N-2, N-3, and N-4 was 30%, 26%, 32%, and 17%, respectively. The compounds demonstrated little pharmacologic activity in the prostate and seminal vesicles, but significantly increased the weight of the levator ani muscle to 105% ±13%, 119% ±16%, 130% ±5%, and 142% ±17%, respectively, of that observed in intact controls. Pharmacokinetic studies showed that the clearance of compounds incorporating a 4-nitro substituent in the A- or B-ring was significantly higher than that of the di-cyano substituted compound (N-4-Compound III described hereinabove).

Inclusion of a 4-nitro substituent in the A-ring of these derivatives increased in vitro AR binding affinity, but resulted in increased in vivo clearance. All compounds demonstrated potent and tissue-selective in vivo pharmacologic effects. In vivo activity did not correlate with in vitro binding affinity. However, N-4 demonstrated the greatest activity and lowest in vivo clearance, corroborating the importance of in vivo pharmacokinetics and metabolism to SARM activity.

Example 18

Synthesis of (S) Enantiomer of Compound of Formula III

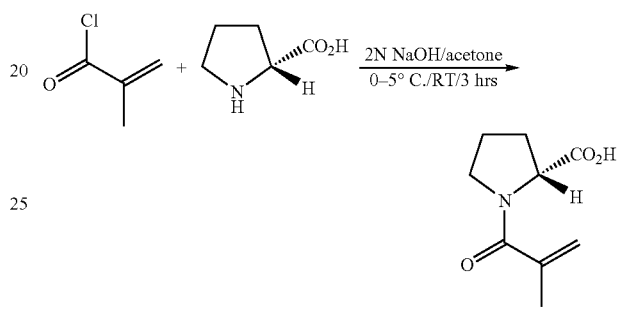

(2R)-1-Methacryloylpyrrolidin-2-carboxylic Acid. D-Proline, 14.93 g, 0.13 mol) was dissolved in 71 mL of 2 N NaOH and cooled in an ice bath; the resulting alkaline solution was diluted with acetone (71 mL). An acetone solution (71 mL) of metacryloly chloride (13.56 g, 0.13 mol) and 2N NaOH solution (71 mL) were simultaneously added over 40 min to the aqueous solution of D-proline in an ice bath. The pH of the mixture was kept at 10-11° C. during the addition of the metacryloly chloride. After stirring (3 h, room temperature), the mixture was evaporated in vacuo at a temperature at 35-45° C. to remove acetone. The resulting solution was washed with ethyl ether and was acidified to pH 2 with concentrated HCl. The acidic mixture was saturated with NaCl and was extracted with EtOAc (100 mL×3). The combined extracts were dried over Na₂SO₄, filtered through Celite, and evaporated in vacuo to give the crude product as a colorless oil. Recrystallization of the oil from ethyl ether and hexanes afforded 16.2 (68%) of the desired compound as colorless crystals: mp 102-103° C. (lit. [214] mp 102.5-103.5° C.); the NMR spectrum of this compound demonstrated the existence of two rotamers of the title compound. $^1$H NMR (300 MHz, DMSO-d₆) δ 5.28 (s) and 5.15 (s) for the first rotamer, 5.15 (s) and 5.03 (s) for the second rotamer (totally 2H for both rotamers, vinyl CH₂), 4.48-4.44 for the first rotamer, 4.24-4.20 (m) for the second rotamer (totally 1H for both rotamers, CH at the chiral canter), 3.57-3.38 (m, 2H, CH₂), 2.27-2.12 (1H, CH), 1.97-1.72 (m, 6H, CH₂, CH, Me); $^{13}$C NMR (75 MHz, DMSO-d₆) δ for major rotamer 173.3, 169.1, 140.9, 116.4, 58.3, 48.7, 28.9, 24.7, 19.5: for minor rotamer 174.0, 170.0, 141.6, 115.2, 60.3, 45.9, 31.0, 22.3, 19.7; IR (KBr) 3437 (OH), 1737 (C=O), 1647 (CO, COOH), 1584, 1508, 1459, 1369, 1348, 1178 cm$^{-1}$; $[\alpha]_D^{26}$+80.8° (c=1, MeOH); Anal. Calcd. for C₉H₁₃NO₃: C 59.00, H 7.15, N, 7.65. Found: C 59.13, H 7.19, N 7.61.

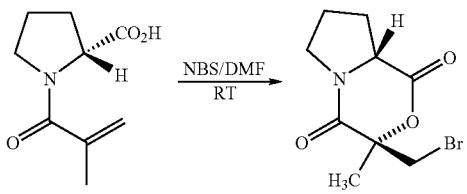

(3R,8aR)-3-Bromomethyl-3-methyl-tetrahydro-pyrrolo[2,1-c][1,4]oxazine-1,4-dione. A solution of NBS (23.5 g, 0.132 mol) in 100 mL of DMF was added dropwise to a stirred solution of the (methyl-acryloyl)-pyrrolidine (16.1 g, 88 mmol) in 70 mL of DMF under argon at room temperature, and the resulting mixture was stirred 3 days. The solvent was removed in vacuo, and a yellow solid was precipitated. The solid was suspended in water, stirred overnight at room temperature, filtered, and dried to give 18.6 (81%) (smaller weight when dried ~34%) of the title compound as a yellow solid: mp 152-154° C. (lit. [214] mp 107-109° C. for the S-isomer); $^1$H NMR (300 MHz, DMSO-$d_6$) δ 4.69 (dd, J=9.6 Hz, J=6.7 Hz, 1H, CH at the chiral center), 4.02 (d, J=11.4 Hz, 1H, CHH$_a$), 3.86 (d, J=11.4 Hz, 1H, CHH$_b$), 3.53-3.24 (m, 4H, CH$_2$), 2.30-2.20 (m, 1H, CH), 2.04-1.72 (m, 3H, CH$_2$ and CH), 1.56 (s, 2H, Me); $^{13}$C NMR (75 MHz, DMSO-$d_6$) δ 167.3, 163.1, 83.9, 57.2, 45.4, 37.8, 29.0, 22.9, 21.6; IR (KBr) 3474, 1745 (C=O), 1687 (C=O), 1448, 1377, 1360, 1308, 1227, 1159, 1062 cm$^{-1}$; [α]$_D^{26}$ +124.5° (c=1.3, chloroform); Anal. Calcd. for C$_9$H$_{12}$BrNO$_3$: C 41.24, H 4.61, N 5.34. Found: C 41.46, H 4.64, N 5.32.

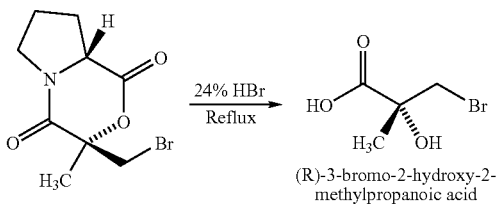

(2R)-3-Bromo-2-hydroxy-2-methylpropanoic Acid. A mixture of bromolactone (18.5 g, 71 mmol) in 300 mL of 24% HBr was heated at reflux for 1 h. The resulting solution was diluted with brine (200 mL), and was extracted with ethyl acetate (100 mL×4). The combined extracts were washed with saturated NaHCO$_3$ (100 mL×4). The aqueous solution was acidified with concentrated HCl to pH=1, which, in turn, was extracted with ethyl acetate (100 mL×4). The combined organic solution was dried over Na$_2$SO$_4$, filtered through Celite, and evaporated in vacuo to dryness. Recrystallization from toluene afforded 10.2 g (86%) of the desired compound as colorless crystals: mp 107-109° C. (lit. [214] mp 109-113° C. for the S-isomer); $^1$H NMR (300 MHz, DMSO-$d_6$) δ 3.63 (d, J=10.1 Hz, 1H, CHH$_a$), 3.52 (d, J=10.1 Hz, 1H, CHH$_b$), 1.35 (s, 3H, Me); IR (KBr) 3434 (OH), 3300-2500 (COOH), 1730 (C=O), 1449, 1421, 1380, 1292, 1193, 1085 cm$^{-1}$; [α]$_D^{26}$ +10.5° (c=2.6, MeOH); Anal. Calcd. for C$_4$H$_7$BrO$_3$: C 26.25, H 3.86. Found: C 26.28, H 3.75.

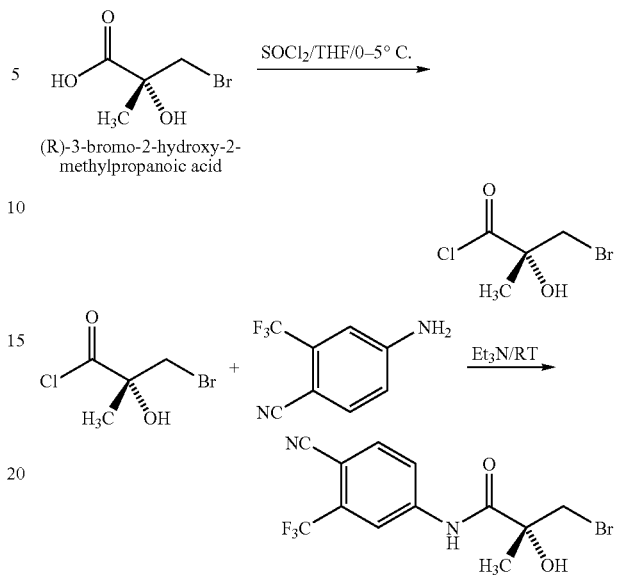

Synthesis of (2R)-3-Bromo-N-[4-cyano-3-(trifluoromethyl)phenyl]-2-hydroxy-2-methylpropanamide. Thionyl chloride (46.02 g, 0.39 mol) was added dropwise to a cooled solution (less than 4° C.) of R-131 (51.13 g, 0.28 mol) in 300 mL of THF under an argon atmosphere. The resulting mixture was stirred for 3 h under the same condition. To this was added Et$_3$N (39.14 g, 0.39 mol) and stirred for 20 min under the same condition. After 20 min, 5-amino-2-cyanobenzotrifluoride (40.0 g, 0.21 mol), 400 mL of THF were added and then the mixture was allowed to stir overnight at room temperature. The solvent was removed under reduced pressure to give a solid which was treated with 300 mL of H$_2$O, extracted with EtOAc (2×400 mL). The combined organic extracts were washed with saturated NaHCO$_3$ solution (2×300 mL) and brine (300 mL). The organic layer was dried over MgSO$_4$ and concentrated under reduced pressure to give a solid which was purified from column chromatography using CH$_2$Cl$_2$/EtOAc (80:20) to give a solid. This solid was recrystallized from CH$_2$Cl$_2$/hexane to give 55.8 g (73.9%) of (2R)-3-Bromo-N-[4-cyano-3-(trifluoromethyl)phenyl]-2-hydroxy-2-methylpropanamide as a light-yellow solid.

$^1$H NMR (CDCl$_3$/TMS) δ 1.66 (s, 3H, CH$_3$), 3.11 (s, 1H, OH), 3.63 (d, J=10.8 Hz, 1H, CH$_2$), 4.05 (d, J=10.8 Hz, 1H, CH$_2$), 7.85 (d, J=8.4 Hz, 1H, ArH), 7.99 (dd, J=2.1, 8.4 Hz, 1H, ArH), 8.12 (d, J=2.1 Hz, 1H, ArH), 9.04 (bs, 1H, NH). Calculated Mass: 349.99, [M−H]$^-$ 349.0. M.p.: 124-126° C.

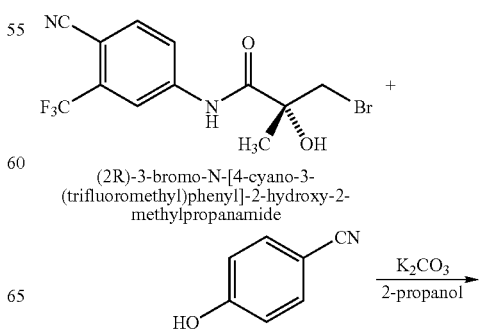

(2R)-3-bromo-N-[4-cyano-3-(trifluoromethyl)phenyl]-2-hydroxy-2-methylpropanamide

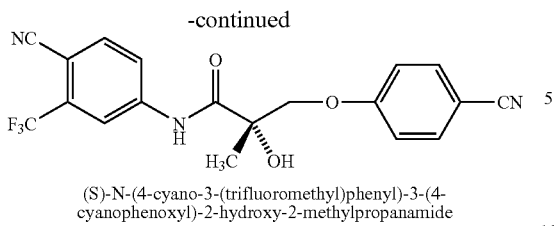

(S)-N-(4-cyano-3-(trifluoromethyl)phenyl)-3-(4-cyanophenoxyl)-2-hydroxy-2-methylpropanamide Synthesis of (S)—N-(4-Cyano-3-(trifluoromethyl)phenyl)-3-(4-cyanophenoxy)-2-hydroxy-2-methylpropanamide. A mixture of bromoamide ((2R)-3-Bromo-N-[4-cyano-3-(trifluoromethyl)phenyl]-2-hydroxy-2-methylpropanamide, 50 g, 0.14 mol), anhydrous $K_2CO_3$ (59.04 g, 0.43 mol), 4-cyanophenol (25.44 g, 0.21 mol) in 500 mL of 2-propanol was heated to reflux for 3 h and then concentrated under reduced pressure to give a solid. The resulting residue was treated with 500 mL of $H_2O$ and then extracted with EtOAc (2×300 mL). The combined EtOAc extracts were washed with 10% NaOH (4×200 mL) and brine. The organic layer was dried over $MgSO_4$ and then concentrated under reduced pressure to give an oil which was treated with 300 mL of ethanol and an activated carbon. The reaction mixture was heated to reflux for 1 h and then the hot mixture was filtered through Celite. The filtrate was concentrated under reduced pressure to give an oil. This oil was purified by column chromatography using $CH_2Cl_2$/EtOAc (80:20) to give an oil which was crystallized from $CH_2Cl_2$/hexane to give 33.2 g (59.9%) of (S)—N-(4-cyano-3-(trifluoromethyl)phenyl)-3-(4-cyanophenoxy)-2-hydroxy-2-methylpropanamide as a colorless solid (a cotton type).

$^1$H NMR (CDC$_3$/TMS) δ 1.63 (s, 3H, CH$_3$), 3.35 (s, 1H,OH), 4.07 (d, J=9.04 Hz, 1H, CH), 4.51 (d, J=9.04 Hz, 1H, CH), 6.97-6.99 (m, 2H, ArH), 7.57-7.60 (m, 2H, ArH), 7.81 (d, J=8.55 Hz, 1H, ArH), 7.97 (dd, J=1.95, 8.55 Hz, 1H, ArH), 8.12 (d, J=1.95 Hz, 1H, ArH), 9.13 (bs, 1H, NH). Calculated Mass: 389.10, [M–H]$^-$ 388.1. Mp: 92-94° C.

Example 19

Influence of the X-Bridge of the SARM Compounds in Terms of Affinity to an AR and Transcriptional Activation A series of SARMs that are p-nitro, m-trifluoromethyl substituted in the A-ring and p-acetamide or p-fluoro substituted in the B-ring with the 2-hydroxy-2-methylpropionanilide linker and a variety of X-position functional groups in the linker were synthesized and analysed (Table 12).

TABLE 12

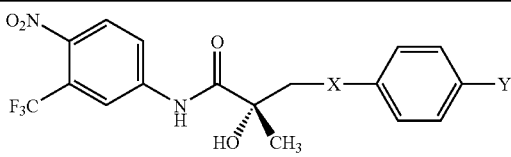

Dependence of % Maximum Efficacy on X- and Y-Positions

| Cmpd. # | X | Y | Affinity (nM)[a] | Efficacy (% max)[b,c] |
|---|---|---|---|---|
| 1 | —O— | NHC(O)CH$_3$ | 3.98 ± 0.70 | 92.92 ± 7.00 |
| 2 | —O— | F | 6.11 ± 0.19 | 43.40 ± 2.60 |

TABLE 12-continued

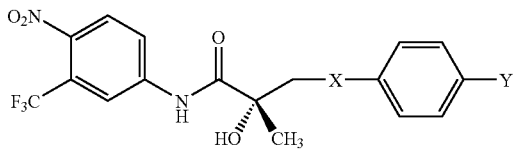

Dependence of % Maximum Efficacy on X- and Y-Positions

| Cmpd. # | X | Y | Affinity (nM)[a] | Efficacy (% max)[b,c] |
|---|---|---|---|---|
| 3 | —S— | NHC(O)CH$_3$ | 4.90 ± 0.20 | 50 |
| 4 | —S— | F | 11 ± 2 | 77.4 ± 5.6 |
| 5 | —SO$_2$— | NHC(O)CH$_3$ | 9.32 ± 0.81 | 45.1 ± 5.2 |
| 6 | —SO$_2$— | F | 28 ± 10 | 18.8 ± 9.3 |
| 7 | —NH— | NHC(O)CH$_3$ | 128 ± 5.97 | 5.18 ± 1.40 |
| 8 | —NH— | F | 7.96 ± 0.43 | 21.33 ± 2.22 |
| 9 | —CH$_2$— | F | 9 ± 0.2[d] | 28.9 ± 2.4[d] |
| 10 | — | F | 26 ± 5[d] | 15.9 ± 1.2[d] |

[a]Intact AR binding affinities were determined using a competitive binding assay using rat ventral prostate cytosol as the source for AR as described previously.
[b]Intact AT in vitro functional activity was examined using a cotransfection assay.
[c]Efficacy (transcriptional activation) was assayed at 10 nM of SARM and activity was expressed as a % maximum transcriptional activation observed for 1 nM dihydrotestosterone (DHT).
[d]Reported as a racemic mixture.

Results

Dihydrotestosterone induced transcriptional activation was suppressed by 33% and 18% for non-hydrogen compounds 9 and 10 (X=CH$_2$), respectively of Table 9, demonstrating that these agents were not strong antagonists of in vitro transcriptional activation. The non-hydrogen bonding AR ligands 9 and 10 of Table 9 were high affinity ligands with K$_i$ values of 9 nM and 26 nM, respectively, but demonstrated reduced in vitro functional activity of 29% and 16%, respectively as seen in Table 9. Shortening the linker by one carbon (10) was detrimental effect to affinity and functional activation.

In addition Y-position effects were seen (Table 9). Of the series of compounds evaluated, the p-acetamide was favorable for affinity and in vitro transcriptional activity. The exceptions to this rule were compounds 7 vs. 8 (X=NH) for affinity and 3 vs. 4 (X=S) for in vitro activation. For these compounds, the Y-position has a hydrogen bonding interaction within the AR binding pocket. It is plausible that with regard to these compounds, the p-acetamide displaces the H$_2$O molecule and interacts directly with the histidine thereby more effectively stabilizing the active conformation of the AR-SARM complex.

The non-hydrogen bonding compounds 9 and 10 reduced in vitro transcriptional activation abilities of 29% and 16%, respectively, despite the high affinities of 9 nM and 26 nM, respectively. Thus, for these compounds, a hydrogen bond acceptor (HBA) X-position ability is critical for AR activation.

It will be appreciated by a person skilled in the art that the present invention is not limited by what has been particularly shown and described hereinabove. Rather, the scope of the invention is defined by the claims that follow.

What is claimed is:

1. A SARM compound represented by the structure of formula (III):

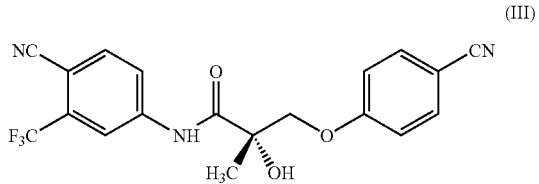

(III)

and/or its isomer, pharmaceutically acceptable salt, or any combination thereof.

2. A composition comprising the SARM compound of claim 1, and/or its isomer, or any combination thereof; and a suitable carrier or diluent.

3. A composition comprising the SARM compound of claim 1, and/or its isomer, or any combination thereof, and/or a pharmaceutically acceptable salt thereof; and a suitable carrier or diluent.

4. A method of binding a SARM compound to an androgen receptor, comprising the step of contacting the androgen receptor with the SARM compound of claim 1 and/or its isomer, pharmaceutically acceptable salt, or any combination thereof, in an amount effective to bind the SARM compound to the androgen receptor.

5. A method of hormone therapy comprising the step of contacting an androgen receptor of a subject with the SARM compound of claim 1 and/or its isomer, pharmaceutically acceptable salt, or any combination thereof, in an amount effective to effect a change in an androgen-dependent condition.

6. A method of treating a subject suffering from prostate cancer, comprising the step of administering to said subject the SARM compound of claim 1 and/or its isomer, pharmaceutically acceptable salt, or any combination thereof, in an amount effective to treat prostate cancer in said subject.

7. A method of delaying the progression of prostate cancer in a subject suffering from prostate cancer, comprising the step of administering to said subject the SARM compound of claim 1 and/or its isomer, pharmaceutically acceptable salt, or any combination thereof, in an amount effective to delay the progression of prostate cancer in said subject.

* * * * *